(12) United States Patent
Bailey et al.

(10) Patent No.: US 6,897,306 B2
(45) Date of Patent: May 24, 2005

(54) 3-HETEROCYCLYLPROPANOHYDROXAMIC ACIDS

(75) Inventors: Simon Bailey, San Diego, CA (US); Stephane Billotte, San Diego, CA (US); Paul Vincent Fish, Faversham (GB); Kim James, Westgate-onSea (GB); Nicholas Murray Thomson, Canterbury (GB); Andrew Michael Derrick, Ramsgate (GB)

(73) Assignee: Pfizer Products, Inc., Groton, CT (US)

( * ) Notice: Subject to any disclaimer, the term of this patent is extended or adjusted under 35 U.S.C. 154(b) by 0 days.

(21) Appl. No.: 10/198,710

(22) Filed: Jul. 16, 2002

(65) Prior Publication Data

US 2003/0119807 A1 Jun. 26, 2003

Related U.S. Application Data

(62) Division of application No. 09/735,968, filed on Dec. 13, 2000, now Pat. No. 6,448,278.
(60) Provisional application No. 60/180,527, filed on Feb. 7, 2000.

(30) Foreign Application Priority Data

Dec. 23, 1999 (GB) .............................. 9930570

(51) Int. Cl.$^7$ ...................... C07D 271/06; C07D 413/14
(52) U.S. Cl. ...................... 544/138; 546/194; 546/223; 546/14; 548/131; 548/236; 548/110
(58) Field of Search .......................... 544/138; 546/194, 546/223; 548/131, 236

(56) References Cited

U.S. PATENT DOCUMENTS 5,861,380 A * 1/1999 Gyorkos et al. .............. 514/19

FOREIGN PATENT DOCUMENTS

| WO | 9705865 | 2/1997 |
|----|---------|--------|
| WO | 9731892 | 4/1997 |
| WO | 9945927 | 9/1999 |

OTHER PUBLICATIONS

D.A. Evans et al, *Journal of Organic Chemistry*, vol. 64, No. 17 Aug. 20, 1999, pp. 6411–6417, "A general method for the synthesis of enantiomerically pure beta–substituted, beta–amino acids through alpha–substituted succinic acid derivatives".

M. Yamamoto et al., *J. of Medicinal Chemistry*, vol. 41, No. 8, Apr. 9, 1998, pp. 1209–1217, "Inhibition of membrane—type 1 matrix metalloproteinase by hydroxamate inhibitors: an examination of the subsite pocket".

D.H. Steinman et al. *Bioorganic & Medicinal Chemistry Letters* vol. 8, No. 16, Aug. 18, 1998, pp. 2087–2092, "The design, synthesis and structure–activity relationships of a series of macrocyclic MMP inhibitors".

C.B. Vu et al, *Bioorganic & Medicinal Chemistry Letters* vol. 9, No. 20, Oct. 18, 1999, pp3009–3014, "Nonpeptidic SH2 Inhibitors of the Tyrosine Kinase ZAP–70".

K. F. McClure et al., *Bioorganic & Medicinal Chemistry Letters* vol.8. No. 2, pp. 143–146, "Alkylation of succinates: synthesis of RO 32–3555, "Alkylation of succinates: synthesis of RO 32–3555.

B. Simoneau, et al., *Bioorganic & Medicinal Chemistry Letters* vol. 7. No. 3, pp. 489–508, "Discovery of Non–peptidic $P_2$–$P_2$ Butanediamide Renin Inhibitors with High Oral Efficcay".

C. D. Floyd et al., SYNLETT, No. 6, Jun. 1998, pp. 637–639, "Rapid synthesis of matrix metalloproteinase Inhibitors via Ugi four–component condensation".

Abstract, Preparation and fromulation of hydroxamic acid detrivatives as matrix metalloproteinase inhibitors, *Chemical Abstracts Service, Columbus, OH,* Database accession No. 1997:594709, XP002163188.

International Search Report for PCT/IB001/01855.

* cited by examiner

*Primary Examiner*—Joseph K. McKane
*Assistant Examiner*—Sonya Wright
(74) *Attorney, Agent, or Firm*—Elsa Djuardi; J. Michael Dixon

(57) ABSTRACT

Compounds of formula (I):

and their salts, solvates, prodrugs, etc., wherein the substituents have the values mentioned herein, are Procollagen C-Proteinase (PCP) inhibitors and have utility in conditions mediated by PCP.

11 Claims, No Drawings

3-HETEROCYCLYLPROPANOHYDROXAMIC ACIDS

This application is a division of and claims priority benefits of a non-provisional application Ser. No. 09/735,968, filed Dec. 13, 2000 now U.S. Pat. No. 6,448,278, which claims priority of a provisional application No. 60/180,527, filed Feb. 7, 2000, which claims priority of a Great Britain application No 9930570.8, filed Dec. 23, 1999.

This invention relates to a certain class of compounds, and the pharmaceutically acceptable salts, solvates and prodrugs thereof, which inhibit Procollagen C-proteinase ("PCP"). They are therefore useful in the treatment of mammals having conditions alleviable by inhibition of PCP. Especially of interest is an antiscarring treatment for wounds.

Fibrotic tissues, including dermal scars, are characterised by excessive accumulation of extracellular matrix, mainly collagen type I. It is thought that inhibition of collagen deposition will reduce formation of scar tissue. Collagen is secreted as the precursor, procollagen, which is transformed into the insoluble collagen by cleavage of the C-terminal propeptide by PCP. PCP is a zinc-dependent metalloprotease which is secreted from TGF-β-activated fibroblasts belonging to the subfamily of astacin-like proteases and able to cleave the C-terminal peptide of types I, II and III procollagens. Furthermore, data suggest that PCP activates lysyl oxidase, an enzyme essential for the formation of covalent cross-links which stabilise the fibrous form of collagen. Therefore, inhibition of PCP may not only reduce collagen deposition but may also make collagen more accessible for degradation.

Collagen is integral to, among other things, the proper formation of connective tissue. Thus, the over- or under-production of collagen or the production of abnormal collagen (including incorrectly processed collagen) has been linked with numerous connective tissue diseases and disorders. Mounting evidence suggests that PCP is an essential key enzyme for the proper maturation of collagen (see for example International Patent Application publication number WO 97/05865).

The present invention relates to substances capable of inhibiting PCP activity in order to regulate, modulate and/or reduce collagen formation and deposition. More specifically, the invention relates to the use of compounds and pharmaceutical compositions thereof for the treatment of various conditions relating to production of collagen.

At present more than nineteen types of collagens have been identified. These collagens, including fibrillar collagen Types I, II, III are synthesized as procollagen precursor molecules which contain amino- and carboxy-terminal peptide extensions. These peptide extensions, referred to as "pro-regions," are designated as N- and C-propeptides, respectively. The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, Annu. Rev. Biochem. 47:129–162; Bornstein and Traub, 1979, in: The Proteins (eds. Neurath, H. and Hill, R. H.), Academic Press, New York, pp. 412–632; Kivirikko et al., 1984, in: Extracellur Matrix Biochemistry (eds. Piez, K. A. and Reddi. A. H.), Elsevier Science Publishing Co., Inc., New York, pp. 83–118; Prockop and Kivirikko, 1984, N. Engl, J. Med. 311:376–383; Kuhn, 1987, in: Structure and Function of Collagen Types (eds. Mayne, R. and Burgeson, R. E.), Academic Press, Inc., Orlando, Fla., pp. 1–42.

An array of conditions has been associated with the inappropriate or unregulated production of collagen, including pathological fibrosis or scarring, including endocardial sclerosis, idiopathic interstitial fibrosis, interstitial pulmonary fibrosis, perimuscular fibrosis, Symmers' fibrosis, pericentral fibrosis, hepatitis, dermatofibroma, cirrhosis such as billary cirrhosis and alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and Pyronie's disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. Other conditions where collagen plays a key role include burns. Fibrosis of lung tissue is also observed in patients suffering from chronic obstructive airways disease (COAD) and asthma. One strategy for the treatment of these diseases and conditions is to inhibit the overproduction and/or deposition and/or unregulation of collagen. Thus, identification and isolation of molecules which control, inhibit and/or modulate the production and deposition of collagen are of major medical interest.

Recent evidence suggests that PCP is the essential key enzyme that catalyzes the cleavage of the Procollagen C-propeptide. This has been demonstrated in fibrillar collagens, including type I, type II, and type III collagen.

PCP was first observed in the culture media of human and mouse fibroblasts (Goldberg et al., 1975, Cell 4:45–50; Kessler and Goldberg, 1978, Anal. Biochem. 86:463–469), and chick tendon fibroblasts (Duskin et al., 1978, Arch. Biochem. Biophys. 185:326–332; Leung et al., 1979, J. Biol, Chem. 254:224–232). An acidic proteinase which removes the C-terminal propeptides from type I procollagen has also been identified (Davidson et al., 1979, Eur. J. Biochem. 100:551).

A partially purified protein having PCP activity was obtained from chick calvaria in 1982. Njieha et al., 1982, Biochemistry 23:757–764. In 1985, chicken PCP was isolated, purified and characterized from conditioned media of chick embryo tendons. Hojima et al., 1985, J. Biol. Chem. 260:15996–16003. Murine PCP has been subsequently purified from media of cultured mouse fibroblasts. Kessler et al., 1986, Collagen Relat. Res. 6:249–266; Kessler and Adar, 1989, Eur. J. Biochem. 186:115–121. Finally, the cDNA encoding human PCP has been identified, as set forth in the above-referenced articles and references disclosed therein.

Experiments conducted with these purified forms of chick and mouse PCP have indicated that the enzyme is instrumental in the formation of functional collagen fibers. Fertala et al., 1994, J. Biol. Chem. 269:11584.

As a consequence of the enzyme's apparent importance to collagen production, scientists have identified a number of PCP inhibitors. See e.g., Hojima et al., supra. For example, several metal chelators have demonstrated activity as PCP inhibitors. Likewise, chymostatin and pepstatin A were found to be relatively strong inhibitors of PCP. Additionally, ($\alpha_2$-Macroglobuline, ovostatin, and fetal bovine serum appear to at least partially inhibit PCP activity.

Dithiothreitol, SDS, concanavalin A, $Zn^{2+}$, $Cu^{2+}$, and $Cd^{2+}$ are similarly reported to be inhibitory at low concentrations. Likewise, some reducing agents, several amino acids, phosphate, and ammonium sulfate were inhibitory at concentrations of 1–10 mM. Further, the enzyme was shown to be inhibited by the basic amino acids lysine and arginine (Leung et al., supra; Ryhänen et al., 1982, Arch. Biochem. Biophys. 215:230–235). Finally, high concentrations of NaCl or Tris-HCL buffer were found to inhibit PCP's activity. For example, it is reported that, with 0.2, 0.3, and 0.5M NaCl, the activity of PCP was reduced 66, 38, and 25%, respectively, of that observed with the standard assay concentration of 0.15M. Tris-HCl buffer in a concentration of 0.2–0.5M markedly inhibited activity (Hojima et al., supra). PCP activity and its inhibition have been determined using a wide array of assays. See e.g., Kessler and Goldberg, 1978, Anal. Biochem. 86:463; Njieha et al., 1982, Biochemistry 21:757–764. As articulated in numerous publications, the enzyme is difficult to isolate by conventional biochemical means and the identity of the cDNA sequence encoding such enzyme was not known until reported in the above referenced and related patent applications.

In view of its essential role in the formation and maturation of collagen PCP appears to be an ideal target for the treatment of disorders associated with the inappropriate or unregulated production and maturation of collagen. However, none of the inhibitors so far disclosed has proven to be an effective therapeutic for the treatment of collagen-related diseases and conditions.

The identification of effective compounds which specifically inhibit the activity of PCP to regulate and modulate abnormal or inappropriate collagen production is therefore desirable and the object of this invention.

Matrix metalloproteases (MMPs) constitute a family of structurally similar zinc-containing metalloproteases, which are involved in the remodelling, repair and degradation of extracellular matrix proteins, both as part of normal physiological processes and in pathological conditions.

Another important function of certain MMPs is to activate other enzymes, including other MMPs, by cleaving the pro-domain from their protease domain. Thus, certain MMPs act to regulate the activities of other MMPs, so that over-production in one MMP may lead to excessive proteolysis of extracellular matrix by another, e.g. MMP-14 activates pro-MMP-2

During the healing of normal and chronic wounds, MMP-1 is expressed by migrating keratinocytes at the wound edges (U. K. Saarialho-Kere, S. O. Kovacs, A. P. Pentland, J. Clin. Invest. 1993, 92, 2858–66). There is evidence which suggests MMP-1 is required for keratinocyte migration on a collagen type I matrix in vitro, and is completely inhibited by the presence of the non-selective MMP inhibitor SC44463 ((N-4-hydroxy)-N-1-[(1S)-2-(4-methoxyphenyl)methyl-1-((1R)-methylamino)carbonyl)]-(2R)-2-(2-methylpropyl)butanediamide) (B. K. Pilcher, J. A. Dumin, B. D. Sudbeck, S. M. Krane, H. G. Welgus, W. C. Parks, J. Cell Biol., 1997, 137, 1–13). Keratinocyte migration in vivo is essential for effective wound healing to occur.

MMP-2 and MMP-9 appear to play important roles in wound healing during the extended remodelling phase and the onset of re-epithelialisation, respectively (M. S. Agren, Brit. J. Dermatology, 1994,131, 634–40; T. Salo, M. Mäkänen, M. Kylmäniemi, Lab. Invest., 1994, 70, 176–82). The potent, non-selective MMP inhibitor BB94 ((2S,3R)-5-methyl-3-{[(1S)-1-(methylcarbamoyl)-2-phenylethyl]carbamoyle}-2-[(2-thienylthio)methyl]hexanohydroxamic acid, batimastat), inhibits endothelial cell invasion of basement membrane, thereby inhibiting angiogenesis (G. Tarboletti, A. Garofalo, D. Belotti, T. Drudis, P. Borsotti, E. Scanziani, P. D. Brown, R. Giavazzi, J. Natl. Cancer Inst., 1995, 87, 293–8). There is evidence that this process requires active MMP-2 and/or 9.

Thus PCP inhibitors which significantly inhibit MMPs 1 and/or 2 and/or 9 would be expected to impair wound healing. MMP-14 is responsible for the activation of MMP-2, and thus inhibition of MMP-14 might also result in impaired wound healing.

For recent reviews of MMPs, see Zask et al, Current Pharmaceutical Design, 1996, 2, 624–661; Beckett, Exp. Opin. Ther. Patents, 1996, 6, 1305–1315; and Beckett et al, Drug Discovery Today, vol 1(no.1), 1996, 16–26.

Alternative names for various MMPs and substrates acted on by these are shown in the table below (Zask et al, supra).

| Enzyme | Other names | Preferred substrates |
| --- | --- | --- |
| MMP-1 | Collagenase-1, interstitial collagenase | Collagens I, II, III, VII, X, gelatins |
| MMP-2 | Gelatinase A, 72kDa gelatinase | Gelatins, collagens IV, V, VII, X, elastin, fibronectin; activates pro-MMP-13 |
| MMP-3 | Stromelysin-1 | Proteoglycans, laminin, fibronectin, gelatins. |
| MMP-7 | Pump, Matrilysin | Proteoglycans, laminin, fibronectin, gelatins, collagen IV, elastin, activates pro-MMP-1 and -2. |
| MMP-8 | Collagenase-2, neutrophil collagenase | Collagens I, II, III |
| MMP-9 | Gelatinase B, 92 kDa gelatinase | Gelatins, collagens IV, V, elastin |
| MMP-12 | Macrophage metalloelastase | Elastin, collagen IV, fibronectin, activates pro-MMP-2 & 3. |
| MMP-13 | Collagenase-3 | Collagens I, II, III, gelatins |
| MMP-14 | MT-MMP-1 | Activates pro-MMP-2 & 13, gelatins |
| MMP-15 | MT-MMP-2 | unknown |
| MMP-16 | MT-MMP-3 | Activates pro-MMP-2 |
| MMP-17 | MT-MMP-4 | unknown |

According to one aspect of the present invention, there are provided compounds of formula (I):

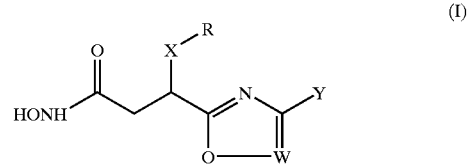

wherein:
X is $C_{1-6}$alkylene or $C_{2-6}$alkenylene, each of which is optionally substituted by one or more fluorine atoms;

R is aryl or $C_{3-8}$cycloalkyl optionally substituted by one or more fluorine atoms;

W is N or CZ;

Y and Z are each independently H, $C_{1-4}$alkyl (optionally substituted by one or more substituents independently selected from halogen, $S(O)_pR^6$, $OR^5$, $CONR^1R^2$, $CO_2R^7$ and aryl), $C_{1-4}$alkanoyl optionally substituted by one or more halogen, $C_{1-4}$alkoxycarbonyl optionally substituted by one or more halogen, or $CONR^1R^2$;

$R^1$ and $R^2$ are each independently selected from H, $C_{3-8}$cycloalkyl, $C_{1-4}$alkyl (optionally substituted by $C_{3-8}$cycloalkyl, aryl, $CO_2H$, $CO_2R^5$ and/or $NR^3R^4$), or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by $C_{1-4}$alkyl, $CO_2H$, $CO_2R^5$, aryl and/or $NR^3R^4$;

$R^3$ and $R^4$ are each independently selected from H, $C_1$–$C_4$alkyl or $C_{1-4}$alkoxycarbonyl optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$alkyl) moiety;

$R^5$ is $C_{1-4}$alkyl optionally substituted by $CO_2R^7$ or $CONR^3R^4$, or $R^5$ is aryl;

$R^6$ is $C_{1-4}$alkyl optionally substituted by one or more halogen, or aryl;

$R^7$ is H or $R^6$;

p is 0, 1 or 2;

"Aryl" is a mono- or bicyclic aromatic carbocyclic or heterocyclic system comprising from 5 to 10 ring atoms, including up to 3 hetero-atoms selected from N, O and S, where, if there is a N atom in the ring, it can be present as the N-oxide, which ring system is optionally substituted by up to 3 substituents independently selected from halogen, $C_{1-4}$alkyl optionally substituted by one or more halogen, $C_{1-4}$alkoxy optionally substituted by one or more halogen, phenyl, pyridyl, $CO_2H$, $CONR^3R^4$, $CO_2(C_{1-4}alkyl)$, $NR^3R^4$, OH and $OC(O)(C_{1-4}alkyl)$;

and the pharmaceutically acceptable salts, solvates (including hydrates) and prodrugs thereof.

"Alkyl", "alkylene", "alkoxy", "alkanoyl", and "alkenylene" groups, including in groups incorporating said moieties, may be straight chain or branched where the number of carbon atoms allows.

Halogen is taken to mean fluorine, chlorine, bromine or iodine.

Pharmaceutically-acceptable salts are well known to those skilled in the art, and for example include those mentioned in the art cited above, and by Berge et al, in *J. Pharm. Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogen phosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate, pamoate, camsylate, and p-toluenesulphonate salts.

Pharmaceutically acceptable base addition salts are well known to those skilled in the art, and for example include those mentioned in the art cited above, and can be formed from bases which form non-toxic salts and include the aluminium, calcium, lithium, magnesium, potassium, sodium and zinc salts, and salts of non-toxic amines such as diethanolamine.

Certain of the compounds of formula (I) may exist in one or more zwitterionic forms. It is to be understood that pharmaceutically acceptable salts includes all such zwitterions.

Certain of the compounds of formula (I), their salts, solvates, prodrugs, etc. may exist in one or more polymorphic forms. It is to be understood that the invention includes all such polymorphs.

The compounds of formula (I), their salts, hydrates, prodrugs etc. can exhibit isotopic variation, e.g. forms with enriched $^2H$, $^3H$, $^{13}C$, $^{14}C$, $^{15}N$, $^{18}O$, etc. may be prepared, for example by suitable variation of the synthetic methods described herein using methods and reagents known in the art or routine modification thereof. All such isotopic variants are included in the scope of the invention.

Prodrug moieties are well-known to those skilled in the art (see for example the article by H Feres, in Drugs of Today, vol 19, no.9 (1983) pp.499–538, especially section A1), and for example include those specifically mentioned in A. A. Sinkula's article in Annual Reports in Medicinal Chemistry, vol 10, chapter 31, pp.306–326, herein incorporated by reference, and the references therein. Specific prodrug moieties which may be specifically mentioned are aliphatic-aromatic, carbonate, phosphate and carboxylic esters, carbamates, peptides, glycoside, acetals and ketals, tetrahydropyranyl and silyl ethers. Such prodrug moieties can be cleaved in situ, e.g. are hydrolysable in physiological conditions, to give compounds of formula (I).

Certain of the compounds of the formula (I) may exist as geometric isomers. The compounds of the formula (I) may possess one or more asymmetric centres, apart from the specified centres in formula (I), and so exist in two or more stereoisomeric forms. The present invention includes all the individual stereoisomers and geometric isomers of the compounds of formula (I) and mixtures thereof.

Preferably the compounds of formula (I) have the following stereochemistry (IA):

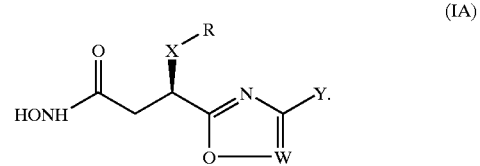

(IA)

Preferably, for compounds of formula (I) where W is CZ, at least one of Y and Z is H or $C_{1-4}$alkyl (optionally substituted by one or more halogen).

Preferably X is a linear $C_{2-4}$alkylene moiety optionally substituted by one or more fluorine atoms. Most preferably X is propylene.

Preferably R is $C_{3-8}$cycloalkyl optionally substituted by one or more fluorine atoms. More preferably R is cyclobutyl or cyclohexyl optionally substituted by one or more fluorine atoms. Yet more preferably R is cyclobutyl or cyclohexyl. Most preferably R is cyclohexyl.

Preferably W is N, CH or $CCH_3$. Most preferably W is N.

Preferably Z is H or $C_{1-4}$alkyl optionally substituted by one or more halogen atoms. More preferably Z is H or methyl optionally substituted by one or more fluorine atoms. Most preferably Z is H or methyl.

Preferably Y is $C_{1-4}$alkyl (optionally substituted by one or more substituents independently selected from halogen, $S(O)_pR^6$, $OR^5$, $CONR^1R^2$, $CO_2R^7$ and aryl), $C_{1-4}$alkoxycarbonyl, or $CONR^1R^2$. More preferably Y is methyl, isopropyl, methoxymethyl, 2-methoxyethyl, (pyrrolidino)$COCH_2$, phenylsulphonylmethyl, 4-chlorophenoxymethyl, (pyridin-2-yl)methyl, (pyridin-3-yl)methyl, (pyridin-4-yl)methyl, (imidazol-2-yl)methyl, $CO_2(C_{1-2}alkyl)$, $CONH_2$, $CONH(C_{1-4}alkyl$ (optionally substituted by $C_{3-8}$cycloalkyl, aryl, $CO_2H$ or $CO_2R^5$)), $CON(C_{1-4}alkyl)(C_{1-4}alkyl$ (optionally substituted by $C_{3-8}$ cycloalkyl, aryl, $CO_2H$ or $CO_2R^5$)), or $CONR^1R^2$ where $R^1$ and $R^2$ are taken together with the nitrogen to which they are attached to represent a 4- to 6-membered heterocyclic ring optionally containing one or two further hetero atoms in the ring independently selected from N, O and S, and which heterocyclic ring is optionally benzo- or pyrido-fused, and which heterocyclic ring is optionally substituted by $C_{1-4}$ alkyl, $CO_2H$, $CO_2R^5$, aryl or $NR^3R^4$. Yet more preferably Y is $CO_2C_2H_5$, $CONH_2$, $CONHCH_3$, $CONH(n-C_3H_7)$, $CONH(1-C_3H_7)$, (cyclopropyl)$CH_2NHCO$, (cyclobutyl) $CH_2NHCO$, (2-methoxyphenyl)$CH_2NHCO$, (4-methoxyphenyl)$CH_2NHCO$, (pyridin-2-yl)$CH_2NHCO$, $CONHCH_2CO_2H$, $CON(CH_3)CH_2CO_2CH_3$, $CON(CH_3)_2$, (4-dimethylaminopiperidinyl)CO, (3-morpholinoazetidinyl) CO, (4-(pyridin-4-yl)piperidino)CO, (pyridin-2-yl)$CH_2N$ $(CH_3)CO$, $CON(CH_3)CH_2CO_2H$, (3-methoxycarbonylazetidinyl)CO, (3-carboxyazetidinyl)CO, methyl, isopropyl, methoxymethyl, 2-methoxyethyl, (pyrrolidino)$COCH_2$, phenylsulphonylmethyl, 4-chlorophenoxymethyl, (pyridin-2-yl)methyl, (pyridin-3-yl)methyl, (pyridin-4-yl)methyl, (imidazol-2-yl)methyl, benzylaminocarbonyl, piperidinocarbonyl, (2,3-dihydroisoindol-2-yl)CO, (1,2,3,4-tetrahydroisoquinolin-2-yl)CO, morpholinocarbonyl, 4-methylpiperazinocarbonyl, (5-aza-1,2,3,4-tetrahydroisoquinolin-2-yl)CO or N-methylbenzylaminocarbonyl. Most preferably Y is $CONH_2$, $CONHCH_3$ or $CON(CH_3)_2$.

A preferred group of compounds is that in which each substituent is as specified in the Examples below.

Another preferred group are the compounds are those of the Examples below (especially Examples 2,3 and 12) and the salts, solvates and prodrugs thereof.

A further aspect of the invention is a PCP inhibitor which is selective against MMP-1 and/or MMP-2 and/or MMP-9 and/or MMP-14. A further aspect of the invention is the use of a PCP inhibitor which is selective against MMP-1 and/or MMP-2 and/or MMP-9 and/or MMP-14 in medicine. Further related to this aspect of the invention is the use of a PCP inhibitor which is selective against MMP-1 and/or MMP-2 and/or MMP-9 and/or MMP-14 in the manufacture of an antiscarring medicament. Further related to this aspect of the invention is a method of treating a condition mediated by PCP and in which MMP-1 and/or MMP-2 and/or MMP-9 and/or MMP-14 have a beneficial effect, with an effective amount of PCP inhibitor which is selective against MMP-1 and/or MMP-2 and/or MMP-9 and/or MMP-14, an example of such a condition being a wound. Preferably the PCP inhibitor mentioned in this aspect of the invention is selective against at least MMP-1, MMP-2 and MMP-9. Most preferably the said PCP inhibitor is selective against MMP-1, MMP-2, MMP-9, and MMP-14. Preferably the said selective PCP inhibitor has an $IC_{50}$ vs. PCP of 0.5 µM or lower, and selectivities vs. MMP-2 and MMP-9 of at least 30-fold, in the tests described herein. Preferably the selective PCP inhibitor has an $IC_{50}$ vs. PCP of 0.1 µM or lower, and selectivities vs. MMP-1, MMP-2, MMP-9 and MMP-14 of at least 300-fold, in the tests described herein.

Another aspect of the invention is the use of the substances of formula (I) described herein, including the salts, solvates and prodrugs thereof, in medicine.

Another aspect of the invention is the use of the substances of formula (I) described herein, including the salts, solvates and prodrugs thereof, in the manufacture of an antiscarring medicament.

Another aspect of the invention is a pharmaceutical composition comprising a PCP inhibitor which is selective vs. MMP-1, MMP-2, MMP-9 and MMP-14, and a pharmaceutically acceptable diluent, carrier or adjuvant.

Another aspect of the invention is a pharmaceutical composition comprising a compound of formula (I), salts thereof, solvates thereof and/or prodrugs thereof, and a pharmaceutically acceptable diluent, carrier or adjuvant.

Another aspect of the invention is the combination of a PCP inhibitor, preferably a compound of formula (I), or a salt, solvate or prodrug thereof, with another material useful in treating wounds, such as:

(i) a growth factor such as TGF-β-3 (Renovo), IGF-1 (Genentech), IGF-1 complex (Celtrix), KGF-2 or FGF-10 (Sumitomo), DWP-401/EGF (Daewoong) or SNK-863 (Sanwa Kagaku Kenkyusho);

(ii) a growth factor agonist such as Noggin (Regeneron);

(iii) a growth factor antibody/antisense material, such as those to: TGF-β-1 or 2 (Renovo, CaT), PDGF (II Yang) or CTGF (Fibrogen);

(iv) a hormone such as DHEAS (Pharmadigm), ConXn/Relaxin (Connetics);

(v) an antibody to adhesion compounds such as ICAM-1 (Boehringer);

(vi) a MMP such as Collagenase ABC (BioSpecifics);

(vii) a barrier such as ADCON (Gliatech);

(viii) skin products such as artificial skin systems such as those based on DermaGraft (Advanced Tissue Sciences Inc.), INTEGRA Artificial Skin (Integra Life Sciences Holding Corp.), cell cultures such as Apligraf/Graftskin (Novartis), those developed by Cell Genesys Inc., AlloDerm (LifeCell) or matrix formulation products such as Argidene gel (Telios Pharmaceuticals Inc.);

(ix) a uPA inhibitor such as those disclosed in WO 99/01451;

(x) a MMP-3 inhibitor such as those disclosed in WO 99/35124, WO 99/29667;

A further aspect of the invention is the use of a substance according to the above definitions for the manufacture of a medicament for the treatment of a condition mediated by PCP.

Yet another aspect of the invention is a method of treatment of a condition mediated by PCP comprising administration of a therapeutically-effective amount of a substance according to the above definitions.

It is to be appreciated that reference to treatment includes prophylaxis as well as the alleviation of established symptoms of PCP-mediated conditions and diseases.

The invention further provides Methods for the production of compounds of the invention, which are described below and in the Examples and Preparations. The skilled man will appreciate that the compounds of the invention could be made by methods other than those specifically described herein, by adaptation of the methods herein described in the sections below and/or adaptation thereof, for example by methods known in the art. Suitable guides to synthesis, functional group transformations, use of protecting groups, etc. are, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), and any updated versions of said standard works.

In the Methods below, unless otherwise specified, the substituents are as defined above with reference to the compounds of formula (I) above.

The compounds of formula (I), where W is N, can be prepared according to the chemistry outlined in the scheme below:

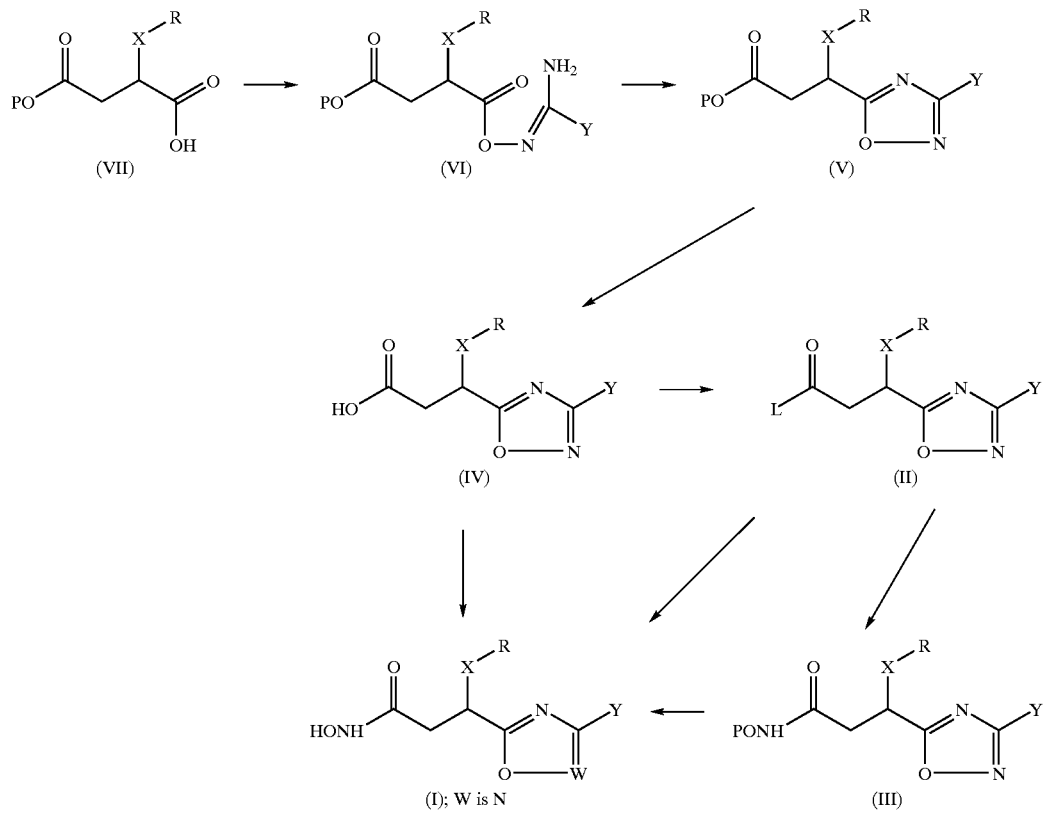

The hydroxamic acid compounds of formula (I) where W is N can be made by reaction of the corresponding activated acid derivative of formula (II), where L is a suitable leaving group, with hydroxylamine.

Suitable leaving groups are generally those which would leave in a more efficient manner than the hydroxide of the parent acid (IV), in a nucleophilic substitution reaction, such as a halide, $C_{1-4}$ alkoxide optionally substituted by halogen, an alkylsulphonate such as methylsulphonate or mesylsulphonate, an arylsulphonate such as p-tosylsulphonate. Other suitable leaving groups are familiar to those working in the field of amino acid coupling.

Such compounds of formula (II) may be made via standard chemistry from the corresponding acid (IV). Compounds of formula (II) where L is a leaving group such as Cl, Br, I, $OCO(C_{1-4}$ alkyl optionally substituted by one or more halogen), mesylate, tosylate, and the like, can be made from the corresponding compound of formula (II) where L is OH by conventional methods, including methods typified in e.g. Examples 2, etc.

The hydroxylamine used in this reaction is suitably generated in situ by treatment of a hydroxylamine salt such as the hydrochloride salt with a suitable base such as triethylamine. Suitably the reaction is carried out in a polar solvent such as DMF. This reaction, leaving groups, solvents, reagents, etc. are exemplified below in Examples 1–4, 12–16, 18, 20–28, 30, 33–40 and 41.

Alternatively the compounds of formula (I) may be made from a NHO-protected compound of formula (III), where P is a suitable O-protecting group, by suitable deprotection.

Suitable O-protecting groups can be found in the text by Greene and Wuts, supra, and include trialkylsilyl (such as trimethylsilyl), benzyl, etc. Compounds of formula (III) can be made in an analogous manner to the compounds of formula (I) from the compounds of formula (II), using a protected hydroxylamine $PONH_2$ or a suitable salt thereof in place of hydroxylamine itself or the hydroxylamine salt. The deprotection method is determined by the protective group used, as is well known in the art. E.g. benzyl groups may be hydrogenated, suitably using a catalytic transfer hydrogenation method. The reagents and conditions for reaction (III)→ (I) are typified in Examples 29, 31, and 32 below, and also in the other Examples where a protected hydroxylamine reagent (e.g. O-trimethylsilylhydroxylamine) was used (e.g.Examples 2, etc.), where conveniently the deprotection is carried out in the same vessel as the previous step.

Other methods of making hydroxamic acids (I) are known and may be used, e.g. those mentioned in the text by J. March, supra, chapters 0–54, 0–57 and 6–4, and relevant references therein.

Acids of formula (IV) may be made by deprotection of the O-protected species of formula (V). Suitable O-protecting groups can be found in the chapter on O-protection in the book by Greene and Wuts, supra, and include $C_{1-4}$ alkoxy such as t-butoxy (as typified in Preparation 4), benzyloxy, trialkylsilyloxy such as trimethylsilyloxy, etc. The deprotection method is determined by the protective group used, as is well known in the art (see Greene and Wuts, supra). E.g. benzyl groups may be removed by hydrogenation, suitably using a catalytic transfer hydrogenation method, t-butyl groups may be removed by treatment with an acid such as trifluoroacetic acid, etc.

Compounds of formula (V), e.g. where P is a t-butoxy can be made for example by condensation reaction of a corresponding compound of formula (VI), for example by heating to elevated temperature in an inert solvent such as in xylene at about 130° C., this reaction being typified by Preparation 3 below.

Compounds of formula (VI) can be made for example by coupling an acid of formula (VII) with a reagent of formula C(NH$_2$)(Y)=NH, which is available via literature methods or adaptation thereof in a conventional manner, such as typified in methods described herein (e.g. see Preparation 2, etc.). Typically the condensation is carried out by adding a solution of the acid (VII) in a suitable inert solvent such as 1,4-dioxane to a suitable agent such as 1-hydroxybenzotriazole hydrate, followed by addition of a suitable coupling agent such as a carbodiimide coupling agent, e.g. N,N'-dicyclohexylcarbodiimide, then treatment with the reagent C(NH$_2$)(Y)=NH. Suitably the coupling is carried out at ambient temperature.

Compounds of formula (VII) can be made by hydrogenation of the corresonding itaconate derivative, which in turn can be made by conventional methods such as the Stobbe condensation. Certain aspects of these preparations related to stereoselective preparation of certain intermediates, such as are disclosed in Preparation 1—Route C, are novel and inventive and constitute a further aspect to this invention.

The compounds of formula (I), where W is CZ, can be prepared according to the chemistry outlined in the scheme below:

reagents, etc. are the same as those mentioned above in relation to the corresponding compounds of formula (I) where W is N.

Such compounds of formula (IX) may be made via standard chemistry from the corresponding acid (X) using the same or similar chemistry to that outlined above in relation to the corresponding compounds of formula (II) where W is N (supra).

Alternatively the compounds of formula (I) may be made from a NHO-protected compound of formula (VIII), where P is a suitable O-protecting group, by suitable deprotection. Suitable O-protecting groups can be found in the text by Greene and Wuts, supra, and include trialkylsilyl (such as trimethylsilyl), benzyl, etc.

Compounds of formula (VIII) can be made in an analogous manner to the compounds of formula (II) from the compounds of formula (II), using a protected hydroxylamine PONH$_2$ or a suitable salt thereof in place of hydroxylamine itself or the hydroxylamine salt. The deprotection method is determined by the protective group used, as is well known in the art. E.g. benzyl groups may be hydrogenated, suitably using a catalytic transfer hydrogenation method. The reagents and conditions for reaction (VIII)→(I) are typified in Examples 29, 31, and 32 below, and also in the other Examples where a protected hydroxylamine reagent (e.g. O-trimethylsilylhydroxylamine) was used (e.g. Examples 2, etc.), where conveniently the deprotection is carried out in the same vessel as the previous step.

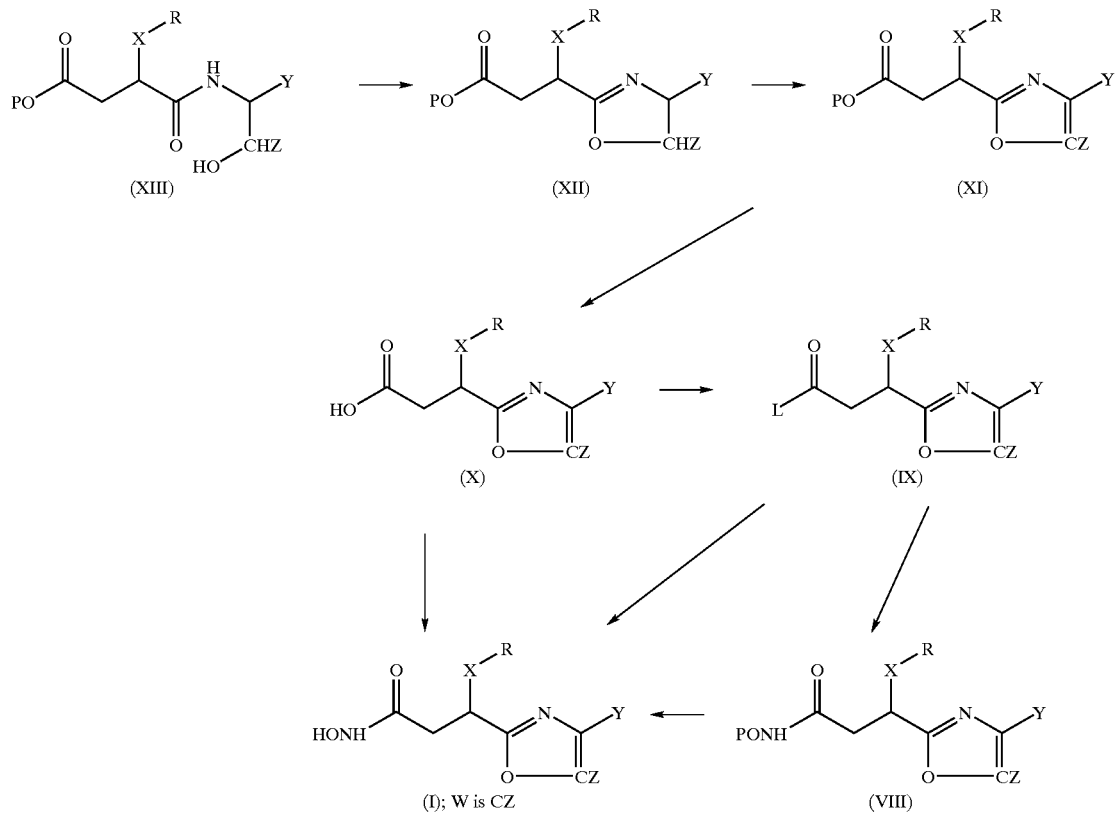

The hydroxamic acid compounds of formula (I) where W is CZ can be made by reaction of the corresponding activated acid derivative of formula (IX), where L⁻ is a suitable leaving group, with hydroxylamine. The leaving groups, Other methods of making hydroxamic acids (I) are known and may be used, e.g. those mentioned in the text by J. March, supra, chapters 0–54, 0–57 and 6–4, and relevant references therein.

Acids of formula (X) may be made by deprotection of the O-protected species of formula (XI). Suitable O-protecting groups can be found in the chapter on O-protection in the book by Greene and Wuts, supra, and include $C_{1-4}$ alkoxy such as t-butoxy (as typified in Preparation 4), benzyloxy, trialkylsilyloxy such as trimethylsilyloxy, etc. The deprotection method is determined by the protective group used, as is well known in the art (see Greene and Wuts, supra). E.g. benzyl groups may be removed by hydrogenation, suitably using a catalytic transfer hydrogenation method, t-butyl groups may be removed by treatment with an acid such as trifluoroacetic acid, etc.

Compounds of formula (XI), e.g. where P is a t-butoxy group can be made for example by oxidation of a compound of formula (XII). Suitably the oxidation is carried out using copper (II) bromide with hexamethylenetetramine and a base such as DBU. The reagents, conditions, etc. are typified in Preparation 62 below.

Compounds of formula (XII) may be made by condensation of compounds of formula (XIII), for example by treatment of the compound of formula (XIII) with s suitable agent such as Burgess Reagent, in an anhydrous solvent such as THF. This reaction is typified in Preparation 61 below.

Compounds of formula (XIII) may be made by condensation of the acid of formula (II) above with an agent of formula $NH_2CH(Y)CH(Z)OH$, as typified in Preparation 60 below. Compounds of formula $NH_2CH(Y)CH(Z)OH$ are available commercially, from the literature or by routine modification thereof.

Certain compounds of formula (I) may be interconverted into other compounds of formula (I)—for Example where Y is an acid, this can be converted to an ester and vice versa—typified in Examples 17 and 19 below.

It will be apparent to those skilled in the art that other protection and subsequent deprotection regimes during synthesis of a compound of the invention may be achieved by conventional techniques, for example as described in the volumes by Greene and Wuts, and Kocienski, supra.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Certain compounds of the invention may be interconverted into certain other compounds of the invention by methods mentioned in the Examples and Preparations, and well-known methods from the literature.

Compounds of the invention are available by either the methods described herein in the Methods, Examples and Preparations or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

The compounds, salts, solvates and prodrugs of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base. In certain cases preferential crystallisation of one of the enantiomers can occur from a solution of a mixture of enantiomers, thus enriching the remaining solution in the other enantiomer.

For human use, the compounds of formula (I) or their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract. The compounds or salts can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, or transdermally, in the form of sterile creams, gels, suspensions, lotions, ointments, dusting powders, sprays, foams, mousses, drug-incorporated dressings, skin patches, ointments such as petrolatum or white soft paraffin based ointments or via a skin patch or other device. They could be administered directly onto a wound. They could be incorporated into a coated suture. For example they can be incorporated into a lotion or cream consisting of an aqueous or oily emulsion of mineral oils; sorbitan monostearate; polysorbate 60; cetyl esters wax; cetearyl alcohol; 2-octyldodecanol; benzyl alcohol; water; polyethylene glycols and/or liquid paraffin, or they can be incorporated into a suitable ointment consisting of one or more of the following—mineral oil; liquid petrolatum; white petrolatum; propylene glycol; polyoxyethylene polyoxypropylene compound; emulsifying wax and water, or as hydrogel with cellulose or polyacrylate derivatives or other viscosity modifiers, or as a dry powder or liquid spray or aerosol with butane/propane, HFA, CFC, $CO_2$ or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly for ophthalmic use e.g. in a lens implant or as an eye drop with appropriate buffers, viscosity modifiers (e.g. cellulose or polyacrylate derivatives), preservatives (e.g. benzalkonium chloride (BZK)) and agents to adjust tonicity (e.g. sodium chloride). Such formulation techniques are well-known in the art.

For certain uses, vaginal, rectal and nasal (e.g. by inhalation of a dry powder or aerosol) administration would be suitable.

All such formulations may also contain appropriate stabilisers and preservatives.

For oral and parenteral administration to human patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

For topical administration to human patients with acute/surgical wounds or scars, the daily dosage level of the compounds, in suspension or other formulation, could be from 0.01 to 50 mg/ml, preferably from 0.3 to 30 mg/ml.

The dosage will vary with the size of the wound, whether or not the wound is open or closed or partially closed, and whether or not the skin is intact.

The physician in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

Biological Test Methods
PCP Inhibition

In order to determine potency of PCP inhibitors a fluorogenic PCP cleavage assay was used. This assay is based on the template of Beekman et al. (FEBS Letters (1996), 390: 221–225) using a fluorogenic substrate. The substrate (Dabcyl-Arg-Tyr-Tyr-Arg-Ala-Asp-Asp-Ala-Asn-Val-Glu (EDANS)—$NH_2$) contains the cleavage site of human PCP (Hojima et al., J Biol Chem (1985), 260: 15996–16003). Human PCP has been purified from supernatant of stable transfected CHO cells using hydrophobic interaction column followed by Superdex 200 gel filtration. 4 µg total protein of this enzyme preparation was incubated with various concentrations of the substance to be tested and $3 \times 10^{-6}$ M substrate in assay buffer (50 mM Tris-Base, pH 7.6 containing 150 mM NaCl, 5 mM $CaCl_2$, 1 µM $ZnCl_2$ and 0.01% Brij 35). The assay was performed in 96-well black fluorimeter plates and fluorescence was read continuously in a fluorimeter over 2.5 hours ($\lambda_{ex}$=340 nm, $\lambda_{em}$=485 nm) at a constant 37° C. with shaking. Release of the fluorogenic signal was in linear correlation to PCP activity. Reading of the mean velocity from 30 min after start of experiment until 2.5 hours was calculated by the Biolise software. $IC_{50}$ values were calculated by plotting % inhibition values against compound concentration using Tessela add in for Excel spreadsheet.

MMP Inhibition

The ability of compounds to inhibit the cleavage of fluorogenic peptides by MMPs 1, 2, 9, and 14 is described below.

The assays for MMPs 2, 9, and 14 are based upon the original protocol described by Knight et al. (Fed.Euro.Biochem.Soc., 296 (3), 263–266; 1992) with the slight modifications given below.

Inhibition of MMP-1
(i) Enzyme Preparation

Catalytic domain MMP-1 was prepared at Pfizer Central Research. A stock solution of MMP-1 (1 µM) was activated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 µM $ZnSO_4$, 0.05% Brij 35) pH 7.5 to a of 10 nM. The final concentration of enzyme used in the assay was 1 nM.

(ii) Substrate

The fluorogenic substrate used in this assay was Dnp-Pro-□-cyclohexyl-Ala-Gly-Cys(Me)-His-Ala-Lys(N-Me-Ala)-$NH_2$ as originally described by Bickett et al (Anal. Biochem, 212, 58–64, 1993). The final substrate concentration used in the assay was 10 µM.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG Lab Technologies, Aylesbury, UK) at an excitation wavelength of 355 nm and emission wavelength of 440 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-2 and MMP-9
(i) Enzyme Preparation

Catalytic domain MMP-2 and MMP-9 were prepared at Pfizer Central Research. A stock solution of MMP-2/MMP-9 (1 □M) was activated by the addition of aminophenylmercuric acetate (APMA). For MMP-2 and MMP-9, a final concentration of 1 mM APMA was added, followed by incubation for 1 hour at 37° C. The enzymes were then diluted in Tris-HCl assay buffer (100 mM Tris, 100 mM NaCl, 10 mM $CaCl_2$ and 0.16% Brij 35, pH 7.5), to a concentration of 10 nM. The final concentration of enzyme used in the assays was 1 nM.

(ii) Substrate

The fluorogenic substrate used in this screen was Mca-Arg-Pro-Lys-Pro-Tyr-Ala-Nva-Trp-Met-Lys(Dnp)-$NH_2$ (Bachem Ltd, Essex, UK) as originally described by Nagase et al (J. Biol. Chem., 269(33), 20952–20957, 1994). This substrate was selected because it has a balanced hydrolysis rate against MMPs 2 and 9 ($k_{cat}/k_m$ of 54,000, 59,400 and 55,300 $s^{-1}$ $M^{-1}$ respectively). The final substrate concentration used in the assay was 5 µM.

(iii) Determination of Enzyme Inhibition

Test compounds were dissolved in dimethyl sulphoxide and diluted with test buffer solution (as above) so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence using a fluorimeter (Fluostar; BMG LabTechnologies, Aylesbury, UK) at an excitation wavelength of 328 nm and emission wavelength of 393 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-14
(i) Enzyme Preparation

Catalytic domain MMP-14 was purchased from Prof. Tschesche, Department of Biochemistry, Faculty of Chemistry, University of Bielefeld, Germany. A 10 □M enzyme stock solution was activated for 20 minutes at 25° C. following the addition of 5 □g/ml of trypsin (Sigma, Dorset, UK). The trypsin activity was then neutralised by the addition of 50 □g/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assay was 1 nM.

(ii) Substrate

The fluorogenic substrate used in this screen was Mca-Pro-Leu-Gly-Leu-Dpa-Ala-Arg-$NH_2$ (Bachem Ltd, Essex, UK) as described by Will et al (J. Biol. Chem., 271(29), 17119–17123, 1996). The final substrate concentration used in the assay was 10 µM.

Determination of enzyme inhibition by test compounds was performed in the same manner as described for MMPs-2 and -9 above.

The compounds of Examples 1–40 and 42–58 had PCP $IC_{50}$ values of 0.5 µM and below, and the compounds of Examples 1–40, 43, 44 and 46 had selectivities vs MMP-2 of more than 100-fold.

All references mentioned herein in this text are incorporated by reference in their entirety.

EXAMPLES AND PREPARATIONS

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (1R) spectra were measured using a Nicolet Magna 550 Fourier transform infra-red spectrometer. Flash chromatography refers to column chromatography on silica gel (Kieselgel 60, 230–400 mesh, from E. Merck, Darmstadt. Kieselgel 60 $F_{254}$ plates from E. Merck were used for TLC, and compounds were visualised using UV light, 5% aqueous potassium permanagate or Dragendorff's reagent (oversprayed with aqueous sodium nitrite). Thermal analyses by Differential Scanning Calorimetry (DSC) and ThermoGravimetric Analysis (TGA) were obtained using Perkin Elmer DSC7 and TGA7. Moisture sorption characteristics were recorded using Surface Measurement Systems Ltd. Automated Water Sorption Analyser DVS 1. Water content was determined on a Mitsubishi CA100 (Coulometric Karl Fisher Titrator). Powder X-ray diffraction (PXRD) pattern was determined using a Siemens D5000 powder X-ray diffractometer fitted with an automatic sample changer, a theta-theta goniometer, automatic beam divergence slits, a secondary monochromator and a scintillation counter. Other measurements were taken using standard equipment. Hexane refers to a mixture of hexanes (hplc grade) b.p. 65–70° C. Ether refers to diethyl ether. Acetic acid refers to glacial acetic acid. 1-Hydroxy-7-aza-1H-1,2,3-benzotriazole (HOAt), N-[(dimethylamino)-1H-1,2,3-triazolo[4,5-b]pyridin-1-ylmethylene]-N-methylmethaninium hexafluorophosphate N-oxide (HATU) and 7-azabenzotriazol-1-yloxytris(pyrrolidino)phosphonium hexafluorophosphate (PyAOP) were purchased from PerSeptive Biosystems U.K. Ltd. "DIPE" refers to diisopropyl ether. Reverse-phase silica gel for flash chromatography was obtained from Fluka (Fluka 100, $C_{18}$, 40–63µ). Pentane refers to High Performance Liquid Chromatography (HPLC) grade n-pentane (b.pt.35–37° C.). Nomenclature has been allocated using a program available from IUPAC. Standard abbreviations are used throughout, e.g. "Me" is methyl, "Et" is ethyl, "Pr" is propyl, "Ph" is phenyl, etc. It was noticed that during certain repetitions of the methods disclosed in the Examples and Preparations that some racemisation appeared to have taken place. It was found in some cases that specific desired enantiomers can be separated from mixtures thereof by routine methods such as by differential crystallisation.

[a]HPLC autopurification performed using 2 columns— Phenomonex LUNA C8 150×21.2 mm, 10 µm and Phenomonex MAGELLEN C18 150×21.2 mm, 51 µm, eluting with a gradient system of organic solvent [ammonium acetate (aq) 100 mM:acetonitrile (1:9)] :aqueous solvent [ammonium acetate (aq) 100 mM:acetonitrile (9:1)]

[b]HPLC autopurification performed using 2 columns— Phenomonex LUNA C8 150×21.2 mm, 10 µm and Phenomonex MAGELLEN C18 150×21.2 mm, 5 µm, eluting with a gradient system of organic solvent (acetonitrile):aqueous solvent (0.1% aqueous trifluoroacetic acid)

Example 1

Ethyl 5-{(1R)-4-cyclohexyl-1-[2-(hydroxyamino)-2-oxoethyl]butyl}-1,2,4-oxadiazole-3-carboxylate

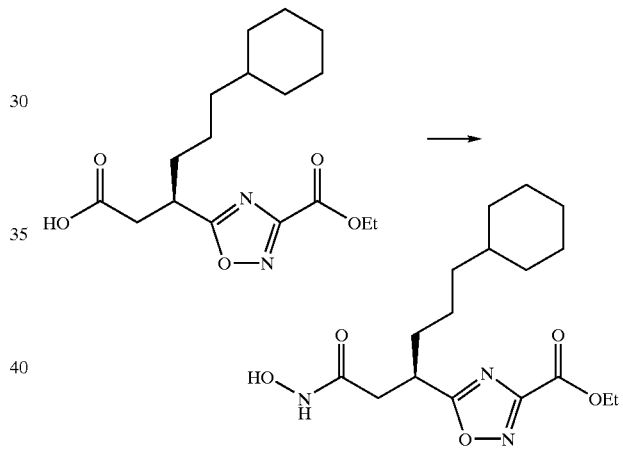

A solution of (3R)-6-cyclohexyl-3-[3-(ethoxycarbonyl)-1,2,4-oxadiazol-5-yl]hexanoic acid (Preparation 4) (140 mg, 0.41 mmol) and N,N-diisopropylethylamine (320 µl, 2.07 mmol) in N,N-dimethylformamide (5 ml) was treated with O-(7-azabenzotriazol-1-yl)-N,N,N',N'-tetramethyluronium hexafluorophosphate (235 mg, 0.61 mmol) and the resulting solution was stirred at room temperature under a nitrogen atmosphere for 30 minutes. Hydroxylamine hydrochloride (113 mg, 0.61 mmol) was then added and the mixture was stirred at room temperature for 20 hours. The mixture was poured into hydrochloric acid (1M, 20 ml) and extracted with ethyl acetate (×3). The combined organic layers were washed sequentially with a saturated aqueous solution of sodium hydrogen carbonate and brine, dried over anhydrous sodium sulphate, filtered and the solvent removed under reduced pressure. The residue was purified by column chromatography on silica gel eluting with a gradient system of dichloromethane:methanol (99.5:0.5) gradually changing to dichloromethane:methanol (97:3) to afford the title compound as a yellow oil (62 mg).

MS: 354 ($MH^+$)

$^1$H-NMR ($CDCl_3$) δ: 4.52 (2H, m), 3.70 (1H, br m), 2.94–2.52 (2H, br m), 1.96–1.00 (18H, m), 0.85 (2H, m).

Example 2(a)

5-{(1R)-4-Cyclohexyl-1-[2-(hydroxyamino)-2-oxoethyl]butyl}-1,2,4-oxadiazole-3-carboxamide

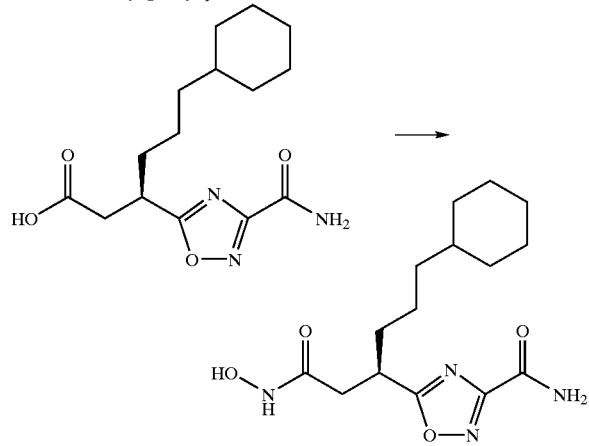

A solution of (3R)-3-[3-(aminocarbonyl)-1,2,4-oxadiazol-5-yl]-6-cyclohexylhexanoic acid (Preparation 6) (6.00 g, 19.42 mmol) in anhydrous tetrahydrofuran (200 ml) was cooled to 0° C. then treated with N-methylmorpholine (2.40 ml, 22.0 mmol) and isobutyl chloroformate (2.8 ml, 22.0 mmol) and stirred under a nitrogen atmosphere for 1 hour. O-(Trimethylsilyl)hydroxylamine (7.0 ml, 60.0 mmol) was added and the mixture was stirred for 18 hours, being allowed to warm to room temperature over this time. The mixture was then treated with methanol (50 ml) and stirred for a further 30 minutes. This mixture was partitioned between ethyl acetate and water. The combined organic layers were washed with brine, dried over anhydrous sodium sulphate, filtered and the solvent removed under reduced pressure. The solid was recrystallised from isopropyl acetate (500 ml) to afford the title compound as a white solid (4.46 g). Chiral HPLC analysis indicated this material to be 87.6% ee. A sample of this material (2.9 g) was dissolved in ethyl acetate (450 ml) at reflux then allowed to cool. The precipitate was filtered off and the solvent was removed from the filtrate under reduced pressure to afford a white solid, which was then recrystallised from isopropyl acetate (120 ml) to afford the title compound (1.42 g). Chiral HPLC analysis showed this material to be 98.3% ee.

MS: 323 (MH⁻)

$^1$H-NMR (DMSO-$d_6$) δ: 10.50 (1H, br s), 8.81 (1H, br s), 8.26 (1H, br s), 8.05 (1H, br s), 3.47 (1H, m), 2.56–2.39 (2H, m), 1.73–1.46 (7H, m), 1.27–0.99 (8H, m), 0.80 (2H, m).

Analysis: Found C, 52.76; H, 7.64; N, 16.34%; $C_{15}H_{24}N_4O_4 \cdot H_2O$ requires C, 52.62; H, 7.65; N, 16.36%

MPt.: 136–138° C.

Example 2(b)

5-{(1R)-4-Cyclohexyl-1-[2-(hydroxyamino)-2-oxoethyl]butyl}-1,2,4-oxadiazole-3-carboxamide Monohydrate

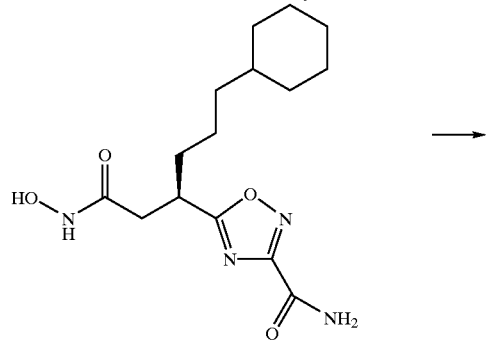

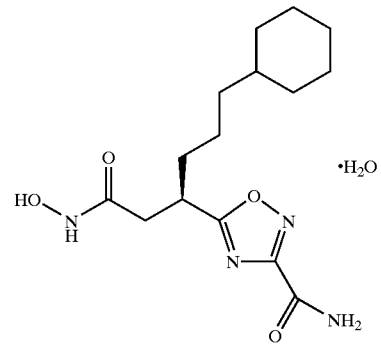

A solution of 5-{(1R)-4-cyclohexyl-1-[2-(hydroxyamino)-2-oxoethyl]butyl}-1,2,4-oxadiazole-3-carboxamide (1.58 Kg, 4.86 mol) in tetrahydrofuran (15 liters) was heated to 40° C. and demineralised water (26 liters) was added to give a hazy solution. The mixture was allowed to cool to ambient temperature where it was stirred for 24 hours. The mixture was cooled to 52° C. and stirred for 1 hour. The precipitate was collected by filtration and dried in vacuo (38° C., 100 mbar) to afford the title compound as a colourless solid (1.37 Kg).

$^1$H-NMR (DMSO-$d_6$) δ: 10.50 (1H, br s), 8.81 (1H, br s), 8.26 (1H, br s), 3.47 (1H, m), 2.56–2.39 (2H, m), 1.73–1.46 (7H, m), 1.27–0.99 (8H, m), 0.80 (2H, m)

Water Content (Coulometric Karl Fisher): 5.0% Dynamic Vapour Sorption: 5.17% w/w @ 20% RH (30° C.), 4.84% w/w @ 2% RH (30° C.), significant dehydration below 1% RH (30° C.). TGA (Weight Loss): 24° C.–117° C.=4.93% 117° C.–160° C.=0.26%

Example 2(c)

5-{(1R)-4-Cyclohexyl-1-[2-(hydroxyamino)-2-oxoethyl]butyl}-1,2,4-oxadiazole-3-carboxamide (Anhydrous)

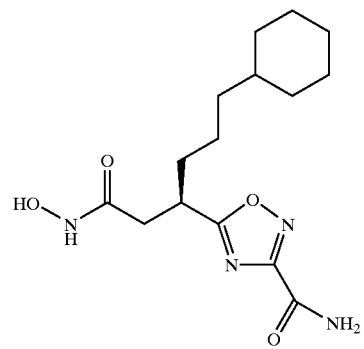

5-{(1R)-4-Cyclohexyl-1-[2-(hydroxyamino)-2-oxoethyl]butyl}-1,2,4-oxadiazole-3-carboxamide (3.20 g, 9.86 mmol) was dissolved in ethyl acetate (80 ml) at reflux. The mixture was allowed to cool to ambient temperature, stirred for 3 hours. The precipitate was collected by filtration and dried in vacuo (40–45° C., 48 hours) to afford the title compound as a colourless solid (2.40 g).

$^1$H-NMR (DMSO-$d_6$) δ: 10.50 (1H, br s), 8.81 (1H, br s), 8.26 (1H, br s), 3.47 (1H, m), 2.56–2.39 (2H, m), 1.73–1.46 (7H, m), 1.27–0.99 (8H, m), 0.80 (2H, m)

Dynamic Vapour Sorption: 0.18% w/w @ 15% RH (30° C.), 0.23% w/w @ 30% RH (30° C.), w/w @ 45% RH (30°

C.). Title compound hydrates slowly at 60% RH (30° C.) converting to the monohydrate (XRD used to confirm), eventually equilibrates at 5.3% w/w at 90% RH (30° C.). TGA (Weight Loss): 25° C.–91° C.=0.22% 91° C.–138° C.=0.33%

Example 3

5-{(1R)-4-Cyclohexyl-1-[2-(hydroxyamino)-2-oxoethyl]butyl}-N-methyl-1,2,4-oxadiazole-3-carboxamide Example 4

5-{(1R)-4-Cyclohexyl-1-[2-(hydroxyamino)-2-oxoethyl]butyl}-N-propyl-1,2,4-oxadiazole-3-carboxamide

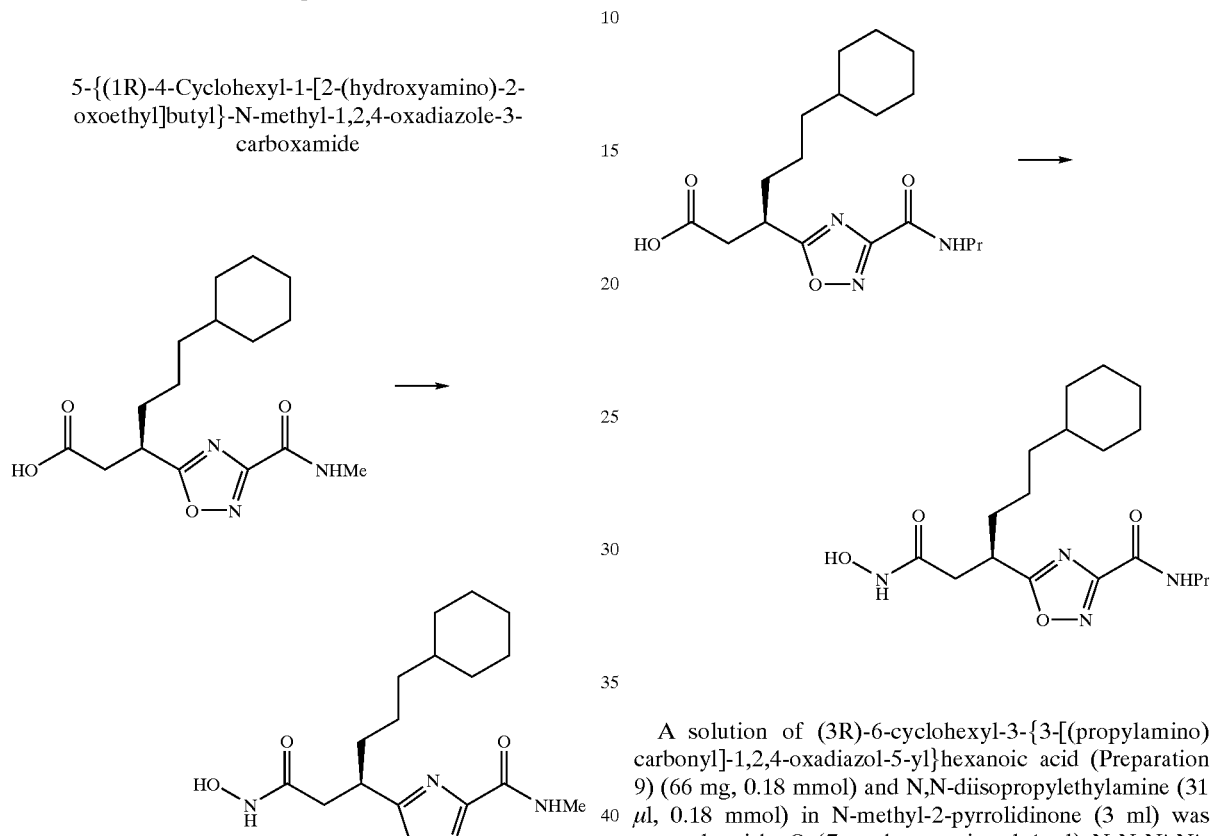

A solution of (3R)-6-cyclohexyl-3-{3-[(methylamino)carbonyl]-1,2,4-oxadiazol-5-yl}hexanoic acid (Preparation 8) (285 mg, 0.88 mmol) and N-methylmorpholine (110 μl, 1.00 mmol) in anhydrous tetrahydrofuran (10 ml) was cooled to 0° C., treated with isobutyl chloroformate (130 μl, 1.00mmol) and stirred under a nitrogen atmosphere for 1 hour. O-(Trimethylsilyl)hydroxylamine (130 μl, 1.06 mmol) was added and the mixture was stirred for 18 hours, being allowed to warm to room temperature over this time. The mixture was then treated with aqueous citric acid solution (10% w/v, 10 ml) and stirred for 2 hours. This mixture was diluted with water and extracted with ethyl acetate (×3). The combined organic layers were washed sequentially with water and brine, dried over anhydrous sodium sulphate, filtered and the solvent removed under reduced pressure. The solid was then recrystallised from hexane:ethyl acetate to afford the title compound as a white solid (130 mg).

¹H-NMR (DMSO-d₆) δ: 10.48 (1H, br s), 8.87 (1H, m), 8.77 (1H, br s), 3.48 (1H, m), 3.19 (2H, m), 2.16 (1H, m), 1.87 (1H, m), 1.57 (9H, m), 1.14 (8H, m), 0.80 (5H, m).

A solution of (3R)-6-cyclohexyl-3-{3-[(propylamino)carbonyl]-1,2,4-oxadiazol-5-yl}hexanoic acid (Preparation 9) (66 mg, 0.18 mmol) and N,N-diisopropylethylamine (31 μl, 0.18 mmol) in N-methyl-2-pyrrolidinone (3 ml) was treated with O-(7-azabenzotriazol-1-yl)-N,N,N',N'-tetramethyluronium hexafluorophosphate (102 mg, 0.27 mmol) and the resulting mixture was stirred at room temperature under a nitrogen atmosphere for 1 hour. N,N-diisopropylethylamine (93 μl, 0.54 mmol) was then added, followed by hydroxylamine hydrochloride (37.5 mg, 0.54 mmol) and the mixture was stirred at room temperature for 18 hours. The mixture was partitioned between ethyl acetate and pH 7 aqueous buffer. The combined organic layers were washed sequentially with aqueous citric acid solution (5% w/v) and brine, dried over anhydrous sodium sulphate, filtered and the solvent removed under reduced pressure. The residue was purified by column chromatography on silica gel eluting with a gradient system of dichloromethane::ethyl acetate (90:10) gradually changing to dichloromethane:ethyl acetate (0:100) then to dichloromethane:methanol (95:5) to afford the title compound as an oil (31 mg).

MS: 367(MH⁺)

¹H-NMR (DMSO-d₆) δ: 10.48 (1H, br s), 8.87 (1H, br t), 8.76 (1H, br s), 3.47 (1H, m), 3.19 (2H, m), 2.16 (1H, m), 1.88 (1H, m), 1.76–1.43 (9H, m), 1.30–1.00 (8H, m), 0.90–70 (5H, m).

Example 5

5-{(1R)-4-Cyclohexyl-1-[2-(hydroxyamino)-2-oxoethyl]butyl}-N-isopropyl-1,2,4-oxadiazole-3-carboxamide

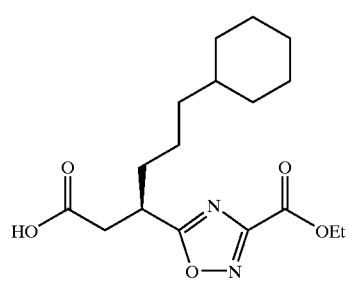

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of isopropylamine (434 mg, 7.35 mmol) in ethanol (2 ml) and the resulting mixture was heated at 80° C. under a nitrogen atmosphere for 10 hours. The solvent was removed under reduced pressure and the residue was dissolved in hydrochloric acid (1M, 10 ml) then extracted with ethyl acetate (×2). The combined organic layers were dried over anhydrous magnesium sulphate, filtered and the solvent removed under reduced pressure. This residue (531 mg) was then dissolved in dichloromethane (15 ml), cooled to 0° C. and treated sequentially with N-methylmorpholine (180 μl.1.63 mmol) and isobutyl chloroformate (210 μl, 1.62 mmol). This mixture was stirred at 0° C. under a nitrogen atmosphere for 1 hour, then treated with O-(trimethylsilyl)hydroxylamine (220 μl, 1.80 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by reverse phase HPLC$^a$ to afford the title compound as a foam (43 mg).

MS: 367(MH$^+$), 389 (MNa$^+$)

$^1$H-NMR (CDCl$_3$) δ: 9.06 (1H, br s), 7.63 (1H, br s), 6.74 (1H, br d), 4.27 (1H, m), 3.70 (1H, m), 2.83–2.60 (2H, m), 1.78–1.52 (7H, m), 1.35–1.07 (14H, m), 0.83 (2H, m).

Example 6

5-{(1R)-4-Cyclohexyl-1-[2-(hydroxyamino)-2-oxoethyl]butyl}-N-(cyclopropylmethyl)-1,2,4-oxadiazole-3-carboxamide

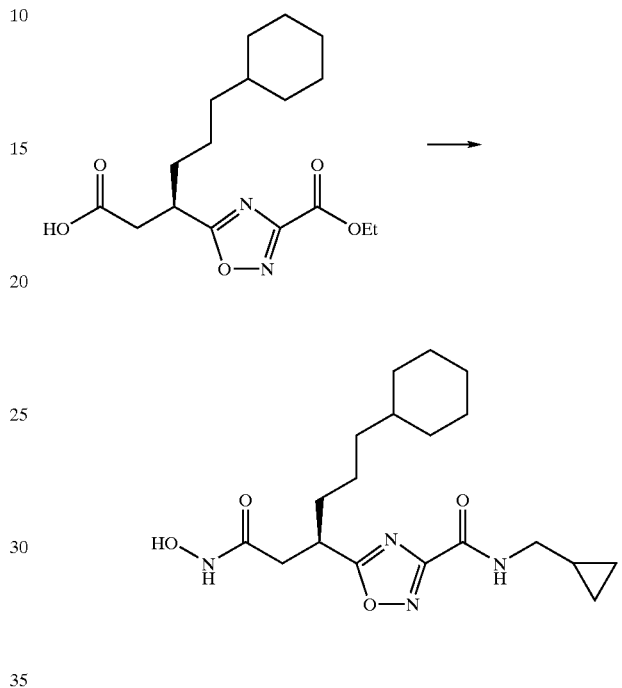

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of cyclopropylmethylamine (522 mg, 7.35 mmol) in ethanol (2 ml) and the resulting solution was heated at 80° C. under a nitrogen atmosphere for 10 hours. The solvent was removed under reduced pressure and the residue was dissolved in hydrochloric acid (1M, 10 ml) then extracted with ethyl acetate (×2). The combined organic layers were dried over anhydrous magnesium sulphate, filtered and the solvent removed under reduced pressure. This residue (349 mg) was then dissolved in dichloromethane (15 ml), cooled to 0° C. and treated sequentially with N-methylmorpholine (120 μl, 1.09 mmol) and isobutyl chloroformate (140 μl, 1.09 mmol). This mixture was stirred at 0° C. under a nitrogen atmosphere for 1 hour, then treated with O-(trimethylsilyl)hydroxylamine (140 μl, 1.15 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by HPLC$^a$ to afford the title compound as a foam (88 mg).

MS: 379 (MH$^+$), 401 (MNa$^+$)

$^1$H-NMR (CDCl$_3$) δ: 9.20 (1H, br s), 7.05 (1H, br s), 3.72 (1H, m), 3.33 (2H, m), 2.87–2.60 (2H, m), 1.88–1.52 (7H, m), 1.40–1.00 (8H, m), 0.83 (3H, m), 0.59 (2H, m) 0.30 (2H, m).

Example 7

N-Cyclobutyl-5-{(1R)-4-cyclohexyl-1-[2-(hydroxyamino)-2-oxoethyl]butyl}-1,2,4-oxadiazole-3-carboxamide

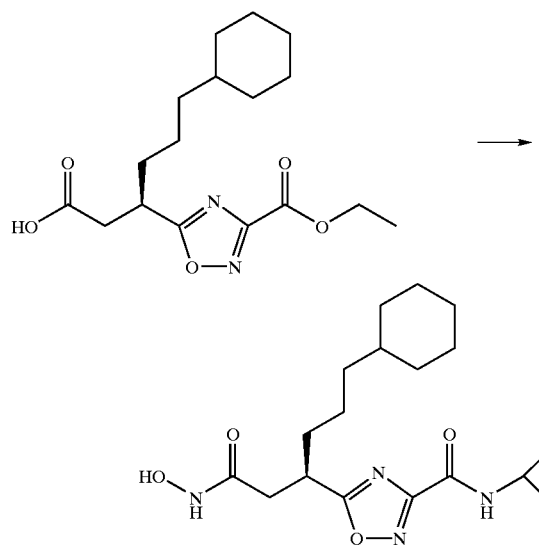

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of cyclobutylamine (522 mg, 7.35 mmol) in ethanol (2 ml) and the resulting solution was heated at 80° C. under a nitrogen atmosphere for 10 hours. The solvent was removed under reduced pressure and the residue was dissolved in hydrochloric acid (1M, 10 ml) then extracted with ethyl acetate (×2). The organic layers were combined, dried over anhydrous magnesium sulphate, filtered and the solvent removed under reduced pressure. This residue (462 mg) was then dissolved in dichloromethane (15 ml), cooled to 0° C. and treated sequentially with N-methylmorpholine (150 µl, 1.36 mmol) and isobutyl chloroformate (180 µl, 1.39 mmol). This mixture was stirred at 0° C. under a nitrogen atmosphere for 1 hour, then treated with O-(trimethylsilyl)hydroxylamine (190 µl, 1.55 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by HPLC$^a$ to afford a residue (63 mg) which was dissolved in dichloromethane (3 ml), cooled to 0° C. and treated sequentially with N-methylmorpholine (20 µl, 0.18 mmol) and isobutyl chloroformate (23 µl, 0.18 mmol). This mixture was stirred at 0° C. under a nitrogen atmosphere for 1 hour, then treated with O-(trimethylsilyl)hydroxylamine (24 µl, 0.20 mmol) and stirring continued for 3 hours. Further O-(trimethylsilyl)hydroxylamine (30 µl, 0.25 mmol) was added and stirring continued for 17 hours. The reaction was quenched with methanol and the solvent removed under reduced pressure. The residue was dissolved in ethyl acetate, washed with water, dried over anhydrous sodium sulphate, filtered and the solvent removed under reduced pressure. The residue was then dissolved in methanol (5 ml), treated with potassium carbonate (110 mg) and stirred at room temperature for 17 hours. The mixture was treated with a few drops of acetic acid and the solvent removed under reduced pressure. The residue was partitioned between ethyl acetate and water. The organic phase was separated, dried over anhydrous sodium sulphate, filtered and the solvent removed under reduced pressure to afford the title compound as a foam (24 mg)

MS: 379 (MH$^+$), 401 (MNa$^+$)

$^1$H-NMR (CDCl$_3$) δ: 8.80 (1H, br s), 7.06 (1H, br d), 4.57 (1H, m), 3.70 (1H, m) 2.85–2.54 (2H, m), 2.43 (1H, m), 2.05 (1H, m), 1.87–1.41 (11H, m), 1.38–0.98 (8H, m), 0.84 (2H, m).

Example 8

5-{(1R)-4-Cyclohexyl-1-[2-(hydroxyamino)-2-oxoethyl]butyl}-N-(2-methoxybenzyl)-1,2,4-oxadiazole-3-carboxamide

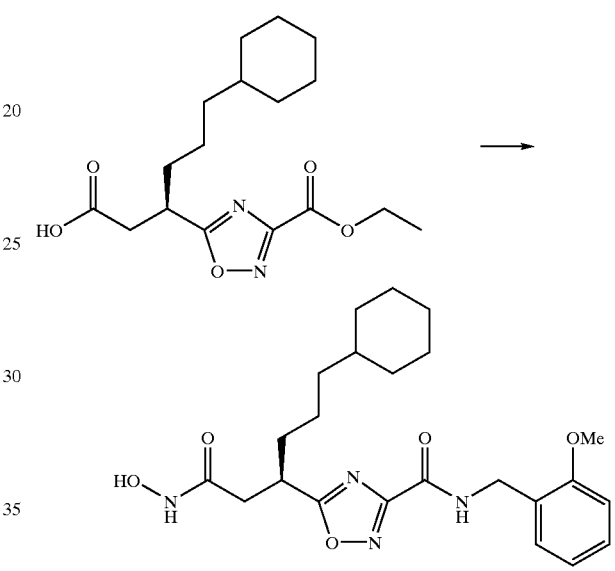

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of 2-methoxybenzylamine (1.00 g, 7.35 mmol) in ethanol (2 ml) and the resulting solution was heated at 80° C. under a nitrogen atmosphere for 10 hours. The solvent was removed under reduced pressure and the residue was dissolved in hydrochloric acid (1M, 10 ml) then extracted with ethyl acetate (×2). The combined organic layers were dried over anhydrous magnesium sulphate, filtered and the solvent removed under reduced pressure. This residue (672 mg) was then dissolved in dichloromethane (15 ml), cooled to 0° C. and treated sequentially with N-methylmorpholine (180 µl, 1.64 mmol) and isobutyl chloroformate (210 µl, 1.63 mmol). This mixture was stirred at 0° C. under a nitrogen atmosphere for 1 hour, then treated with O-(trimethylsilyl)hydroxylamine (220 µl, 1.80 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by HPLC$^a$ to afford the title compound as a foam (140 mg).

MS: 445 (MH$^+$), 462 (MNH$_4^+$)

$^1$H-NMR (CDCl$_3$) δ: 7.44 (1H, br s), 7.29 (2H, m), 6.91 (2H, m), 4.63 (2H, d, J=5 Hz), 3.89 (3H, s), 3.71 (1H, m), 2.86–2.54 (2H, m), 1.90–1.48 (7H, m), 1.39–1.00 (8H, m), 0.83 (2H, m).

Example 9

5-{(1R)-4-Cyclohexyl-1-[2-(hydroxyamino)-2-oxoethyl]butyl}-N-(4-methoxybenzyl)-1,2,4-oxadiazole-3-carboxamide

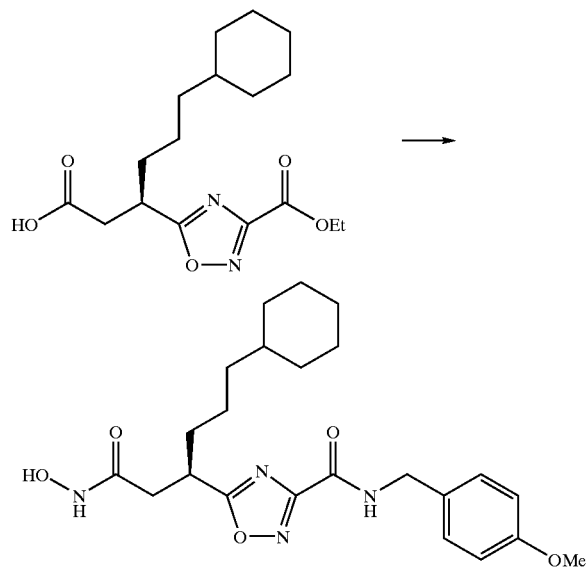

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of 4-methoxybenzylamine (1.00 g, 7.35 mmol) in ethanol (2 ml) and the resulting solution was heated at 80° C. under a nitrogen atmosphere for 10 hours. The solvent was removed under reduced pressure and the residue was dissolved in hydrochloric acid (1M, 10 ml) then extracted with ethyl acetate (×2). The combined organic layers were dried over anhydrous magnesium sulphate, filtered and the solvent removed under reduced pressure. This residue (578 mg) was then dissolved in dichloromethane (15 ml), cooled to 0° C. and treated sequentially with N-methylmorpholine (160 μl, 1.45 mmol) and isobutyl chloroformate (190 μl, 1.47 mmol). This mixture was stirred at 0° C. under a nitrogen atmosphere for 1 hour, then treated with O-(trimethylsilyl)hydroxylamine (195 μl, 1.60 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by HPLC[a] to afford the title compound as a foam (74 mg).

MS: 445 (MH+), 462 (MNH$_4^+$)

$^1$H-NMR (CD$_3$OD): δ: 7.37 (2H, d, J=8 Hz), 6.89 (2H, d, J=8 Hz), 4.50 (2H, s), 3.76 (3H, s), 3.60 (1H, m), 2.73–2.50 (2H, m), 1.86–1.66 (7H, m), 1.40–1.09 (8H, m), 0.85 (2H, m).

Example 10

5-{(1R)-4-Cyclohexyl-1-[2-(hydroxyamino)-2-oxoethyl]butyl}-N-(2-pyridinylmethyl)-1,2,4-oxadiazole-3-carboxamide

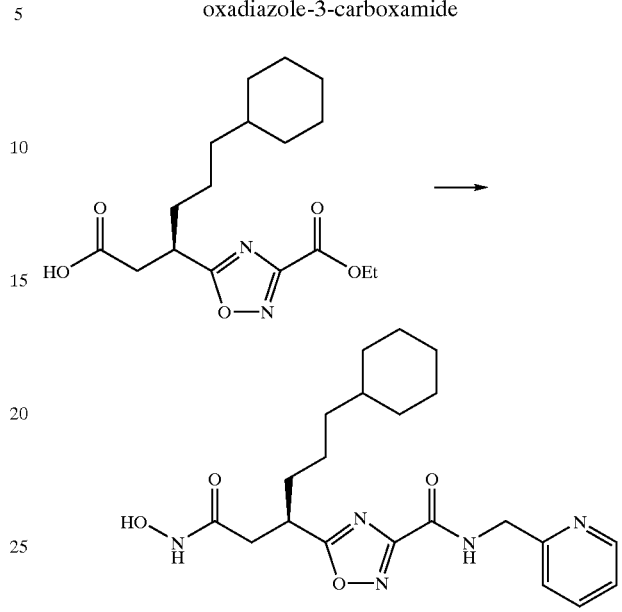

A solution of (3R)-6-cyclohexyl-3-[3-(ethoxycarbonyl)-1,2,4-oxadiazol-5-yl]hexanoic acid (Preparation 4) (500 mg, 1.47 mmol) in ethanol (13 ml) was treated with a solution of 2-aminomethylpyridine (794 mg, 7.35 mmol) in ethanol (2 ml) and the resulting solution was heated at 80° C. under a nitrogen atmosphere for 10 hours. The solvent was removed under reduced pressure. The residue was dissolved in hydrochloric acid (1M, 10 ml), neutralised to pH 4 with a saturated aqueous solution of ammonium hydroxide then extracted with ethyl acetate (×2). The combined organic layers were dried over anhydrous magnesium sulphate, filtered and the solvent removed under reduced pressure. This residue (467 mg) was then dissolved in dichloromethane (15 ml), cooled to 0° C. and treated sequentially with N-methylmorpholine (140 μl, 1.27 mmol) and isobutyl chloroformate (165 μl, 1.28 mmol). This mixture was stirred at 0° C. under a nitrogen atmosphere for 1 hour, then treated with O-(trimethylsilyl)hydroxylamine (170 μl, 1.39 mmol) and stirring continued for 10 minutes at 0° then for 17 hours at room temperature. The mixture was then treated with trifluoroacetic acid:water (5 ml, 9:1) and the solution stirred for 30 minutes. The solvent was removed under reduced pressure and the residue azeotroped from toluene (×2). The residue was purified by reverse phase HPLC[b] to afford a solid (130 mg) which was dissolved in dichloromethane (5 ml), cooled to 0° C. and treated sequentially with N-methylmorpholine (33 μl, 0.30 mmol) and isobutyl chloroformate (38 μl, 0.30 mmol). This mixture was stirred at 0° C. under a nitrogen atmosphere for 1 hour, then treated with O-(trimethylsilyl)hydroxylamine (40 μl, 0.32 mmol) and stirring continued for 3 hours. The reaction was quenched with methanol and the solvent removed under reduced pressure. The residue was dissolved in ethyl acetate, washed with water, dried over anhydrous sodium sulphate, filtered and the solvent removed under reduced pressure. The residue was dissolved in methanol (5 ml), treated with potassium carbonate (110 mg, 0.80 mmol) and stirred at room temperature for 17 hours. The mixture was treated with a few drops of acetic acid and the solvent removed under reduced pressure. The residue was partitioned between ethyl acetate and water. The organic phase was separated, dried over anhydrous sodium sulphate, filtered and the solvent removed under reduced pressure. The residue was purified by HPLC[a] to afford the title compound as a solid (34 mg).

MPt.: 128–130° C.

MS: 416 (MH⁺)

¹H-NMR (CDCl₃) δ: 8.50 (2H, m), 7.72 (1H, dd, J=7, 7 Hz), 7.40–7.18 (2H, m), 4.74 (2H, d, J=5 Hz), 3.67 (1H, m), 2.83–2.50 (2H, m), 1.86–1.42 (7H, m), 1.40–0.97 (8H, m), 0.80 (2H, m).

Example 11

2-{[(5-{(1R)-4-Cyclohexyl-1-[2-(hydroxyamino)-2-oxoethyl]butyl}-1,2,4-oxadiazol-3-yl)carbonyl]amino}acetic Acid

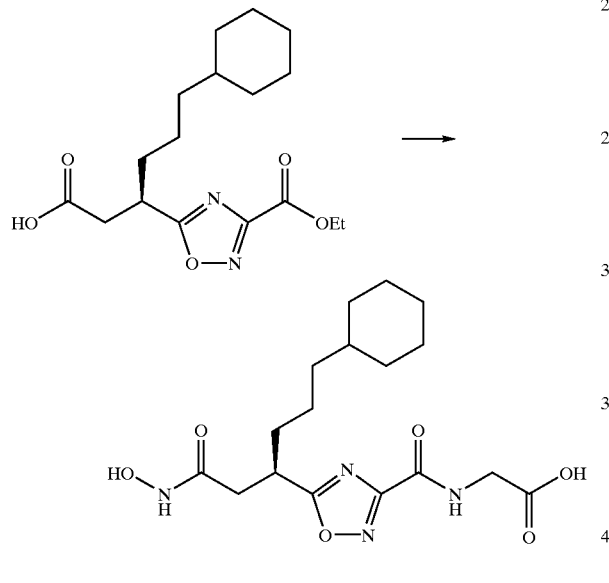

A solution of (3R)-6-cyclohexyl-3-[3-(ethoxycarbonyl)-1,2,4-oxadiazol-5-yl]hexanoic acid (Preparation 4) (527 mg, 1.56 mmol) in ethanol (20 ml) was treated with triethylamine (508 mg, 5.02 mmol) and glycine t-butyl ester hydrochloride (743 mg, 4.43 mmol) and the resulting solution was heated at 80° C. under a nitrogen atmosphere for 30 hours. The solvent was removed under reduced pressure and the residue was dissolved in hydrochloric acid (1M, 20 ml) then extracted with ethyl acetate (×2). The combined organic layers were dried over anhydrous sodium sulphate, filtered and the solvent removed under reduced pressure. The residue was purified by column chromatography on silica gel eluting with dichloromethane:ethyl acetate (1:1) then dichloromethane:methanol (19:1). This residue (430 mg, 1.02 mmol) was dissolved in dichloromethane (10 ml), cooled to 0° C. and treated sequentially with N-methylmorpholine (130 μl, 1.20 mmol) and isobutyl chloroformate (150 μl, 1.20 mmol). This mixture was stirred at 0° C. under a nitrogen atmosphere for 1 hour, then treated with O-(trimethylsilyl)hydroxylamine (160 μl, 1.30 mmol). The mixture was stirred for 17 hours being allowed to warm to room temperature over this time. The mixture was diluted with dichloromethane, washed with aqueous citric acid solution (10% w/v), dried over anhydrous magnesium sulphate, filtered and the solvent removed under reduced pressure. The residue was dissolved in dichloromethane (10 ml), treated with trifluoroacetic acid (10 ml) and the solution was stirred for 2.5 hours at room temperature. The solvent was removed under reduced pressure and the residue azeotroped from toluene (×2). The residue was purified by HPLC[b] to afford the title compound as a white solid (350 mg).

MPt.: 141–142° C.

MS: 383 (MH⁺), 405 (MNa⁺)

Analysis: Found C, 50.80; H, 7.00; N, 13.90%; C₁₇H₂₆N₄O₆.H₂O requires C, 50.99; H, 7.05; N, 13.99%

¹H-NMR (CD₃OD) δ: 4.10 (2H, s), 3.63 (1H, m), 2.72–2.51 (2H, m), 1.85–1.60 (7H, m), 1.38–1.10 (8H, m), 0.86 (2H, m).

Example 12

5-{(1R)-4-Cyclohexyl-1-[2-(hydroxyamino)-2-oxoethyl]butyl}-N,N-dimethyl-1,2,4-oxadiazole-3-carboxamide

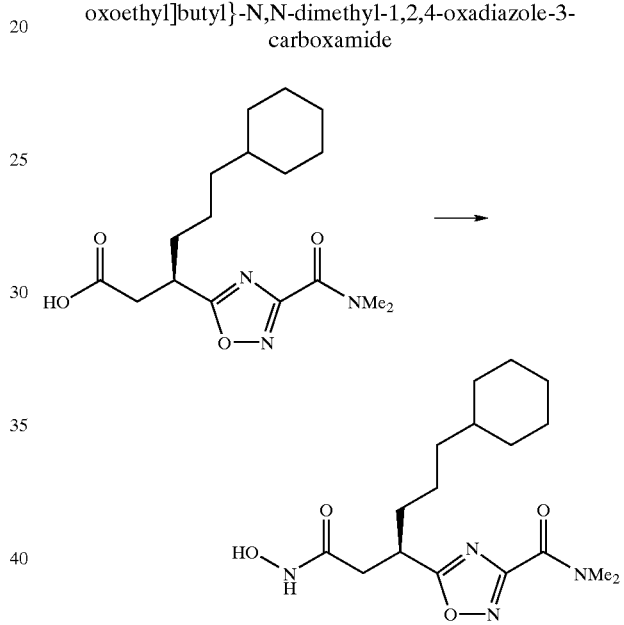

A solution of (3R)-6-cyclohexyl-3-{3-[(dimethylamino)carbonyl]-1,2,4-oxadiazol-5-yl}hexanoic acid (Preparation 11) (60 mg, 0.18 mmol) and N,N-diisopropylethylamine (30 μl, 0.18 mmol) in N—N-dimethylformamide (3 ml) was treated with O-(7-azabenzotriazol-1-yl)-N,N,N',N'-tetramethyluronium hexafluorophosphate (100 mg, 0.27 mmol) and the resulting mixture was stirred at room temperature under a nitrogen atmosphere for 1 hour. Further N,N-diisopropylethylamine (90 μl, 0.52 mmol) was then added, followed by hydroxylamine hydrochloride (35 mg, 0.52 mmol) and the mixture was stirred at room temperature for 18 hours. The mixture was partitioned between ethyl acetate and pH 7 aqueous buffer. The layers were separated and the aqueous phase extracted with ethyl acetate (×2). The combined organic layers were washed sequentially with aqueous citric acid solution (5% w/v) and brine, dried over anhydrous sodium sulphate, filtered and the solvent removed under reduced pressure. The residue was purified by column chromatography on silica gel eluting with a gradient system of dichloromethane:ethyl acetate (90:10) gradually changing to dichloromethane:ethyl acetate (50:50) then to dichloromethane:methanol (95:5). The residue was further purified by column chromatography on silica gel eluting with a gradient system of dichloromethane:methanol (99:1) gradually changing to dichloromethane:methanol (95:5) to afford the title compound as an oil which crystallised on standing (35 mg).

MS: 353 (MH⁺)

¹H-NMR (DMSO-d$_6$) δ: 10.50 (1H, br s), 8.81 (1H, br s), 3.48 (1H, m), 3.03 (3H, s), 2.93 (3H, s), 2.50 (2H, m), 1.76–1.52 (7H, m), 1.32–1.03 (8H, m), 0.80 (2H, m).

Example 13

(3R)-6-Cyclohexyl-3-(3-{[4-(dimethylamino)-1-piperidinyl]carbonyl}-1,2,4-oxadiazol-5-yl)-N-hydroxyhexanamide

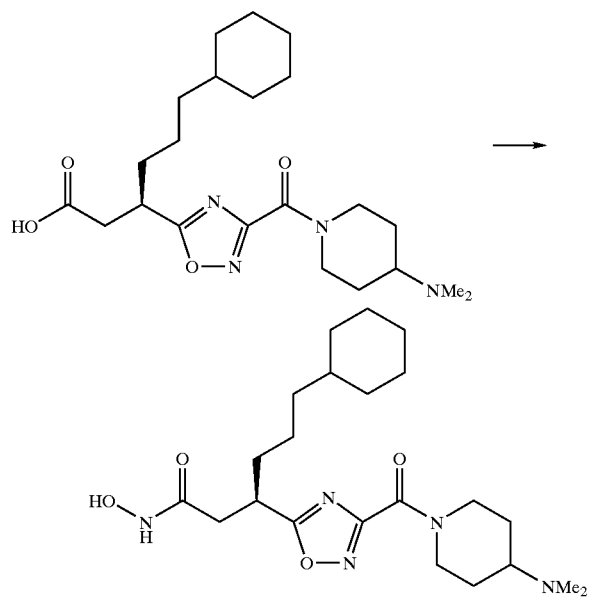

A solution of (3R)-6-cyclohexyl-3-(3-{[4-(dimethylamino)-1-piperidinyl]carbonyl}-1,2,4-oxadiazol-5yl) hexanoic acid trifluoroacetate (Preparation 26) (702 mg, 1.31 mmol) and N-methylmorpholine (159 μl, 1.45 mmol) in N,N-dimethylformamide (15 ml) was cooled to 0° C. and then treated with dropwise with isobutyl chloroformate (188 μl, 1.45 mmol). The resulting solution was stirred at 0° C. under a nitrogen atmosphere for 45 minutes. Hydroxylamine hydrochloride (274 mg, 3.94 mmol) was then added followed by further N-methylmorpholine (433 μl, 3.94 mmol) and the mixture was stirred for 18 hours being allowed to warm to room temperature over this time. The solvent was removed under reduced pressure and the residue was dissolved in a saturated aqueous solution of sodium carbonate. The pH of the solution was adjusted to 9 by dropwise addition of acetic acid and the product was then extracted with ethyl acetate (×2). The combined organic phases were washed with brine, dried over anhydrous sodium sulphate, filtered and the solvent removed under reduced pressure. The residue was purified by column chromatography on silica gel eluting with a gradient system of dichloromethane:methanol:0.88 ammonia (90:10:1) then dichloromethane:methanol:0.88 ammonia (80:20:2) to afford the title compound as an oil (23 mg)

MS: 436 (MH⁺)

¹H-NMR (CD$_3$OD) δ: 4.68 (1H, m), 3.95 (1H, m), 3.48 (1H, m), 3.18 (1H, m), 2.91 (1H, m) 2.72–2.54 (3H, m), 2.36 (6H, s), 2.04 (1H, m), 1.96 (1H, m), 1.84–1.60 (7H, m), 1.50 (2H, m), 1.35–1.10 (8H, m), 0.88 (2H, m).

Example 14

(3R)-6-Cyclohexyl-N-hydroxy-3-(3-{[3-(4-morpholinyl)-1-azetidinyl]carbonyl}-1,2,4-oxadiazol-5-yl)hexanamide

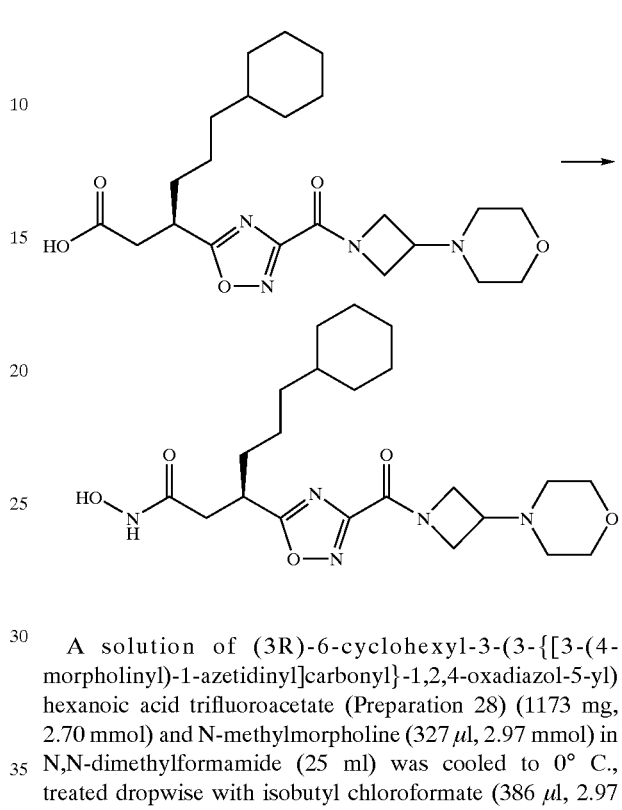

A solution of (3R)-6-cyclohexyl-3-(3-{[3-(4-morpholinyl)-1-azetidinyl]carbonyl}-1,2,4-oxadiazol-5-yl) hexanoic acid trifluoroacetate (Preparation 28) (1173 mg, 2.70 mmol) and N-methylmorpholine (327 μl, 2.97 mmol) in N,N-dimethylformamide (25 ml) was cooled to 0° C., treated dropwise with isobutyl chloroformate (386 μl, 2.97 mmol) and stirred under a nitrogen atmosphere at 0° C. for 45 minutes. Hydroxylamine hydrochloride (564 mg, 8.11 mmol) was then added followed by further N-methylmorpholine (891 μl, 8.11 mmol) and the mixture was stirred for 18 hours being allowed to warm to room temperature over this time. The solvent was removed under reduced pressure and the residue dissolved in a saturated aqueous solution of sodium carbonate. The pH of the solution was adjusted to 9 by dropwise addition of acetic acid. Water was added (75 ml) and the product was then extracted with ethyl acetate (×2). The combined organic phases were washed with brine, dried over anhydrous sodium sulphate, filtered and the solvent removed under reduced pressure. The residue was purified by column chromatography on silica gel eluting with a gradient system of dichloromethane:methanol:0.88 ammonia (90:10:1) then dichloromethane:methanol:0.88 ammonia (80:20:2). The product was further purified by HPLC to afford the title compound as a white solid (151 mg)

MS: 450 (MH⁺)

Analysis: Found C, 56.19; H, 7.61; N, 14.81%; C$_{22}$H$_{35}$N$_5$O$_5$.H$_2$O requires C, 56.51; H, 7.96; N, 14.98%

¹H-NMR (CD$_3$OD) δ: 4.63 (1H, m), 4.42 (1H, m), 4.44 (1H, m), 4.03 (1H, m), 3.75 (4H, m), 3.41 (1H, m), 3.30 (1H, m), 2.72–2.53 (2H, m), 2.45 (4H, m), 1.83–1.56 (7H, m), 1.36–1.07 (8H, m), 0.87 (2H, m).

MPt.: 52–63° C.

Example 15

(3R)-6-Cyclohexyl-N-hydroxy-3-(3-{[4-(4-pyridinyl)-1-piperidinyl]carbonyl}-1,2,4-oxadiazol-5-yl)hexanamide

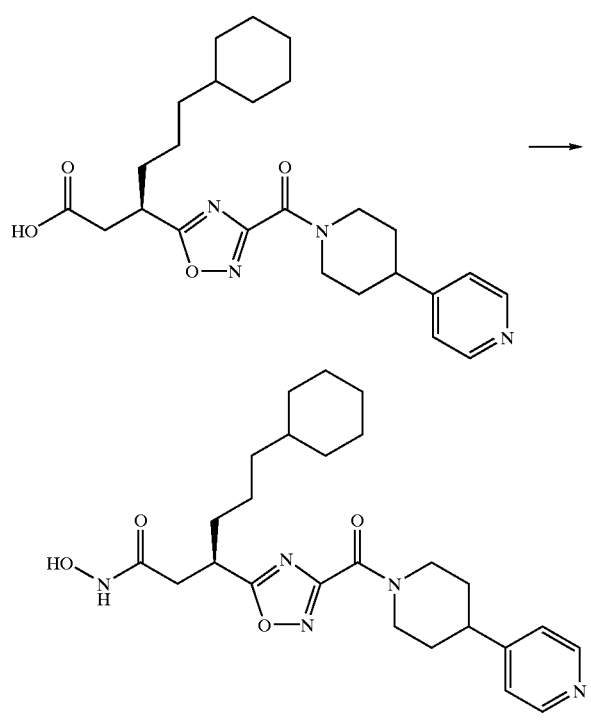

A solution of (3R)-6-cyclohexyl-3-(3-{[4-(4-pyridinyl)-1-piperidinyl]carbonyl}-1,2,4-oxadiazol-5-yl)hexanoic acid (Preparation 32) (311 mg, 0.68 mmol) and N-methylmorpholine (83 µl, 0.75 mmol) in N,N-dimethylformamide (15 ml) was cooled to 0° C., treated dropwise with isobutyl chloroformate (98 µl, 0.75 mmol) and the resulting solution was stirred at 0° C. for 45 minutes. Hydroxylamine hydrochloride (142 mg, 2.05 mmol) was then added followed by further N-methylmorpholine (226 µl, 2.05 mmol) and the mixture was stirred for 18 hours being allowed to warm to room temperature over this time. The solvent was removed under reduced pressure and the residue partitioned between ethyl acetate (50 ml) and water (50 ml). The layers were separated and the aqueous phase extracted with ethyl acetate (×2). The combined organic phases were washed with brine, dried over anhydrous sodium sulphate, filtered and the solvent removed under reduced pressure. The residue was purified by HPLC to afford a residue that was partitioned between ethyl acetate and water. The organic phase was separated, dried over anhydrous sodium sulphate, filtered and the solvent removed under reduced pressure. The residue was triturated with diethyl ether to yield the title compound as a white solid (94 mg).

MS: 470 (MH$^+$)

$^1$H-NMR (CD$_3$OD) δ: 8.45 (2H, d, J=4 Hz), 7.37 (2H, d, J=4 Hz), 4.79 (1H, m), 4.00 (1H, m), 3.60 (1H, m), 3.32 (1H, m), 3.00 (2H, m), 2.70–2.52 (2H, m), 2.06–1.85 (2H, m), 1.83–1.60 (9H, m), 1.39–1.12 (8H, m), 0.86 (2H, m).

Example 16

5-{(1R)-4-Cyclohexyl-1-[2-(hydroxyamino)-2-oxoethyl]butyl}-N-methyl-N-(2-pyridinylmethyl)-1,2,4-oxadiazole-3-carboxamide

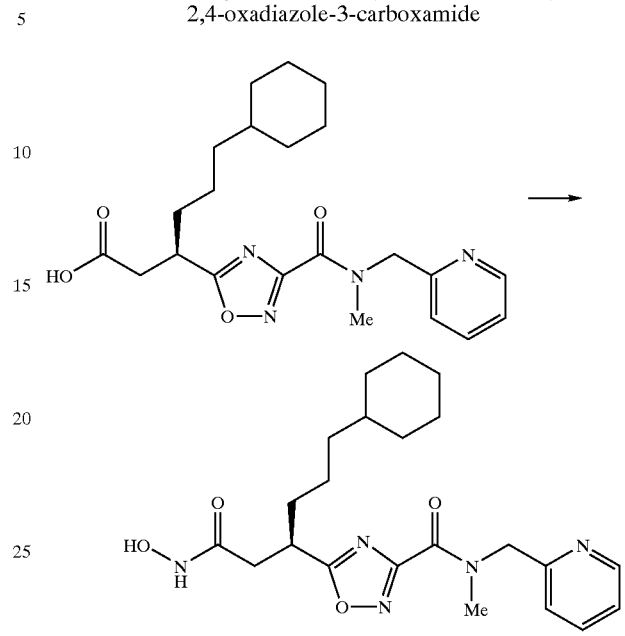

A solution of (3R)-6-cyclohexyl-3-(3-{[methyl(2-pyridinylmethyl)amino]carbonyl}-1,2,4-oxadiazol-5-yl)hexanoic acid (Preparation 36) (453 mg, 1.09 mmol) and N-methylmorpholine (132 µl, 1.20 mmol) in anhydrous tetrahydrofuran (10 ml) was cooled to 0° C., treated with isobutyl chloroformate (155 µl, 1.20 mmol) and stirred under a nitrogen atmosphere for 2 hours. O-(trimethylsilyl)hydroxylamine (160 µl, 1.31 mmol) was added and the mixture was stirred for 18 hours, being allowed to warm to room temperature over this time. The mixture was then treated with saturated aqueous ammonium chloride solution (10 ml) and stirred for 1 hour. This mixture was then diluted with water and extracted with ethyl acetate (×3). The combined organic layers were sequentially washed with water and brine, dried over anhydrous sodium sulphate, filtered and the solvent removed under reduced pressure. The residue was purified by column chromatography on silica gel eluting with ethyl acetate:isopropanol (95:5) then a gradient system of dichloromethane:methanol (90:10) to dichloromethane:methanol (80:20) to afford a residue (260 mg, 0.31 mmol) which was dissolved in methanol (5 ml) and treated with potassium carbonate (138 mg, 1.00 mmol) and the mixture was stirred at room temperature for 17 hours. The solvent was removed under reduced pressure and the residue partitioned between ethyl acetate and a saturated aqueous solution of ammonium chloride. The layers were separated and the aqueous layer was extracted with ethyl acetate (×4). The combined organic layers were washed with brine, dried over anhydrous sodium sulphate, filtered and the solvent removed under reduced pressure. The residue was purified by HPLC$^a$ to afford the title compound as a white solid (84 mg)

MS: 430 (MH$^+$)

$^1$H-NMR (CDCl$_3$) (mixture of rotamers) δ: 8.55 (1H, m), 7.72 (1H, m), 7.42–7.20 (2H, m), 4.84 (2H, m), 3.64 (1H, m), 3.24 (1.2H, s), 3.18 (1.8H, s), 2.84–2.53 (2H, m), 1.86–1.45 (7H, m), 1.39–0.88 (8H, m), 0.80 (2H, m).

Example 17

2-[[(5-{(1R)-4-Cyclohexyl-1-[2-(hydroxyamino)-2-oxoethyl]butyl}-1,2,4-oxadiazol-3-yl)carbonyl](methyl)amino]acetic Acid

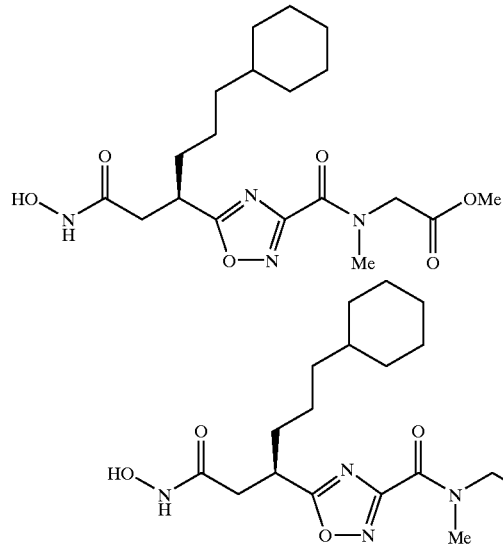

A solution of methyl 2-[[(5-{(1R)-4-cyclohexyl-1-[2-(hydroxyamino)-2-oxoethyl]butyl}-1,2,4-oxadiazol-3-yl)carbonyl](methyl)amino]acetate (Preparation 40) (180 mg, 0.44 mmol) in 1,4-dioxane (4 ml) was cooled to 0° C. and treated with lithium hydroxide monohydrate (42 mg, 1 mmol). The mixture was stirred for 1 hour being allowed to warm to room temperature over this time. The mixture was then treated with hydrochloric acid (2M), diluted with water and extracted with ethyl acetate (×2). The combined organic layers were washed with brine, dried over anhydrous sodium sulphate, filtered and the solvent removed under reduced pressure. The residue was purified by HPLC$^b$ to afford the title compound as a white foam (95 mg).

MS: 397(MH$^+$), 419 (MNa$^+$)

$^1$H-NMR (CD$_3$OD) (mixture of rotamers) δ: 4.39 (1H, s), 4.27 (1H, s), 3.60 (1H, m), 3.23 (1.5H, s), 3.16 (1.5H, s), 2.73–2.50 (2H, m), 1.86–1.58 (7H, m), 1.39–1.08 (8H, m), 0.87 (2H, m).

Example 18

Methyl 1-[(5-{(1R)-4-cyclohexyl-1-[2-(hydroxyamino)-2-oxoethyl]butyl}-1,2,4-oxadiazol-3-yl)carbonyl]-3-azetidinecarboxylate

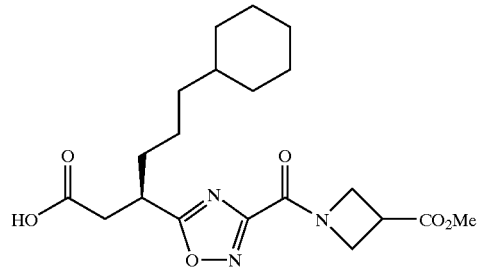

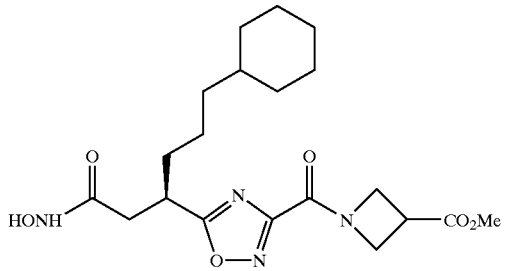

A solution of (3R)-6-cyclohexyl-3-(3-{[3-(methoxycarbonyl)-1-azetidinyl]carbonyl}-1,2,4-oxadiazol-5-yl)hexanoic acid (Preparation 43) (200 mg, 0.49 mmol) and N-methylmorpholine (59 μl, 0.54 mmol) in anhydrous dichloromethane (7 ml) was cooled to 0° C., treated with isobutyl chloroformate (70 μl, 0.54 mmol) and stirred under a nitrogen atmosphere for 1 hour. O-(Trimethylsilyl) hydroxylamine (175 μl, 1.47 mmol) was added and the mixture was for 18 hours, being allowed to warm to room temperature over this time. The mixture was then treated with aqueous citric acid solution (10% w/v, 10 ml) and stirred for 2 hours. This mixture was then diluted with water and extracted with ethyl acetate (×3). The combined organic layers were washed with water and brine, dried over anhydrous sodium sulphate, filtered and the solvent removed under reduced pressure. The residue was purified by HPLC to afford the title compound as a foam (150 mg).

MS: 423 (MH$^+$), 440 (MNH$_4^+$)

$^1$H-NMR (CD$_3$OD) δ: 4.80–4.62 (2H, m), 4.46–4.25 (2H, m), 3.77 (3H, s), 3.63 (2H, m), 2.75–2.50 (2H, m), 1.83–1.57 (7H, m), 1.39–1.08 (8H, m), 0.86 (2H, m).

Example 19

1-[(5-{(1R)-4-Cyclohexyl-1-[2-(hydroxyamino)-2-oxoethyl]butyl}-1,2,4-oxadiazol-3-yl)carbonyl]-3-azetidinecarboxylic Acid

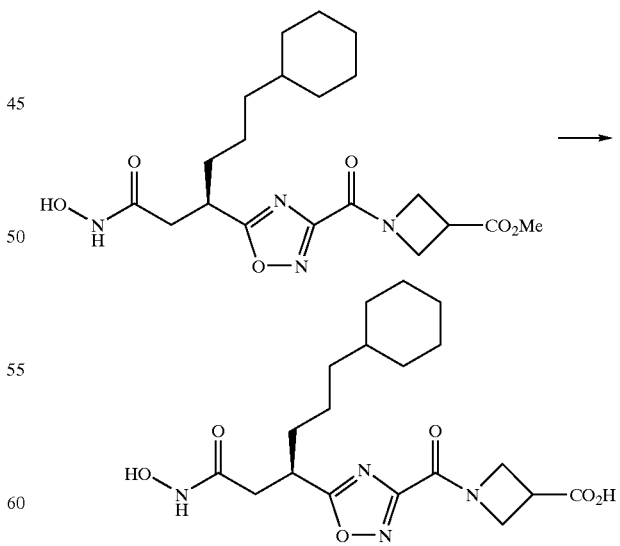

A solution of methyl 1-[(5-{(1R)-4-cyclohexyl-1-[2-(hydroxyamino)-2-oxoethyl]butyl}-1,2,4-oxadiazol-3-yl)carbonyl]-3-azetidinecarboxylate (Example 18) (130 mg, 0.31 mmol) in 1,4-dioxane (3 ml) was cooled to 0° C. and treated with lithium hydroxide monohydrate (25 mg, 0.60 mmol). The mixture was stirred for 1 hour being allowed to warm to room temperature over this time. Further lithium hydroxide monohydrate (25 mg, 0.60 mmol) was added and the mixture stirred for 3 hours. The mixture was then treated with hydrochloric acid (2M), diluted with water and extracted with ethyl acetate (×2). The combined organic layers were washed with brine, dried over anhydrous sodium sulphate, filtered and the solvent removed under reduced pressure. The residue was purified by HPLC[b] to afford the title compound as a foam (110 mg).

MS: 409 (MH$^+$), 431 (MNa$^+$)

$^1$H-NMR (CDCl$_3$) δ: nmr—needs redoing 4.71 (2H, m), 4.35 (2H, m), 3.69–3.43 (2H, m), 2.86–2.56 (2H, m), 1.90–1.52 (7H, m), 1.40–0.99 (8H, m), 0.83 (2H, m).

Example 20

(3R)-6-Cyclohexyl-N-hydroxy-3-(3-methyl-1,2,4-oxadiazol-5-yl)hexanamide

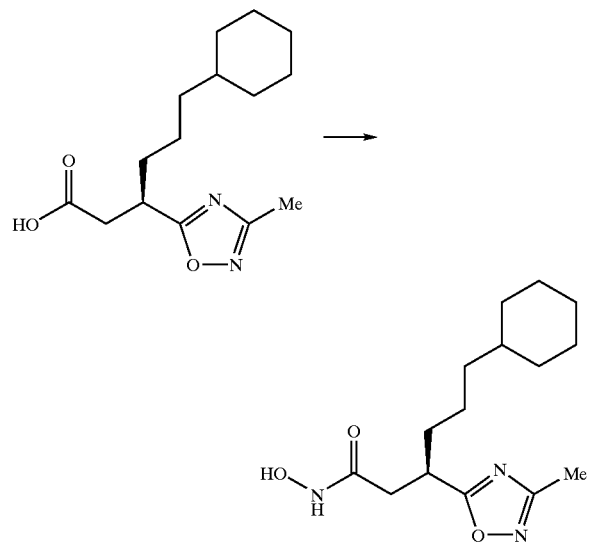

A solution of (3R)-6-cyclohexyl-3-(3-methyl-1,2,4-oxadiazol-5-yl)hexanoic acid (Preparation 45) (170 mg, 0.61 mmol) in anhydrous tetrahydrofuran (2 ml) was treated with 1,1'-carbonyldiimidazole (98 mg, 0.61 mmol) and the mixture stirred at room temperature under a nitrogen atmosphere for 20 minutes. Hydroxylamine hydrochloride (42 mg, 0.61 mmol) was then added and the mixture stirred for 18 hours. The solvent was removed under reduced pressure and the residue partitioned between hydrochloric acid (0.5M) and ethyl acetate. The layers were separated and the organic phase was washed with water, dried over anhydrous sodium sulphate, filtered and solvent removed under reduced pressure. The residue was purified by column chromatography on silica gel eluting with dichloromethane:methanol (98:2) to afford the title compound as an oil (82 mg).

MS: 296 (MH$^+$)

$^1$H-NMR (CDCl$_3$) δ: 3.56 (1H, m), 2.70 (1H, m), 2.58 (1H, m), 2.38 (3H, s), 1.88–1.42 (7H, m), 1.39–1.03 (8H, m), 0.83 (2H, m)

Example 21

(3R)-6-Cyclohexyl-N-hydroxy-3-(3-isopropyl-1,2,4-oxadiazol-5-yl)hexanamide

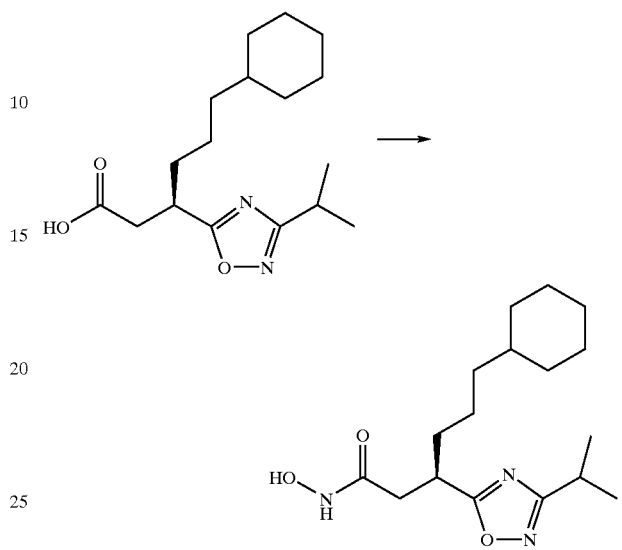

A solution of (3R)-6-cyclohexyl-3-(3-isopropyl-1,2,4-oxadiazol-5-yl)hexanoic acid (Preparation 47) (175 mg, 0.57 mmol) in anhydrous tetrahydrofuran (10 ml) was treated with 1,1'-carbonyldiimidazole (93 mg, 0.57 mmol) and the mixture stirred at room temperature under a nitrogen atmosphere for 1 hour. Hydroxylamine hydrochloride (40 mg, 0.57 mmol) was then added and the mixture stirred for 18 hours. The mixture was filtered and the solvent was removed from the filtrate under reduced pressure. The residue was purified by column chromatography on silica gel eluting with dichloromethane:methanol:0.88 ammonia (95:5:0.5) to afford the title compound as an oil (44 mg).

MS: 324 (MH$^+$)

$^1$H-NMR (CDCl$_3$) δ: 3.54 (1H, m), 3.06 (1H, m), 2.75–2.48 (2H, m), 1.88–1.58 (7H, m), 1.39–1.05 (14H, m), 0.83 (2H, m)

Example 22

(3R)-6-Cyclohexyl-N-hydroxy-3-[3-(methoxymethyl)-1,2,4-oxadiazol-5-yl]hexanamide

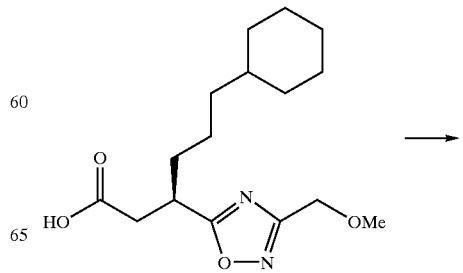

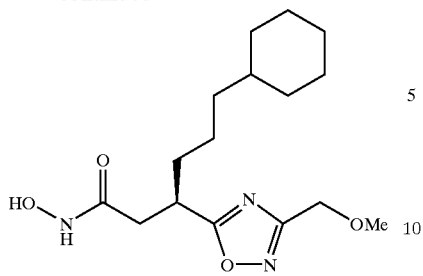

A solution of (3R)-6-cyclohexyl-3-[3-(methoxymethyl)-1,2,4-oxadiazol-5-yl]hexanoic acid (Preparation 49) (250 mg, 0.81 mmol) in anhydrous tetrahydrofuran (10 ml) was treated with 1,1'-carbonyldiimidazole (130 mg, 0.81 mmol) and the mixture stirred at room temperature under a nitrogen atmosphere for 2 hours. Hydroxylamine hydrochloride (56 mg, 0.81 mmol) was then added and the mixture stirred for 18 hours. The solvent was removed under reduced pressure and the residue was purified by column chromatography on silica gel eluting with dichloromethane:methanol:0.88 ammonia (95:5:0.5) to afford the title compound as an oil (75 mg).

MS: 326 (MH$^+$), 348 (MNa$^+$)

$^1$H-NMR (CDCl$_3$) δ: 4.57 (2H, s), 3.62 (1H, m), 3.46 (3H, s), 2.80–2.52 (2H, m), 1.88–1.42 (7H, m), 1.39–1.03 (8H, m), 0.83 (2H, m)

Example 23

(3R)-6-Cyclohexyl-N-hydroxy-3-[3-(2-methoxyethyl)-1,2,4-oxadiazol-5-yl]hexanamide

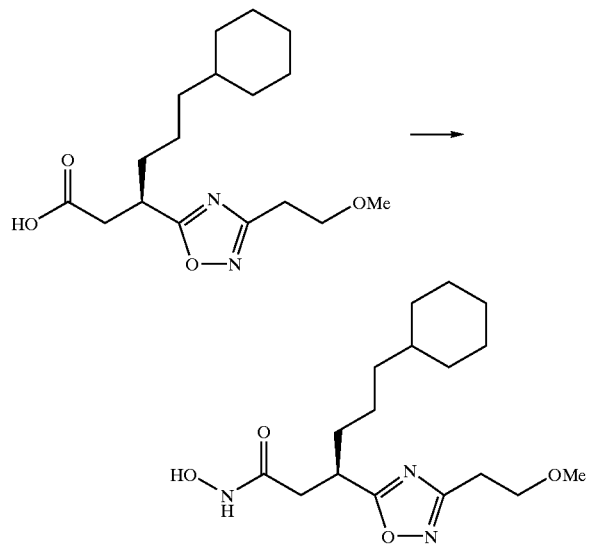

A solution of ((3R)-6-cyclohexyl-3-[3-(2-methoxyethyl)-1,2,4-oxadiazol-5-yl]hexanoic acid (Preparation 51) (245 mg, 0.76 mmol) in anhydrous tetrahydrofuran (10 ml) was treated with 1,1'-carbonyldiimidazole (123 mg, 0.76 mmol) and the mixture stirred at room temperature under a nitrogen atmosphere for 1 hour. Hydroxylamine hydrochloride (53 mg, 0.76 mmol) was then added and the mixture stirred for 18 hours. The solvent was removed under reduced pressure and the residue was purified by column chromatography on silica gel eluting with dichloromethane:methanol:0.88 ammonia (95:5:0.5). The residue was dissolved in ethyl acetate, washed with hydrochloric acid (1M), dried over anhydrous magnesium sulphate, filtered and the solvent removed under reduced pressure to afford the title compound as an oil (100 mg)

MS: 340 (MH$^+$), 362 (MNa$^+$)

$^1$H-NMR (CDCl$_3$) δ: 3.77 (2H, m), 3.55 (1H, m), 3.36 (3H, s), 3.00 (2H, t, J=6 Hz), 2.80–2.52 (2H), m), 1.88–1.52 (7H, m), 1.39–1.05 (8H, m), 0.83 (2H, m)

Example 24

(3R)-6-Cyclohexyl-N-hydroxy-3-{3-[2-oxo-2-(1-pyrrolidinyl)ethyl]-1,2,4-oxadiazol-5-yl}hexanamide

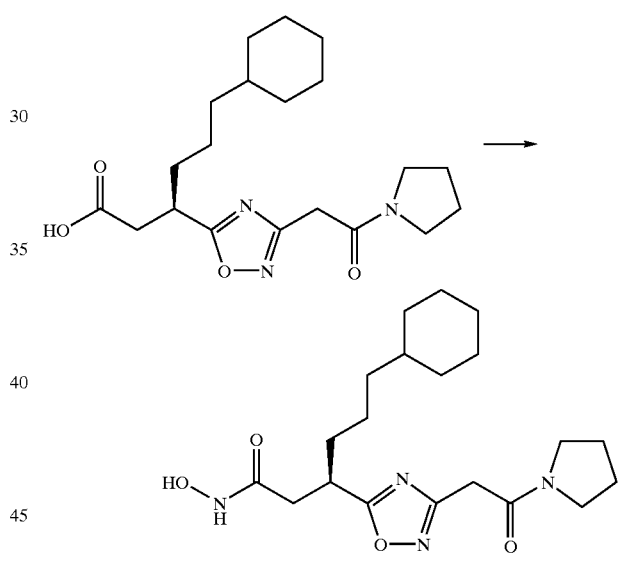

A solution of (3R)-6-cyclohexyl-3-{3-[2-oxo-2-(1-pyrrolidinyl)ethyl]-1,2,4-oxadiazol-5yl}hexanoic acid (Preparation 53) (200 mg, 0.53 mmol) in anhydrous tetrahydrofuran (10 ml) was treated with 1,1'-carbonyldiimidazole (86 mg, 0.53 mmol) and the mixture stirred at room temperature under a nitrogen atmosphere for 2 hours. Hydroxylamine hydrochloride (37 mg, 0.53 mmol) was then added and the mixture stirred for 18 hours. The solvent was removed under reduced pressure and the residue was purified by column chromatography on silica gel eluting with dichloromethane:methanol:0.88 ammonia (90:10:1) to afford the title compound as a colourless oil (50 mg).

$^1$H-NMR (CDCl$_3$) δ: 3.80 (2H, m), 3.67–3.40 (5H, m), 2.80–2.52 (2H, m), 2.13–0.98 (19H, m), 0.83 (2H, m)

Example 25

(3R)-6-Cyclohexyl-N-hydroxy-3-{3-[(phenylsulfonyl)methyl]-1,2,4-oxadiazol-5-yl}hexanamide

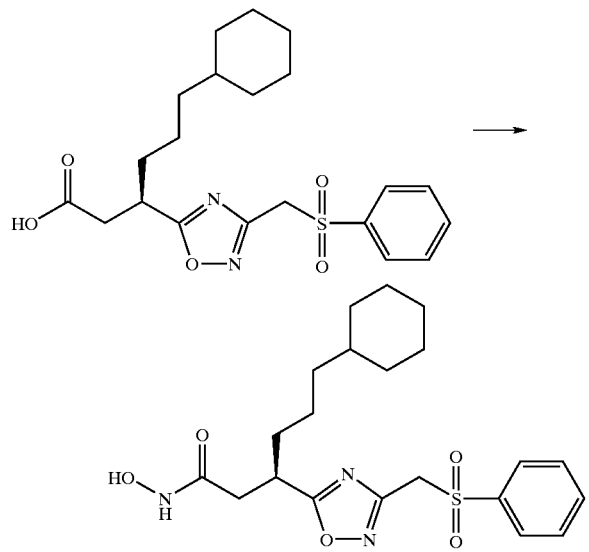

A solution of (3R)-6-cyclohexyl-3-{3-[(phenylsulfonyl)methyl]-1,2,4-oxadiazol-5-yl}hexanoic acid (Preparation 55) (60 mg, 0.14 mmol) in anhydrous tetrahydrofuran (4 ml) was treated with 1,1'-(25 mg, 0.15 mmol) and the mixture stirred at room temperature under a nitrogen atmosphere for 2 hours. Hydroxylamine hydrochloride (10 mg, 0.14 mmol) was then added and the mixture was stirred for 18 hours. The solvent was removed under reduced pressure and the residue was purified by column chromatography on silica gel eluting with dichloromethane:methanol:0.88 ammonia (95:5:0.5) to afford the title compound as an oil (15 mg).

MS: 436 (MH$^+$), 453 (MNH$_4$$^+$)

$^1$H-NMR (CDCl$_3$) δ: 8.93 (1H, br s), 8.01–7.40 (5H, m), 4.53 (2H, S), 3.60 (1H, m), 2.85–2.52 (2H, m), 1.84–1.43 (7H, m), 1.39–1.00 (8H, m), 0.85 (2H, m)

Example 26

(3R)-3-{3-[(4-Chlorophenoxy)methyl]-1,2,4-oxadiazol-5-yl}-6-cyclohexyl-N-hydroxyhexanamide

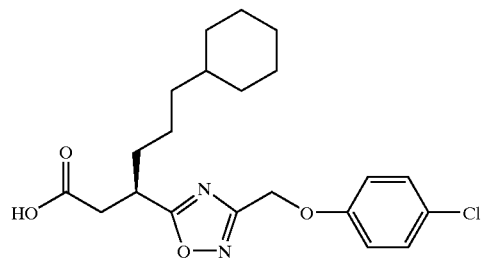

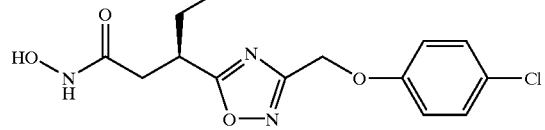

A solution of (3R)-3-{3-[(4-chlorophenoxy)methyl]-1,2,4-oxadiazol-5-yl}-6-cyclohexylhexanoic acid (Preparation 57) (180 mg, 0.44 mmol) in anhydrous tetrahydrofuran (10 ml) was treated with 1,1'-carbonyldiimidazole (71 mg, 0.44 mmol) and the mixture stirred at room temperature under a nitrogen atmosphere for 2 hours. Hydroxylamine hydrochloride (30 mg, 0.44 mmol) was then added and the mixture stirred for 18 hours. The solvent was removed under reduced pressure and the residue was partitioned between ethyl acetate and water. The layers were separated and the organic phase was washed with brine, dried over anhydrous magnesium sulphate, filtered and the solvent removed under reduced pressure. The residue was purified by column chromatography on silica gel eluting with dichloromethane:methanol:0.88 ammonia (95:5:0.5) to afford the title compound as a glass (53 mg).

$^1$H-NMR (CDCl$_3$) δ: 7.24 (2H, m), 6.94 (2H, d, J=8 Hz), 5.13 (2H, s), 3.70–3.44 (1H, m), 3.00–2.50 (2H, m), 1.85–1.53 (7H, m), 1.37–1.02 (8H, m), 0.82 (2H, m)

Example 27

(3R)-6-Cyclohexyl-N-hydroxy-3-[3-(2-pyridinylmethyl)-1,2,4-oxadiazol-5-yl]hexanamide

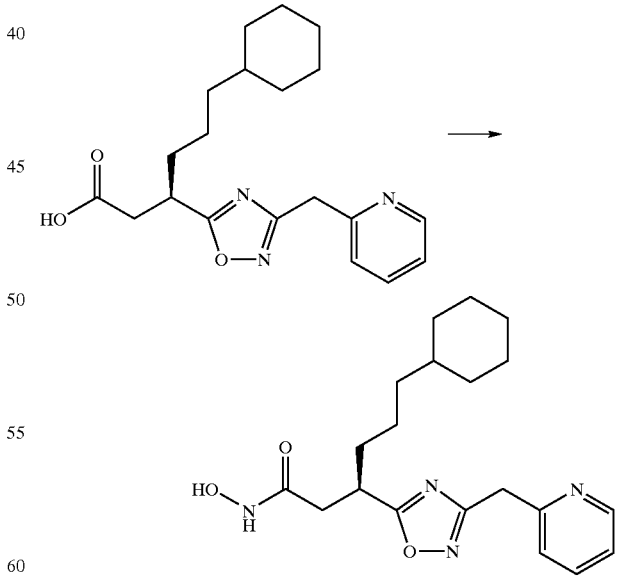

A solution of (3R)-6-cyclohexyl-3-[3-(2-pyridinylmethyl)-1,2,4-oxadiazol-5-yl]hexanoic acid trifluoroacetate (Preparation 59) (214 mg, 0.45 mmol) in anhydrous tetrahydrofuran (5 ml) was treated with 1,1'-carbonyldiimidazole (194 mg, 1.20 mmol) and the mixture stirred at room temperature under a nitrogen atmosphere for 2 hours. Hydroxylamine hydrochloride (83 mg, 1.20 mmol) was then added and the mixture stirred for 18 hours. The solvent was removed under reduced pressure and the residue was partitioned between ethyl acetate and water. The layers were separated and the organic phase was washed with water then brine, dried over anhydrous magnesium sulphate, filtered and the solvent removed under reduced pressure. The residue was purified by column chromatography on silica gel eluting with dichloromethane:methanol:0.88 ammonia (95:5:0.5) to afford the title compound as a colourless oil (120 mg).

MS: 373 (MH$^+$), 395 (MNa$^+$)

$^1$H-NMR (DMSO-d$_6$) δ: 8.79 (1H, br s), 8.45 (1H, d, J=5 Hz), 7.74 (1H, t, J=5 Hz), 7.38–7.20 (2H, m), 4.20 (2H, s), 3.40 (1H, m), 2.48–2.31 (2H, m), 1.89–1.43 (7H, m), 1.29–0.95 (8H, m), 0.76 (2H, m)

Example 28

Ethyl 2-{(1R)-4-cyclohexyl-1-[2-(hydroxyamino)-2-oxoethyl]butyl}-1,3-oxazole-4-carboxylate

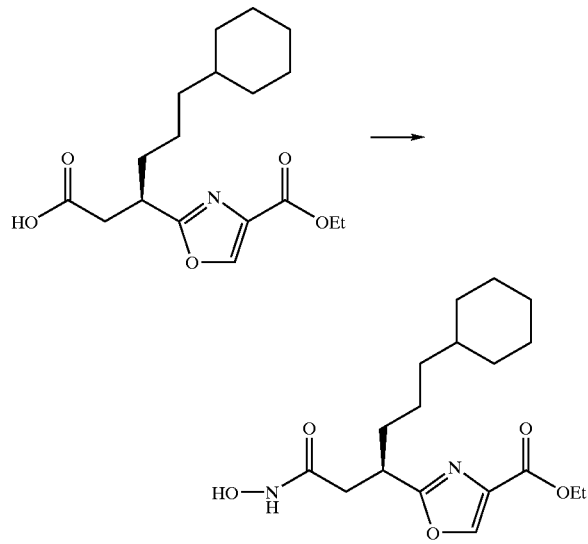

A solution of (3R)-6-cyclohexyl-3-[4-(ethoxycarbonyl)-1,3-oxazol-2-yl]hexanoic acid (Preparation 63) (130 mg, 0.39 mmol) and N,N-diisopropylethylamine (67 μl, 0.39 mmol) in N,N-dimethylformamide (6 ml) was treated with O-(7-azabenzotriazol-1-yl)-N,N,N',N'-tetramethyluronium hexafluorophosphate (220 mg, 0.58 mmol) and the resulting mixture was stirred at room temperature under a nitrogen atmosphere for 45 minutes. Further N,N-diisopropylethylamine (270 μl, 1.54 mmol) was then added, followed by hydroxylamine hydrochloride (80 mg, 1.16 mmol) and the mixture was stirred at room temperature for 18 hours. The solvent was removed under reduced pressure and the residue partitioned between ethyl acetate and pH 7 aqueous buffer. The organic layer was separated, washed sequentially with water and brine, dried over anhydrous magnesium sulphate, filtered and the solvent removed under reduced pressure. The residue was purified by column chromatography on silica gel eluting with a gradient system of dichloromethane:methanol (99:1) gradually changing to dichloromethane:methanol (98:2) to afford the title compound (20 mg).

MS: 353 (MH$^+$)

$^1$H-NMR (CDCl$_3$) δ: 8.14 (1H, s), 4.37 (2H, q, J=7 Hz), 3.50 (1H, m), 2.76 (1H, m), 2.57 (1H, m), 1.88–1.52 (7H, m), 1.37 (3H, t, J=7 Hz), 1.32–1.02 (8H, m), 0.83 (2H, m).

Example 29

2-{(1R)-4-Cyclohexyl-1-[2-(hydroxyamino)-2-oxoethyl]butyl}-N,N-dimethyl-1,3-oxazole-4-carboxamide

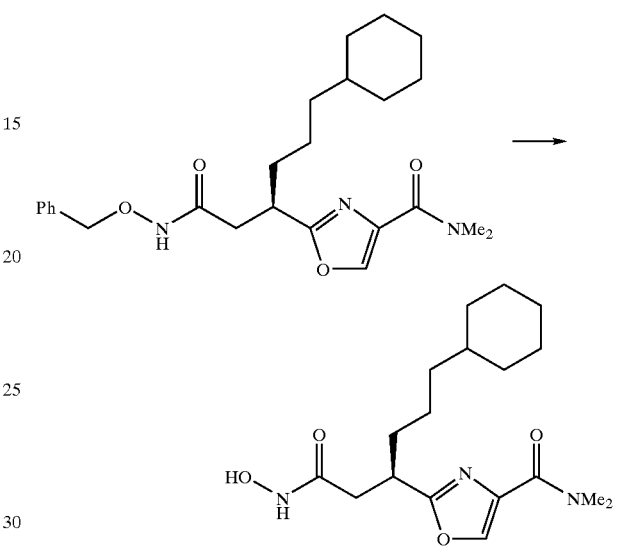

A solution of 2-((1R)-1-{2-[(benzyloxy)amino]-2-oxoethyl}-4-cyclohexylbutyl) —N,N-dimethyl-1,3-oxazole-4-carboxamide (Preparation 66) (100 mg, 0.23 mmol) in ethanol (5 ml) was treated with 5% palladium on barium sulphate (50 mg), pressurised to 1 atm with hydrogen in a sealed vessel and the mixture was stirred at room temperature for 2 hours. The solution was filtered through Arbocel® and the solvent removed from the filtrate under reduced pressure. The residue was azeotroped from dichloromethane (×3) then dichloromethane:ether (1 ml:4 ml) to afford the title compound as a foam (75 mg).

MS: 351 (M$^+$)

$^1$H-NMR (CDCl$_3$) δ: 7.94 (1H, s), 3.52 (1H, m), 3.38–2.94 (6H, br d), 2.73–2.45 (2H, m), 1.85–1.47 (7H, m), 1.41–0.98 (8H, m), 0.83 (2H, m).

Example 30

(3R)-6-Cyclohexyl-N-hydroxy-3-[3-(1-pyrrolidinylcarbonyl)-1,2,4-oxadiazol-5-yl]hexanamide

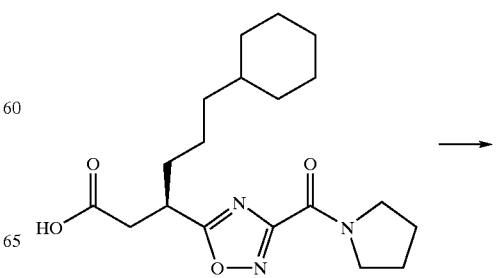

45

-continued

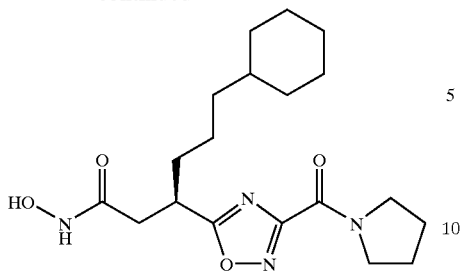

A solution of (3R)-6-cyclohexyl-3-[3-(1-pyrrolidinylcarbonyl)-1,2,4-oxadiazol-5-yl]hexanoic acid (Preparation 13) (288 mg, 0.79 mmol) and N,N-diisopropylethylamine (138 µl, 0.79 mmol) in N,N-dimethylformamide (6 ml) was treated with O-(7-azabenzotriazol-1-yl)-N,N,N',N'-tetramethyluronium hexafluorophosphate (452 mg, 1.19 mmol) and the resulting mixture was stirred at room temperature under a nitrogen atmosphere for 1 hour. Further N,N-diisopropylethylamine (552 µl, 3.16 mmol) was then added, followed by the hydroxylamine hydrochloride (165 mg, 2.38 mmol) and the mixture stirred at room temperature for 18 hours. The solvent was removed under reduced pressure and the residue wasa partitioned between ethyl acetate and pH 7 aqueous buffer. The organic layer was separated, washed sequentially with water and brine, dried over anhydrous magnesium sulphate, filtered and the solvent removed under reduced pressure. The residue was purified by column chromatography on silica gel eluting with dichloromethane:methanol (98:2) to afford the title compound as a foam (126 mg).

MS: 379 (MH⁺), 396 (MNH₄⁺)

¹H-NMR (CD₃OD) δ: 3.75 (2H, m), 3.60 (3H, m), 2.66 (1H, dd, J=13, 8 Hz), 2.57 (1H, dd, J=13, 3 Hz), 1.98 (4H, m), 1.86–1.58 (7H, m), 1.40–1.07 (8H, m), 0.87 (2H, m).

Example 31

2-{(1R)-4-Cyclohexyl-1-[2-(hydroxyamino)-2-oxoethyl]butyl}-N,N,5-trimethyl-1,3-oxazole-4-carboxamide

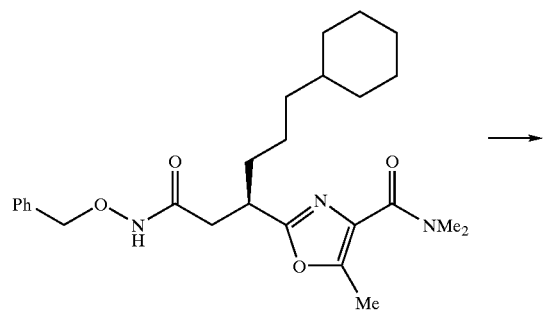

46

-continued

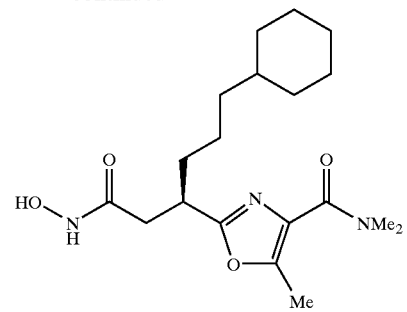

A solution of 2-((1R)-1-{2-[(benzyloxy)amino]-2-oxoethyl}-4-cyclohexylbutyl)-N,N,5-trimethyl-1,3-oxazole-4carboxamide (Preparation 73) (105 mg, 0.23 mmol) in ethanol (5 ml) was treated with 5% palladium on barium sulphate (45 mg) and ammonium formate (73 mg, 1.15 mmol) and the mixture was heated at 45° C. for 17 hours. Further palladium on barium sulphate (30 mg) and ammonium formate (60 mg, mmol) were added and the heating was continued for 2 hours. The solution was filtered through Arbocel® and the solvent removed from the filtrate under reduced pressure. The residue was azeotroped from dichloromethane (×3) then purified by column chromatography on silica gel eluting with dichloromethane:methanol:0.88 ammonia (98:2:0.2 to 90:10:1) to afford the title compound as a foam (25 mg).

MS: 366(MH⁺), 388 (MNa⁺)

Analysis: Found C, 61.77; H, 8.62; N, 11.22%; C₁₉H₃₁N₃O₄.0.1H₂O requires C, 62.14; H, 8.56; N, 11.44%

¹H-NMR (CD₃) δ: 10.37 (1H, br s), 8.66 (1H, br s), 3.25 (1H, m), 3.14 (3H, br s), 2.91 (3H, br s), 2.43–2.21 (5H, m), 1.66–1.50 (7H, m), 1.24–1.00 (8H, m), 0.79 (2H, m).

Example 32

2-{(1R)-4-Cyclohexyl-1-[2-(hydroxyamino)-2-oxoethyl]butyl}-5-methyl-1,3-oxazole-4-carboxamide

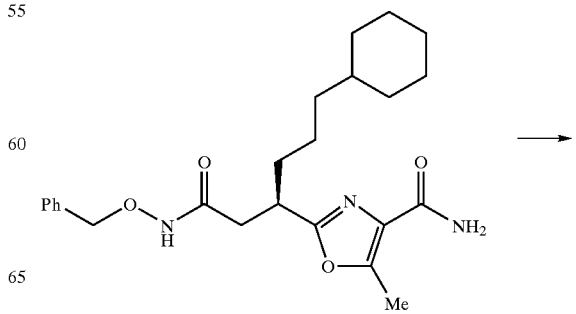

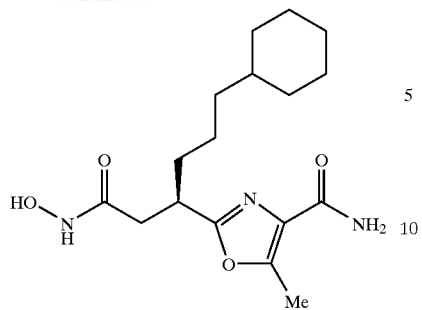

A solution of 2-((1R)-1-{2-[(benzyloxy)amino]-2-oxoethyl}-4-cyclohexylbutyl)-5-methyl-1,3-oxazole-4-carboxamide (Preparation 74) (133 mg, 0.31 mmol) in ethanol (6 ml) was treated with 5% palladium on barium sulphate (80 mg) and ammonium formate (196 mg, 3.10 mmol) and the mixture was heated at 45° C. for 2.5 hours. The solution was filtered through Arbocel® and the solvent removed from the filtrate under reduced pressure. The residue was azeotroped from dichloromethane (×3) then purified by column chromatography on silica gel eluting with dichloromethane:methanol:0.88 ammonia (98:2:0.2 to 90:10:1) to afford the title compound as a white solid (56 mg).

MS: 338 (MH$^+$), 360 (MNa$^+$)

Analysis: Found C, 61.77; H, 8.62; N, 11.22%; $C_{19}H_{31}N_3O_4 \cdot 0.1H_2O$ requires C, 62.14; H, 8.56; N, 11.44%

$^1$H-NMR (DMSO-d$_6$) δ: 7.12 (2H, br s), 3.52 (1H, m), 2.56–2.21 (2H, m), 1.67–1.49 (7H, m), 1.23–1.00 (8H, m), 0.79 (2H, m).

Other compounds prepared by the same general method, using appropriate starting materials (see Preparations section below), are listed in Table 1 below.

TABLE 1

| Example | R' | Elemental Analysis | LRMS | $^1$H, δ |
|---|---|---|---|---|
| 33 | NHCH$_2$Ph | Found C, 62.93; H, 7.37; N, 13.29%; C$_{22}$H$_{30}$N$_4$O$_4$·0.25H$_2$O requires C, 63.06, H, 7.34; N, 13.37% | 415(MH$^+$) 432(MNH$_4^+$) | (CD$_3$OD): 7.40–7.21(5H, m), 4.57(2H, s), 3.60 (1H, m), 2.72–2.53(2H, m), 1.86–1.59(7H, m), 1.40–1.10(8H, m), 0.86(2H, m) |
| 34 | piperidinyl | | 393(MH$^+$) 410(MNH$_4^+$) | (CD$_3$OD): 3.73(2H, m), 3.60(1H, m), 3.47 (2H, m), 2.73–2.50(2H, m), 1.91–1.53(13H, m), 1.43–1.05(8H, m), 0.86(2H, m). |
| 35 | isoindolinyl | | 428(M2H$^+$) | (CD$_3$OD): 7.42–7.27(4H, m), 5.20(2H, s), 4.98 (2H, s), 3.64(1H, m), 2.70(1H, dd, J=13, 8Hz), 2.50(1H, dd, J=13, 4Hz), 1.89–1.58(7H, m), 1.40–1.10(8H, m), 0.88(2H, m). |
| 36 | tetrahydroisoquinolinyl | Found C, 64.53; H, 7.43; N, 12.58%; C$_{24}$H$_{32}$N$_4$O$_4$·0.25H$_2$O requires C, 64.77, H, 7.36; N, 12.59% | 441(MH$^+$), 463(MNa$^+$) | (CD$_3$OD): (mixture of rotamers) 7.32–7.04(4H, m), 4.83(1.2H, s), 4.73(0.8H, s), 4.00(0.8H, m), 3.83(1.2H, m), 3.64(1H, m), 3.00(2H, m), 2.77–2.54(2H, m), 1.90–1.53(7H, m), 1.44–1.02(8H, m), 0.88(2H, m) |
| 37 | morpholinyl | | 395(MH$^+$), 412(MNH$_4^+$) | (CD$_3$OD): 3.75(4H, m), 3.71–3.53(5H, m), 2.62(2H, m), 1.87–1.58(7H, m), 1.40–1.06(8H, m), 0.86(2H, m) |
| 38 | N-methylpiperazinyl | | 408(MH$^+$) | (CD$_3$OD): 3.80(2H, m), 2.60(3H, m), 2.72–2.43(6H, m), 2.33(3H, s), 1.82–1.58(7H, m), 1.40–1.09(8H, m), 0.87(2H, m) |
| 39 | tetrahydronaphthyridinyl | | 442(MH$^+$) | (CD$_3$OD): (mixture of rotamers[1:2]) 8.39(1H, m), 7.73(0.67H, d, J=7Hz), 7.62(0.33H, d, J=7Hz), 7.32(1H, m), 4.94(1.34H, m), 4.85(0.66H, m), 4.12(0.66H, t, J=4Hz), 3.95(1.34H, t, J=4Hz), 3.63(1H, m), 3.10(2H, t, J=4Hz), 2.75–2.54(2H, m), 1.86–1.59(7H, m), 1.40–1.07(8H, m), 0.89(2H, m) |

TABLE 1-continued

| Example | R' | Elemental Analysis | LRMS | ¹H, δ |
|---|---|---|---|---|
| 40 | ![structure: N(Me)CH2Ph] | | 429(MH+) | (CD₃OD) (mixture of rotamers[1:1]) 7.40–7.23(5H, m), 4.80(1H, s), 4.64(1H, s), 3.62(1H, m), 3.03(1.5H, s), 2.99(1.5H, s), 2.72–2.51(2H, m), 1.86–1.55(7H, m), 1.38–1.03(8H, m), 0.84(2H, m). |

Example 41/Preparation 40

Methyl 2-[[(5-{(1R)-4-cyclohexyl-1-[2-(hydroxyamino)-2-oxoethyl]butyl}-1,2,4-oxadiazol-3-yl)carbonyl](methyl)amino]acetate

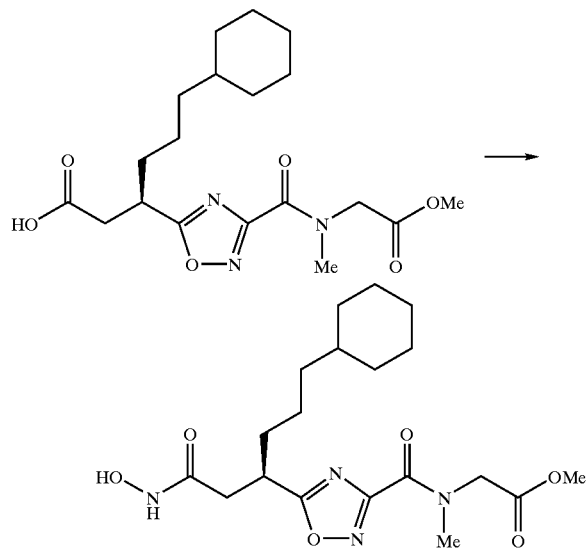

A solution of (3R)-6-cyclohexyl-3-(3-{[(2-methoxy-2-oxoethyl)(methyl)amino]carbonyl}-1,2,4-oxadiazol-5-yl)hexanoic acid (Preparation 39) (273 mg, 0.70 mmol) and N-methylmorpholine (85 μl, 0.77 mmol) in anhydrous dichloromethane (10 ml) was cooled to 0° C., treated with isobutyl chloroformate (100 μl, 0.77 mmol) and the resulting mixture was stirred under a nitrogen atmosphere for 30 minutes. O-(Trimethylsilyl)hydroxylamine (250 μl, 2.10 mmol) was then added and the mixture stirred under a nitrogen atmosphere for 1 hour, being allowed to warm to room temperature over this time. The mixture was then quenched with methanol (10 ml) and stirred for 10 minutes. The solvent was removed under reduced pressure and the residue partitioned between ethyl acetate and water. The layers were separated and the organic layer was sequentially washed with water and brine, dried over anhydrous sodium sulphate, filtered and the solvent removed under reduced pressure. The residue was purified by HPLC$^a$ to afford the title compound as a colourless oil (187 mg).

MS: 411 (MH⁺), 433 (MNa⁺)

¹H-NMR (CDCl₃) δ: (mixture of rotamers) 4.50–4.21 (2H, m), 3.84–3.60 (4H, m), 3.32 (1.8H, s), 3.21 (1.2H, s), 2.81–2.56 (2H, m), 1.90–1.50 (7H, m), 1.40–1.03 (8H, m), 0.82 (2H, m).

Example 42

(3R)-6-Cyclohexyl-3-(3-{[3-(dimethylamino)-1-azetidinyl]carbonyl}-1,2,4-oxadiazol-5-yl)-N-hydroxyhexanamide

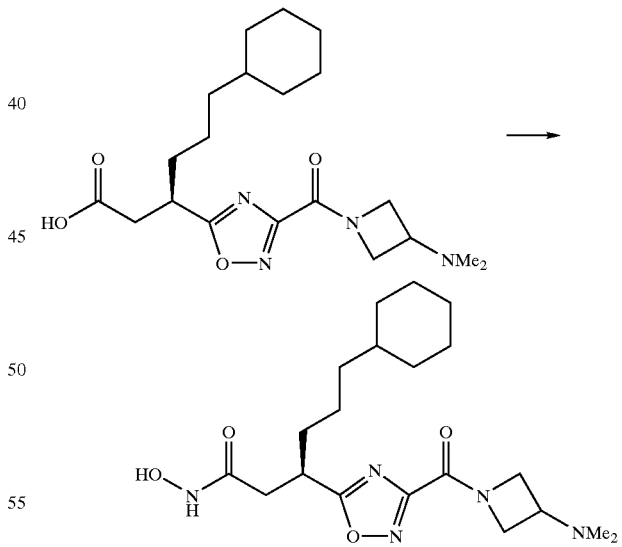

A solution of (3R)-6-cyclohexyl-3-(3-{[3-(dimethylamino)-1-azetidinyl]carbonyl}-1,2,4-oxadiazol-5-yl)hexanoic acid (Preparation 76) (200 mg, 0.51 mmol) and N-methylmorpholine (112 μl, 1.00 mmol) in anhydrous tetrahydrofuran (15 ml) was cooled to 0° C., treated with isobutyl chloroformate (79 μl, 0.69 mmol) and stirred under a nitrogen atmosphere for 2 hours. O-(Trimethylsilyl) hydroxylamine (85 μl, 0.61 mmol) was added and the mixture was stirred for 18 hours, being allowed to warm to room temperature over this time. The mixture was then treated with methanol and stirred at room temperature for 2 hours. The solvent was removed under reduced pressure. The residue was dissolved in ethyl acetate (100 ml) and washed with water (2×25 ml) and brine (25 ml), dried over anhydrous sodium sulphate, filtered and the solvent removed under reduced pressure to afford the title compound as a foam (180 mg).

MS: 408 (MH+)

$^1$H-NMR (CD$_3$OD) δ: 4.60 (1H, m), 4.38 (1H, m), 4.22 (1H, m), 3.99 (1H, m), 3.60 (1H, m), 3.24 (1H, m), 2.64 (1H, dd), 2.57 (1H, dd), 2.20 (6H, s), 1.58–1.80 (6H, m), 1.08–1.36 (7H, m), 0.85 (2H, m).

Example 43 tert-Butyl 3-{[(5-{(1R)-4-cyclohexyl-1-[2-(hydroxyamino)-2-oxoethyl]butyl}-1,2,4-oxadiazol-3-yl)carbonyl]amino}-1-azetidinecarboxylate

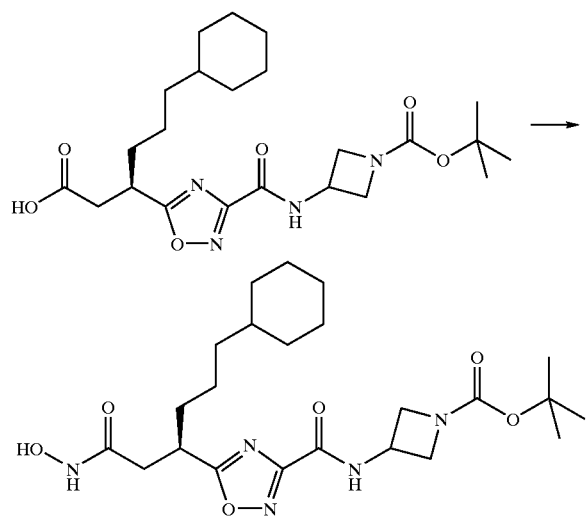

A solution of (3R)-3-[3-({[1-(tert-butoxycarbonyl)-3-azetidinyl]amino}carbonyl)-1,2,4-oxadiazol-5-yl]-6-cyclohexylhexanoic acid (Preparation 79) (350 mg, 0.75 mmol) and N-methylmorpholine (163 μl, 1.48 mmol) in anhydrous tetrahydrofuran (15 ml) was cooled to 0° C., treated with isobutyl chloroformate (116 μl, 0.89 mmol) and stirred under a nitrogen atmosphere for 2 hours. O-(Trimethylsilyl)hydroxylamine (272 μl, 2.22 mmol) was added and the mixture was stirred for 18 hours, being allowed to warm to room temperature over this time. The mixture was then treated with methanol and stirred at room temperature for 2 hours. The solvent was removed under reduced pressure. The residue was dissolved in ethyl acetate (100 ml) and washed with water (2×25 ml) and brine (25 ml), dried over anhydrous sodium sulphate, filtered and the solvent removed under reduced pressure. The solid was purified by column chromatography on silica gel eluting with a gradient system of 98.75:1.25:0.13 (dichloromethane:methanol:ammonia) gradually changing to 90:10:1 (dichloromethane:methanol:ammonia) to afford the title compound as a glass.

MS: 497 (MNH$_4^+$)

$^1$H-NMR (CD$_3$OD) δ: 4.23 (2H, t), 3.98 (2H, t), 3.59 (1H, m), 2.64 (1H, dd), 2.57 (1H, dd), 1.58–1.83 (7H, m), 1.41 (9H, s), 1.08–1.37 (8H, m), 0.84 (2H, m).

Example 44

N-(3-Azetidinyl)-5-{(1R)-4-cyclohexyl-1-[2-(hydroxyamino)-2-oxoethyl]butyl}-1,2,4-oxadiazole-3-carboxamide

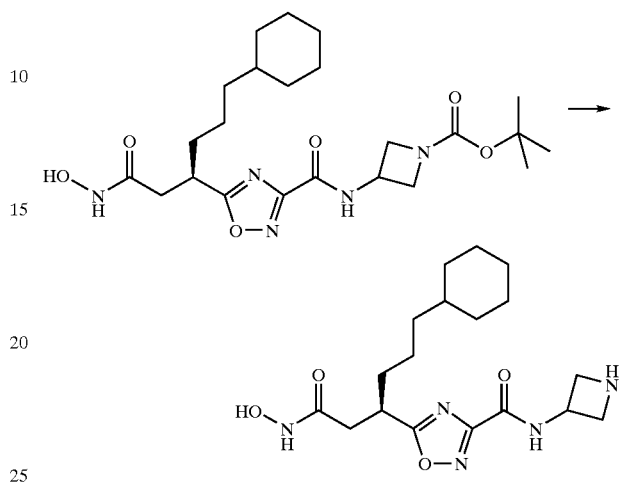

A solution of tert-butyl 3-{[(5-{(1R)-4-cyclohexyl-1-[2-(hydroxyamino)-2-oxoethyl]butyl}-1,2,4-oxadiazol-3-yl)carbonyl]amino}-1-azetidinecarboxylate (Example 43) (160 mg, 0.33 mmol) in dichloromethane (10 ml) was cooled to 0° C. and treated with trifluoroacetic acid (7 ml) and the resulting mixture was stirred at 0° C. under a nitrogen atmosphere for 45 minutes. The solvent was removed under reduced pressure and the residue azeotroped from dichloromethane (×2). The residue was triturated with diethylether, filtered and dried to afford the title compound as a white solid (123 mg).

MS: 380 (MH+)

$^1$H-NMR (CD$_3$OD) δ: 4.83 (1H, m), 4.30 (4H, d), 3.58 (1H, m), 2.50–2.70 (2H), 1.77 (2H, m), 1.62 (5H, m), 1.08–1.39 (8H, m), 0.83 (2H, m).

Example 45

Di(tert-butyl) 1-[(5-{(1R)-4-cyclohexyl-1-[2-(hydroxyamino)-2-oxoethyl]butyl}-1,2,4-oxadiazol-3-yl)carbonyl]-3-azetidinylimidodicarbonate

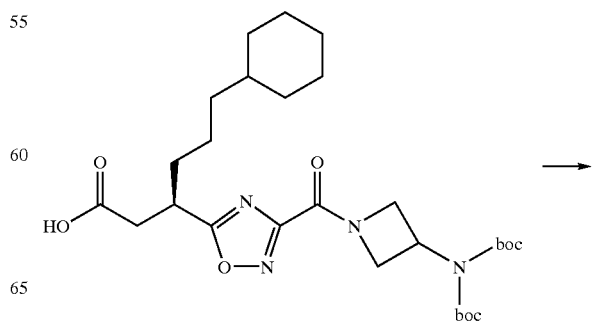

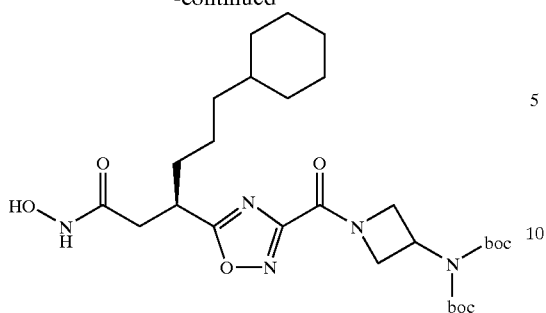

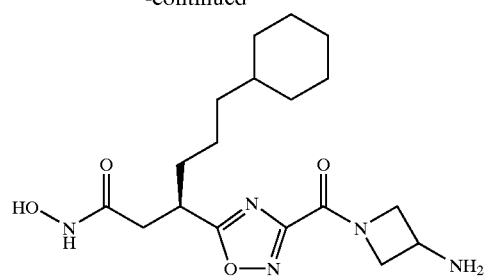

A solution of (3R)-3-[3-({3-[bis(tert-butoxycarbonyl)amino]-1-azetidinyl}carbonyl)-1,2,4-oxadiazol-5-yl]-6-cyclohexylhexanoic acid (Preparation 80) (430 mg, 0.76 mmol) and N-methylmorpholine (167 µl, 1.52 mmol) in anhydrous tetrahydrofuran (20 ml) was cooled to 0° C., treated with isobutyl chloroformate (120 µl, 0.93 mmol) and stirred under a nitrogen atmosphere for 2 hours. O-(Trimethylsilyl)hydroxylamine (280 µl, 2.29 mmol) was added and the mixture was stirred for 18 hours, being allowed to warm to room temperature over this time. The mixture was then treated with methanol and stirred at room temperature for 2 hours. The solvent was removed under reduced pressure. The residue was dissolved in ethyl acetate (100 ml) and washed with water (2×25 ml) and brine (25 ml), dried over anhydrous sodium sulphate, filtered and the solvent removed under reduced pressure. The solid was purified by column chromatography on silica gel eluting with a gradient system of 98.75:1.25:0.13 (dichloromethane:methanol:ammonia) gradually changing to 90:10:1 (dichloromethane:methanol:ammonia) to afford the title compound as a sticky foam.

MS: 578 (M−H⁻)

¹H-NMR (CD₃OD) δ: 4.88 (1H, m), 4.62 (1H,m), 4.40 (1H, t), 4.24 (1H,m), 3.60 (1H, m), 2.65 (1H, dd), 2.56 (1H, dd), 1.58–1.80 (6H, m), 1.50 (18H, s), 1.08–1.35 (9H, m), 0.83 (2H, m).

Example 46

(3R)-3-{3-[(3-Amino-1-azetidinyl)carbonyl]-1,2,4-oxadiazol-5-yl}-6-cyclohexyl-N-hydroxyhexanamide

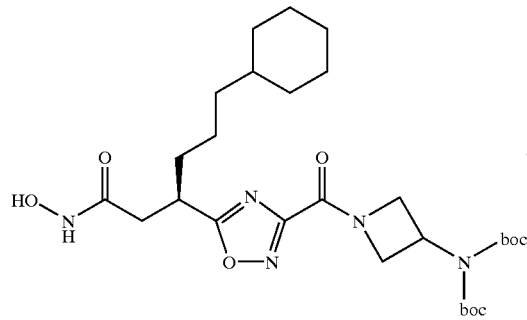

A solution of di(tert-butyl) 1-[(5-{(1R)-4-cyclohexyl-1-[2-(hydroxyamino)-2-oxoethyl]butyl}-1,2,4-oxadiazol-3-yl)carbonyl]-3-azetidinylimidodicarbonate (Example 45) (250 mg, 0.43 mmol) in dichloromethane (10 ml) was cooled to 0° C. and treated with trifluoroacetic acid (7 ml) and the resulting mixture was stirred at 0° C. under a nitrogen atmosphere for 45 minutes. The solvent was removed under reduced pressure and the residue azeotroped from dichloromethane (×2). The residue was triturated with diethylether, filtered and dried to afford the title compound as a white solid.

MS: 380 (MH⁺)

¹H-NMR (CD₃OD) δ: 4.90 (1H, m), 4.53 (2H, m), 4.19 (2H, m), 3.58 (1H, m), 2.58–2.65 (2H, m), 1.76 (2H, m), 1.66 (5H, m), 1.06–1.38 (8H, m), 0.84 (2H,m).

Example 47

5-{(1R)-4-Cyclohexyl-1-[2-(hydroxyamino)-2-oxoethyl]butyl}-N-[2-(dimethylamino)ethyl]-N-methyl-1,2,4-oxadiazole-3-carboxamide

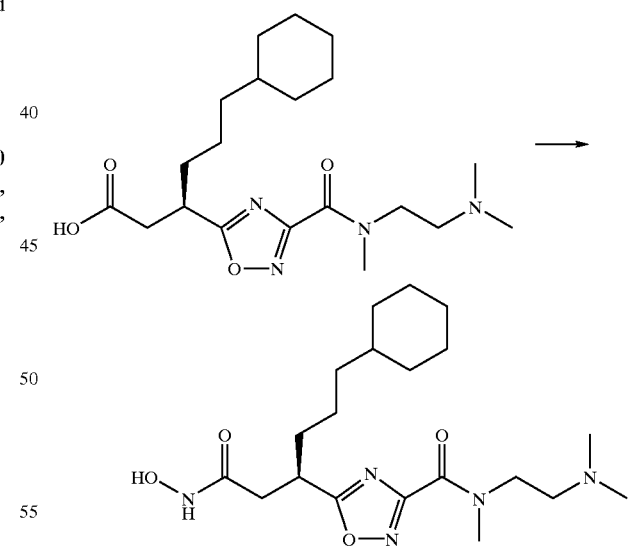

A solution (3R)-6-cyclohexyl-3-(3-{[[2-(dimethylamino)ethyl](methyl)amino]carbonyl}-1,2,4-oxadiazol-5-yl)hexanoic acid (Preparation 82) (450 mg, 0.72 mmol) and N-methylmorpholine (284 µl, 2.53 mmol) in dichloromethane (10 ml) was cooled to 0° C., treated with isobutyl chloroformate (112 µl, 0.87 mmol) and stirred under an argon atmosphere for 1 hour. O-(Trimethylsilyl)hydroxylamine (355 µl, 2.90 mmol) was added and the mixture was stirred for 3.5 hours, being allowed to warm to room temperature over this time. The mixture was then treated with methanol (2.5 ml) and stirred at room temperature for 20 minutes. The solvent was removed under reduced pressure. The residue was dissolved in ethyl acetate (100 ml) and washed with water (20 ml), dried over anhydrous magnesium sulphate, filtered and the solvent removed under reduced pressure. The solid was purified by column chromatography on silica gel eluting with a gradient system of 97:3:0.3 (dichloromethane:methanol:ammonia) gradually changing to 90:10:1 (dichloromethane:methanol:ammonia) to afford the title compound as a gum (123 mg).

MS: 410 (MH$^+$)

Analysis: Found, C, 57.02; H, 8.50; N, 16.43%; $C_{20}H_{35}N_5O_4.0.25H_2O.0.1CH_2Cl_2$ requires C, 58.35; H, 8.72; N, 16.14%

$^1$H-NMR (CDCl$_3$) δ: 3.36–3.76 (3H, br d), 3.11 (3H, s), 2.45–2.74 (3H, m), 2.30 (1H, s), 2.25–2.35 (7H, m), 1.60–1.85 (7H, m), 1.05–1.40 (8H, m), 0.83 (2H, m).

Example 48

5-{(1R)-4-Cyclohexyl-1-[2-(hydroxyamino)-2-oxoethyl]butyl}-N-[3-(dimethylamino)propyl]-N-methyl-1,2,4-oxadiazole-3-carboxamide

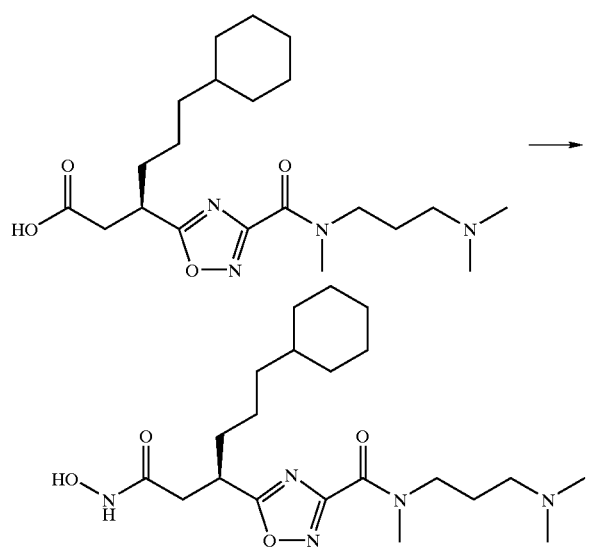

A solution (3R)-6-cyclohexyl-3-(3-{[[3-(dimethylamino)propyl](methyl)amino]carbonyl}-1,2,4-oxadiazol-5-yl)hexanoic acid (Preparation 84) (566 mg, 0.88 mmol) and N-methylmorpholine (390 µl, 3.52 mmol) in dichloromethane (10 ml) was cooled to 0° C., treated with isobutyl chloroformate (340 µl, 2.64 mmol) and stirred under an argon atmosphere for 1 hour. O-(Trimethylsilyl)hydroxylamine (540 µl, 4.40 mmol) was added and the mixture was stirred for 4.5 hours, being allowed to warm to room temperature over this time. The mixture was then treated with methanol (2.5 ml) and stirred at room temperature for 20 minutes. The solvent was removed under reduced pressure. The residue was dissolved in ethyl acetate (100 ml) and washed with water (20 ml), dried over anhydrous magnesium sulphate, filtered and the solvent removed under reduced pressure. The solid was purified by column chromatography on silica gel eluting with a gradient system of 97:3:0.3 (dichloromethane:methanol:ammonia) gradually changing to 90:10:1 (dichloromethane:methanol:ammonia) to afford the title compound (150 mg).

MS: 424 (MH$^+$)

Analysis: Found, C, 58.30; H, 8.64; N, 15.33%; $C_{21}H_{37}N_5O_4.0.2 H_2O.0.08 CH_2Cl_2$ requires C, 57.14; H, 8.50; N, 16.57%

$^1$H-NMR (CDCl$_3$) δ: 3.68 (2H, m), 3.30 (2H, m), 3.18 (3H, s), 2.28–2.40 (3H, m), 2.23 (6H, s), 1.58–1.88 (9H, m), 1.08–1.40 (8H, m), 0.88 (2H, m).

Example 49

Ethyl [(5-{(1R)-4-cyclohexyl-1-[2-(hydroxyamino)-2-oxoethyl]butyl}-1,2,4-oxadiazol-3-yl)methoxy]acetate

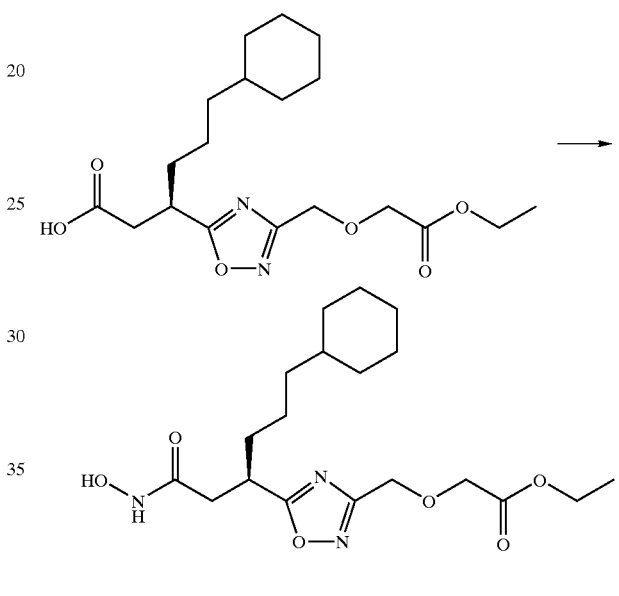

A solution of (3R)-6-cyclohexyl-3-{3-[(2-ethoxy-2-oxoethoxy)methyl]-1,2,4-oxadiazol-5-yl}hexanoic acid (Preparation 87) (330 mg, 0.86 mmol) and N-methylmorpholine (160 µl, 1.46 mmol) in anhydrous tetrahydrofuran (14 ml) was cooled to 0° C., treated with isobutyl chloroformate (120 µl, 0.93 mmol) and stirred under a nitrogen atmosphere for 2.5 hours. O-(Trimethylsilyl)hydroxylamine (350 µl, 2.86 mmol) was added and the mixture was stirred for 18 hours, being allowed to warm to room temperature over this time. The mixture was then treated with methanol and stirred at room temperature for 1 hour. The solvent was removed under reduced pressure. The residue was dissolved in ethyl acetate and washed with water and brine, dried over anhydrous sodium sulphate, filtered and the solvent removed under reduced pressure. The oil was purified by column chromatography on silica gel eluting with a gradient system of 98:2 (dichloromethane:methanol) gradually changing to 90:10 (dichloromethane:methanol) to afford the title compound as a colourless oil (272 mg).

MS: 420 (MNa$^+$)

$^1$H-NMR (CD$_3$OD) δ: 4.70 (2H, s), 4.20 (4H, m), 3.54 (1H, m), 2.61 (1H, dd), 2.50 (1H, dd), 1.60–1.80 (7H, m), 1.10–1.30 (11H, m), 0.82 (2H, m).

Example 50

[(5-{(1R)-4-Cyclohexyl-1-[2-(hydroxyamino)-2-oxoethyl]butyl}-1,2,4-oxadiazol-3-yl)methoxy]acetic Acid

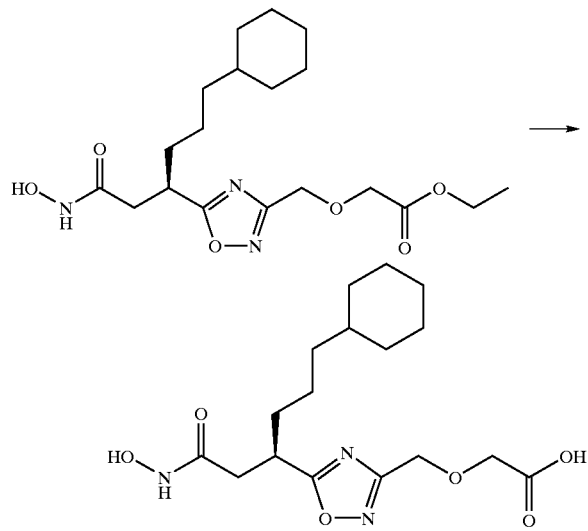

A solution of ethyl [(5-{(1R)-4-cyclohexyl-1-[2-(hydroxyamino)-2-oxoethyl]butyl}-1,2,4-oxadiazol-3-yl)methoxy]acetate (Example 49) (158 mg, 0.40 mmol) in 1,4-dioxan (4 ml) and water (2 ml) was treated with lithium hydroxide monohydrate (2 mg, 0.48 mmol) and stirred at room temperature for 2 hours. The reaction mixture was diluted with water and washed with diethylether (×2). The aqueous layer was acidified to pH 1 with hydrochloric acid (2M) and washed with ethyl acetate (×3). The combined organic layers were washed with brine, dried over anhydrous sodium sulphate, filtered and the solvent was removed under reduced pressure to afford the title compound as a colourless oil (141 mg).

MS: 370 (MH$^+$)

$^1$H-NMR (CD$_3$OD) δ: 4.70 (2H, s), 4.20 (2H, s), 3.55 (1H, m), 2.60 (1H, dd), 2.50 (1H, dd), 1.60–1.80 (7H, m), 1.10–1.30 (8H, m), 0.84 (2H, m).

Example 51

Ethyl 2-[(5-{(1R)-4-cyclohexyl-1-[2-(hydroxyamino)-2-oxoethyl]butyl}-1,2,4-oxadiazol-3-yl)methoxy]propanoate

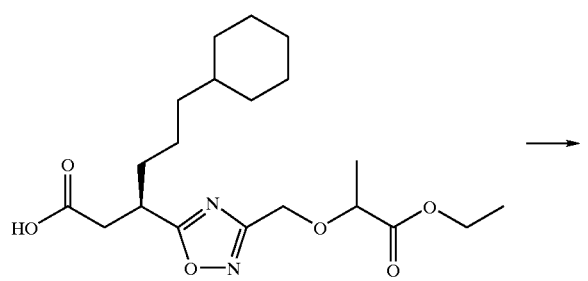

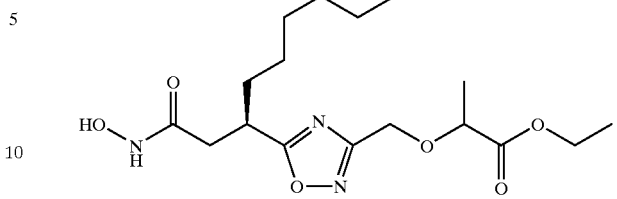

A solution of (3R)-6-cyclohexyl-3-{3-[(2-ethoxy-1-methyl-2-oxoethoxy)methyl]-1,2,4-oxadiazol-5-yl}hexanoic acid (Preparation 89) (370 mg, 0.93 mmol) and N-methylmorpholine (170 μl, 1.54 mmol) in anhydrous tetrahydrofuran (15 ml) was cooled to 0° C., treated with isobutyl chloroformate (130 μl, 1.00 mmol) and stirred under a nitrogen atmosphere for 2.5 hours. O-(Trimethylsilyl)hydroxylamine (380 μl, 3.10 mmol) was added and the mixture was stirred for 18 hours, being allowed to warm to room temperature over this time. The mixture was then treated with methanol (4 ml) and stirred at room temperature for 1 hour. The solvent was removed under reduced pressure. The residue was dissolved in ethyl acetate and washed with water and brine, dried over anhydrous sodium sulphate, filtered and the solvent removed under reduced pressure. The oil was purified by column chromatography on silica gel eluting with a gradient system of 100:0 (dichloromethane:methanol) gradually changing to 90:10 (dichloromethane:methanol) to afford the title compound as a colourless oil (330 mg).

MS: 434 (MNa$^+$)

Analysis: Found, C, 57.55; H, 8.14; N, 9.81%; C$_{20}$H$_{33}$N$_3$O$_6$.0.1 H$_2$O.0.05 DCM requires C, 57.68; H, 8.04; N, 10.06%

$^1$H-NMR (CD$_3$OD) δ: 4.75 (1H, d), 4.59 (1H, d), 4.20 (3H, m), 3.55 (1H, m), 6.61 (1H, dd), (2.50 (1H, dd), 1.69–1.80 (7H, m), 1.38 (3H, d), 1.10–1.30 (11H, m), 0.82 (2H, m).

Example 52

2-[(5-{(1R)-4-Cyclohexyl-1-[2-(hydroxyamino)-2-oxoethyl]butyl}-1,2,4-oxadiazol-3-yl)methoxy]propanoic Acid

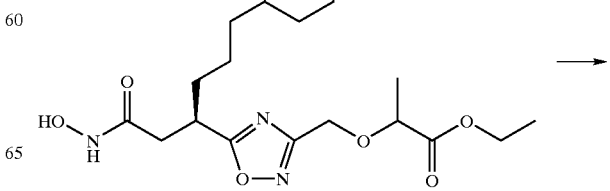

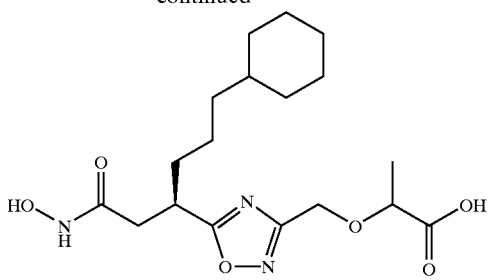

A solution of ethyl 2-[(5-{(1R)-4-cyclohexyl-1-[2-(hydroxyamino)-2-oxoethyl]butyl}-1,2,4-oxadiazol-3-yl)methoxy]propanoate (Example 51) (184 mg, 0.45 mmol) in 1,4-dioxan (4 ml) and water (2 ml) was cooled to 0° C. and treated with lithium hydroxide monohydrate (2 mg, 0.48 mmol) and stirred at 0° C. for 2 hours. The solvent was partially removed under reduced pressure and diluted with water and washed with diethylether (×2). The aqueous layer was acidified to pH 1 with hydrochloric acid (2M) and washed with ethyl acetate (×2). The combined organic layers were washed with brine, dries over anhydrous sodium sulphate, filtered and the solvent was removed under reduced pressure to afford the title compound as a colourless oil (160 mg).

MS: 384 (MH$^+$)

$^1$H-NMR (CD$_3$OD) δ: 4.77 (1H, d), 4.59 (1H, d), 4.17 (3H, q), 3.45 (1H, m), 2.61 (1H, dd), 2.50 (1H, dd), 1.60–1.80 (7H, m), 1.39 (3H, d), 1.07–1.30 (8H, m), 0.83 (2H, m).

Example 53

(3R)-3-{3-[(2-Amino-2-oxoethoxy)methyl]-1,2,4-oxadiazol-5-yl}-6-cyclohexyl-N-hydroxyhexanamide

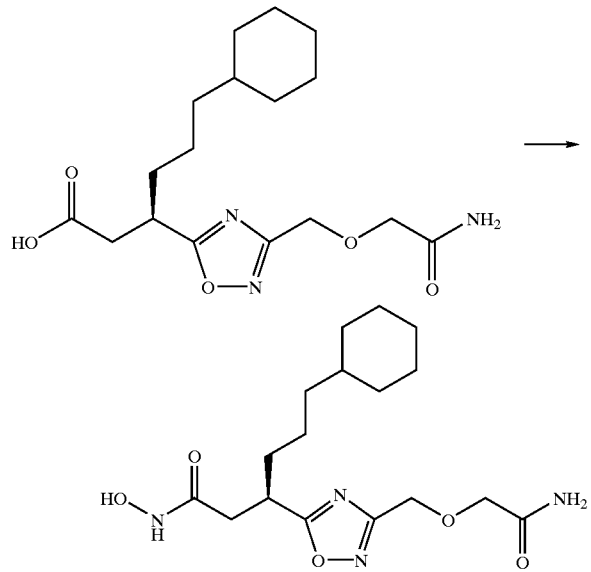

A solution of (3R)-3-{3-[(2-amino-2-oxoethoxy)methyl]-1,2,4-oxadiazol-5-yl}-6-cyclohexylhexanoic acid (Preparation 91) (178 mg, 0.50 mmol) and N-methylmorpholine (100 μl, 0.91 mmol) in anhydrous tetrahydrofuran (8 ml) was cooled to 0° C., treated with isobutyl chloroformate (70 μl, 0.54 mmol) and stirred under a nitrogen atmosphere for 2.5 hours. O-(Trimethylsilyl)hydroxylamine (200 μl, 1.63 mmol) was added and the mixture was stirred for 18 hours, being allowed to warm to room temperature over this time. The mixture was then treated with methanol and stirred at room temperature for 1 hour. The solvent was removed under reduced pressure. The residue was dissolved in ethyl acetate and washed with water and brine, dried over anhydrous sodium sulphate, filtered and the solvent removed under reduced pressure. The oil was purified by column chromatography on silica gel eluting with a gradient system of 98:2 (dichloromethane:methanol) gradually changing to 90:10 (dichloromethane:methanol) and then neat methanol to afford the title compound as a colourless oil (60 mg).

MS: 391 (MH$^+$)

Analysis: Found, C, 53.67; H, 7.55; N, 14.19%; C$_{17}$H$_{28}$N$_4$O$_5$.0.2 CH$_2$Cl$_2$ requires C, 53.60; H, 7.43; N, 14.54%

$^1$H-NMR (CD$_3$OD) δ: 4.70 (2H, s), 4.08 (2H, s), 3.55 (1H, m), 2.45–2.70 (2H, m), 1.60–1.80 (7H, m), 1.10–1.30 (8H, m), 0.82 (2H, m).

Example 54

Ethyl 3-(5-{(1R)-4-cyclohexyl-1-[2-(hydroxyamino)-2-oxoethyl]butyl}-1,2,4-oxadiazol-3-yl)propanoate

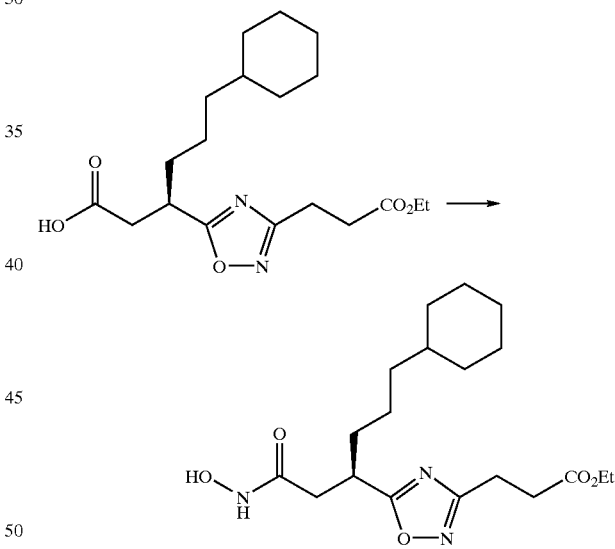

A solution of 3R)-6-cyclohexyl-3-[3-(3-ethoxy-3-oxopropyl)-1,2,4-oxadiazol-5-yl]hexanoic acid (Preparation 94) (110 mg, 0.30 mmol) and N-methylmorpholine (60 μl, 0.54 mmol) in anhydrous tetrahydrofuran (6 ml) was cooled to 0° C., treated with isobutyl chloroformate (42 μl, 0.32 mmol) and stirred under a nitrogen atmosphere for 2.5 hours. O-(Trimethylsilyl)hydroxylamine (120 μl, 1.00 mmol) was added and the mixture was stirred for 18 hours, being allowed to warm to room temperature over this time. The mixture was then treated with methanol and stirred at room temperature for 3 hours. The solvent was removed under reduced pressure. The residue was dissolved in ethyl acetate and washed with water and brine, dried over anhydrous sodium sulphate, filtered and the solvent removed under reduced pressure. The oil was purified by column chromatography on silica gel eluting with a gradient system of 100:0 (dichloromethane:methanol) gradually changing to 90:10 (dichloromethane:methanol) to afford the title compound as a yellow oil (94 mg).

MS: 404 (MNa+)

¹H-NMR (CDCl₃) δ: 4.15 (2H, q), 3.52 (1H, m), 3.03 (2H, t), 2.78 (4H, m), 2.58 (1H, dd), 1.60–1.80 (7H, m), 1.10–1.35 (11H, m), 0.82 (2H, m).

Example 55

3-(5-{(1R)-4-Cyclohexyl-1-[2-(hydroxyamino)-2-oxoethyl]butyl}-1,2,4-oxadiazol-3-yl)propanoic Acid

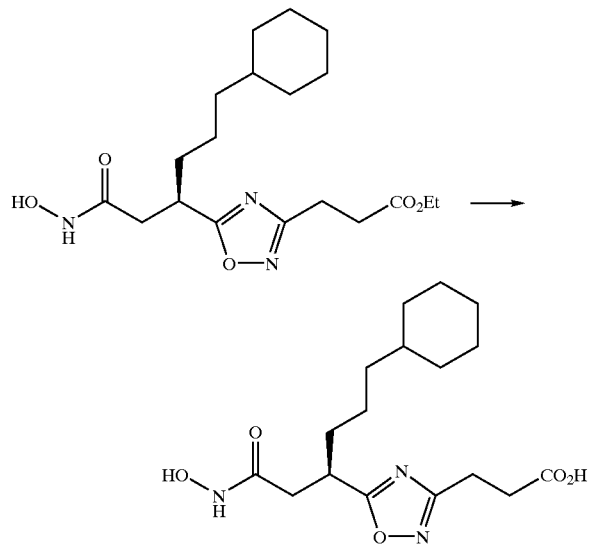

A solution of ethyl 3-(5-{(1R)-4-cyclohexyl-1-[2-(hydroxyamino)-2-oxoethyl]butyl}-1,2,4-oxadiazol-3-yl)propanoate (Example 54) (58 mg, 0.1 5 mmol) in 1,4-dioxan (2 ml) and water (1 ml) was treated with lithium hydroxide monohydrate (13 mg, 0.31 mmol) and stirred at room temperature for 2 hours. The reaction mixture was diluted with water and washed with diethylether (×2). The aqueous layer was acidified with hydrochloric acid (2M) (2 ml) and washed with ethyl acetate (×2). The combined organic layers were washed with brine, dried over anhydrous sodium sulphate, filtered and the solvent was removed under reduced pressure. The oil was purified by column chromatography on silica gel eluting with a gradient system of 100:0:0 (dichloromethane:methanol:acetic acid) gradually changing to 90:10:1 (dichloromethane:methanol:acetic acid) to afford the title compound as an orange gum (36 mg).

MS: 376 (MNa+)

Analysis: Found, C, 55.98; H, 7.61; N, 11.12%; C₁₇H₂₇N₃O₅.0.2 CH₂Cl₂ require C, 55.77: H, 7.46; N, 11.34%

¹H-NMR (CD₃OD) δ: 3.50 (1H, m), 2.98 (2H, t), 2.76 (2H, t), 2.59 (1H, dd), 2.48 (1H, dd), 1.60–1.80 (7H, m), 1.07–1.35 (8H, m), 0.81 (2H, m).

Example 56

(3R)-6-Cyclohexyl-N-hydroxy-3-{3-[(propylsulfonyl)methyl]-1,2,4-oxadiazol-5-yl}hexanamide

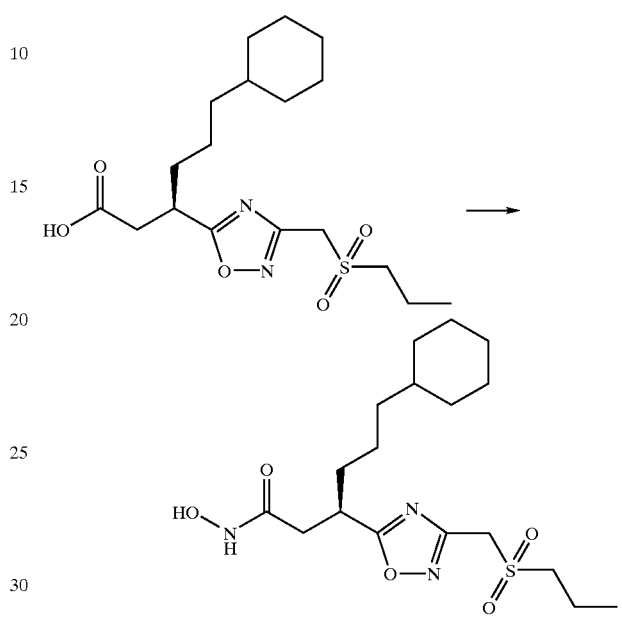

A solution of (3R)-6-cyclohexyl-3-{3-[(propylsulfonyl)methyl]-1,2,4-oxadiazol-5-yl}hexanoic acid (Preparation 97) (298 mg, 0.77 mmol) and 2,6-lutidine (135 μl, 1.16 mmol) in dichloromethane (10 ml) was cooled to 0° C., treated with isobutyl chloroformate (100 μl, 0.77 mmol) and stirred under a nitrogen atmosphere for 1 hour. O-(Trimethylsilyl)hydroxylamine (310 μl, 2.31 mmol) was added and the mixture was stirred for 4 hours, being allowed to warm to room temperature over this time. The mixture was then treated with methanol (5 ml) and stirred at room temperature for 1 hour. The solvent was removed under reduced pressure. The residue was dissolved in ethyl acetate and washed with hydrochloric acid (1 M) and brine, dried over anhydrous magnesium sulphate, filtered and the solvent removed under reduced pressure. The oil was purified by column chromatography on silica gel eluting with a gradient system of 100:0 (dichloromethane:methanol) gradually changing to 95:5 (dichloromethane:methanol) to afford the title compound as a white solid (140 mg).

MS: 424 (MNa+)

Analysis: Found, C, 53.65; H, 7.80; N, 10.26%; C₁₈H₃₁N₃O₅S requires C, 53.84; H, 7.78; N, 10.47%

¹H-NMR (DMSO) δ: 10.39 (1H, br s), 8.65 (1H, br s), 4.70 (2H, s), 3.45 (1H, m), 3.20 (2h, obs), 2.50 (2H, obs), 1.76 (1H, m), 1.50–1.70 (7H, m), 1.08–1.25 (8H, m), 0.98 (3H, t), 0.80 (2H, m).

Example 57

2-{(1R)-4-Cyclohexyl-1-[2-(hydroxyamino)-2-oxoethyl]butyl}-N-[2-(dimethylamino)ethyl]-5-methyl-1,3-oxazole-4-carboxamide

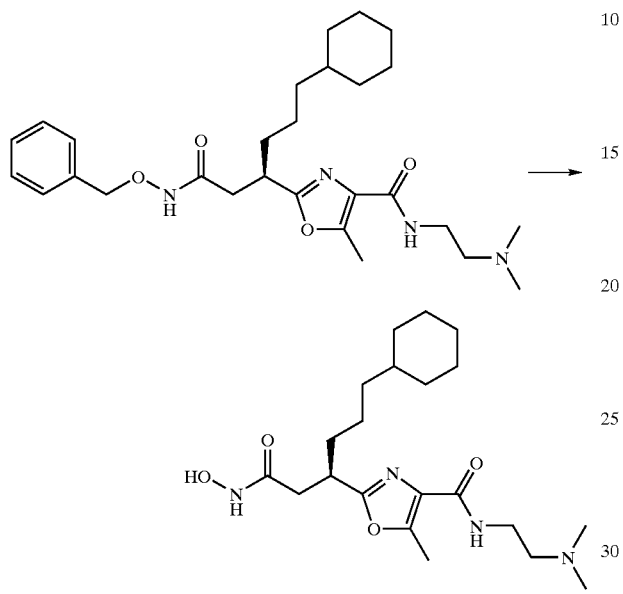

A solution 2-((1R)-1-{2-[(benzyloxy)amino]-2-oxoethyl}-4-cyclohexylbutyl)-N-[2-(dimethylamino)ethyl]-5-methyl-1,3-oxazole-4-carboxamide (Preparation 98) (193 mg, 0.39 mmol) in ethanol (10 ml) was treated with ammonium formate (244 mg, 3.90 mmol) and 5% palladium on barium sulphate (100 mg) and heated at 43° C., under a nitrogen atmosphere for 2 hours. The reaction mixture was filtered and the solvent removed under reduced pressure. The residue was purified by column chromatography on silica gel eluting with a gradient system of 98:2:0.2 (dichloromethane:methanol:ammonia) gradually changing to 90:10:1 (dichloromethane:methanol:ammonia) to afford the title compound as a white solid (80 mg).

MS: 409 (MH$^+$)

Analysis: Found, C, 60.93; H, 9.06; N, 13.54%; $C_{21}H_{36}N_4O_4 \cdot 0.2 H_2O$ requires C, 61.20; H, 8.90; N, 13.59%

$^1$H-NMR (d$_6$-DMSO) δ: 8.61 (1H, br s), 7.59 (1H, br s), 3.28 (2H, q), 3.18 (1H, obs), 2.45 (2H, obs), 2.35 (2H, t), 2.17 (6H, s), 1.50–1.65 (7H, m), 1.10–1.20 (7H, m), 0.80 (2H, m).

Example 58

{[(2-{(1R)-4-Cyclohexyl-1-[2-(hydroxyamino)-2-oxoethyl]butyl}-5-methyl-1,3-oxazol-4-yl)carbonyl]amino}acetic Acid

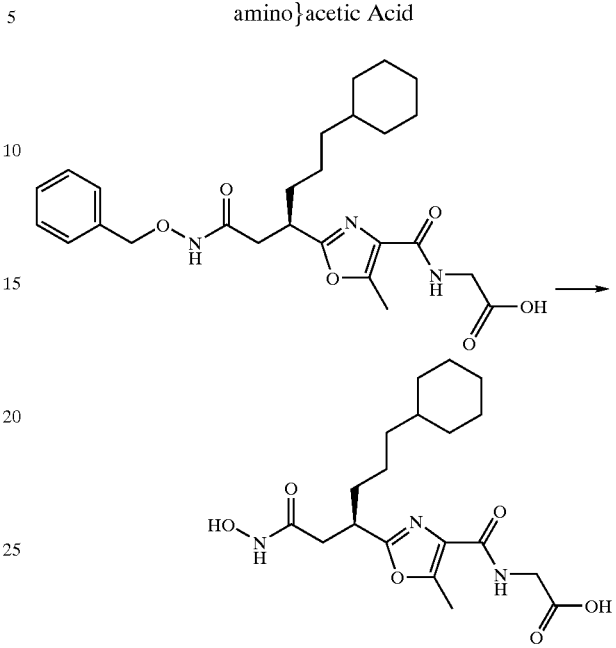

A solution ({[2-((1R)-1-{2-[(benzyloxy)amino]-2-oxoethyl}-4-cyclohexylbutyl)-5-methyl-1,3-oxazol-4-yl]carbonyl}amino)acetic acid (Preparation 100) (60 mg, 0.12 mmol) in ethanol (3 ml) was treated with ammonium formate (78 mg, 1.23 mmol) and palladium hydroxide (20 mg) and heated at 43° C., under a nitrogen atmosphere for 4 hours. The reaction mixture was filtered and the solvent removed under reduced pressure. The residue was purified by column chromatography on silica gel eluting with a gradient system of 99:1:0.1 (dichloromethane:methanol:acetic acid) gradually changing to 90:10:1 (dichloromethane:methanol:acetic acid) to afford the title compound as a white solid (17 mg).

MS: 394 (M–H)$^-$ $^1$H-NMR (CDCl$_3$) δ: 7.68 (1H, br s), 4.95–4.10 (2H, m), 3.34 (1H, m), 2.40–2.60 (5H, m), 1.50–1.80 (7H, m), 1.05–1.35 (8H, m), 0.81 (2H, m).

Example 59

(3R)-6-Cyclohexyl-N-hydroxy-3-[3-(1H-imidazol-2-ylmethyl)-1,2,4-oxadiazol-5-yl]hexanamide

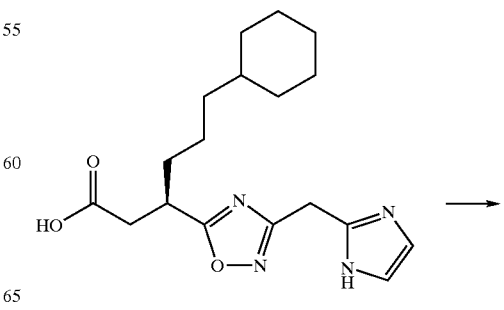

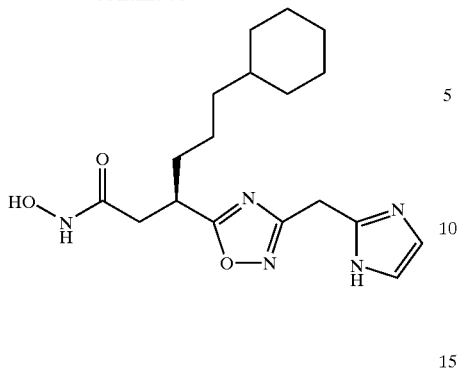

A solution of (3R)-6-cyclohexyl-3-[3-(1H-imidazol-2-ylmethyl)-1,2,4-oxadiazol-5-yl]hexanoic acid (Preparation 103) (200 mg, 0.43 mmol) in anhydrous tetrahydrofuran (5 ml) was treated with 1,1'-carbonyldiimidazole (77 mg, 0.48 mmol) and stirred under a nitrogen atmosphere for 30 minutes. O-(Trimethylsilyl)hydroxylamine (160 µl, 1.30 mmol) was added and the mixture was stirred for 18 hours. The mixture was then treated with methanol (4 ml) and stirred at room temperature for 1 hour. The solvent was removed under reduced pressure. The residue was purified by column chromatography on silica gel eluting with 90:10:1 (dichloromethane:methanol:ammonia) to afford a colourless oil which began to crystallise once a little methanol and dichloromethane were added. The solid was triturated with dichloromethane and dried under reduced pressure to afford the title compound as a solid (49 mg).

MS: 362 (MH$^+$)

Analysis: Found, C, 59.24; H, 7.42; N, 19.13%; $C_{18}H_{27}N_5O_3 \cdot 0.2H_2O$ requires C, 59.22; H, 7.57; N, 19.18%

$^1$H-NMR (d$_6$-DMSO) δ: 10.38 (1H, s), 8.65 (1H, s), 7.70 (1H, s), 7.17 (1H, s), 6.88 (1H, s), 5.39 (2H, s), 3.42 (1H, m), 2.45 (2H, m), 1.5–1.70 (7H, m), 1.00–1.15 (8H, m), 0.78 (2H, m).

Example 60

(3R)-6-cyclohexyl-N-hydroxy-3-[3-(4-pyridinylmethyl)-1,2,4-oxadiazol-5-yl]hexanamide

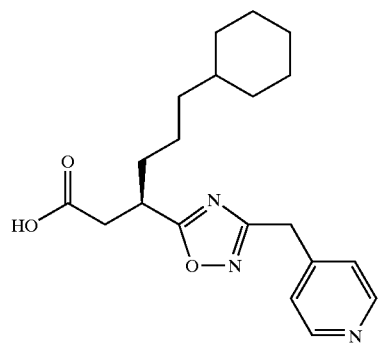

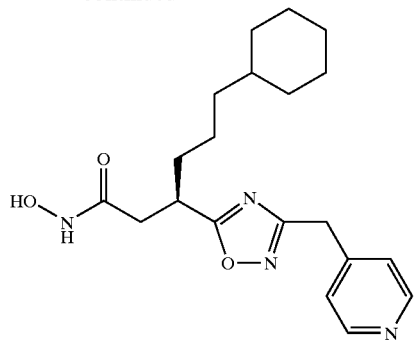

A solution of (3R)-6-cyclohexyl-3-[3-(4-pyridinylmethyl)-1,2,4-oxadiazol-5-yl]hexanoic acid (Preparation 106) (380 mg, 0.96 mmol) in dichloromethane (10 ml) was treated with 1,1'-carbonyldiimidazole (156 mg, 0.96 mmol) and stirred under a nitrogen atmosphere for 1 hour. O-(Trimethylsilyl)hydroxylamine (388 µl, 2.89 mmol) was added and the mixture was stirred for 3.5 hours. The mixture was then treated with methanol (5 ml) and stirred at room temperature for 2 hours. The solvent was removed under reduced pressure. The residue was dissolved in ethyl acetate and washed with water and brine, dried over anhydrous magnesium sulphate, filtered and the solvent removed under reduced pressure. The residue was purified by column chromatography on silica gel eluting with 95:5 (dichloromethane:methanol) to afford a white solid. Analysis suggests that 10% imidazole remains. The solid was dissolved in ethyl acetate and washed with water, dried over anhydrous magnesium sulphate, filtered and the solvent was removed under reduced pressure to afford the title compound as a white solid (128 mg).

MS: 373 (MH$^+$)

Analysis: Found, C, 64.13; H, 7.59; N, 14.86%; $C_{20}H_{28}N_4O_3$ requires C, 64.49; H, 7.58; N, 15.04%

$^1$H-NMR (d$_6$-DMSO) δ: 10.38 (1H, s), 8.65 (1H, s), 8.49 (2H, d), 7.25 (2H, d), 4.10 (2H, s), 3.39 (1H, m), 2.20 (2H, m), 1.50–1.65 (7H, m), 1.00–1.20 (8H, m), 0.87 (2H, m).

Example 61

(3R)-6-Cyclohexyl-N-hydroxy-3-[3-(3-pyridinylmethyl)-1,2,4-oxadiazol-5-yl]hexanamide

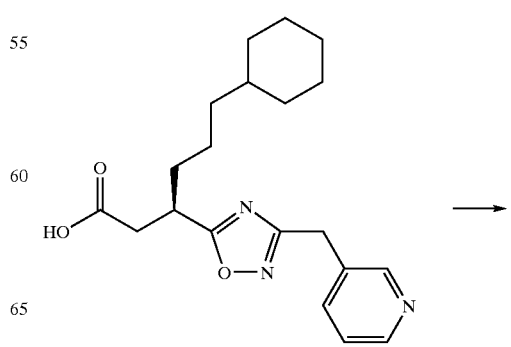

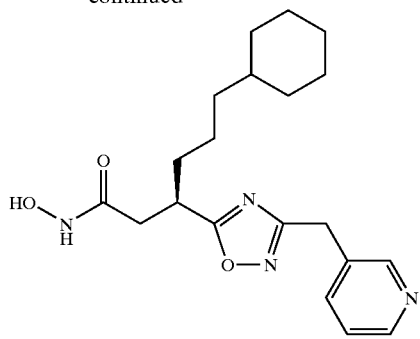

A solution of (3R)-6-cyclohexyl-3-[3-(3-pyridinylmethyl)-1,2,4-oxadiazol-5-yl]hexanoic acid (Preparation 109) (410 mg, 1.04 mmol) in dichloromethane (10 ml) was treated with 1,1'-carbonyldiimidazole (169 mg, 1.04 mmol) and stirred under a nitrogen atmosphere for 1 hour. O-(Trimethylsilyl)hydroxylamine (418 μl, 3.12 mmol) was added and the reation mixture was stirred for 18 hours. The reaction mixture was then treated with methanol (5 ml) and stirred at room temperature for 3 hours. The solvent was removed under reduced pressure. The residue was dissolved in ethyl acetate and washed with water (3×30 ml) and brine, dried over anhydrous magnesium sulphate, filtered and the solvent removed under reduced pressure. The residue was purified by column chromatography on silica gel eluting with a solvent gradient of 100:0 (dichloromethane:methanol) gradually changing to 95:5 (dichloromethane:methanol) to afford a white waxy solid. The solid was recrystallised from ethyl acetate to afford the title compound as a white solid (128 mg).

MS: 373 (MH+)

Analysis: Found, C, 64.53; H, 7.63; N, 14.53%; $C_{20}H_{28}N_4O_3$.0.15 EtOAc requires C, 64.15; H, 7.63; N, 14.53%

$^1$H-NMR ($d_6$-DMSO) δ: 10.36 (1H, s), 8.62 (1H, s), 8.54 (1H, s), 8.43 (1H, d), 7.65 (1H, d), 7.30 (1H, m), 4.10 (2H, s), 3.40 (1H, m), 2.70 (1H, m), 2.40 (1H, m), 1.50–1.70 (7H, m), 1.00–1.20 (8H, m), 0.76 (2H, m).

Example 62

2-{(1R)-4-Cyclobutyl-1-[2-(hydroxyamino)-2-oxoethyl]butyl}-N,N-dimethyl-1,3-oxazole-4-carboxamide

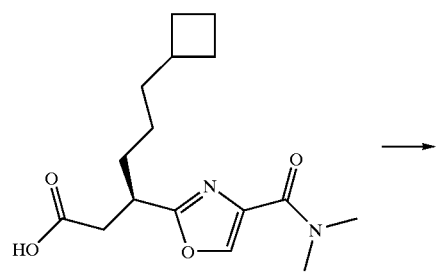

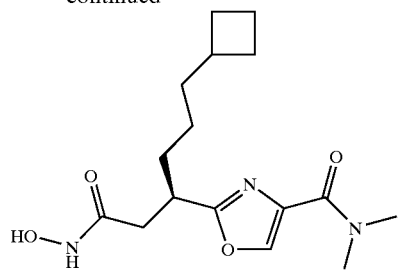

A solution of (3R)-6-cyclobutyl-3-{4-[(dimethylamino)carbonyl]-1,3-oxazol-2-yl}hexanoic acid (Preparation 121) (155 mg, 0.50 mmol) and N-methylmorpholine (90 μl, 0.82 mmol) in anhydrous tetrahydrofuran (8 ml) was cooled to 0° C., treated with isobutyl chloroformate (90 μl, 0.70 mmol) and stirred under a nitrogen atmosphere for 2 hours. O-(Trimethylsilyl)hydroxylamine (200 μl, 1.63 mmol) was added and the mixture was stirred for 18 hours, being allowed to warm to room temperature over this time. The mixture was then treated with methanol (2 ml) and stirred at room temperature for 10 minutes. The solvent was removed under reduced pressure. The residue was dissolved in ethyl acetate and washed with water, dried over anhydrous sodium sulphate, filtered and the solvent removed under reduced pressure. The oil was purified by column chromatography on silica gel eluting with a gradient system of 98:2 (dichloromethane:methanol) gradually changing to 90:10 (dichloromethane:methanol). The solid was triturated with diethyl ether, filtered and dried under reduced pressure to afford the title compound as a white solid (64 mg).

MS: 346 (MNa+)

Analysis: Found, C, 59.03; H, 7.81; N, 12.92%; $C_{16}H_{25}N_3O_4$.0.1 $H_2O$ requires C, 59.10; H, 7.81; N, 12.92%

$^1$H-NMR ($d_6$-DMSO) δ: 10.45 (1H, s), 8.78 (1H, s), 8.38 (1H, s), 3.25 (1H, t), 3.28 (3H, s), 2.90 (3H, s), 2.40 (1H, dd), 2.28 (1H, dd), 2.12 (1H, m), 1.91 (2H, m), 1.70 (2H, m), 1.57 (2H, m), 1.45 (2H, m), 1.27 (2H, m), 1.02 (2H, m).

Preparation 1: (2R)-2-[2-(tert-Butoxy)-2-oxoethyl]-5-cyclohexylpentanoic Acid

Route A: (2R)-2-[2-(tert-butoxy)-2-oxoethyl]-5-cyclohexylpentanoic Acid

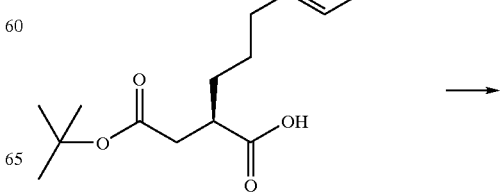

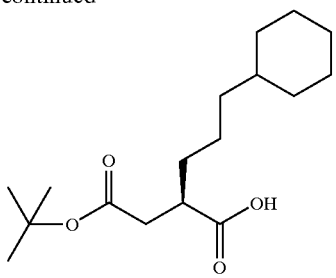

A solution of (2R)-2-[2-(tert-butoxy)-2-oxoethyl]-5-phenylpentanoic acid (Syn. Lett.; 1998; 637–639) (10.00 g, 34.2 mmol) in acetic acid (120 ml) was treated with 5% Rhodium on alumina catalyst, pressurised to 60 psi with hydrogen in a sealed vessel and stirred at room temperature for 17 hours. The mixture was filtered through a pad of Arbocel® and the solvent was removed from the filtrate under reduced pressure. The residue was azeotroped from toluene to afford the title compound (7.53 g).

MS: 299 (MH$^+$)

$^1$H-NMR (CDCl$_3$) δ: 2.80 (1H, m), 2.61 (1H, m), 2.38 (1H, m), 1.75–1.56 (7H, m), 1.55–1.04 (17H, m), 0.84 (2H, m).

Route B: (4S)-4-Benzyl-3-(5-cyclohexylpentanoyl)-1,3-oxazolidin-2-one

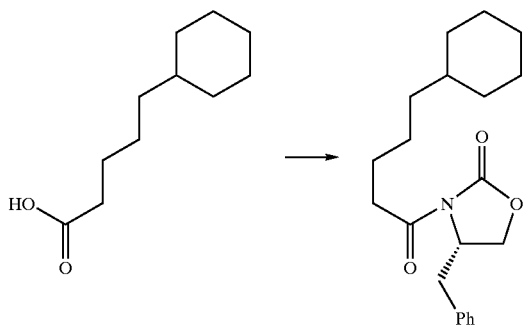

A solution of 5-cyclohexylpentanoic acid (63.50 g, 345 mmol) in N,N-dimethylformamide (0.5 ml) and dichloromethane (350 ml) was cooled to 5° C. and treated dropwise with oxalyl chloride (31.6 ml, 362 mmol) over 30 minutes. The mixture was stirred at 0° C. for 3 hours then the solvent was removed under reduced pressure to afford 5-cyclohexylpentanoyl chloride as a pale yellow solid (70.0 g).

A solution of n-butyllithium (100 ml, 250 mmol, 2.5M in hexanes) was added via a cannula to a solution of (4S)-4-benzyl-1,3-oxazolidin-2-one (44.30 g, 250 mmol) in anhydrous tetrahydrofuran (400 ml) at −78° C. The yellow solution was then stirred for 45 minutes. A solution of 5-cyclohexylpentanoyl chloride (55.5 g, 275 mmol) in tetrahydrofuran (100 ml) was then added over 1 hour. The mixture was stirred at −78° C. for 30 minutes then warmed to room temperature over 1 hour. The mixture was quenched with an aqueous solution of ammonium chloride (20% w/v, 400 ml) and extracted with ethyl acetate. The layers were separated and the organic layer was washed with brine, dried over anhydrous sodium sulphate and the solvent removed under reduced pressure. The solid was recrystallised from hexane (500 ml) to afford the title compound as a white solid (81.0 g).

MS: 344 (MH$^+$)

$^1$H-NMR (CDCl$_3$) δ: 7.41–7.13 (5H, m), 4.68 (1H, m), 4.27–4.02 (2H, m), 3.31 (1H, dd, J=16, 4 Hz), 3.06–2.70 (3H, m), 1.81–1.53 (7H, m), 1.49–1.04 (8H, m), 0.88 (2H, m)

tert-Butyl 3-{[(4S)-4-benzyl-2-oxo-1,3-oxazolidin-3-yl]carbonyl}-6-cyclohexylhexanoate

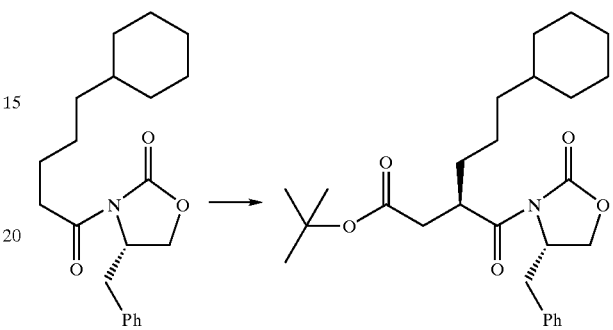

A solution of (4S)-4-benzyl-3-(5-cyclohexylpentanoyl)-1,3-oxazolidin-2-one (70.0 g, 204 mmol) in anhydrous tetrahydrofuran (650 ml) was cooled to −70° C. and treated dropwise with sodium hexamethyldisilazide (1 M in tetrahydrofuran, 224 ml, 224 mmol) over 45 minutes. The mixture was stirred for a further 45 minutes before being treated with t-butylbromoacetate (31.6 ml, 214 mmol). This mixture was stirred at −70° C. for 30 minutes then warmed to −30° C. and quenched with an aqueous solution of ammonium chloride (20%w/v, 400 ml) and warmed to room temperature. The mixture was extracted with ethyl acetate and the combined organic extracts were washed with brine, dried over anhydrous sodium sulphate and the solvent removed under reduced pressure. The solid was recrystallised from hexane to afford the title compound as a white solid (71.4 g).

MS: 458(MH$^+$)

$^1$H-NMR (CDCl$_3$) δ: 7.41–7.13 (5H, m), 4.66 (1H, m), 4.23–4.03 (3H, m), 3.35 (1H, dd, J=16, 4 Hz), 2.95–2.68 (3H, m), 2.47 (1H, m), 1.80–1.07 (24H, m), 0.85 (2H, m)

2-[2-(tert-Butoxy)-2-oxoethyl]-5-cyclohexylpentanoic Acid

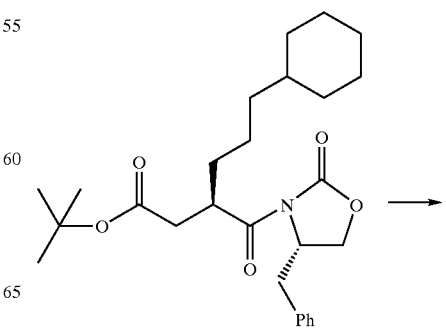

-continued

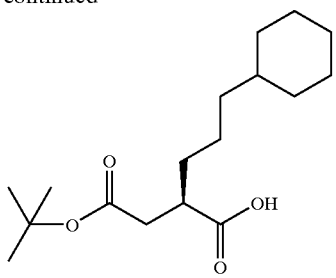

A solution of tert-butyl 3-{[(4S)-4-benzyl-2-oxo-1,3-oxazolidin-3-yl]carbonyl}-6-cyclohexylhexanoate (64.0 g, 139.9 mmol) in tetrahydrofuran:water (3:1, 800 ml) was cooled to 5° C. then treated sequentially with hydrogen peroxide (30%w/v water, 87 ml, 769 mmol) then lithium hydroxide hydrate (10.0 g, 238 mmol). The reaction was stirred for 1 hour then quenched by dropwise addition of an aqueous solution of sodium thiosulphate (500 ml) keeping the temperature below 20° C. The mixture was extracted with ethyl acetate (discarded) and the aqueous phase was acidifed to pH 2 with solid citric acid and extracted with ethyl acetate. The combined organic phases were washed with brine, dried over anhydrous sodium sulphate and the solvent removed under reduced pressure. The residue was purified by column chromatography on silica gel eluting with a gradient system of hexane:ethyl acetate (2:1) gradually changing to hexane:ethyl acetate (1:1) to afford the title compound (40.7 g)

Route C: 3-(Diethoxyphosphoryl)succinic Acid 1-tert-butyl Ester

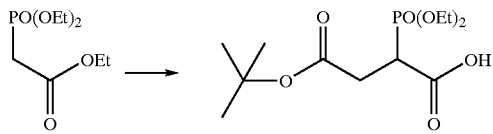

Triethylphosphonoacetate (102 g, 0.45 mol) was added dropwise over 11 min to a stirred solution of potassium tert-butoxide (60 g, 0.54 mol) in THF (500 ml), at 0° C., under nitrogen. The mixture was stirred for 1 hour at 0° C. and then dichloromethane (300 ml) was added and the reaction mixture was warmed to 25–30° C. The mixture was stirred at 25–30° C. for 1 hour and then added dropwise over 33 minutes to a solution of tert-butyl bromoacetate (96 g, 0.49 mol) in THF (500 ml), at 0° C., under nitrogen. The mixture was stirred at 0–5° C. for 2 hours and then a solution of citric acid (174 g, 0.91 mol) in demineralised water (250 ml) was added. The mixture was concentrated in vacuo to remove most of the THF and then toluene (750 ml) was added. The organic phase was separated, washed with brine (2×150 ml) and concentrated in vacuo to leave a colourless oil. The oil was taken up in ethanol and a solution of potassium hydroxide (36. g, 0.64 mol) in demineralised water (150 ml) was added dropwise over 15 mins. The mixture was stirred at 0° C. for 4 hours and then a solution of citric acid (158 g, 0.82 mol) in demineralised water (600 ml), and toluene (600 ml), were added. The organic phase was separated and the aqueous phase was re-extracted with toluene (600 ml). The combined organic phases were washed with demineralised water (2×150 ml) and concentrated in vacuo to leave a white solid. Toluene (150 ml) was added and the slurry was re-concentrated in vacuo to leave a white solid. The product was purified by crystallisation from tert-butylmethyl ether (300 ml) and cyclohexane (600 ml) to give the title compound as a solid (79 g).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

Alternative Preparation

Triethylphosphonoacetate (12.0 Kg, 53.5 mol) was added over 30 minutes to a stirred solution of potassium tert-butoxide (7.20 Kg, 64.2 mol) in THF (118 liters), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 liters), between 0 and 5° C., under nitrogen. The mixture was stirred at 0–5° C. for 1 hour and then demineralised water (6.1 liters) and ethanol (30 liters) were added. A solution of potassium hydroxide (4.2 Kg, 75.0 mol) in demineralised water (84 liters) was then added over 2 hours, between −5 and 0° C. The mixture was stirred at −10° C. for 16 hours and then a solution of citric acid (16.5 Kg, 85.8 mol) in demineralised water (32 liters) was added. The mixture was concentrated in vacuo to a volume of 180 liters and then ethyl acetate (90 liters) was added. The organic phase was separated and the aqueous phase was re-extracted with ethyl acetate (30 liters). The combined organic phases were washed with water (30 liters) and then stripped and replaced with cyclohexane by distillation at atmospheric pressure, at a constant volume of 72 liters. tert-Butylmethyl ether (18 liters) was added and the mixture was stirred at ambient temperature for 12 hours and then filtered. The residue was washed with a mixture of cyclohexane (16 liters) and tert-butylmethyl ether (3.6 liters) then dried in vacuo for 16 hours to give the title compound as a colourless solid (10.0 Kg, 60%).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

(E)-2-[2-(tert-Butoxy)-2-oxoethyl]-5-phenyl-2-pentenoic Acid

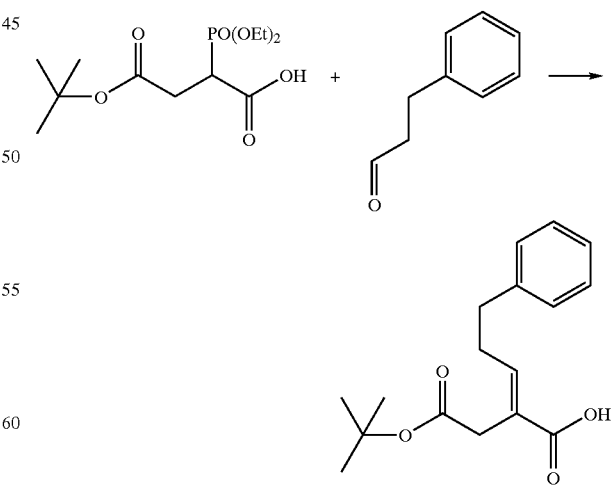

A solution of 3-(diethoxyphosphoryl)succinic acid 1-tert-butyl ester (100 g, 0.32 mol) in THF (300 ml) was added dropwise over 15 min to a stirred solution of potassium tert-butoxide (110 g, 0.98 mol) in THF (300 ml), between −10 and −5° C., under nitrogen. The mixture was stirred at −10° C. for 15 min and then a solution of hydrocinnamaldehyde (46.8 g, 0.35 mmol) in THF (100 ml) was added dropwise over 15 min, between −13 and −8° C. The mixture was stirred at −10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colourless solid (76 g, 81%).

MS: 289 [(M−H)]⁻

¹H-NMR (CDCl₃) δ: 7.33–7.16 (5H, m), 7.05 (1H, br t), 3.20 (2H, s), 2.89 (2H, br t), 2.50 (2H, br dd), 1.41 (9H, s)

(R)-2-[2-(tert-Butoxy)-2-oxoethyl]-5-phenylpentanoic Acid

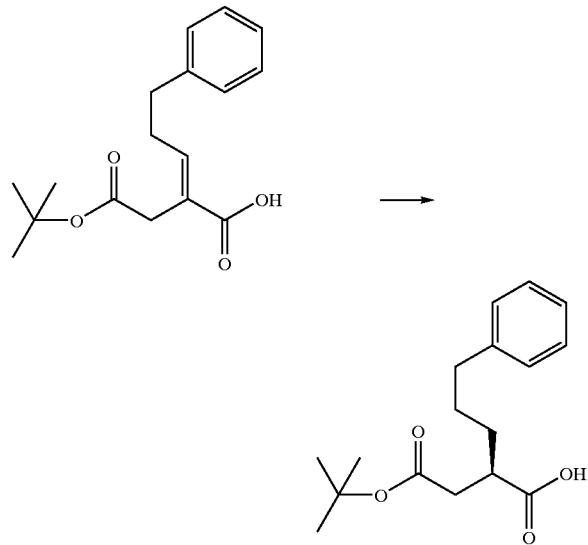

A stirred solution of (E)-2-[2-(tert-butoxy)-2-oxoethyl]-5-phenyl-2-pentenoic acid (100 g, 0.34 mol), cyclohexylamine (39 ml, 0.34 mol) and [(S)-2,2'-bis(diphenylphosphino-1,1'-binaphthyl]chloro(p-cymene)ruthenium chloride (0.64 g, 0.69 mmol) in methanol (1000 ml) was heated to 60° C., under hydrogen (60 p.s.i.), for 42 hours and then allowed to cool to room temperature. The mixture was filtered through celite and then concentrated in vacuo to a yellow solid which was purified by re-crystallisation from acetone (850 ml). The resulting solid was partitioned between ethyl acetate (1200 ml) and citric acid solution (10%, 1200 ml) and the organic phase was separated, washed with demineralised water (1200 ml) and concentrated in vacuo to leave the title compound as an oil (80 g).

¹H-NMR (CDCl₃) δ: 7.30–7.17 (5H, m), 2.85–2.78 (1H, m), 2.66–2.58 (3H, m), 2.37 (1H, br dd), 1.75–1.51 (4H, m), 1.40 (9H, s)

Preparation of Cyclohexylamine Salt

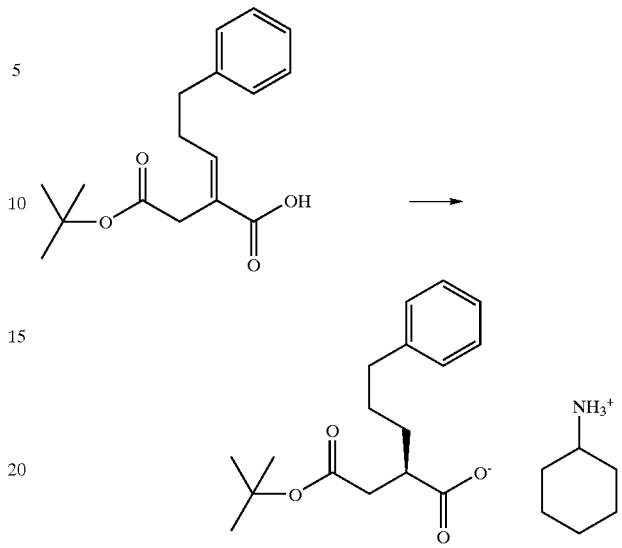

A stirred solution of cyclohexylamine (266 ml, 2.32 mol), (E)-2-[2-(tert-butoxy)-2-oxoethyl]-5-phenyl-2-pentenoic acid (688 g, 2.37 mol) and [(S)-2,2'-bis(diphenylphosphino-1,1'-binaphthyl]chloro(p-cymene)ruthenium chloride (4.4 g, 4.7 mmol) in methanol (6.9 liters) was heated to 60° C., under hydrogen (60 p.s.i.), for 47 hours and then allowed to cool to room temperature (enantiomeric excess=88%). The mixture was filtered through celite and then the solvent was stripped and replaced with acetone by distillation at atmospheric pressure, at a constant volume of 4.2 liters. The resulting suspension was cooled to room temperature where it was stirred for 4 hours and then filtered. The residue was washed with acetone (2×1 liter) and then dried in vacuo at 45° C. for 16 hours to leave the title compound as a colourless solid (590 g, 64%, enantiomeric excess=98.9%).

¹H-NMR (CD₃OD) δ: 7.23–7.09 (5H, m), 3.05–2.98 (1H, m), 2.64–2.56 (3H, m), 2.53 (1H, dd, J 15.2, 7.2 Hz), 2.23 (1H, dd, J 15.2, 7.2 Hz), 2.00–1.97, (2H, m), 1.85–1.81 (2H, m), 1.72–1.20 (10H, m), 1.40 (9H, s)

(R)-2-[2-(tert-Butoxy)-2-oxoethyl]-5-cyclohexylpentanoic Acid Cyclohexylamine Salt

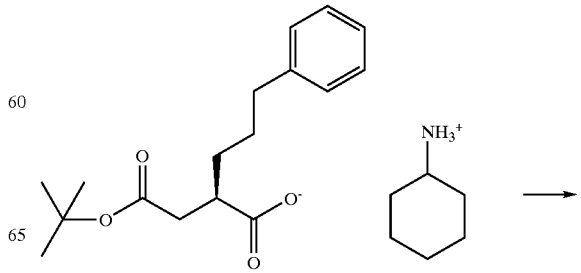

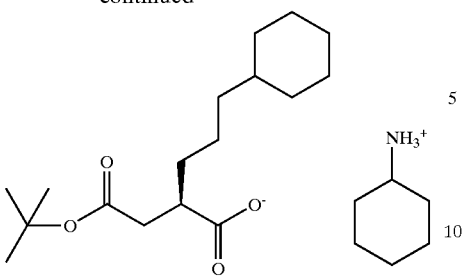

(R)-2-[2-(tert-Butoxy)-2-oxoethyl]-5-phenylpentanoic acid cyclohexylamine salt (691 g, 1.77 mol) and ethyl acetate (7.0 liters) were added to an aqueous solution of citric acid (10%, 6.3 liters) and the organic phase was separated, washed with water (7.0 liters) and concentrated in vacuo to a yellow oil. A solution of the oil and 5% rhodium on carbon (51.6 g) in methanol (7.0 liters) was stirred at ambient temperature, under hydrogen (150 p.s.i.) for 48 hours and then filtered through celite. To the filtrate was added cyclohexylamine (202 ml, 1.77 mol) and the methanol solution was stripped and replaced with methylethyl ketone by distillation at atmospheric pressure, to a volume of 5.5 liters. The mixture was allowed to cool to ambient temperature where it was stirred for 48 hours and then filtered. The residue was washed with methylethyl ketone (2×500 ml) and then dried in vacuo at 45° C. for 4 hours to leave the title compound as a colourless solid (495 g, 71%).

$^1$H-NMR (CD$_3$OD) δ: 3.06–2.99 (1H, m), 2.63–2.56 (1H, m), 2.53 (1H, dd, J 15.2, 7.2 Hz), 2.23 (1H, dd, J 15.2, 7.2 Hz), 2.02–1.97 (2H, m), 1.77–1.15 (21H, m), 1.43 (9H, s), 0.93–0.82 (2H, m)

(R)-2-[2-(tert-Butoxy)-2-oxoethyl]-5-cyclohexylpentanoic Acid

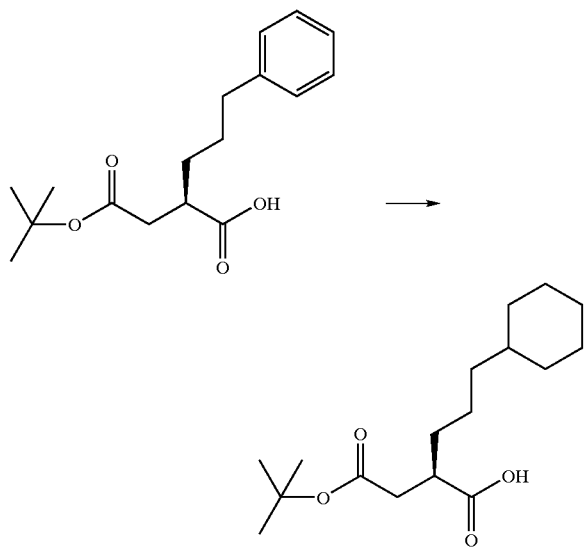

A solution of (R)-2-[2-(tert-butoxy)-2-oxoethyl]-5-phenylpentanoic acid (2.2 g, 7.5 mmol) and 5%Rh/C (0.22 g) in methanol (220 ml) was stirred at room temperature, under hydrogen (150 p.s.i.) for 24 hours and then filtered through celite. The filtrate was concentrated in vacuo to leave the title compound as an oil (2.0 g).

$^1$H-NMR (CDCl$_3$) δ: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

Preparation 2: tert-Butyl (3R)-3-[({[(Z)-1-amino-2-ethoxy-2-oxoethylidene]amino}oxy)carbonyl]-6-cyclohexylhexanoate

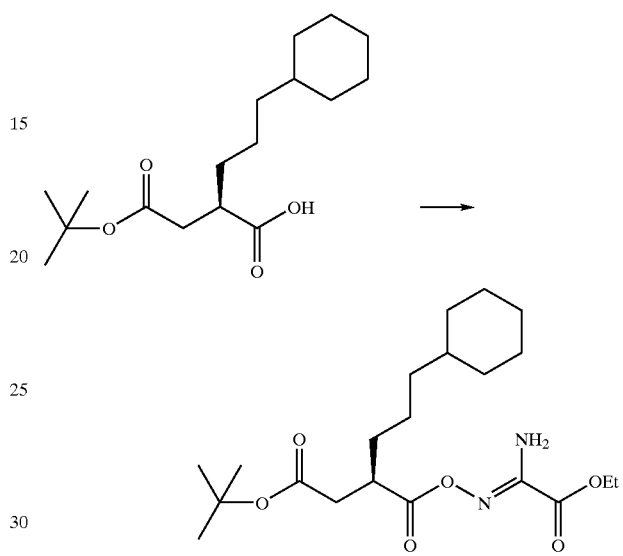

A solution of (2R)-2-[2-(tert-butoxy)-2-oxoethyl]-5-cyclohexylpentanoic acid (Preparation 1) (7.53 g, 25.2 mmol) in 1,4-dioxane (175 ml) was treated with 1-hydroxybenzotriazole hydrate (3.75 g, 27.8 mmol) and the mixture cooled to 0° C. N,N'-Dicyclohexylcarbodiimide (5.47 g, 26.5 mmol) was then added and the mixture was stirred for 3 hours being allowed to warm to room temperature over this time. The mixture was then filtered and washed with 1,4-dioxane (2×50 ml). The filtrate was then treated with sodium carbonate (4.01 g, 37.8 mmol) and ethyl 2-amino-2-(hydroxyimino)acetate (J.Org.Chem.;23; 1958; 1794) (3.33 g, 25.2 mmol). The resulting mixture was stirred at room temperature for 17 hours. The solvent was removed under reduced pressure and the residue was partitioned between ethyl acetate and water. The layers were separated and the aqueous phase was extracted with ethyl acetate (×2). The combined organic layers were dried over anhydrous magnesium sulphate, filtered and the solvent removed under reduced pressure. The residue was purified by column chromatography on silica gel eluting with a gradient system of ethyl acetate:pentane (30:70) gradually changing to ethyl acetate:pentane (50:50) to afford the title compound as a white solid (6.50 g).

MS: 413 (MH$^+$)

$^1$H-NMR (CDCl$_3$) δ: 5.71 (2H, br s), 4.39 (2H, q), 2.92 (1H, m), 2.67 (1H, dd), 2.44 (1H, dd), 1.75–1.32 (22H, m), 1.26–1.04 (5H, m), 0.84 (2H, m).

Preparation 3: Ethyl 5-{(1R)-1-[2-(tert-butoxy)-2-oxoethyl]-4-cyclohexylbutyl}-1,2,4-oxadiazole-3-carboxylate

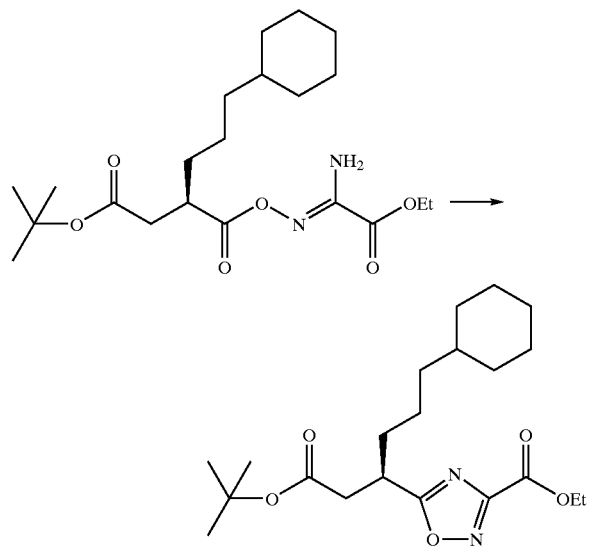

A solution of tert-Butyl (3R)-3-[({[(Z)-1-amino-2-ethoxy-2-oxoethylidene]amino}oxy)carbonyl]-6-cyclohexylhexanoate (Preparation 2) (21.0 g, 50.82 mmol) in xylene (400 ml) was heated at 130° C. for 17 hours, then allowed to cool to room temperature. The residue was purified by column chromatography on silica gel eluting with a gradient system of ethyl acetate:pentane (5:95) gradually changing to ethyl acetate:pentane (20:80) to afford the title compound as a colourless oil (20.0 g).

MS: 395 (MH$^+$), 412 (MNH$_4^+$)

$^1$H-NMR (CDCl$_3$) δ: 4.51 (2H, m), 3.54 (1H, m), 2.86 (1H, dd), 2.65 (1H, dd), 1.86–1.57 (7H, m), 1.50–1.33 (12H, m), 1.30–1.03 (8H, m), 0.82 (2H, m).

Preparation 4: (3R)-6-Cyclohexyl-3-[3-(ethoxycarbonyl)-1,2,4-oxadiazol-5-yl]hexanoic Acid

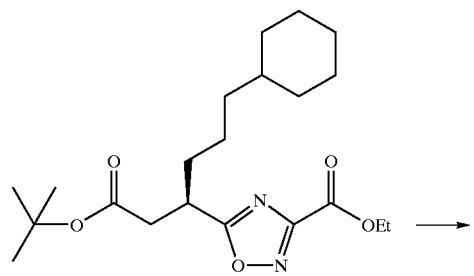

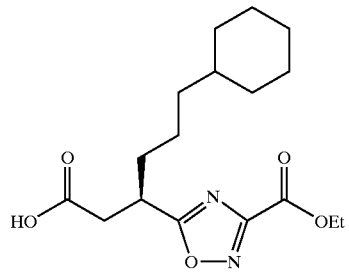

A solution of ethyl 5-{(1R)-1-[2-(tert-butoxy)-2-oxoethyl]-4-cyclohexylbutyl}-1,2,4-oxadiazole-3-carboxylate (Preparation 3) (820 mg, 2.08 mmol) in dichloromethane (10 ml) was cooled to 0° C. and treated with trifluoroacetic acid (5 ml). The mixture was stirred for 2.5 hours being allowed to warm to room temperature over this time. The solvent was removed under reduced pressure and the residue azeotroped with toluene (×2). The residue was then dissolved in ethyl acetate, washed sequentially with an aqueous solution of sodium dihydrogen citrate and brine, dried over anhydrous sodium sulphate, filtered and the solvent removed under reduced pressure to afford the title compound as an oil (740 mg).

MS: 339 (MH$^+$)

$^1$H-NMR (CDCl$_3$) δ: 4.49 (2H, q J=7 Hz), 3.57 (1H, m), 3.05 (1H, dd J=17, 8 Hz), 2.81 (1H, dd J=17, 4 Hz), 1.92–1.55 (7H, m), 1.45 (3H, t J=7 Hz), 1.35–1.02 (8H, m), 0.84 (2H, m)

Preparation 5: tert-Butyl (3R)-3-[3-(aminocarbonyl)-1,2,4-oxadiazol-5-yl]-6-phenylhexanoate

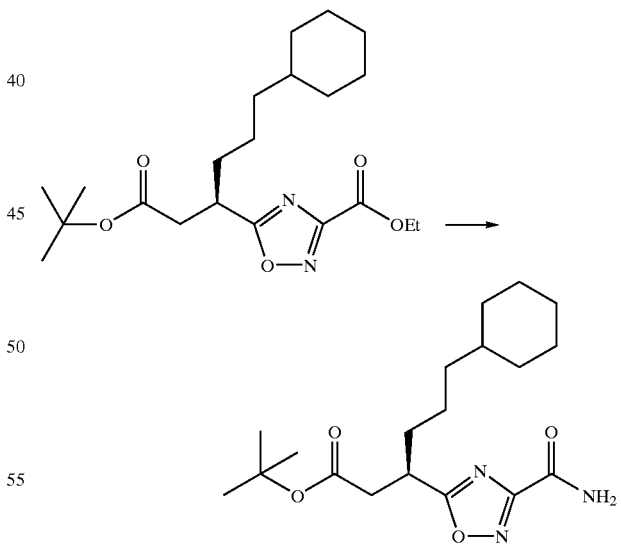

A solution of ethyl 5-{(1R)-1-[2-(tert-butoxy)-2-oxoethyl]-4-cyclohexylbutyl}-1,2,4-oxadiazole-3-carboxylate (Preparation 3) (400 mg, 1.01 mmol) in ethanol saturated with ammonia gas (20 ml) was stirred at room temperature for 18 hours. The solvent was removed under reduced pressure and the residue was purified by column chromatography on silica gel eluting with a gradient system of hexane:ethyl acetate (90:10) gradually changing to hexane:ethyl acetate (60:40) to afford the title compound as a white solid (260 mg).

MPt: 77–79° C.

MS: 366 (MH+), 383 (MNa+)

Analysis: Found C, 62.42; H, 8.59; N, 11.48%; $C_{19}H_{31}N_3O_4$ requires C, 62.44; H, 8.55; N, 11.50%

$^1$H-NMR (CDCl$_3$) δ: 6.80 (1H, br s), 5.90 (1H, br s), 3.53 (1H, m), 2.87 (1H, dd, J=17, 9 Hz), 2.66 (1H, dd, J=17, 5 Hz), 1.90–1.50 (7H, m), 1.46–1.02 (17H, m), 0.83 (2H, m).

Alternative Preparation of tert-butyl (3R)-3-[3-(aminocarbonyl)-1,2,4-oxadiazol-5-yl]-6-cyclohexyl-hexanoate

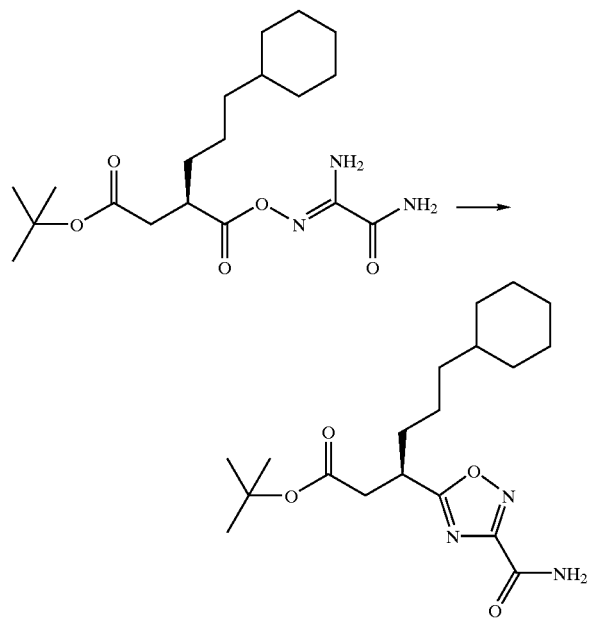

tert-Butyl(3R)-3-[({[(Z)-1,2-diamino-2-oxoethylidene]amino}oxy)carbonyl]-6-cyclohexyl-hexanoate (Preparation 101) (4.10 g, 10.7 mmol) in mixed xylenes (25 ml) was heated to reflux for 48 hours. The solvent was removed under reduced pressure and the residue was purified by column chromatography on silica gel eluting with isocratic system of n-hexane:ethyl acetate (75:25) to afford a yellow oil. The oil was crystallised from cyclohexane to afford the title compound as a colourless solid (0.60 g).

$^1$H-NMR (CDCl$_3$) δ: 6.80 (1H, br s), 5.90 (1H, br s), 3.53 (1H, m), 2.87 (1H, dd, J=17, 9 Hz), 2.66 (1H, dd, J=17, 5 Hz), 1.90–1.50 (7H, m), 1.46–1.02 (17H, m), 0.93–0.82 (2H, m).

Preparation 6: (3R)-3-[3-(Aminocarbonyl)-1,2,4-oxadiazol-5-yl]-6-cyclohexylhexanoic Acid

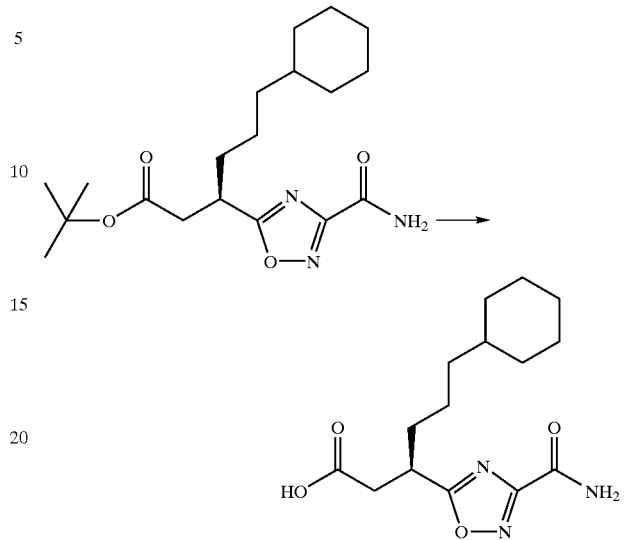

A solution of tert-butyl (3R)-3-[3-(aminocarbonyl)-1,2,4-oxadiazol-5-yl]-6-phenylhexanoate (Preparation 5) (250 mg, 0.68 mmol) in dichloromethane (10 ml) was cooled to 0° C. and treated with trifluoroacetic acid (5 ml). The mixture was stirred for 2 hours, being allowed to warm to room temperature over this time. The solvent was removed under reduced pressure and the residue was azeotroped with toluene (×2) then hexane to afford the title compound as a white solid (204 mg).

MPt.: 172–174° C.

Analysis: Found C, 58.03; H, 7.48; N, 13.38%; $C_{15}H_{23}N_3O_4$ requires C, 58.24; H, 7.49; N, 13.19%

$^1$H-NMR (CD$_3$OD) δ: 3.55 (1H, m), 2.93 (1H, dd, J=17, 9 Hz), 2.80 (1H, dd, J=17, 4 Hz), 1.84–1.59 (7H, m), 1.40–1.08 (8H, m), 0.86 (2H, m).

Preparation 7: tert-Butyl (3R)-6-cyclohexyl-3-{3-[(methylamino)carbonyl]-1,2,4-oxadiazol-5-yl}hexanoate

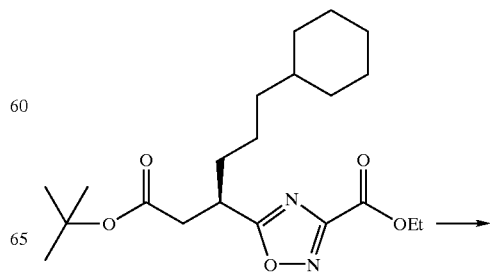

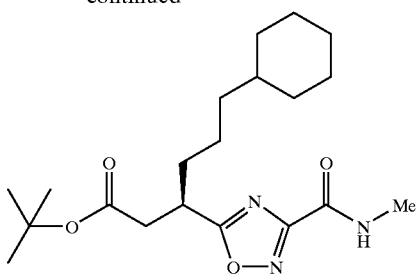

A solution of ethyl 5-{(1R)-1-[2-(tert-butoxy)-2-oxoethyl]-4-cyclohexylbutyl}-1,2,4-oxadiazole-3-carboxylate (Preparation 3) (4.70 g, 11.9 mmol) in ethanol (80 ml) was treated with methylamine (33% w/v in ethanol, 12.0 ml, 96.0 mmol) and the solution was stirred at room temperature for 18 hours. The solvent was removed under reduced pressure and the residue was purified by column chromatography on silica gel eluting with a gradient system of dichloromethane:ethyl acetate (9:1) gradually changing to dichloromethane:ethyl acetate (8:2) to afford the title compound as a pale yellow oil which crystallised on standing (4.23 g).

MS: 380 (MH⁺)

$^1$H-NMR (CDCl$_3$) δ: 6.97 (1H, br m), 3.48 (1H, m), 3.04 (3H, d), 2.84 (1H, dd, J=17, 9 Hz), 2.66 (1H, dd, J=17, 4 Hz), 1.84–1.55 (7H, m), 1.39 (9H, s), 1.33–1.02 (8H, m), 0.83 (2H, m).

Preparation 8: (3R)-6-Cyclohexyl-3-{3-[(methylamino)carbonyl]-1,2,4-oxadiazol-5-yl}hexanoic Acid

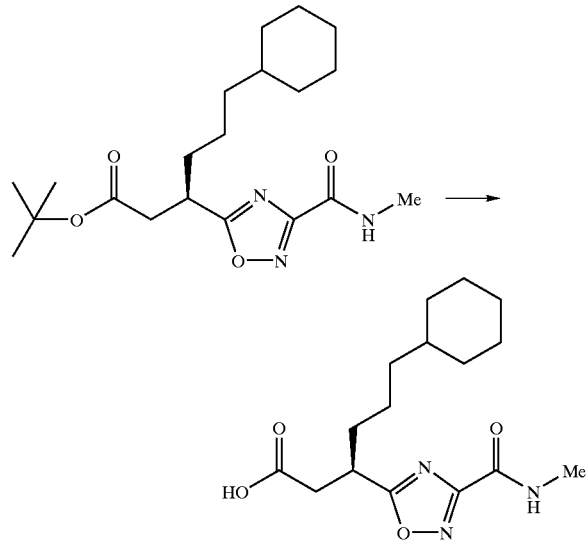

A solution of tert-butyl (3R)-6-cyclohexyl-3-{3-[(methylamino)carbonyl]-1,2,4-oxadiazol-5-yl}hexanoate (Preparation 7, 380 mg, 1.00 mmol) in dichloromethane (10 ml) was treated with trifluoroacetic acid (5 ml) and the mixture was stirred at room temperature for 3.5 hours. The solvent was removed under reduced pressure and the residue azeotroped with toluene (×2). The residue was dissolved in ethyl acetate and washed sequentially with a saturated aqueous solution of sodium citrate then brine. The organic layer was dried over anhydrous sodium sulphate, filtered and the solvent removed under reduced pressure. The residue was crystallised from hexane to afford the title compound as a white solid (310 mg).

MPt.: 83–86° C.

MS: 341 (MNH$_4$⁺)

Analysis: Found C, 59.24; H, 7.75; N, 12.77%; C$_{16}$H$_{25}$N$_3$O$_4$ requires C, 59.43; H, 7.79; N, 12.79

$^1$H-NMR (CDCl$_3$) δ: 6.94 (1H, br m), 3.55 (1H, m), 3.01 (4H, m), 2.79 (1H, dd, J=14, 3), 1.86–1.53 (7H, m), 1.35–1.06 (8H, m), 0.83 (2H, m).

Preparation 9: (3R)-6-Cyclohexyl-3-{3-[(propylamino)carbonyl]-1,2,4-oxadiazol-5-yl}hexanoic Acid

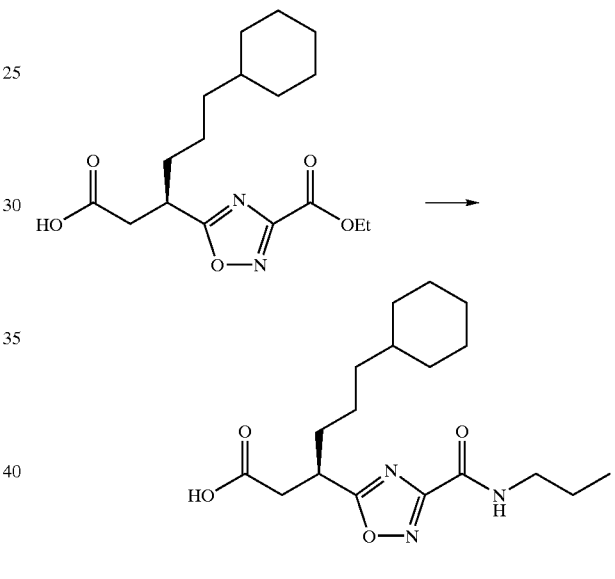

A solution of (3R)-6-cyclohexyl-3-[3-(ethoxycarbonyl)-1,2,4-oxadiazol-5-yl]hexanoic acid (Preparation 4) (107 mg, 0.31 mmol) in toluene (2 ml) was treated with n-propylamine (250 μl, 3.10 mmol) and the mixture was heated at 125° C. in a sealed vessel for 2 hours. The mixture was cooled to room temperature, diluted with ethyl acetate and washed sequentially with aqueous citric acid solution (5%w/v), water and brine, dried over anhydrous sodium sulphate, filtered and the solvent removed under reduced pressure. The residue was purified by column chromatography on silica gel eluting with a gradient system of dichloromethane:ethyl acetate (80:20) gradually changing to dichloromethane:ethyl acetate (60:40) then to dichloromethane:methanol (90:10) to afford the title compound as an oil (76 mg).

MS: 352 (MH⁺)

$^1$H-NMR (DMSO-d$_6$) δ: 8.90 (1H, m), 3.64–3.00 (3H, m), 2.80 (2H, m), 1.81–1.43 (9H, m), 1.39–1.00 (8H, m), 0.83 (5H, m).

Preparation 10: tert-Butyl (3R)-6-cyclohexyl-3-{3-[(dimethylamino)carbonyl]-1,2,4-oxadiazol-5-yl}hexanoate

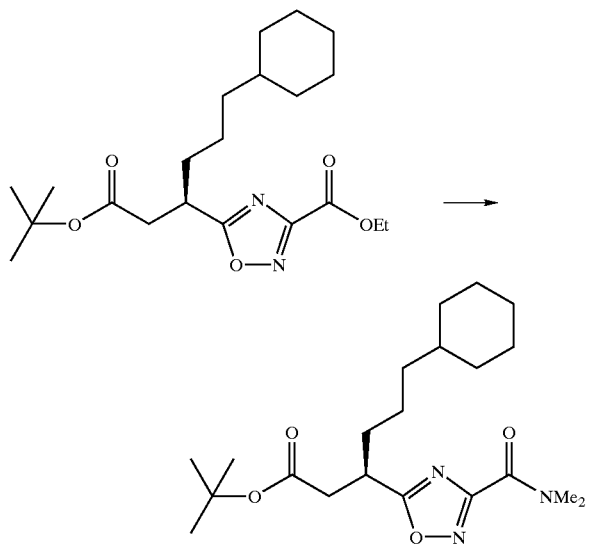

A solution of ethyl 5-{(1R)-1-[2-(tert-butoxy)-2-oxoethyl]-4-cyclohexylbutyl}-1,2,4-oxadiadole-3-carboxylate (Preparation 3) (1.00 g, 2.53 mmol) in ethanol (8 ml) was cooled to 0° C. and treated dropwise with dimethylamine (5.6M in ethanol, 4.50 ml, 25.3 mmol). The solution was stirred for 17 hours being allowed to warm up to room temperature over this time. The solvent was removed under reduced pressure and the residue was purified by column chromatography on silica gel eluting with dichloromethane:ethyl acetate (4:1) to afford the title compound as a yellow oil (0.93 g).

MS: 394 (MH$^+$), 411 (MNH$_4^+$)

$^1$H-NMR (CDCl$_3$) δ: 3.50 (1H, m), 3.12 (6H, d), 2.85 (1H, dd, J=16, 7 Hz), 2.65 (1H, dd, J=16, 5 Hz), 1.84–1.57 (7H, m), 1.39 (9H, s), 1.34–1.05 (8H, m), 0.83 (2H, m).

Preparation 11: (3R)-6-Cyclohexyl-3-{3-[(dimethylamino)carbonyl]-1,2,4-oxadiazol-5-yl}hexanoic Acid

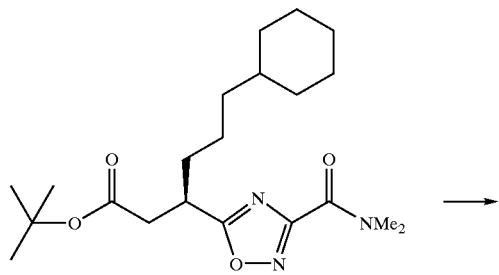

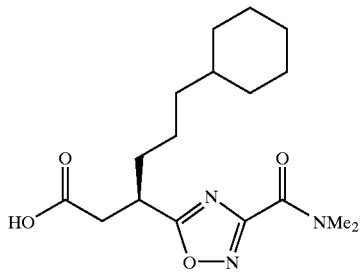

A solution of tert-butyl (3R)-6-cyclohexyl-3-{3-[(dimethylamino)carbonyl]-1,2,4-oxadiazol-5-yl}hexanoate (Preparation 10) (2.35 g, 5.97 mmol) in dichloromethane (10 ml) was treated with trifluoroacetic acid (2 ml) and the resulting mixture was stirred at room temperature under a nitrogen atmosphere for 17 hours. The solvent was removed under reduced pressure and the residue azeotroped from dichloromethane. The residue was purified by column chromatography on silica gel eluting with dichloromethane:methanol (98:2) to afford the title compound (1.27 g).

MS: 360 (MNa$^+$), 355 (MNH$_4^+$)

Analysis: Found C, 60.63; H, 8.16; N, 12.30%; C$_{17}$H$_{27}$N$_3$O$_4$ requires C, 60.51; H, 8.07; N, 12.45%

$^1$H-NMR (DMSO-d$_6$) δ: 3.45 (1H, m), 2.99 (3H, s), 3.91 (3H, s), 2.76 (2H, m), 1.73–1.52 (7H, m), 1.30–1.02 (8H, m), 0.80 (2H, m).

Preparation 12: tert-Butyl (3R)-6-cyclohexyl-3-[3-(1-pyrrolidinylcarbonyl)-1,2,4-oxadiazol-5-yl]hexanoate

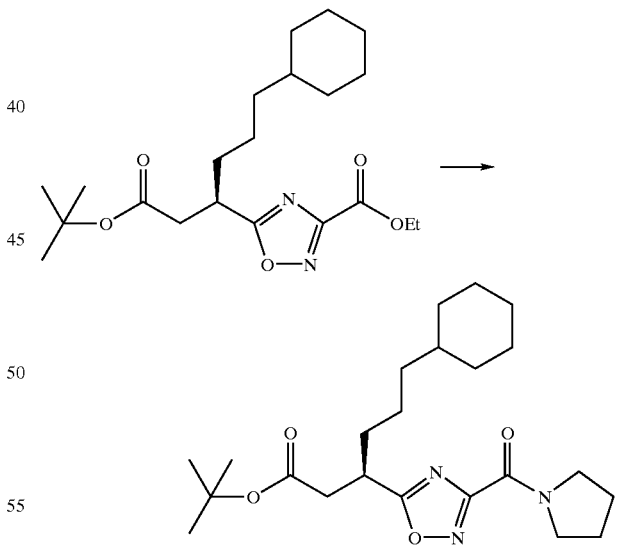

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated dropwise with pyrrolidine (0.63 ml, 7.60 mmol) and the resulting solution was heated at 60° C. for 9 hours. The solvent was removed under reduced pressure and the residue was purified by column chromatography on silica gel eluting with dichloromethane:ethyl acetate (4:1) to afford the title compound as a pale yellow oil (360 mg).

MS: 420 (MH$^+$), 437 (MNH$_4^+$)

$^1$H-NMR (CDCl$_3$) δ: 3.71 (4H, m), 3.50 (1H, m), 2.86 (1H, dd, J=16, 8 Hz), 2.64 (1H, dd, J=16, 3 Hz), 1.96 (4H, m), 1.74–1.55 (7H, m), 1.38 (9H, s), 1.33–1.04 (8H, m), 0.82 (2H, m).

Preparation 13: (3R)-6-Cyclohexyl-3-[3-(1-pyrrolidinylcarbonyl)-1,2,4-oxadiazol-5-yl]hexanoic Acid

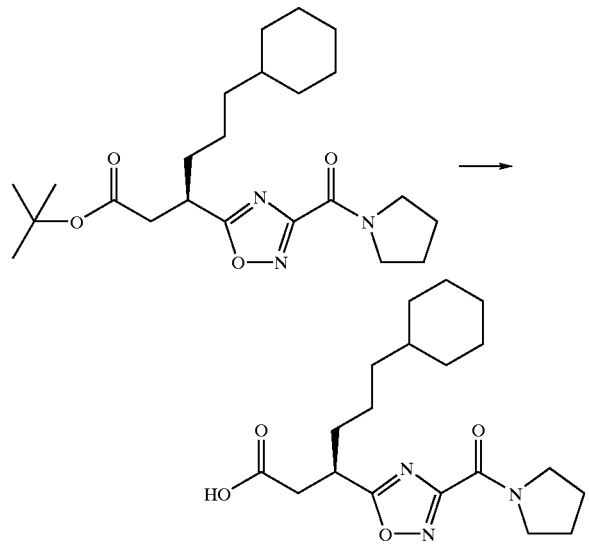

A solution of tert-butyl (3R)-6-cyclohexyl-3-[3-(1-pyrrolidinylcarbonyl)-1,2,4-oxadiazol-5-yl]hexanoate (Preparation 12) (356 mg, 0.85 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound (288 mg).

MS: 364 (MH$^+$), 381 (MNH$_4^+$)

$^1$H-NMR (CD$_3$OD) δ: 3.83–3.45 (5H, m), 2.94 (1H, dd, J=16, 8 Hz), 2.81 (1H, dd, J=16, 4 Hz), 1.98 (4H, m), 1.87–1.54 (7H, m), 1.44–1.06 (8H, m), 0.88 (2H, m).

Preparation 14: tert-Butyl (3R)-6-cyclohexyl-3-[3-(1-piperidinylcarbonyl)-1,2,4-oxadiazol-5-yl]hexanoate

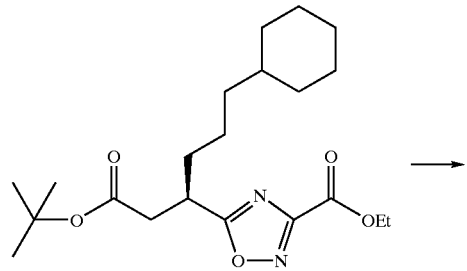

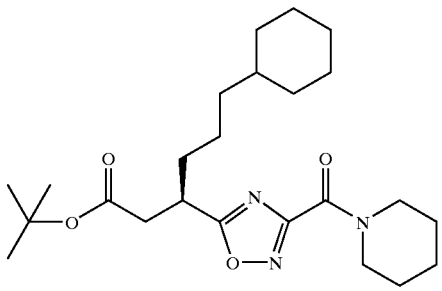

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated dropwise with piperidine (0.75 ml, 7.60 mmol) and the resulting mixture was heated at 60° C. under a nitrogen atmosphere for 9 hours. The mixture was cooled and the solvent removed under reduced pressure. The residue was purified by column chromatography on silica gel eluting with dichloromethane:ethyl acetate (80:20) to afford the title compound as a pale yellow oil (334 mg).

MS: 434 (MH$^+$), 451 (MNH$_4^+$)

$^1$H-NMR (CDCl$_3$) δ: 3.72 (2H, m), 3.48 (3H, m), 2.84 (1H, dd, J=14, 8 Hz), 2.65 (1H, dd, J=14, 4 Hz), 1.86–1.53 (13H, m), 1.39 (9H, s), 1.33–1.05 (8H, m), 0.82 (2H, m).

Preparation 15: (3R)-6-Cyclohexyl-3-[3-(1-piperidinylcarbonyl)-1,2,4-oxadiazol-5-yl]hexanoic Acid

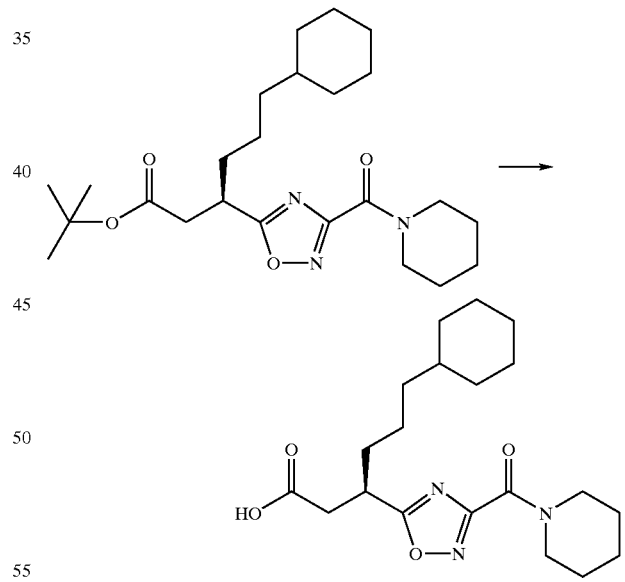

A solution of tert-butyl (3R)-6-cyclohexyl-3-[3-(1-piperidinylcarbonyl)-1,2,4-oxadiazol-5-yl]hexanoate (Preparation 14) (334 mg, 0.77 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound as a beige solid (266 mg).

MS: 378 (MH$^+$), 395 (MNH$_4^+$)

¹H-NMR (CD₃OD) δ: 3.73 (2H, m), 3.55 (1H, m), 3.43 (2H, m), 2.97–2.75 (2H, m), 1.86–1.57 (13H, m), 1.40–1.07 (8H, m), 0.87 (2H, m).

Preparation 16a: tert-Butyl (3R)-6-cyclohexyl-3-[3-(1,3-dihydro-2H-isoindol-2-ylcarbonyl)-1,2,4-oxadiazol-5-yl]hexanoate Preparation 16b: tert-Butyl (3R)-3-{3-[(benzylamino)carbonyl]-1,2,4-oxadiazol-5-yl}-6-cyclohexylhexanoate

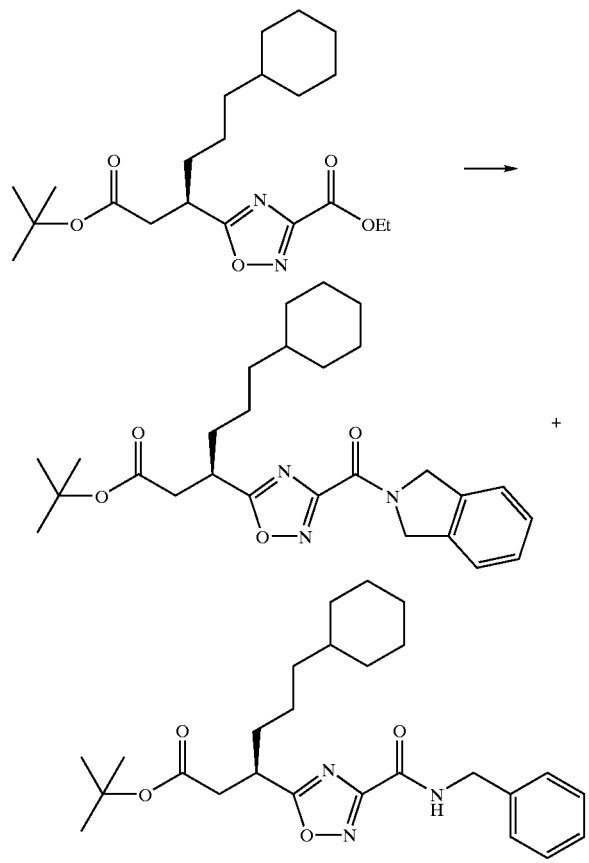

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated with isoindoline hydrochloride (0.59 g, 3.80 mmol) (which also contained benzylamine) and triethylamine (0.74 ml, 5.32 mmol) and the resulting mixture was heated at 60° C. under a nitrogen atmosphere for 16 hours. The solvent was removed under reduced pressure and the residue was purified by column chromatography on silica gel eluting with dichloromethane:ethyl acetate (90:10). The residue was further purified by column chromatography on silica gel eluting with a gradient system of dichloromethane:ethyl acetate (99:1) to afford the title compound 16a (91 mg).

MS: 468 (MH⁺), 485 (MNH₄⁺)

¹H-NMR (CDCl₃) δ: 7.33 (4H, m), 5.19 (2H, s), 5.04 (2H, s), 3.56 (1H, m), 2.92 (1H, dd, J=15, 7 Hz), 2.71 (1H, dd, J=15, 3 Hz), 1.90–1.58 (7H, m), 1.41 (9H, s), 1.38–1.05 (8H, m), 0.83 (2H, m).

Further elution with dichloromethane:ethyl acetate (95:5) then gave compound 16b (173 mg)

MS: 473 (MNH₄⁺)

¹H-NMR (CDCl₃) δ: 7.41–7.17 (5H, m), 4.66 (2H, d, J=5 Hz), 3.50 (1H, m), 2.84 (1H, dd, J=15, 8 Hz), 2.65 (1H, dd, J=15, 3 Hz), 1.83–1.57 (7H, m), 1.39 (9H, s), 1.34–1.04 (8h, m), 0.83 (2H, m).

Preparation 17: (3R)-6-Cyclohexyl-3-[3-(1,3-dihydro-2H-isoindol-2-ylcarbonyl)-1,2,4-oxadiazol-5-yl]hexanoic Acid

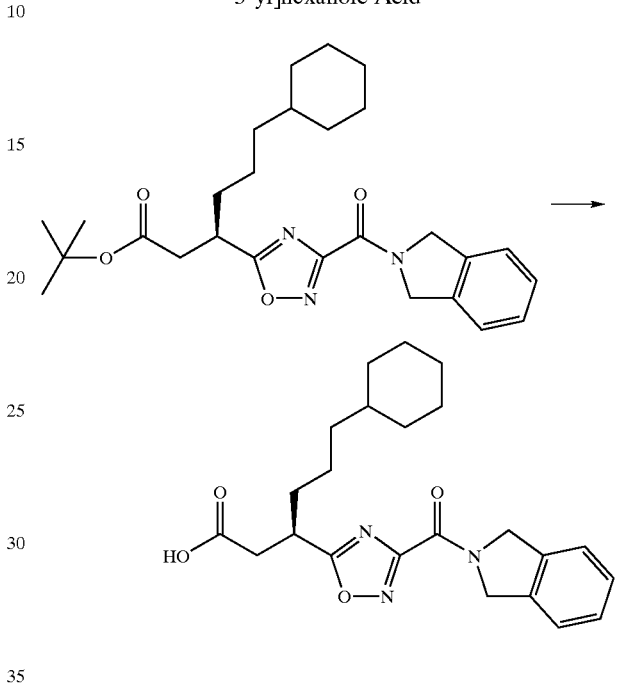

A solution of tert-butyl (3R)-6-cyclohexyl-3-[3-(1,3-dihydro-2H-isoindol-2-ylcarbonyl)-1,2,4-oxadiazol-5-yl]hexanoate (Preparation 16a) (91 mg, 0.19 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound as a beige solid (82 mg).

MS: 412 (MH⁺), 429 (MNH₄⁺)

¹H-NMR (CD₃OD) δ: 7.46–7.25 (4H, m), 5.19 (2H, s), 4.99 (2H, s), 3.62 (1H,m), 2.98 (1H, dd, J=17, 9 Hz), 2.84 (1H, dd, J=17, 5 Hz), 2.94–2.77 (7H, m), 1.47–1.06 (8H, m), 0.90 (2H, m).

Preparation 18: (3R)-3-{3-[(Benzylamino)carbonyl]-1,2,4-oxadiazol-5-yl}-6-cyclohexylhexanoic Acid

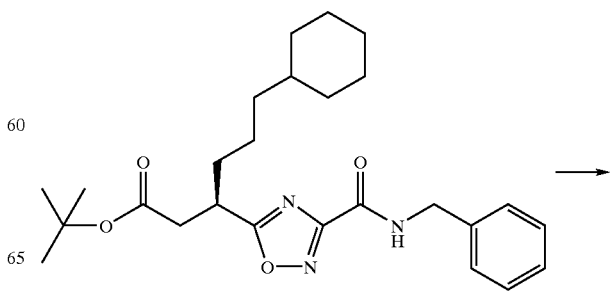

-continued

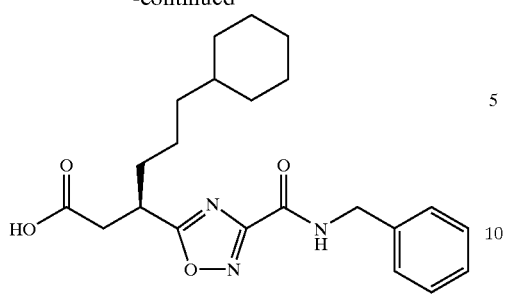

A solution of tert-butyl (3R)-3-{3-[(benzylamino)carbonyl]-1,2,4-oxadiazol-5-yl}-6-cyclohexylhexanoate (Preparation 16b) (173 mg, 0.38 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound as a beige solid (155 mg).

MS: 400 (MH$^+$), 417 (MNH$_4^+$)
$^1$H-NMR (CD$_3$OD) δ: 7.40–7.20 (5H, m), 4.56 (2H, s), 3.54 (1H, m), 2.93 (1H, dd, J=16, 8 Hz), 2.80 (1H, dd, J=16, 3 Hz), 1.83–1.67 (7H, m), 1.40–1.06 (8H, m), 0.86 (2H, m).

Preparation 19: tert-Butyl (3R)-6-cyclohexyl-3-{3-[3,4-dihydro-2(1H)-isoquinolinylcarbonyl]-1,2,4-oxadiazol-5-yl}hexanoate

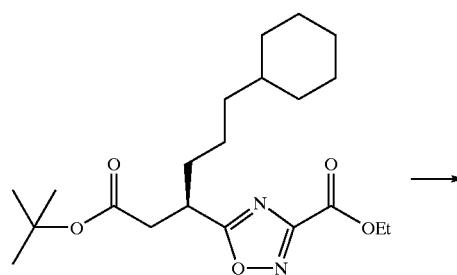

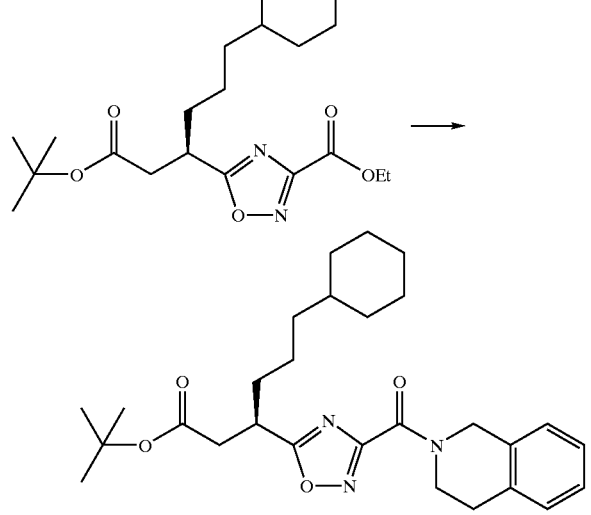

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated with 1,2,3,4-tetrahydroisoquinoline (0.95 ml, 7.60 mmol) and the resulting mixture was heated at 60° C. under a nitrogen atmosphere for 9 hours. The mixture was cooled and the solvent removed under reduced pressure. The residue was purified by column chromatography on silica gel eluting with dichloromethane:ethyl acetate (80:20). The residue was further purified by column chromatography on silica gel eluting with a gradient system of pentane:ethyl acetate (90:10) gradually changing to pentane:ethyl acetate (70:30) to afford the title compound (343 mg).

MS: 482 (MH$^+$), 499 (MNH$_4^+$)
$^1$H-NMR (CDCl$_3$) δ: (mixture of rotamers) 7.26–6.97 (4H, m), 4.92 (1.2H, s), 4.80 (0.8H, s), 4.00 (0.8H, m), 3.82 (1.2H, m), 3.53 (1H, m), 3.01–2.83 (3H, m), 2.67 (1H, dd, J=15, 3 Hz), 1.87–1.58 (7H, m), 1.40 (9H, s), 1.36–1.08 (8H, m), 0.83 (2H, m)

Preparation 20: (3R)-6-Cyclohexyl-3-{3-[3,4-dihydro-2(1H)-isoquinolinylcarbonyl]-1,2,4-oxadiazol-5-yl}hexanoic Acid

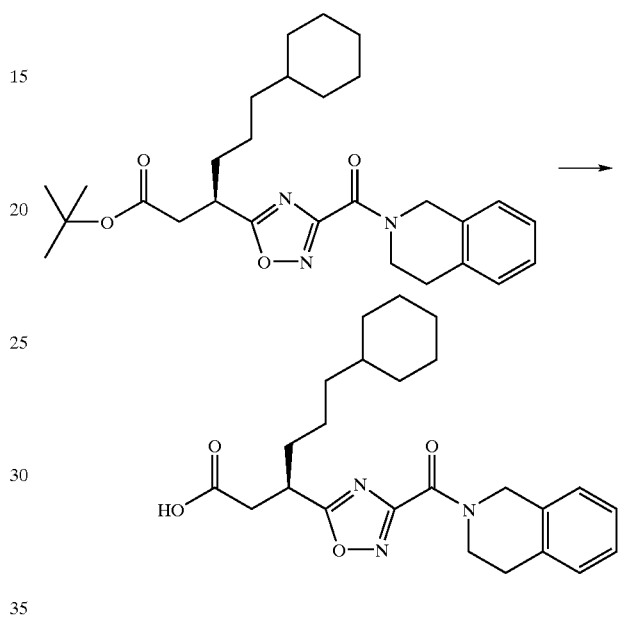

A solution of tert-butyl (3R)-6-cyclohexyl-3-{3-[3,4-dihydro-2(1H)-isoquinolinylcarbonyl]-1,2,4-oxadiazol-5-yl}hexanoate (Preparation 19) (343 mg, 0.71 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound (281 mg).

MS: 426 (MH$^+$), 443 (MNH$_4^+$)
$^1$H-NMR (CD$_3$OD) δ: (mixture of rotamers) 7.28–7.00 (4H, m), 4.87 (1.2H, s), 4.74 (0.8H, s), 3.99 (0.8H, m), 3.78 (1.2H, m), 3.57 (1H, m), 3.05–2.78 (4H, m), 1.86–1.57 (7H, m), 1.45–1.08 (8H, m), 0.87 (2H, m)

Preparation 21: tert-Butyl (3R)-6-cyclohexyl-3-[3-(4-morpholinylcarbonyl)-1,2,4-oxadiazol-5-yl]hexanoate

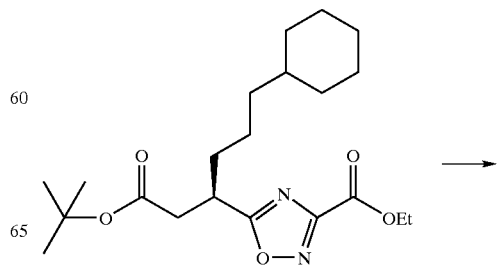

-continued

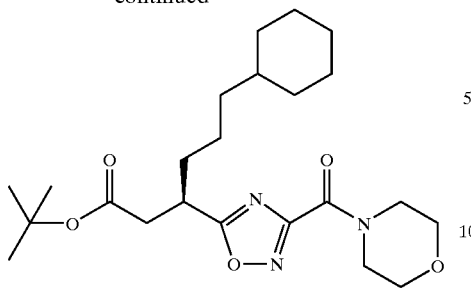

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was cooled to 0° C. then treated with morpholine (0.066 ml, 7.60 mmol). The resulting mixture was warmed to room temperature and stirred under a nitrogen atmosphere for 17 hours. Further morpholine (0.53 ml, 6.08 mmol) was added and the mixture heated to 60° C. for 8 hours. The mixture was cooled and the solvent was removed under reduced pressure. The residue was purified by column chromatography on silica gel eluting with dichloromethane-:ethyl acetate (80:20) to afford title compound as a yellow oil (269 mg)

MS: 436 (MH$^+$), 453 (MNH$_4^+$)

$^1$H-NMR (CDCl$_3$) δ: 3.80 (4H, m), 3.67 (4H, m), 3.49 (1H, m), 2.84 (2H, dd, J=14, 8 Hz), 2.65 (1H, dd, J=14, 3 Hz), 1.84–1.57 (7H, m), 1.39 (9H, s), 1.33–1.06 (8H, m), 0.81 (2H, m)

Preparation 22: (3R)-6-Cyclohexyl-3-[3-(4-morpholinylcarbonyl)-1,2,4-oxadiazol-5-yl]hexanoic Acid

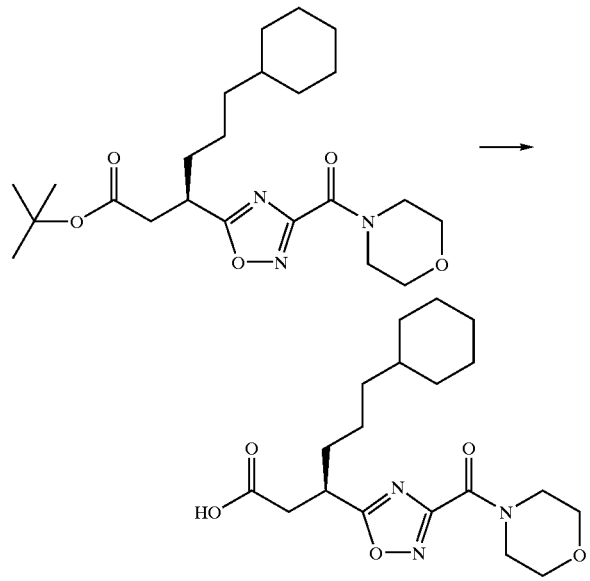

A solution of tert-butyl (3R)-6-cyclohexyl-3-[3-(4-morpholinylcarbonyl)-1,2,4-oxadiazol-5-yl]hexanoate (Preparation 21) (269 mg, 0.62 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound (219 mg).

MS: 380 (MH$^+$), 397 (MNH$_4^+$)

$^1$H-NMR (CDCl$_3$) δ: 3.80 (4H, m), 3.68 (4H, m), 3.54 (1H, m), 3.00 (1H, dd, J=14, 8 Hz), 2.78 (1H, dd, J=14, 3 Hz), 1.88–1.57 (7H, m), 1.40–1.04 (8H, m), 0.85 (2H, m)

Preparation 23: tert-Butyl (3R)-6-cyclohexyl-3-{3-[(4-methyl-1-piperazinyl)carbonyl]-1,2,4-oxadiazol-5-yl}hexanoate

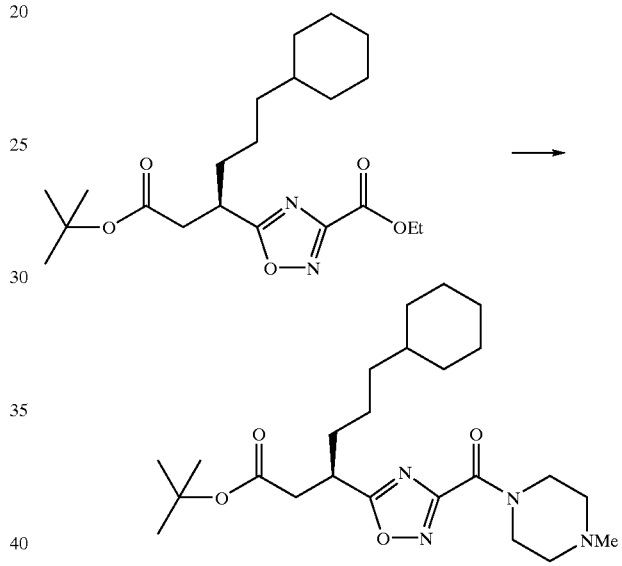

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated with 1-methylpiperazine (0.84 ml, 7.60 mmol) and the resulting mixture was heated at 60° C. under a nitrogen atmosphere for 16 hours. The mixture was cooled and the solvent removed under reduced pressure. The residue was purified by column chromatography on silica gel eluting with a gradient system of dichloromethane:methanol (98:2) gradually changing to dichloromethane:methanol (95:5) to afford the title compound (312 mg).

MS: 449 (MH$^+$)

$^1$H-NMR (CDCl$_3$) δ: 3.80 (2H, m), 3.59 (2H, m), 3.47 (1H, m), 2.85 (1H, m), 2.65 (1H, m), 2.54–2.36 (4H, m), 2.30 (3H, s), 1.85–1.54 (7H, m), 1.37 (9H, s), 1.33–1.04 (8H, m), 0.81 (2H, m)

Preparation 24: (3R)-6-Cyclohexyl-3-{3-[(4-methyl-1-piperazinyl)carbonyl]-1,2,4-oxadiazol-5-yl}hexanic Acid Trifluoroacetate

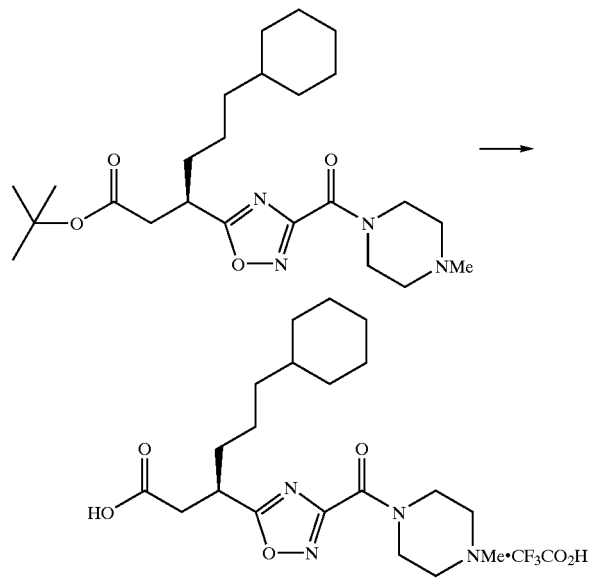

A solution of tert-butyl (3R)-6-cyclohexyl-3-{3-[(4-methyl-1-piperazinyl)carbonyl]-1,2,4-oxadiazol-5-yl}hexanoate (Preparation 23) (312 mg, 0.70 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound as a white foam (320 mg).

MS: 393 (MH⁺)

$^1$H-NMR (CD$_3$OD) δ: 4.03 (4H, br m), 3.56 (1H, m), 3.41 (4H, m), 2.98–2.78 (5H, m), 1.83 (1H, m), 1.40–1.12 (8H, m), 0.87 (2H, m)

Preparation 25: tert-Butyl (3R)-6-cyclohexyl-3-(3-{[4-(dimethylamino)-1-piperidinyl]carbonyl}-1,2,4-oxadiazol-5-yl)hexanoate

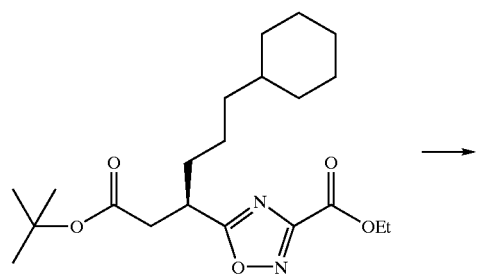

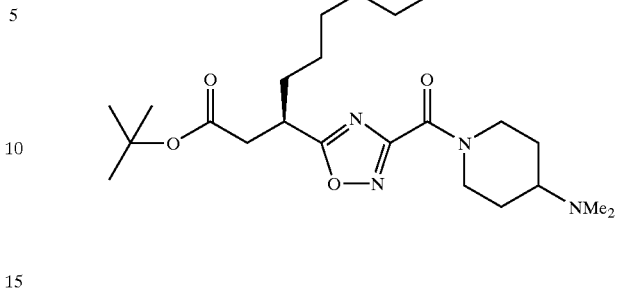

A solution of ethyl 5-{(1R)-1-[2-(tert-butoxy)-2-oxoethyl]-4-cyclohexylbutyl}-1,2,4-oxadiazole-3-carboxylate (Preparation 3) (800 mg, 2.03 mmol) in ethanol (10 ml) was treated with N,N-dimethyl-N-(4-piperidinyl)amine (1.23 g, 9.61 mmol) and the resulting mixture was heated under reflux under a nitrogen atmosphere for 3 hours. The solvent was removed under reduced pressure and the residue was partitioned between ethyl acetate and water. The layers were separated and the aqueous layer was extracted with ethyl acetate. The combined organic layers were washed sequentially with water and brine, dried over anhydrous sodium sulphate, filtered and the solvent was removed under reduced pressure. The residue was purified by column chromatography on silica gel eluting with dichloromethane:methanol (90:10) to give a residue which was further purified by column chromatography on silica gel eluting with dichloromethane:methanol:0.88 ammonia (90:10:0.5) to afford the title compound as a yellow oil (653 mg).

MS: 477 (MH⁺)

$^1$H-NMR (CDCl$_3$) δ: 4.77 (1H, m), 4.05 (1H, m), 3.50 (1H, m), 3.13 (1H, m), 2.92–2.60 (4H, m), 2.40 (6H, s), 2.04–1.50 (9H, m), 1.40 (9H, s), 1.36–1.07 (10H, m), 0.84 (2H, m)

Preparation 26: (3R)-6-Cyclohexyl-3-(3-{[4-(dimethylamino)-1-piperidinyl]carbonyl}-1,2,4-oxadiazol-5-yl)hexanoic Acid Trifluoroacetate

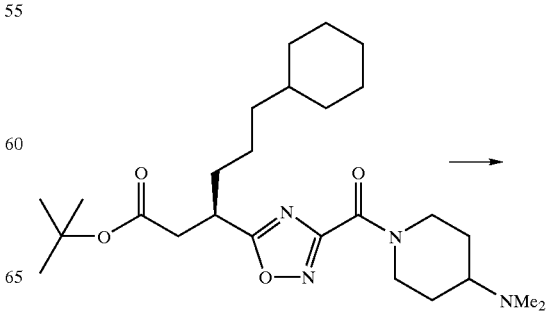

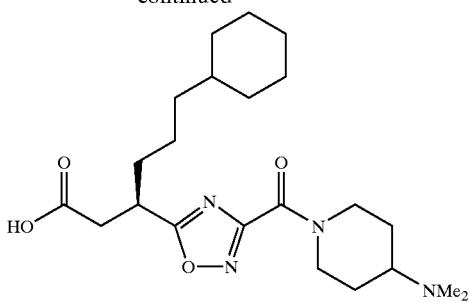

A solution of tert-butyl (3R)-6-cyclohexyl-3-(3-{[4-(dimethylamino)-1-piperidinyl]carbonyl}-1,2,4-oxadiazol-5-yl)hexanoate (Preparation 25) (652 mg, 1.37 mmol) in dichloromethane (15 ml) was cooled to 0° C. and treated with trifluoroacetic acid (5 ml). The resulting mixture was stirred for 2 hours being allowed to warm to room temperature over this time. The solvent was removed under reduced pressure and the residue azeotroped from toluene. The residue was purified by column chromatography on silica gel eluting with a gradient system of dichloromethane:methanol:0.88 ammonia (90:10:1) gradually changing to dichloromethane:methanol:0.88 ammonia (70:30:2) to afford the title compound as a colourless oil (702 mg).

MS: 421 (MH$^+$)

$^1$H-NMR (CD$_3$OD) δ: 4.80 (1H, m), 4.09 (1H, m), 3.55 (1H, m), 3.22 (2H, m), 2.93 (1H, m), 2.83–2.60 (8H, m), 2.20–2.00 (2H, m), 1.82–1.54 (9H, m), 1.41–1.07 (8H, m), 0.87 (2H, m)

Preparation 27: tert-Butyl (3R)-6-cyclohexyl-3-(3-{[3-(4-morpholinyl)-1-azetidinyl]carbonyl}-1,2,4-oxadiazol-5-yl)hexanoate

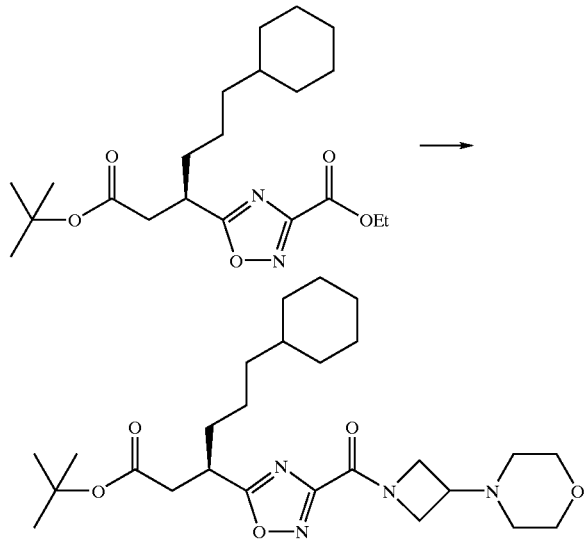

A solution of ethyl 5-{(1R)-1-[2-(tert-butoxy)-2-oxoethyl]-4-cyclohexylbutyl}-1,2,4-oxadiazole-3-carboxylate (Preparation 3) (1.00 g, 2.54 mmol) in ethanol (10 ml) was treated with 4-(3-azetidinyl)morpholine dihydrochloride (2.72 g, 12.6 mmol) and triethylamine (2.56 g, 25 mmol) and the resulting mixture was heated under reflux under a nitrogen atmosphere for 24 hours. The solvent was removed under reduced pressure and the residue was partitioned between ethyl acetate and water. The layers were separated and the aqueous layer was extracted with ethyl acetate. The combined organic layers were washed sequentially with water and brine, dried over anhydrous sodium sulphate, filtered and the solvent removed under reduced pressure. The residue was purified by column chromatography on silica gel eluting with a gradient system of dichloromethane:methanol (97:3) gradually changing to dichloromethane:methanol (95:5) to afford the title compound as a colourless oil (1.32 g).

MS: 491 (MH$^+$), 508 (MNH$_4^+$)

$^1$H-NMR (CD$_3$OD) δ: 4.64 (1H, m), 4.43 (1H, m), 4.25 (1H, m), 4.05 (1H, m), 3.73 (4H, m), 3.52 (1H, m), 3.31 (1H, m), 2.84–2.66 (2H, m), 2.45 (4H, m), 1.85–1.55 (7H, m), 1.46–1.05 (17H, m), 0.86 (2H, m)

Preparation 28: (3R)-6-Cyclohexyl-3-(3-{[3-(4-morpholinyl)-1-azetidinyl]carbonyl}-1,2,4-oxadiazol-5-yl)hexanoic Acid Trifluoroacetate

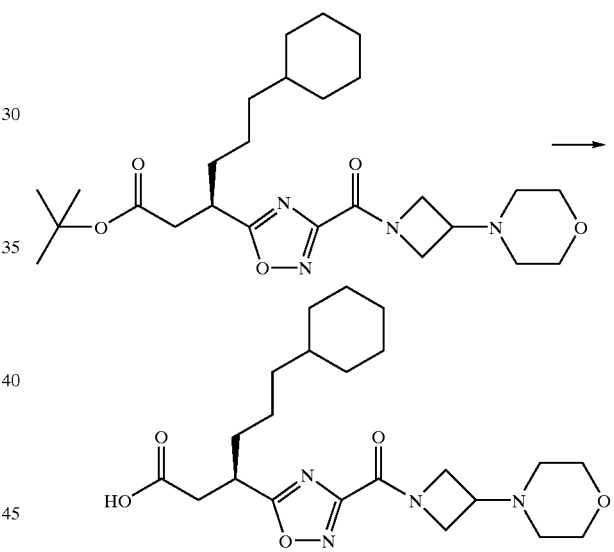

A solution of tert-butyl (3R)-6-cyclohexyl-3-(3-{[3-(4-morpholinyl)-1-azetidinyl]carbonyl}-1,2,4-oxadiazol-5-yl)hexanoate (Preparation 27) (1.32 g, 2.70 mmol) in dichloromethane (15 ml) was cooled to 0° C. and treated with trifluoroacetic acid (5 ml). The resulting mixture was stirred for 3 hours being allowed to warm to room temperature over this time. The solvent was removed under reduced pressure and the residue azeotroped from toluene (×3) then dichloromethane to afford the title compound as a white foam (1.31 g).

MS: 435 (MH$^+$)

$^1$H-NMR (CD$_3$OD) δ: 4.86 (1H, m), 4.50 (1H, m), 4.39 (1H, m), 4.14 (1H, m), 3.92 (4H, m), 3.56 (1H, m), 3.37–3.17 (5H, m), 2.93 (1H, dd, J=13, 8 Hz), 2.82 (1H, dd, J=13, 3 Hz), 1.83–1.59 (7H, m), 1.39–1.09 (8H, m), 0.86 (2H, m)

Preparation 29: tert-Butyl (3R)-6-cyclohexyl-3-{3-[7,8-dihydro[1,6]naphthyridin-6(5H)-ylcarbonyl]-1,2,4-oxadiazol-5-yl}hexanoate

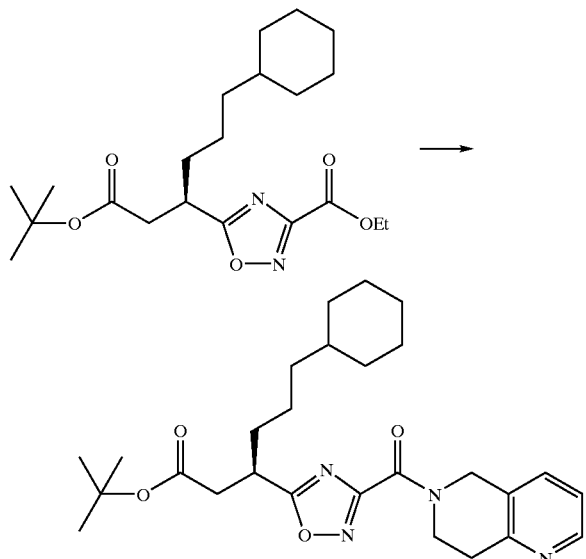

A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated with 5,6,7,8-tetrahydro[1,6]naphthyridine dihydrochloride (Chem.Pharm.Bull.; 32; 7; 1984; 2522–2529) (0.79 g, 3.80 mmol) and triethylamine (1.27 ml, 9.13 mmol) and the resulting mixture was heated at 60° C. under a nitrogen atmosphere for 16 hours. The mixture was cooled and the solvent removed under reduced pressure. The residue was purified by column chromatography on silica gel eluting with a gradient system of dichloromethane:ethyl acetate (90:10) gradually changing to dichloromethane:ethyl acetate (50:50) to afford the title compound (281 mg).

MS: 483 (MH+), 505 (MNa+)

$^{1}$H-NMR (CDCl$_{3}$) δ: (mixture of rotamers) 8.44 (1H, d, J=3 Hz), 7.48 (0.67H, d, J=6 Hz), 7.33 (0.33H, d, J=6 Hz), 7.20–7.10 (1H, m), 4.92 (1.34H, s), 4.83 (0.66H, S), 4.13 (0.66H, t,J=5 Hz), 3.94 (1.34H, t, J=5 Hz), 3.52 (1H, m), 3.13 (2H, m), 2.87 (1H, dd, J=14, 7 Hz), 2.67 (1H, dd, J=14, 3 Hz), 1.85–1.56 (7H, m), 1.39 (9H, d), 1.35–1.04 (8H, m), 0.83 (2H, m)

Preparation 30: (3R)-6-Cyclohexyl-3-{3-[7,8-dihydro[1,6]naphthyridin-6(5H)-ylcarbonyl]-1,2,4-oxadiazol-5-yl}hexanoic Acid Trifluoroacetate

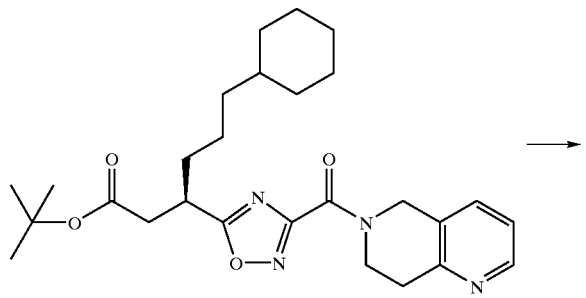

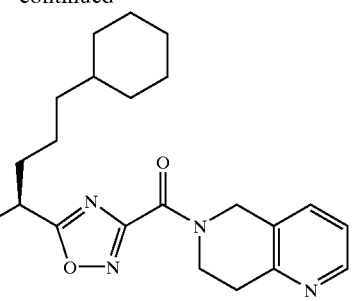

A solution of tert-butyl (3R)-6-cyclohexyl-3-{3-[7,8-dihydro[1,6]naphthyridin-6(5H)-ylcarbonyl]-1,2,4-oxadiazol-5-yl}hexanoate (Preparation 29) (281 mg, 0.58 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound (245 mg).

MS: 427 (MH+)

$^{1}$H-NMR (CD$_{3}$OD) δ: (mixture of rotamers) 8.56 (1H, d, 5 Hz), 8.17 (0.67H, d, J=8 Hz), 8.01 (0.33H, d, J=8 Hz), 7.73–7.56 (1H, m), 5.05 (1.34H, s), 5.00 (0.66H, s), 4.16 (0.66H, m), 4.01 (1.34H, m), 3.59 (1H, m), 3.24 (2H, m), 3.04–2.76 (2H, m), 1.92–1.55 (7H, m), 1.46–1.06 (8H, m), 0.87 (2H, m)

Preparation 31: tert-Butyl (3R)-6-cyclohexyl-3-(3-{[4-(4-pyridinyl)-1-piperidinyl]carbonyl}-1,2,4-oxadiazol-5-yl)hexanoate

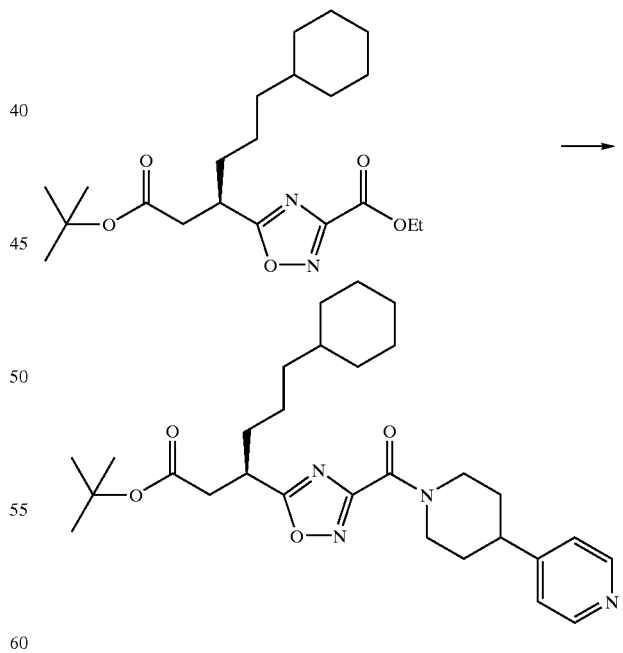

A solution of ethyl 5-{(1R)-1-[2-(tert-butoxy)-2-oxoethyl]-4-cyclohexylbutyl}-1,2,4-oxadiazole-3-carboxylate (Preparation 3) (0.50 g, 1.27 mmol) in ethanol (10 ml) was treated with 4-(4-pyridinyl)piperidine (Monatsh.Chem.; 3; 1882; 867) (0.41 g, 2.54 mmol) and the resulting mixture was heated under reflux under a nitrogen atmosphere for 72 hours. Further 4-(4-pyridinyl)piperidine (0.21 g, 1.27 mmol) was added and the mixture heated under reflux for 24 hours. The solvent was removed under reduced pressure and the residue was partitioned between ethyl acetate and water. The layers were separated and the aqueous layer extracted with ethyl acetate. The combined organic layers were washed sequentially with water and brine, dried over anhydrous sodium sulphate, filtered and the solvent removed under reduced pressure. The residue was purified by column chromatography on silica gel eluting with a gradient system of dichloromethane:methanol (99:1) gradually changing to dichloromethane:methanol (95:5) to afford the title compound as a pale yellow oil (0.39 g).

MS: 511 (MH$^+$)

$^1$H-NMR (CD$_3$OD) δ: 8.44 (2H, d, J=4 Hz), 7.35 (2H, d, J=4 Hz), 4.79 (1H, m), 4.00 (1H, m), 3.53 (1H, m), 3.34 (1H, m), 3.00 (2H, m), 2.84 (1H, dd, J=14, 8 Hz), 2.75 (1H, dd, 14, 5 Hz), 2.02 (1H, m), 1.92 (1H, m), 1.83–1.58 (9H, m), 1.44–1.09 (17H, m), 0.86 (2H, m)

Preparation 32: (3R)-6-Cyclohexyl-3-(3-{[4-(4-pyridinyl)-1-piperidinyl]carbonyl}-1,2,4-oxadiazol-5-yl)hexanoic Acid

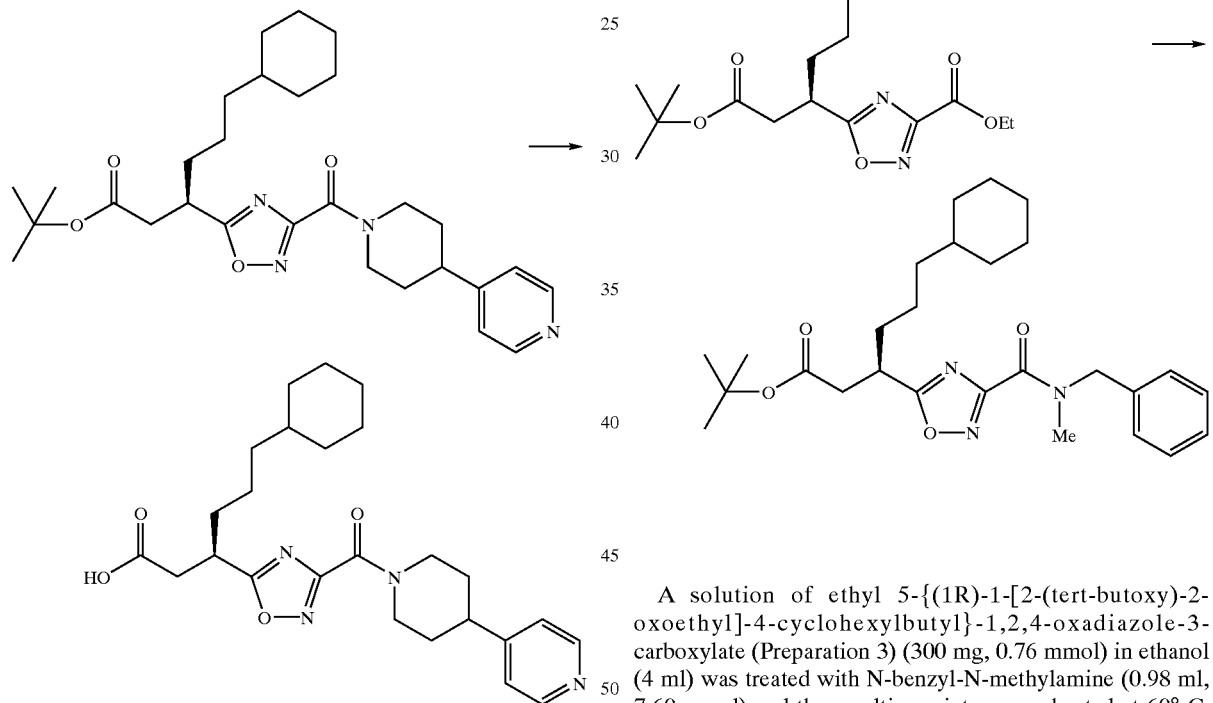

A solution of tert-butyl (3R)-6-cyclohexyl-3-(3-{[4-(4-pyridinyl)-1-piperidinyl]carbonyl}-1,2,4-oxadiazol-5-yl) hexanoate (Preparation 31) (376 mg, 0.74 mmol) in dichloromethane (15 ml) was cooled to 0° C. and treated with trifluoroacetic acid (5 ml). The resulting mixture was stirred for 3 hours being allowed to warm to room temperature over this time. The solvent was removed under reduced pressure and the residue azeotroped from toluene (×3) then dichloromethane. A saturated solution of sodium carbonate was added to the residue until a pH of 12 was achieved followed by dropwise addition of an aqueous citric acid solution solution (10% w/v) until the pH became 3.5. The solution was then diluted with water and extracted with ethyl acetate (×3). The combined organic layers were washed with brine, dried over anhydrous sodium sulphate, filtered and the solvent removed under reduced pressure to afford the title compound as a white solid (310 mg).

MS: 455 (MH$^+$)

$^1$H-NMR (CD$_3$OD) δ: 8.44 (2H, d, J=4 Hz), 7.36 (2H, d, J=4 Hz), 4.78 (1H, m), 3.97 (1H, m), 3.56 (1H, m), 3.34 (1H, m), 3.06–2.75 (4H, m), 2.01 (1H, m), 1.92 (1H, m), 1.83–1.56 (9H, m), 1.40–1.04 (8H, m), 0.85 (2H, m)

Preparation 33: tert-Butyl (3R)-3-(3-{[benzyl (methyl)amino]carbonyl}-1,2,4-oxadiazol-5-yl)-6-cyclohexylhexanoate A solution of ethyl 5-{(1R)-1-[2-(tert-butoxy)-2-oxoethyl]-4-cyclohexylbutyl}-1,2,4-oxadiazole-3-carboxylate (Preparation 3) (300 mg, 0.76 mmol) in ethanol (4 ml) was treated with N-benzyl-N-methylamine (0.98 ml, 7.60 mmol) and the resulting mixture was heated at 60° C. under a nitrogen atmosphere for 16 hours. The mixture was cooled and the solvent removed under reduced pressure. The residue was purified by column chromatography on silica gel eluting with a gradient system of dichloromethane:ethyl acetate (100:0) gradually changing to dichloromethane:ethyl acetate (95:5) to afford the title compound (296 mg).

MS: 470 (MH$^+$), 487 (MNH$_4^+$)

$^1$H-NMR (CD$_3$OD) δ: (mixture of rotamers) 7.42–7.21 (5H, m), 4.79 (1H, d, J=15 Hz), 4.63 (1H, d, J=15 Hz), 3.52 (1H, m), 3.00 (3H, m), 2.90–2.67 (2H, m), 1.85–1.57 (7H, m), 1.41–1.04 (17H, m), 0.84 (2H, m)

Preparation 34: (3R)-3-(3-{[Benzyl(methyl)amino]carbonyl}-1,2,4-oxadiazol-5-yl)-6-cyclohexylhexanoic Acid

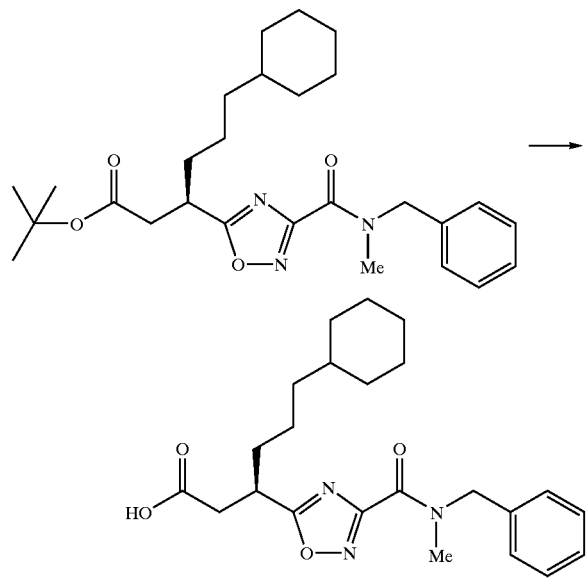

A solution of tert-butyl (3R)-3-(3-{[benzyl(methyl)amino]carbonyl}-1,2,4-oxadiazol-5-yl)-6-cyclohexylhexanoate (Preparation 33) (296 mg, 0.63 mmol) in dichloromethane (4 ml) was treated with trifluoroacetic acid (1 ml) and the resulting mixture was stirred at room temperature under a nitrogen atmosphere for 17 hours. The solvent was removed under reduced pressure and the residue azeotroped from toluene to afford the title compound (226 mg).

MS: 414 (MH$^+$), 431 (MNH$_4^+$)

$^1$H-NMR (CD$_3$OD) δ: (mixture of rotamers) 7.42–7.22 (5H, m), 4.79 (1H, d, J=15 Hz), 4.58 (1H, d, 15 Hz), 3.56 (1H, m), 3.00 (3H, d), 2.97–2.73 (2H, m), 1.84–1.55 (7H, m), 1.41–1.03 (8H, m), 0.83 (2H, m)

Preparation 35: tert-Butyl (3R)-6-cyclohexyl-3-(3-{[methyl(2-pyridinylmethyl)amino]carbonyl}-1,2,4-oxadiazol-5-yl)hexanoate

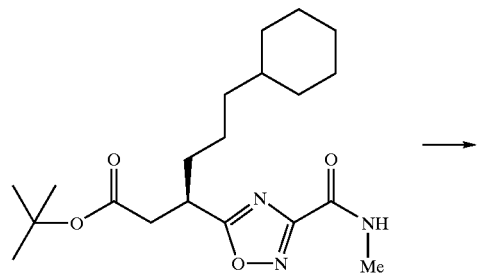

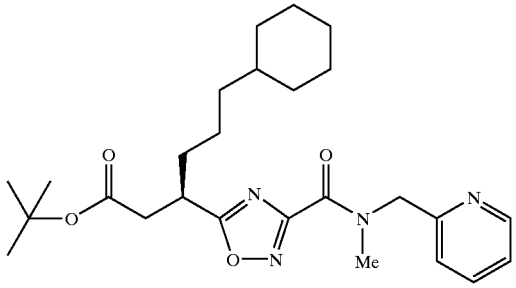

1-1'-Azobis(N,N-dimethylformamide) (645 mg, 3.75 mmol) was added to a cooled solution of tert-butyl (3R)-6-cyclohexyl-3-{3-[(methylamino)carbonyl]-1,2,4-oxadiazol-5-yl}hexanoate (Preparation 7) (1.42 g, 3.75 mmol), tributylphosphine (930 μl, 3.75 mmol) and 2-hydroxymethylpyridine (240 μl, 2.50 mmol) in toluene (10 ml) and the resulting mixture was stirred at 0° C. under a nitrogen atmosphere for 15 minutes, then at room temperature for 72 hours. The mixture was filtered and the solvent removed from the filtrate under reduced pressure. The residue was purified by column chromatography on silica gel eluting with a gradient system of hexane:ethyl acetate (90:10) gradually changing to hexane:ethyl acetate (50:50) to afford the title compound as a pale yellow oil (530 mg).

MS: 472 (MH$^+$)

$^1$H-NMR (CDCl$_3$) δ: (mixture of rotamers) 8.54 (1H, m), 7.68 (1H, m), 7.44–7.15 (2H, m), 4.68 (1H, s), 4.79 (1H, s), 3.51 (1H, m), 3.16 (1.5H, s), 3.10 (1.5H, s), 2.84 (1H, m), 2.63 (1H, m), 1.89–1.52 (7H, m), 1.36 (9H, d), 1.31–1.00 (8H, m), 0.81 (2H, m)

Preparation 36: (3R)-6-Cyclohexyl-3-(3-{[methyl(2-pyridinylmethyl)amino]carbonyl}-1,2,4-oxadiazol-5-yl)hexanoic Acid

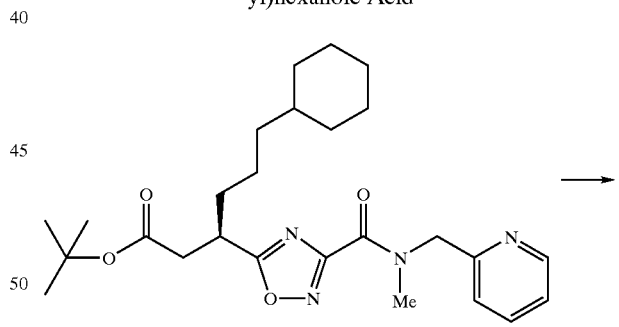

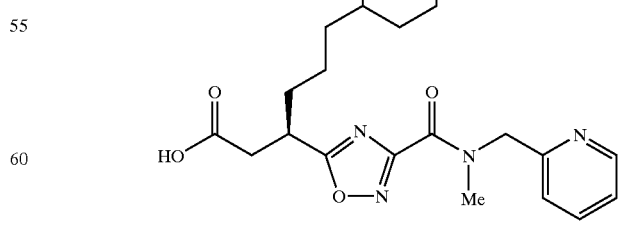

A solution of tert-butyl (3R)-6-cyclohexyl-3-(3-{[methyl(2-pyridinylmethyl)amino]carbonyl}-1,2,4-oxadiazol-5-yl)hexanoate (Preparation 35) (527 mg, 1.12 mmol) in dichloromethane (20 ml) was treated with trifluoroacetic acid (10 ml) and the resulting mixture was stirred at room temperature under a nitrogen atmosphere for 2 hours. The solvent was removed under reduced pressure and the residue was azeotroped from toluene. The residue was dissolved in a saturated aqueous solution of sodium hydrogen carbonate (3 ml) and the pH was adjusted to pH 4 with aqueous citric acid solution (10%w/v). The aqueous phase was extracted with ethyl acetate (×2) and the combined organic layers were washed with brine, dried over anhydrous sodium sulphate, filtered and the solvent removed under reduced pressure to afford the title compound as a yellow oil (456 mg)

MS: 414 (M$^+$)

$^1$H-NMR (CDCl$_3$) δ: (mixture of rotamers) 8.51 (1H, m), 7.75 (1H, m), 7.47 (0.5H, d, J=6 Hz), 7.40 (0.5H, d, J=6 Hz), 7.23 (1H, m), 4.96–4.66 (2H, m), 3.51 (1H, m), 3.10 (3H, d), 3.05–2.66 (2H, m), 1.89–1.52 (7H, m), 1.40–1.01 (8H, m), 0.82 (2H, m)

Preparation 37: tert-Butyl (3R)-6-cyclohexyl-3-(3-{[(2-methoxy-2-oxoethyl)amino]carbonyl}-1,2,4-oxadiazol-5-yl)hexanoate

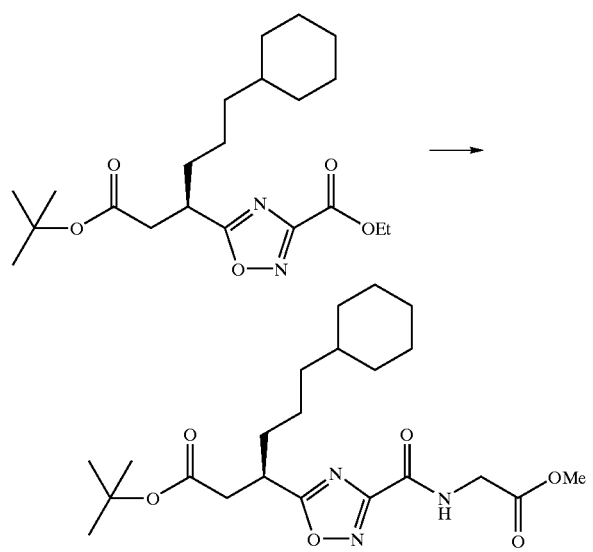

A solution of ethyl 5-{(1R)-1-[2-(tert-butoxy)-2-oxoethyl]-4-cyclohexylbutyl}-1,2,4-oxadiazole-3-carboxylate (Preparation 3) (1.18 g, 3.00 mmol) and triethylamine (1.51 g, 15.00 mmol) in ethanol (30 ml) was treated with glycine methyl ester hydrochloride (1.88 g, 15.00 mmol) and the resulting mixture was heated at 80° C. under a nitrogen atmosphere for 16 hours. The mixture was cooled and the solvent removed under reduced pressure. The residue was partitioned between water and ethyl acetate. The combined organic layers were washed with brine, dried over anhydrous sodium sulphate, filtered and the solvent removed under reduced pressure. The residue was purified by column chromatography on silica gel eluting with a gradient system of hexane:ethyl acetate (90:10) gradually changing to hexane:ethyl acetate (50:50) to afford the title compound (456 mg).

MS: 455 (MNH$_4^+$)

$^1$H-NMR (CDCl$_3$) δ: 7.42 (1H, br t), 4.25 (2H, d, J=4 Hz), 3.80 (3H, s), 3.51 (1H, m), 2.84 (1H, dd, J=14, 9 Hz), 2.66 (1H, dd, J=14, 3 Hz), 1.83–1.55 (7H, m), 1.38 (9H, s), 1.34–1.07 (8H, m), 0.84 (2H, m)

Preparation 38: tert-Butyl (3R)-6-cyclohexyl-3-(3-{[(2-methoxy-2-oxoethyl)(methyl)amino]carbonyl}-1,2,4-oxadiazol-5-yl)hexanoate

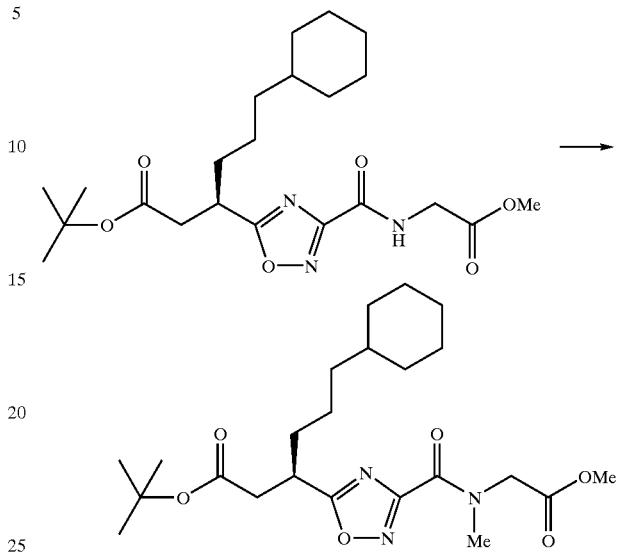

A solution of tert-butyl (3R)-6-cyclohexyl-3-(3-{[(2-methoxy-2-oxoethyl)amino]carbonyl}-1,2,4-oxadiazol-5-yl)hexanoate (Preparation 37) (440 mg, 1.00 mmol) in anhydrous dimethylsulphoxide (10 ml) was treated with iodomethane (310 μl, 5.00 mmol) and cesium carbonate (975 mg, 3.00 mmol) and the resulting mixture was heated at 40° under a nitrogen atmosphere for 3 hours then stirred at room temperature for 17 hours. The mixture was diluted with water and extracted with diethyl ether (×3). The combined organic extracts were washed with brine, dried over anhydrous sodium sulphate, filtered and the solvent removed under reduced pressure. The residue was purified by column chromatography on silica gel eluting with hexane:ethyl acetate (2:1) to afford the title compound as a colourless oil (315 mg)

MS: 452 (MH$^+$)

$^1$H-NMR (CDCl$_3$) δ: (mixture of rotamers) 4.36 (1H, s), 4.30 (1H, s), 3.76 (3H, d), 3.51 (1H, m), 3.25 (1.5H, s), 3.20 (1.5H, s), 2.86 (1H, m), 2.66 (1H, m), 1.85–1.57 (7H, m), 1.39 (9H, s), 1.34–1.04 (8H, m), 0.84 (2H, m)

Preparation 39: (3R)-6-Cyclohexyl-3-(3-{[(2-methoxy-2-oxoethyl)(methyl)amino]carbonyl}-1,2,4-oxadiazol-5-yl)hexanoic Acid

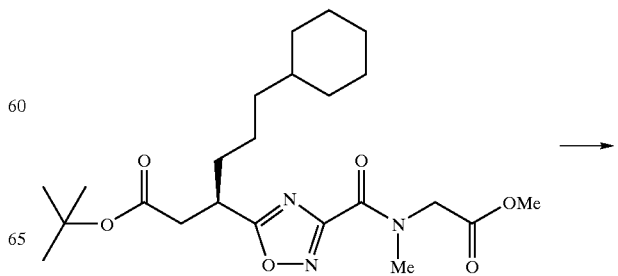

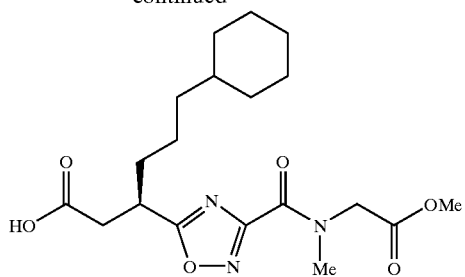

A solution of tert-butyl (3R)-6-cyclohexyl-3-(3-{[(2-methoxy-2-oxoethyl)(methyl)amino]carbonyl}-1,2,4-oxadiazol-5-yl)hexanoate (Preparation 38) (315 mg, 0.70 mmol) in dichloromethane (10 ml) was treated with trifluoroacetic acid (5 ml) and the resulting mixture was stirred at room temperature under a nitrogen atmosphere for 2 hours. The solvent was removed under reduced pressure and the residue azeotroped from toluene. The residue was dissolved in ethyl acetate and washed with a saturated aqueous solution of sodium citrate and brine, dried over anhydrous sodium sulphate, filtered and the solvent removed under reduced pressure to afford the title compound as an oil (273 mg)

MS: 396 (MH$^+$), 418 (MNa$^+$)

$^1$H-NMR (CDCl$_3$) δ: (mixture of rotamers) 4.26 (1.6H, m), 4.11 (0.4H, m), 3.75 (3H, d), 3.52 (1H, m), 3.21 (3H, d), 3.00 (1H, m), 2.78 (1H, m), 1.89–1.41 (7H, m), 1.38–0.95 (8H, m), 0.80 (2H, m)

Preparation 40/Example 41: Methyl 2-[[(5-{(1R)-4-cyclohexyl-1-[2-(hydroxyamino)-2-oxoethyl]butyl}-1,2,4-oxadiazol-3-yl)carbonyl](methyl)amino]acetate

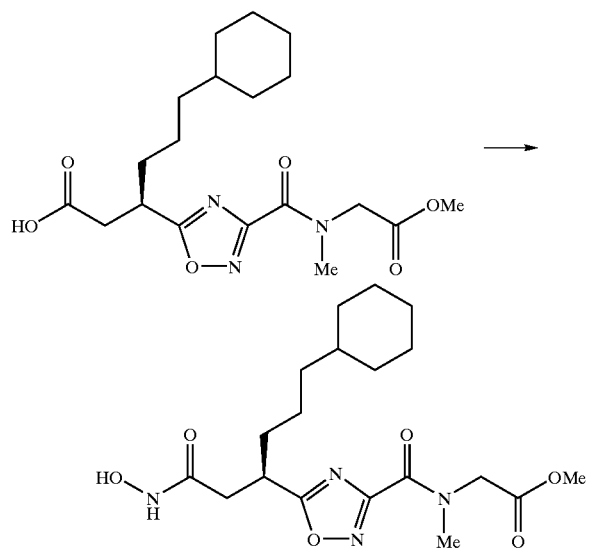

A solution of (3R)-6-cyclohexyl-3-(3-{[(2-methoxy-2-oxoethyl)(methyl)amino]carbonyl}-1,2,4-oxadiazol-5-yl)hexanoic acid (Preparation 39) (273 mg, 0.70 mmol) and N-methylmorpholine (85 μl, 0.77 mmol) in anhydrous dichloromethane (10 ml) was cooled to 0° C., treated with isobutyl chloroformate (100 μl, 0.77 mmol) and the resulting mixture was stirred under a nitrogen atmosphere for 30 minutes. O-(Trimethylsilyl)hydroxylamine (250 μl, 2.10 mmol) was then added and the mixture stirred under a nitrogen atmosphere for 1 hour, being allowed to warm to room temperature over this time. The mixture was then quenched with methanol (10 ml) and stirred for 10 minutes. The solvent was removed under reduced pressure and the residue partitioned between ethyl acetate and water. The layers were separated and the organic layer was sequentially washed with water and brine, dried over anhydrous sodium sulphate, filtered and the solvent removed under reduced pressure. The residue was purified by HPLC$^a$ to afford the title compound as a colourless oil (187 mg).

MS: 411 (MH$^+$), 433 (MNa$^+$)

$^1$H-NMR (CDCl$_3$) δ: (mixture of rotamers) 4.50–4.21 (2H, m), 3.84–3.60 (4H, m), 3.32 (1.8H, s), 3.21 (1.2H, s), 2.81–2.56 (2H, m), 1.90–1.50 (7H, m), 1.40–1.03 (8H, m), 0.82 (2H, m)

Preparation 41: 1-[(5-{(1R)-1-[2-(tert-Butoxy)-2-oxoethyl]-4-cyclohexylbutyl}-1,2,4-oxadiazol-3-yl)carbonyl]-3-azetidinecarboxylic Acid

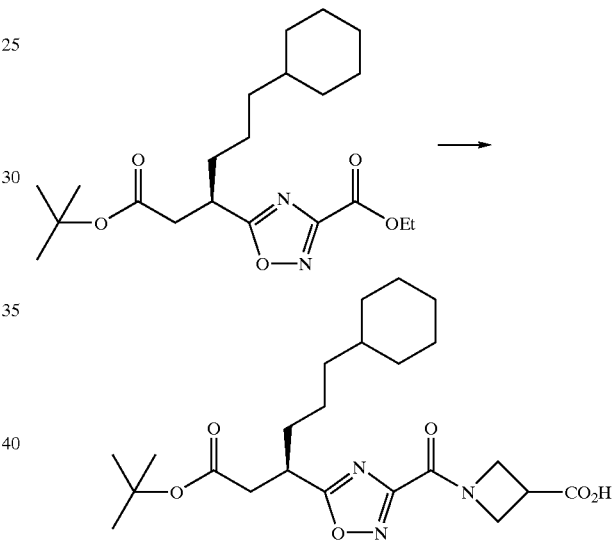

A solution of ethyl 5-{(1R)-1-[2-(tert-butoxy)-2-oxoethyl]-4-cyclohexylbutyl}-1,2,4-oxadiazole-3-carboxylate (Preparation 3) (790 mg, 2.00 mmol) in dimethylsulphoxide (25 ml) was treated with 3-azetidine carboxylic acid (505 mg, 5.00 mmol) and potassium carbonate (690 mg, 5.00 mmol) and the resulting mixture was heated at 95° C. under a nitrogen atmosphere for 16 hours. The mixture was cooled and the mixture treated with hydrochloric acid (1M, 25 ml) then diluted further with water (25 ml) and extracted with ethyl acetate (×3). The combined organic layers were washed with brine, dried over anhydrous sodium sulphate, filtered and the solvent removed under reduced pressure. The residue was purified by column chromatography on silica gel eluting with a gradient system of dichloromethane:methanol (99:1) gradually changing to dichloromethane:methanol (90:10) to afford the title compound as a pale yellow oil (490 mg).

$^1$H-NMR (CDCl$_3$) δ: 4.76 (2H, m), 4.45 (2H, m), 3.64–3.43 (2H, m), 2.89 (1H, dd, J=15, 8 Hz), 2.65 (1H, dd, J=15, 4 Hz), 1.84–1.56 (7H, m), 1.38 (9H, s), 1.34–1.03 (8H, m), 0.84 (2H, m)

Preparation 42: Methyl 1-[(5-{(1R)-1-[2-(tert-butoxy)-2-oxoethyl]-4-cyclohexylbutyl}-1,2,4-oxadiazol-3-yl)carbonyl]-3-azetidinecarboxylate

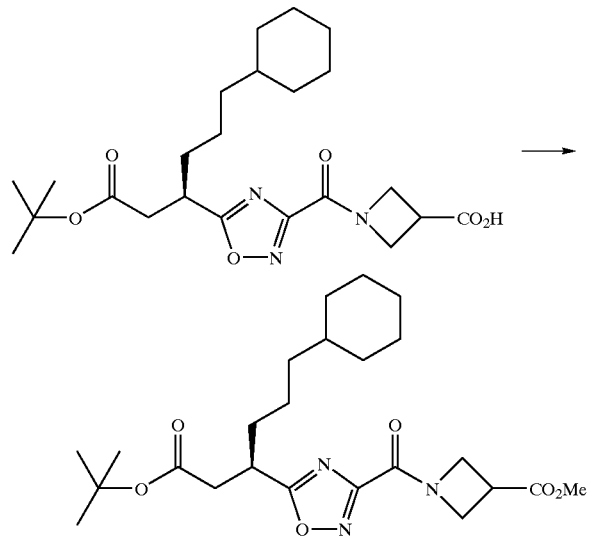

A solution of 1-[(5-{(1R)-1-[2-(tert-butoxy)-2-oxoethyl]-4-cyclohexylbutyl}-1,2,4-oxadiazol-3-yl)carbonyl]-3-azetidinecarboxylic acid (Preparation 41) (480 mg, 1.07 mmol) and N-methylmorpholine (130 μl, 1.17 mmol) in dichloromethane (10 ml) was cooled to 0° C. and then treated with isobutyl chloroformate (150 μl, 1.17 mmol). The mixture was stirred at 0° C. for 30 minutes then allowed to warm to room temperature over 1 hour. The mixture was quenched with methanol (5 ml) and the solvent removed under reduced pressure. The residue was partitioned between ethyl acetate and hydrochloric acid (1M). The combined organic layers were washed with brine, dried over anhydrous sodium sulphate, filtered and the solvent removed under reduced pressure. The residue was purified by column chromatography on silica gel eluting with a gradient system of dichloromethane:ethyl acetate (95:5) gradually changing to dichloromethane:ethyl acetate (90:10) to afford the title compound (230 mg)

MS: 464 (MH$^+$)

$^1$H-NMR (CDCl$_3$) δ: 4.73 (2H, m), 4.40 (2H, m), 3.78 (3H, s), 3.52 (2H, m), 2.86 (1H, dd, J=15, 8 Hz), 2.64 (1H, dd, J=15, 3 Hz), 1.83–1.58 (7H, m), 1.38 (9H, s), 1.33–1.06 (8H, m), 0.83 (2H, m)

Preparation 43: (3R)-6-Cyclohexyl-3-(3-{[3-(methoxycarbonyl)-1-azetidinyl]carbonyl}-1,2,4-oxadiazol-5-yl)hexanoic Acid

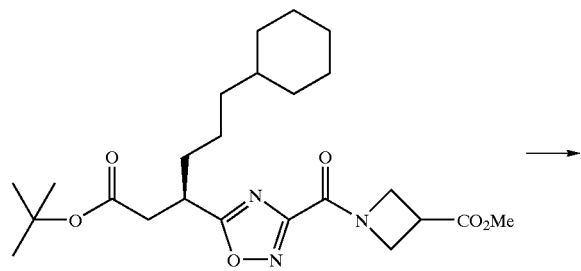

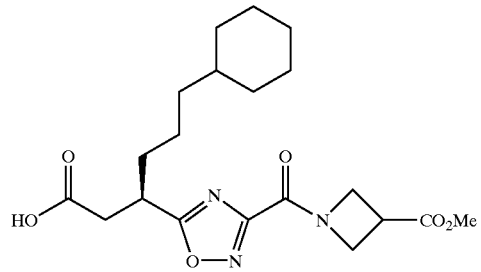

A solution of methyl 1-[(5-{(1R)-1-[2-(tert-butoxy)-2-oxoethyl]-4-cyclohexylbutyl}-1,2,4-oxadiazol-3-yl)carbonyl]-3-azetidinecarboxylate (Preparation 42) (225 mg, 0.48 mmol) in dichloromethane (8 ml) was treated with trifluoroacetic acid (4 ml) and the resulting mixture was stirred at room temperature under a nitrogen atmosphere for 5 hours. The solvent was removed under reduced pressure and the residue azeotroped from toluene (×2). The residue was dissolved in ethyl acetate and washed sequentially with a saturated aqueous solution of sodium citrate and brine, dried over anhydrous sodium sulphate, filtered and the solvent removed under reduced pressure to afford the title compound as an oil (200 mg).

MS: 408 (MH$^+$), 430 (MNa$^+$)

$^1$H-NMR (CDCl$_3$) δ: 4.73 (2H, m), 4.40 (2H, m), 3.78 (3H, s), 3.53 (2H, m), 3.04 (1H, m), 2.80 (1H, m), 1.87–1.41 (7H, m), 1.36–1.00 (8H, m), 0.83 (2H, m)

Preparation 44: tert-Butyl (3R)-6-cyclohexyl-3-(3-methyl-1,2,4-oxadiazol-5-yl)hexanoate

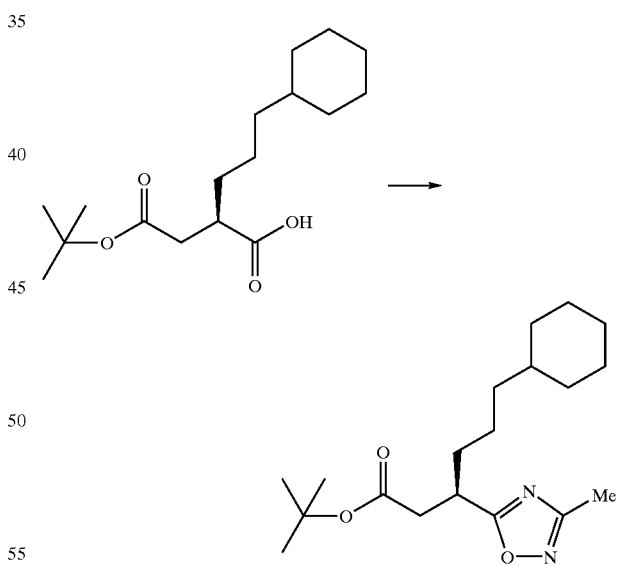

A solution of (2R)-2-[2-(tert-butoxy)-2-oxoethyl]-5-cyclohexylpentanoic acid (Preparation 1) (596 mg, 2.00 mmol) in dichloromethane (8 ml) was treated with 1,1'-carbonyldiimidazole (364 mg, 2.25 mol) and the solution was stirred at room temperature for 15 minutes. The N-hydroxy-acetamidine (Chem.Ber.; 17; 1884; 2746) (148 mg, 2.00 mmol) was then added and the mixture was stirred for 1 hour. The solvent was removed under reduced pressure and the residue was heated neat under a nitrogen atmosphere for 90 minutes. The crude product was then purified by column chromatography on silica gel eluting with dichloromethane to afford the title compound (385 mg).

MS: 337 (MH+)

1H-NMR (CDCl3) δ: 3.41 (1H, m), 2.76 (1H, dd, J=14, 8 Hz), 2.60 (1H, dd, J=14, 5 HZ), 2.36 (3H, s), 1.76–1.56 (7H, m), 1.39 (9H, s), 1.32–1.04 (8H, m), 0.82 (2H, m)

Preparation 45: (3R)-6-Cyclohexyl-3-(3-methyl-1,2,4-oxadiazol-5-yl)hexanoic Acid

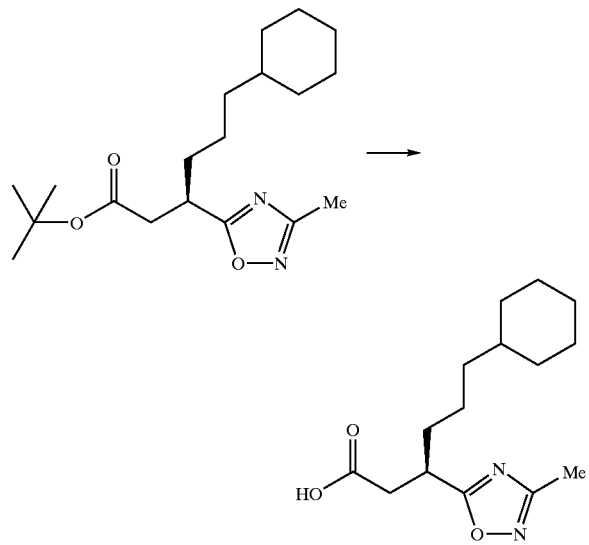

tert-Butyl (3R)-6-cyclohexyl-3-(3-methyl-1,2,4-oxadiazol-5-yl)hexanoate (Preparation 44) (350 mg, 1.04 mmol) was treated with trifluoroacetic acid (3 ml) and the resulting mixture was stirred at room temperature under a nitrogen atmosphere for 45 minutes. The solvent was removed under reduced pressure and the residue azeotroped from toluene then dichloromethane to afford the title compound (185 mg).

MS: 298 (MNH4+)

1H-NMR (CDCl3) δ: 3.41 (1H, m), 2.96 (1H, dd, J=16, 8 Hz), 2.75 (1H, dd, J=16, 6 Hz), 2.36 (3H, s), 1.80–1.40 (7H, m), 1.35–0.93 (8H, m), 0.82 (2H, m)

Preparation 46: tert-Butyl (3R)-6-cyclohexyl-3-(3-isopropyl-1,2,4-oxadiazol-5-yl)hexanoate

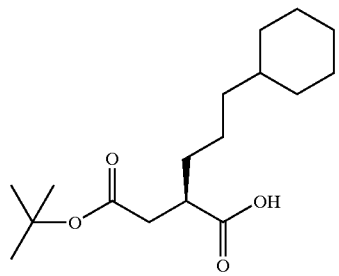

-continued

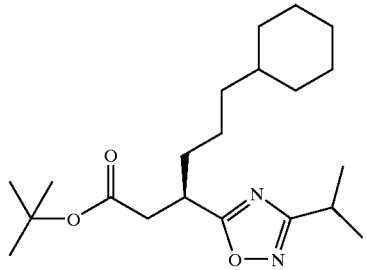

A solution of (2R)-2-[2-(tert-butoxy)-2-oxoethyl]-5-cyclohexylpentanoic acid (Preparation 1) (500 mg, 1.70 mmol) in dichloromethane (30 ml) was treated with 1,1'-carbonyldiimidazole (272 mg, 1.70 mol) and the solution was stirred at room temperature for 1 hour. The N'-hydroxy-2-methylpropanimidamide (Monatsh.Chem.; 113; 1982; 781–792) (174 mg, 1.70 mmol) was then added and the mixture was stirred for 30 minutes. The solvent was removed under reduced pressure and the residue was heated neat at 120° C. under a nitrogen atmosphere for 18 hours. The crude product was then purified by column chromatography on silica gel eluting with dichloromethane to afford the title compound as a colourless oil (250 mg).

MS: 365 (MH+)

1H-NMR (CDCl3) δ: 3.42 (1H, m), 3.05 (1H, m), 2.78 (1H, dd, J=16, 8 Hz), 2.60 (1H, dd, J=16, 4 Hz), 1.70–1.57 (7H, m), 1.39 (9H, s), 1.34–1.06 (14H, m), 0.81 (2H, m)

Preparation 47: (3R)-6-Cyclohexyl-3-(3-isopropyl-1,2,4-oxadiazol-5-yl)hexanoic Acid

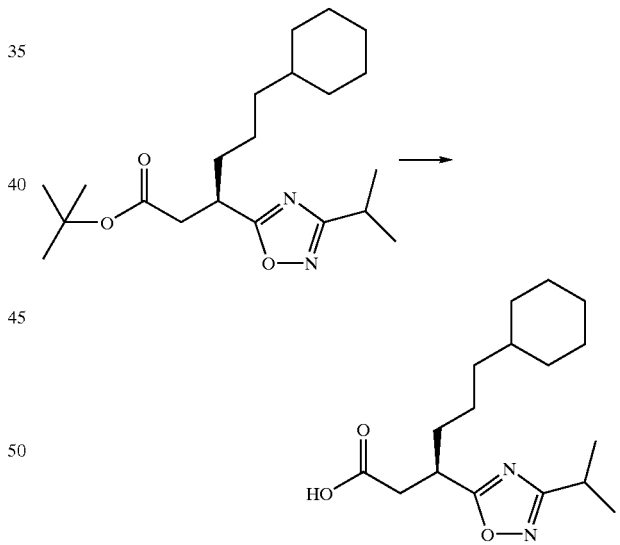

tert-Butyl (3R)-6-cyclohexyl-3-(3-isopropyl-1,2,4-oxadiazol-5-yl)hexanoate (Preparation 46) (250 mg, 0.69 mmol) was treated with trifluoroacetic acid (5 ml) and the resulting mixture was stirred at room temperature under a nitrogen atmosphere for 45 minutes. The solvent was removed under reduced pressure and the residue azeotroped from toluene then dichloromethane to afford the title compound as a white solid (220 mg).

MS: 309 (MH+)

1H-NMR (CDCl3) δ: 3.50 (1H, m), 3.09 (1H, m), 2.95 (2H, dd, J=16, 8 Hz), 2.76 (1H, dd, J=16, 4 Hz), 1.84–1.56 (7H, m), 1.40–1.05 (14H, m), 0.81 (2H, m)

Preparation 48: tert-Butyl (3R)-6-cyclohexyl-3-[3-(methoxymethyl)-1,2,4-oxadiazol-5-yl]hexanoate

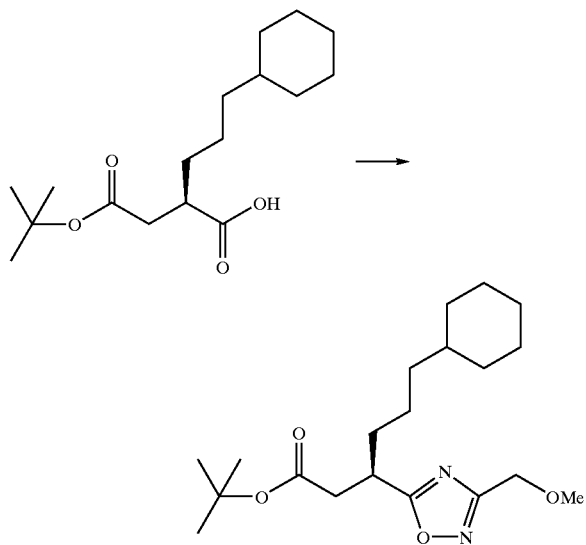

A solution of (2R)-2-[2-(tert-butoxy)-2-oxoethyl]-5-cyclohexylpentanoic acid (Preparation 1) (500 mg, 1.70 mmol) in dichloromethane (30 ml) was treated with 1,1'-carbonyldiimidazole (272 mg, 1.70 mol) and the solution was stirred at room temperature for 1 hour. The N'-hydroxy-2-methoxyethanimidamide (J.Med.Chem,; 40; 8; 1997; 1230–1246) (177 mg, 1.70 mmol) was then added and the mixture was stirred for 17 hours. The solvent was removed under reduced pressure and the residue was heated neat at 120° C. under a nitrogen atmosphere for 2 hours. The crude product was then purified by column chromatography on silica gel eluting with dichloromethane:methanol (99:1) to afford the title compound as an oil (350 mg).

MS: 367 (MH$^+$), 389 (MNa$^+$)

$^1$H-NMR (CDCl$_3$) δ: 4.56 (2H, s), 3.49 (4H, m), 2.84 (1H, dd, J=16, 8 Hz), 2.65 (1H, dd, J=16, 5 Hz), 1.85–1.52 (7H, m), 1.40 (9H, s), 1.36–1.05 (8H, m), 0.84 (2H, m)

Preparation 49: (3R)-6-Cyclohexyl-3-[3-(methoxymethyl)-1,2,4-oxadiazol-5-yl]hexanoic Acid

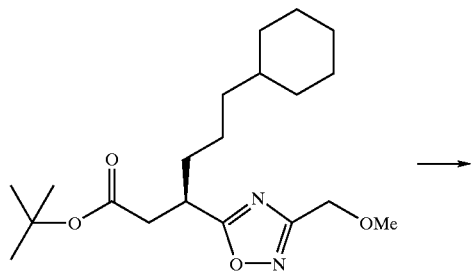

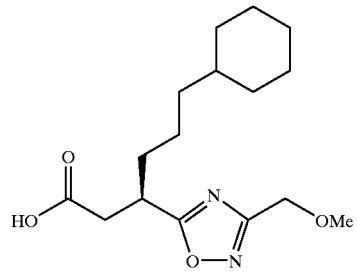

tert-Butyl (3R)-6-cyclohexyl-3-[3-(methoxymethyl)-1,2,4-oxadiazol-5-yl]hexanoate (Preparation 48) (350 mg, 0.96 mmol) was treated with trifluoroacetic acid (3 ml) and the resulting mixture was stirred at room temperature under a nitrogen atmosphere for 2 hours. The solvent was removed under reduced pressure and the residue azeotroped from toluene then dichloromethane to afford the title compound as a colourless oil (250 mg).

MS: 311 (MH$^+$), 333 (MNa$^+$)

$^1$H-NMR (CDCl$_3$) δ: 4.57 (2H, s), 3.50 (4H, m), 3.00 (1H, m), 2.89 (1H, m), 1.90–1.51 (7H, m), 1.40–1.01 (8H, m), 0.84 (2H, m)

Preparation 50: tert-Butyl (3R)-6-cyclohexyl-3-[3-(2-methoxyethyl)-1,2,4-oxadiazol-5-yl]hexanoate

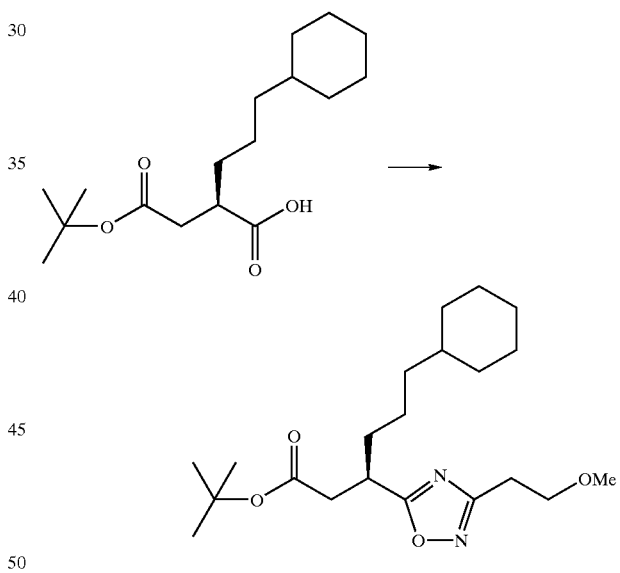

A solution of (2R)-2-[2-(tert-butoxy)-2-oxoethyl]-5-cyclohexylpentanoic acid (Preparation 1) (500 mg, 1.70 mmol) in dichloromethane (30 ml) was treated with 1,1'-carbonyldiimidazole (272 mg, 1.70 mmol) and the solution was stirred at room temperature for 1 hour. N'-hydroxy-3-methoxypropanimidamide (J.Amer.Chem.Soc.; 80; 1958; 3769–3771) (201 mg, 1.70 mmol) was then added and the mixture was stirred for 1 hour. The solvent was removed under reduced pressure and the residue was heated neat at 120° C. under a nitrogen atmosphere for 2 hours. The crude product was then purified by column chromatography on silica gel eluting with dichloromethane:methanol (99:1) to afford the title compound as a colourless oil (410 mg).

MS: 381 (MH$^+$), 403 (MNa$^+$)

$^1$H-NMR (CDCl$_3$) δ: 3.73 (2H, t, J=6 Hz), 3.42 (1H, m), 3.34 (3H, s), 2.98 (2H, t, J=6 Hz), 2.77 (1H, dd, J=16, 9 Hz), 2.61 (1H, dd, J=16, 5 Hz), 1.79–1.54 (7H, m), 1.38 (9H, s), 1.32–1.03 (8H, m), 0.81 (2H, m)

Preparation 51: (3R)-6-Cyclohexyl-3-[3-(2-methoxyethyl)-1,2,4-oxadiazol-5-yl]hexanoic Acid

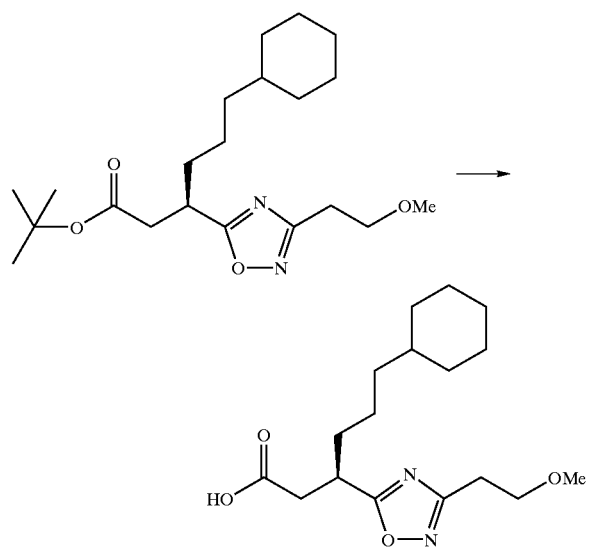

tert-Butyl (3R)-6-cyclohexyl-3-[3-(2-methoxyethyl)-1,2,4-oxadiazol-5-yl]hexanoate (Preparation 50) (410 mg, 1.08 mmol) was treated with trifluoroacetic acid (3 ml) and the resulting mixture was stirred at room temperature under a nitrogen atmosphere for 1 hour. The solvent was removed under reduced pressure and the residue azeotroped from toluene then dichloromethane to afford the title compound (250 mg).

MS: 325 (MH⁺)

¹H-NMR (CDCl₃) δ: 7.46 (1H, br s), 2.77 (2H, t, J=6 Hz), 3.48 (1H, m), 3.36 (3H, s), 3.07–2.87 (3H, m), 2.75 (1H, dd, J=16, 5 Hz), 1.86–1.53 (7H, m), 1.38–1.02 (8H, m), 0.83 (2H, m)

Preparation 52: tert-Butyl (3R)-6-cyclohexyl-3-{3-[2-oxo-2-(1-pyrrolidinyl)ethyl]-1,2,4-oxadiazol-5-yl}hexanoate

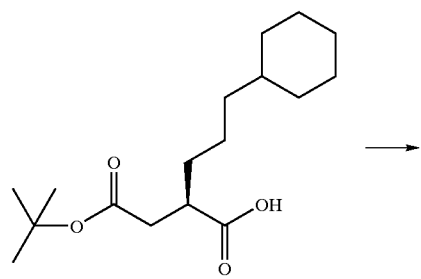

-continued

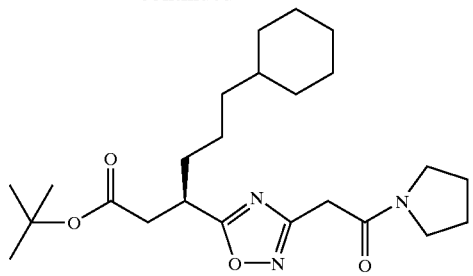

A solution of (2R)-2-[2-(tert-butoxy)-2-oxoethyl]-5-cyclohexylpentanoic acid (Preparation 1) (500 mg, 1.70 mmol) in dichloromethane (30 ml) was treated with 1,1'-carbonyldiimidazole (272 mg, 1.70 mmol) and the solution was stirred at room temperature for 1 hour. N'-hydroxy-3-oxo-3-(1-pyrrolidinyl)propanimidamide (Patent FR 73-36858 731016) (291 mg, 1.70 mmol) was then added and the mixture was stirred for 17 hours. The solvent was removed under reduced pressure and the residue was heated neat at 110° C. under a nitrogen atmosphere for 2 hours. The crude product was then purified by column chromatography on silica gel eluting with dichloromethane:methanol (99:1) to afford the title compound as a colourless oil (309 mg).

MS: 434 (MH⁺)

¹H-NMR (CDCl₃) δ: 3.76 (2H, s), 3.56–3.39 (5H, m), 2.80 (1H, dd, J=15, 8 Hz), 2.61 (1H, m) J=15, 4 Hz), 1.97 (2H, m), 1.86 (2H, m), 1.81–1.58 (7H, m), 1.41–1.05 (17H, m), 0.83 (2H, m)

Preparation 53: (3R)-6-Cyclohexyl-3-{3-[2-oxo-2-(1-pyrrolidinyl)ethyl]-1,2,4-oxadiazol-5-yl}hexanoic Acid

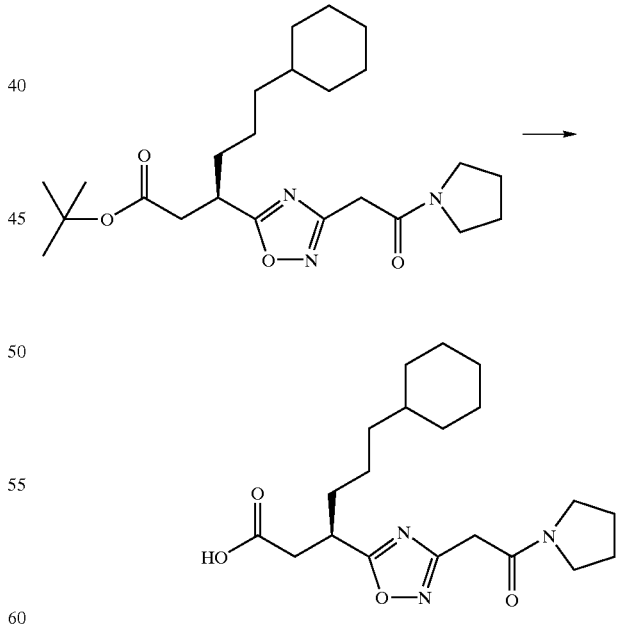

tert-Butyl (3R)-6-cyclohexyl-3-{3-[2-oxo-2-(1-pyrrolidinyl)ethyl]-1,2,4-oxadiazol-5-yl}hexanoate (Preparation 52) (309 mg, 0.71 mmol) was treated with trifluoroacetic acid (2 ml) and the resulting mixture was stirred at room temperature under a nitrogen atmosphere for 2 hours. The solvent was removed under reduced pressure and the residue azeotroped from toluene to afford the title compound as a pale yellow oil (200 mg).

MS: 378 (MH⁺), 400 (MNa⁺)

¹H-NMR (CDCl₃) δ: 3.83 (2H, s), 3.64–3.40 (5H, m), 2.93 (1H, dd, J=17, 8 Hz), 2.76 (1H, dd, J=17, 5 Hz), 2.11–1.50 (11H, m), 1.43–1.02 (8H, m), 0.84 (2H, m)

Preparation 54: tert-Butyl (3R)-6-cyclohexyl-3-{3-[(phenylsulfonyl)methyl]-1,2,4-oxadiazol-5-yl}hexanoate

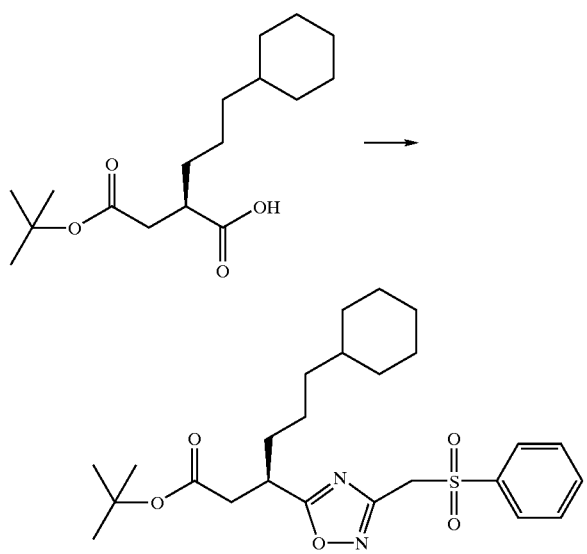

A solution of (2R)-2-[2-(tert-butoxy)-2-oxoethyl]-5-cyclohexylpentanoic acid (Preparation 1) (300 mg, 1.00 mmol) in dichloromethane (15 ml) was treated with 1,1'-carbonyldiimidazole (162 mg, 1.00 mmol) and the solution was stirred at room temperature for 2 hours. N-hydroxy-2-(phenylsulfonyl)ethanimidamide (J.Heterocycl.Chem.; 16; 1979; 1197–1200) (214 mg, 1.00 mmol) was then added and the mixture was stirred for 17 hours. The solvent was removed under reduced pressure and the residue was heated neat at 130° C. under a nitrogen atmosphere for 2 hours. The crude product was then purified by column chromatography on silica gel eluting with dichloromethane:methanol (99:1) to afford the title compound (78 mg).

MS: 499 (MNa⁺)

¹H-NMR (CDCl₃) δ: 7.83 (2H, d, J=7 Hz), 7.69 (1H, dd, J=7, 7 Hz), 7.54 (2H, dd, J=7, 7 Hz), 4.52 (2H, s), 3.43 (1H, m), 2.78 (1H, dd, J=16, 9 Hz), 2.60 (1H, dd, J=16, 5 Hz), 1.78–1.58 (7H, m), 1.40 (9H, s), 1.30–1.06 (8H, m), 0.85 (2H, m)

Preparation 55: (3R)-6-Cyclohexyl-3-{3-[(phenylsulfonyl)methyl]-1,2,4-oxadiazol-5-yl}hexanoic Acid

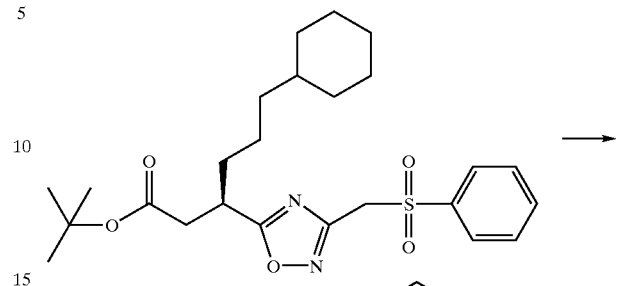

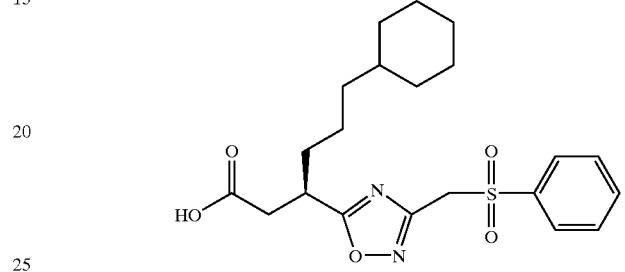

tert-Butyl (3R)-6-cyclohexyl-3-{3-[(phenylsulfonyl)methyl]-1,2,4-oxadiazol-5-yl}hexanoate (Preparation 54) (78 mg, 0.16 mmol) was treated with trifluoroacetic acid (2 ml) and the resulting mixture was stirred at room temperature under a nitrogen atmosphere for 4 hours. The solvent was removed under reduced pressure and the residue azeotroped from toluene then dichloromethane to afford the title compound as an oil which crystallised on standing (60 mg).

MS: 421 (MH⁺), 438 (MNH₄⁺)

¹H-NMR (CDCl₃) δ: 7.80 (2H, d, J=7 Hz), 7.66 (1H, dd, J=7, 7 Hz), 7.53 (2H, dd, J=7, 7 Hz), 4.53 (2H, s), 3.45 (1H, m), 2.91 (1H, dd, J=16, 9 Hz), 2.73 (1H, dd, J=5 Hz), 1.80–1.52 (7H, m), 1.39–1.01 (8H, m), 0.84 (2H, m)

Preparation 56: tert-Butyl (3R)-3-{3-[(4-chlorophenoxy)methyl]-1,2,4-oxadiazol-5-yl}-6-cyclohexylhexanoate

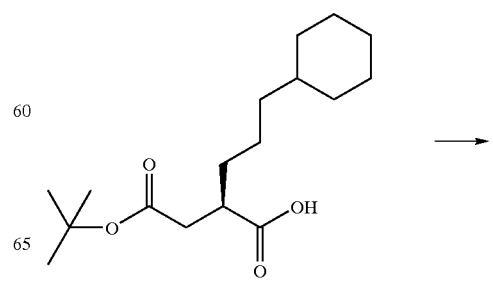

-continued

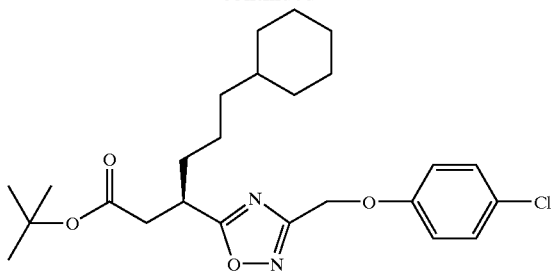

A solution of (2R)-2-[2-(tert-butoxy)-2-oxoethyl]-5-cyclohexylpentanoic acid (Preparation 1) (300 mg, 1.00 mmol) in dichloromethane (15 ml) was treated with 1,1'-carbonyldiimidazole (162 mg, 1.00 mmol) and the solution was stirred at room temperature for 2 hours. 2-(4-chlorophenoxy)-N'-hydroxyethanimidamide (U.S. Pat. No. 97-815671 970313) (197 mg, 0.98 mmol) was then added and the mixture was stirred for 17 hours. The solvent was removed under reduced pressure and the residue was heated neat at 120° C. under a nitrogen atmosphere for 2 hours. The crude product was then purified by column chromatography on silica gel eluting with dichloromethane:methanol (99:1) to afford the title compound as a colourless oil (220 mg).

$^1$H-NMR (CDCl$_3$) δ: 7.25 (2H, d, J=8 Hz), 6.93 (2H, d, J=8 Hz), 5.13 (2H, s), 3.48 (1H, m), 2.82 (1H, dd, J=17, 9 Hz), 2.64 (1H, dd, J=17, 4 Hz), 1.81–1.57 (7H, m), 1.36 (9H, s), 1.33–1.03 (8H, m), 0.83 (2H, m)

Preparation 57: (3R)-3-{3-[(4-Chlorophenoxy)methyl]-1,2,4-oxadiazol-5-yl}-6-cyclohexylhexanoic Acid

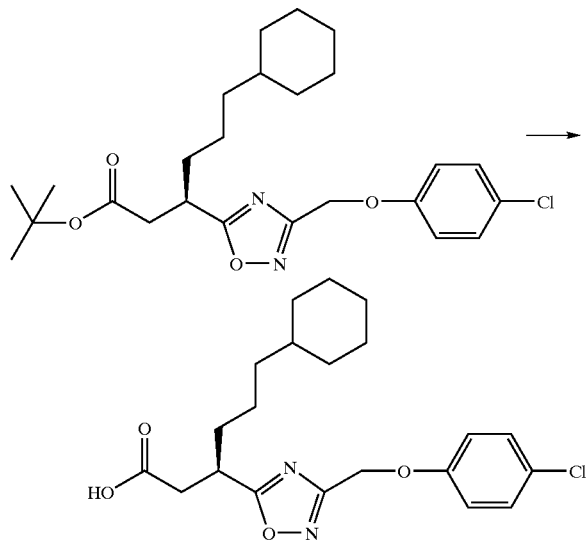

tert-Butyl (3R)-3-{3-[(4-chlorophenoxy)methyl]-1,2,4-oxadiazol-5-yl}-6-cyclohexylhexanoate (Preparation 56) (215 mg, 0.46 mmol) was treated with trifluoroacetic acid (5 ml) and the resulting mixture was stirred at room temperature under a nitrogen atmosphere for 4 hours. The solvent was removed under reduced pressure and the residue azeotroped from toluene to afford the title compound (189 mg).

$^1$H-NMR (CDCl$_3$) δ: 7.25 (2H, d, J=9 Hz), 6.94 (2H, d, J=9 Hz), 5.14 (2H, s), 3.53 (1H, m), 2.99 (1H, dd, J=15, 9 Hz), 2.78 (1H, dd, J=15, 4 Hz), 1.85–1.56 (7H, m), 1.35–1.04 (8H, m), 0.84 (2H, m)

Preparation 58: tert-Butyl (3R)-6-cyclohexyl-3-[3-(2-pyridinylmethyl)-1,2,4-oxadiazol-5-yl]hexanoate

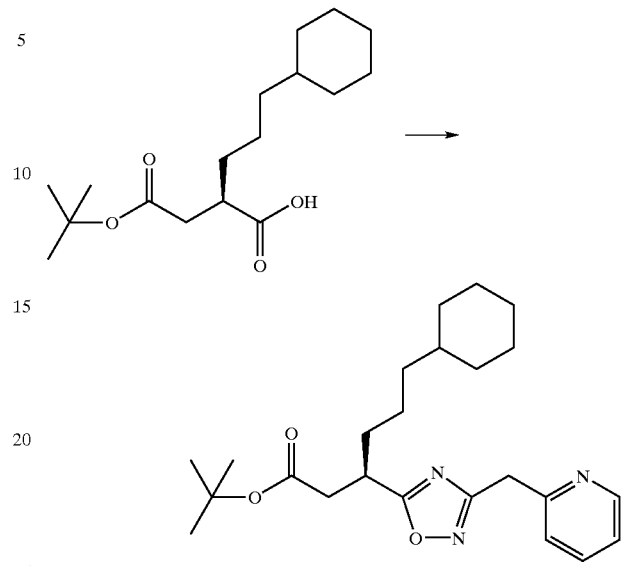

A solution of (2R)-2-[2-(tert-butoxy)-2-oxoethyl]-5-cyclohexylpentanoic acid (Preparation 1) (300 mg, 1.00 mmol) in dichloromethane (15 ml) was treated sequentially with 1-[3-(dimethylamino)propyl]-3-ethylcarbodiimide hydrochloride (192 mg, 1.00 mmol), 4-(dimethylamino)pyridine (125 mg, 1.02 mmol) and N-hydroxy-2-(2-pyridinyl)ethanimidamide (Chem.Pharm.Bull.; 21; 10; 1973; 2146–2160) (152 mg, 1.00 mmol). The resulting mixture was stirred at room temperature for 17 hours. The solvent was removed under reduced pressure and the residue was heated neat at 120° C. under a nitrogen atmosphere for 2 hours. The crude product was then purified by column chromatography on silica gel eluting with dichloromethane:methanol (99:1). The residue was further purified by column chromatography on silica gel eluting with ethyl acetate:pentane (30:70) to afford the title compound as an oil (107 mg).

MS: 414 (MNa$^+$), 436 (MNa$^+$)

$^1$H-NMR (CDCl$_3$) δ: 8.55 (1H, d, J=5 Hz), 7.62 (1H, dd, J=7, 7 Hz), 7.32–7.10 (2H, s), 3.45 (1H, m), 2.79 (1H, dd, J=16, 8 Hz), 2.60 (1H, dd, J=16, 5 Hz), 1.83–1.51 (7H, m), 1.41–1.00 (17H, m), 0.82 (2H, m)

Preparation 59: (3R)-6-Cyclohexyl-3-[3-(2-pyridinylmethyl)-1,2,4-oxadiazol-5-yl]hexanoic Acid Trifluoroacetate

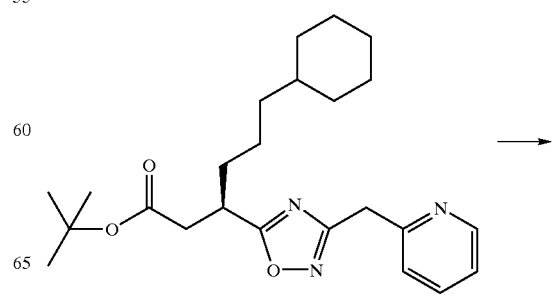

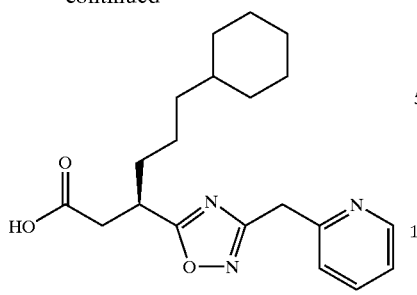

tert-Butyl (3R)-6-cyclohexyl-3-[3-(2-pyridinylmethyl)-1,2,4-oxadiazol-5-yl]hexanoate (Preparation 58) (247 mg, 0.60 mmol) was treated with trifluoroacetic acid (7 ml) and the resulting mixture was stirred at room temperature under a nitrogen atmosphere for 4 hours. The solvent was removed under reduced pressure and the residue azeotroped from toluene then dichloromethane to afford the title compound as an oil (262 mg).

MS: 358 (MH$^+$)

$^1$H-NMR (CDCl$_3$) δ: 8.75 (1H, d, J=5 Hz), 8.04 (1H, dd, J=7, 7 Hz), 7.55 (2H, m), 4.48 (2H, s), 3.49 (1H, m), 2.99–2.61 (2H, m), 1.84–1.44 (7H, m), 1.42–1.00 (8H, m), 0.84 (2H, m)

Preparation 60: tert-Butyl (3R)-6-cyclohexyl-3-({[(1S)-2-ethoxy-1-(hydroxymethyl)-2-oxoethyl]amino}carbonyl)hexanoate

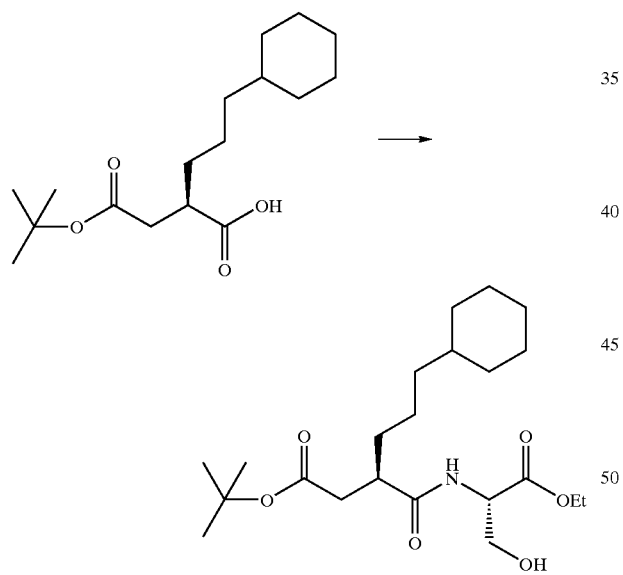

A solution of (2R)-2-[2-(tert-butoxy)-2-oxoethyl]-5-cyclohexylpentanoic acid (Preparation 1) (5.00 g, 16.76 mmol) in dichloromethane (75 ml) was treated sequentially with 1-hydroxybenzotriazole hydrate (2.49 g, 18.43 mmol), serine ethyl ester hydrochloride (3.13 g, 18.43 mmol) and N,N-diisopropylethylamine (6.13 ml, 35.19 mmol) and the resulting mixture was stirred at 0° C. under a nitrogen atmosphere for 15 minutes. 1-[3-(dimethylamino)propyl]-3-ethylcarbodiimide hydrochloride (3.53 g, 18.43 mmol) was then added and the mixture was stirred for 48 hours being allowed to warm to room temperature over this time. The mixture was diluted with dichloromethane (200 ml), washed sequentially with water, aqueous citric acid solution (10% w/v), a saturated aqueous solution of sodium hydrogen carbonate and brine, dried over anhydrous magnesium sulphate, filtered and the solvent removed under reduced pressure. The residue was then purified by column chromatography on silica gel eluting a gradient system of ethyl acetate:pentane (10:90) to (50:50) to afford the title compound as a colourless oil (5.41 g).

MS: 413 (M$^+$)

Analysis: Found C, 63.20; H, 9.52; N, 3.27%; C$_{22}$H$_{39}$NO$_6$.0.33 EtOAc requires C, 63.28; H, 9.48; N, 3.16%

$^1$H-NMR (CDCl$_3$) δ: 6.50 (1H, br d, J=6 Hz), 4.60 (1H, m), 4.26 (2H, q, J=8 Hz), 4.09 (1H, m), 3.85 (1H, m), 3.18 (1H, m), 2.70 (1H, dd, J=18, 9 Hz), 2.51 (1H, m), 2.37 (1H, dd, J=18, 3 Hz), 1.78–1.52 (7H, m), 1.50–1.02 (20H, m), 0.85 (2H, m)

Preparation 61: Ethyl (4S)-2-{(1R)-1-[2-(tert-butoxy)-2-oxoethyl]-4-cyclohexylbutyl}-4,5-dihydro-1,3-oxazole-4-carboxylate

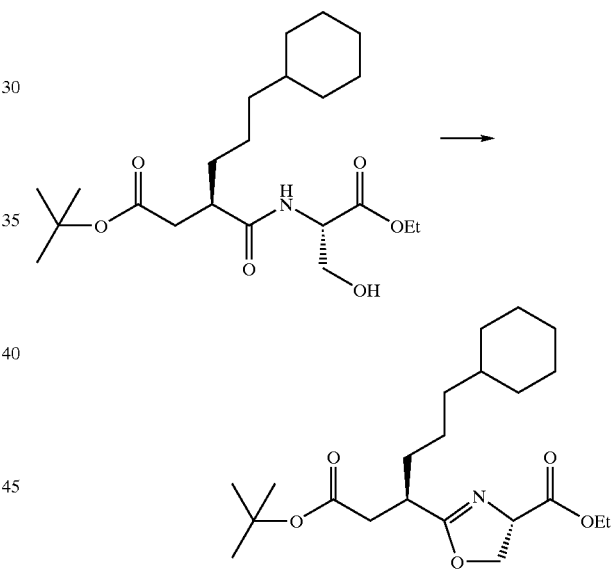

A solution of tert-butyl (3R)-6-cyclohexyl-3-({[(1S)-2-ethoxy-1-(hydroxymethyl)-2-oxoethyl]amino}carbonyl)hexanoate (Preparation 60) (4.14 g, 10 mmol) in anhydrous tetrahydrofuran (40 ml) was treated with (methoxycarbonylsulfamoyl)triethylammonium hydroxide, inner salt [Burgess Reagent] (2.62 g, 11 mmol) and the resulting mixture was heated under reflux under a nitrogen atmosphere for 1 hour. The solvent was removed under reduced pressure and the residue purified by column chromatography on silica gel eluting with a gradient system of pentane:ethyl acetate (80:20) to (50:50) to afford the title compound as a colourless oil (3.10 g)

$^1$H-NMR (CDCl$_3$) δ: 4.69 (1H, m), 4.52–4.33 (2H, m), 4.22 (2H, m), 2.87 (1H, m), 2.63 (1H, dd, J=16, 7 Hz), 2.40 (1H, dd, J=16, 6 Hz), 1.76–1.03 (27H, m), 0.85 (2H, m)

Preparation 62: Ethyl 2-{(1R)-1-[2-(tert-butoxy)-2-oxoethyl]-4-cyclohexylbutyl}-1,3-oxazole-4-carboxylate

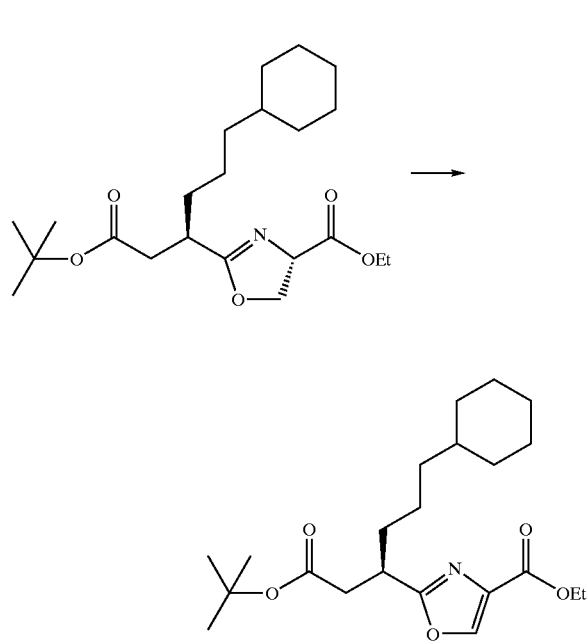

A suspension of copper (II) bromide (2.08 g, 9.31 mmol) and hexamethylenetetramine (1.30 g, 9.31 mmol) in degassed dichloromethane (25 ml) was treated with 1,8-diazabicyclo[5.4.0]undec-7-ene (1.39 ml, 9.31 mmol) and then cooled in a cold water bath and stirred for 5 minutes. This suspension was then treated dropwise with a solution of ethyl (4S)-2-{(1R)-1-[2-(tert-butoxy)-2-oxoethyl]-4-cyclohexylbutyl}-4,5-dihydro-1,3-oxazole-4-carboxylate (Preparation 61) (0.92 g, 2.33 mmol) in dichloromethane (5 ml) and the resulting mixture was stirred at room temperature under a nitrogen atmosphere for 17 hours. The solvent was removed under reduced pressure and the residue partitioned between ethyl acetate and a solution of 0.88 ammonia:saturated aqueous solution of ammonium chloride (1:1, 100 mls). The layers were separated and the aqueous layer was extracted with ethyl acetate (×2). The organic layers were combined, washed sequentially with hydrochloric acid (2M), saturated aqueous sodium hydrogen carbonate solution and brine, dried over anhydrous magnesium sulphate, filtered and the solvent removed under reduced pressure. The residue was purified by column chromatography on silica gel eluting with ethyl acetate:pentane (10:90) to afford the title compound as a pale yellow oil (0.59 g).

MS: 394 (MH$^+$)

$^1$H-NMR (CDCl$_3$) δ: 8.13 (1H, s), 4.39 (2H, q, J=7 Hz), 3.39 (1H, m), 2.80 (1H, dd, J=17, 8 Hz), 2.58 (1H, dd, J=17, 6 Hz), 1.84–1.53 (7H, m), 1.49–1.02 (20H, m), 0.84 (2H, m)

Preparation 63: (3R)-6-Cyclohexyl-3-[4-(ethoxycarbonyl)-1,3-oxazol-2-yl]hexanoic Acid Trifluoroacetate

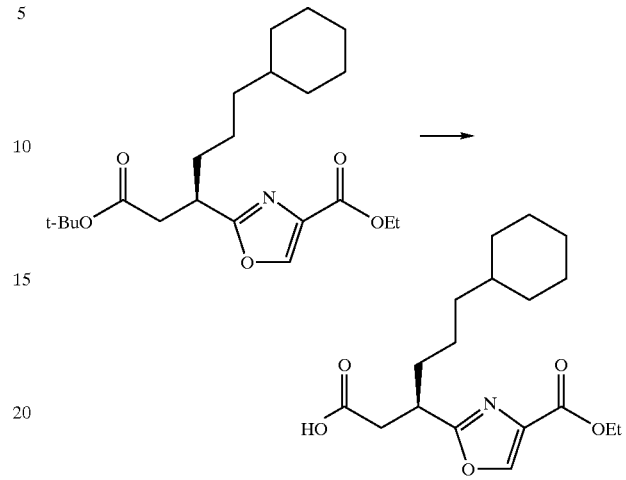

A solution of ethyl 2-{(1R)-1-[2-(tert-butoxy)-2-oxoethyl]-4-cyclohexylbutyl}-1,3-oxazole-4-carboxylate (Preparation 62) (1.58 g, 4.01 mmol) in anhydrous dichloromethane (25 ml) was treated with trifluoroacetic acid (7 ml) and the resulting mixture was stirred at room temperature under a nitrogen atmosphere for 4 hours. The solvent was removed under reduced pressure and the residue azeotroped from dichloromethane to afford the title compound (1.66 g).

MS: 338 (MH$^+$)

$^1$H-NMR (CDCl$_3$) δ: 9.62 (1H, br s), 8.12 (1H, s), 4.34 (2H, q, J=7 Hz), 3.39 (1H, m), 2.93 (1H, dd, J=17, 8 Hz), 2.67 (1H, dd, J=17, 5 Hz), 1.84–1.47 (7H, m), 1.34 (3H, t, J=7 Hz), 1.29–0.98 (8H, m), 0.80 (2H, m)

Preparation 64: Ethyl 2-((1R)-1-{2-[(benzyloxy)amino]-2-oxoethyl}-4-cyclohexylbutyl)-1,3-oxazole-4-carboxylate

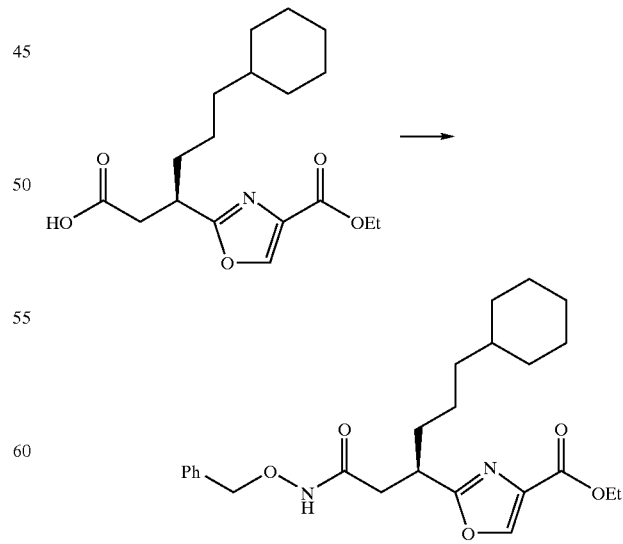

A mixture of (3R)-6-cyclohexyl-3-[4-(ethoxycarbonyl)-1,3-oxazol-2-yl]hexanoic acid trifluoroacetate (Preparation 63) (1.66 g, 3.68 mmol), 1,1'-carbonyldiimidazole (0.80 g, 4.93 mmol), O-benzylhydroxylamine hydrochloride (1.57 g, 9.84 mmol) and N,N-diisopropylethylamine (1.71 ml, 9.82 mmol) in anhydrous tetrahydrofuran (10 ml) was stirred at room temperature for 72 hours. The mixture was diluted with ethyl acetate (50 ml) and washed sequentially with a saturated solution of sodium hydrogen carbonate, aqueous citric acid solution (10% w/v) and brine, dried over anhydrous magnesium sulphate, filtered and the solvent removed under reduced pressure. The residue was purified by column chromatography on silica gel eluting with dichloromethane:methanol (98:2) then further purified by column chromatography on silica gel eluting with ethyl acetate:pentane (50:50) to afford the title compound as an orange oil (1.41 g)

MS: 443 (MH+), 465 (MNa+)

$^1$H-NMR (CDCl$_3$) δ: 8.07 (1H, s), 7.40–7.22 (5H, m), 4.85 (2H, s), 4.36 (2H, q, J=7 Hz), 3.45 (1H, m), 2.89–2.40 (2H, m), 1.82–1.56 (7H, m), 1.36 (3H, t, J=7 Hz), 1.32–1.05 (8H, m), 0.84 (2H, m)

Preparation 65: 2-((1R)-1-{2-[(Benzyloxy)amino]-2-oxoethyl}-4-cyclohexylbutyl)-1,3-oxazole-4-carboxylic Acid

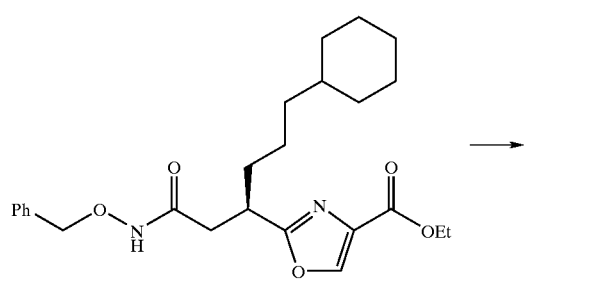

A solution of ethyl 2-((1R)-1-{2-[(benzyloxy)amino]-2-oxoethyl}-4-cyclohexylbutyl)-1,3-oxazole-4-carboxylate (Preparation 64) (1.31 g, 2.96 mmol) in 1,4-dioxane:water (10 ml:5 ml) was treated with lithium hydroxide monohydrate (0.19 g, 4.44 mmol) and stirred in a cold water bath for 3.5 hours. The mixture was diluted with water (100 ml) and washed with ethyl acetate. The layers were separated and the aqueous layer was acidified with solid citric acid then extracted with ethyl acetate. The layers were separated and the organic layer was dried over anhydrous sodium sulphate, filtered and the solvent removed under reduced pressure to afford the title compound as a white solid (0.75 g).

MS: 415 (MH+), 437 (MNa+)

$^1$H-NMR (DMSO-d$_6$) δ: 12.87 (1H, br s), 11.03 (1H, br s), 8.58 (1H, s), 7.41–7.20 (5H, m), 4.70 (2H, s), 3.26 (1H, m), 2.50–2.26 (2H, m), 1.67–1.45 (7H, m), 1.22–0.99 (8H, m), 0.79 (2H, m)

Preparation 66: 2-((1R)-1-{2-[(Benzyloxy)amino]-2-oxoethyl}-4-cyclohexylbutyl)-N,N-dimethyl-1,3-oxazole-4-carboxamide

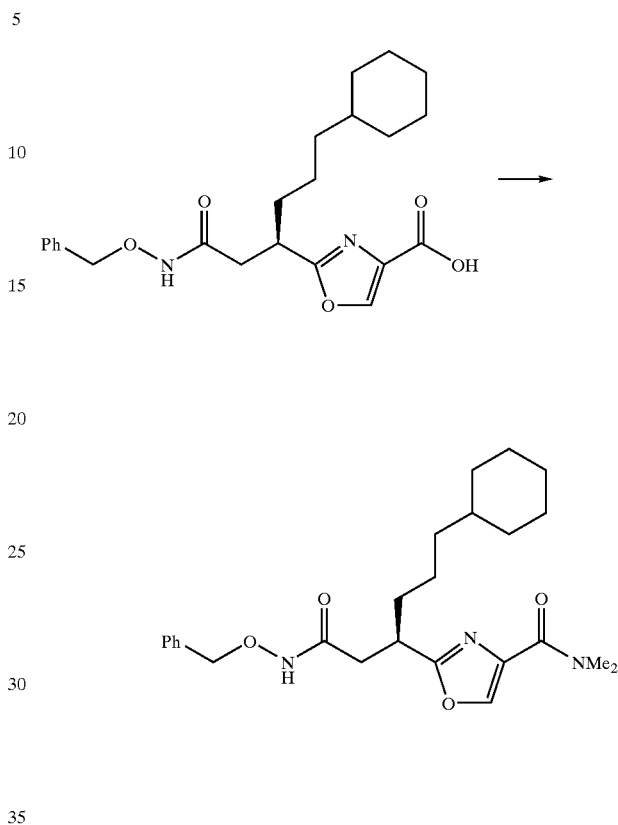

A solution of 2-((1R)-1-{2-[(benzyloxy)amino]-2-oxoethyl}-4-cyclohexylbutyl)-1,3-oxazole-4-carboxylic acid (Preparation 65) (200 mg, 0.48 mmol) in dichloromethane (6 ml) was treated sequentially with 1-hydroxybenzotriazole hydrate (72 mg, 0.53 mmol), dimethylamine hydrochloride (79 mg, 0.96 mmol), N-methylmorpholine (160 µl, 1.45 mmol) and 1-[3-(dimethylamino)propyl]-3-ethylcarbodiimide hydrochloride (111 mg, 0.58 mmol) and the resulting mixture was stirred at room temperature under a nitrogen atmosphere for 4 hours. The solvent was removed under reduced pressure and the residue was dissolved in ethyl acetate and washed sequentially with aqueous citric acid solution (10% w/v), a saturated aqueous solution of sodium hydrogen carbonate and brine, dried over anhydrous magnesium sulphate, filtered and the solvent removed under reduced pressure. The residue was then purified by column chromatography on silica gel eluting with dichloromethane:methanol:0.88 ammonia (95:5:0.5) to afford the title compound as a colourless oil (200 mg).

MS: 442 (MH+), 464 (MNa+)

$^1$H-NMR (CDCl$_3$) δ: 7.99 (1H, s), 7.43–7.20 (5H, m), 4.85 (2H, s), 3.44 (1H, m), 3.39–2.91 (6H, br m), 2.80–2.32 (2H, m), 1.80–1.51 (7H, m), 1.37–1.04 (8H, m), 0.84 (2H, m)

Preparation 67: tert-Butyl (3R)-6-cyclohexyl-3-({[2-hydroxy-1-(methoxycarbonyl)propyl]amino}carbonyl)hexanoate

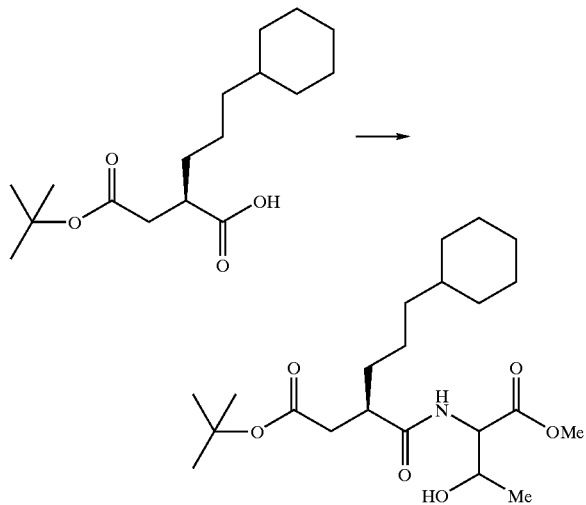

An ice-cooled solution of (2R)-2-[2-(tert-butoxy)-2-oxoethyl]-5-cyclohexylpentanoic acid (Preparation 1) (6.40 g, 21.45 mmol) in dichloromethane (75 ml) was treated sequentially with 1-hydroxybenzotriazole hydrate (3.19 g, 23.60 mmol), threonine methyl ester hydrochloride (4.00 g, 23.60 mmol), N,N-diisopropylethylamine (7.85 ml, 45.10 mmol) and 1-[3-(dimethylamino)propyl]-3-ethylcarbodiimide hydrochloride (4.52 g, 23.58 mmol) and the mixture was stirred for 17 hours being allowed to warm to room temperature over this time. The solvent was removed under reduced pressure and the residue was dissolved in ethyl acetate then washed sequentially with water, aqueous citric acid solution (10% w/v), a saturated aqueous sodium hydrogen carbonate solution and brine, dried over anhydrous magnesium sulphate, filtered and the solvent removed under reduced pressure. The residue was dissolved in diethyl ether (100 ml) and treated with pentane (150 ml) to produce a white precipitate. This was filtered off and washed with pentane to afford the title compound as a white powder (6.48 g).

MS: 436 (MNa$^+$)

$^1$H-NMR (CDCl$_3$) δ: 6.35 (1H, br d), 4.63 (1H, m), 4.26 (1H, m), 3.76 (3H, s), 2.73–2.53 (2H, m), 2.34 (1H, m), 1.73–1.56 (7H, m), 1.45–1.09 (20H, m), 0.84 (2H, m)

Preparation 68: tert-Butyl (3R)-6-cyclohexyl-3-({[1-(methoxycarbonyl)-2-oxopropyl]amino}carbonyl)hexanoate

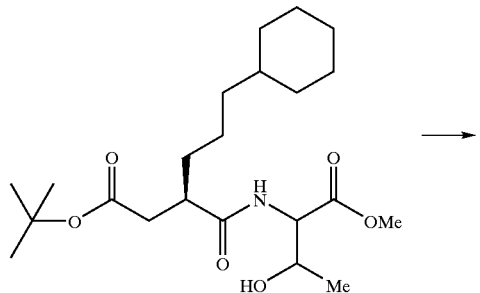

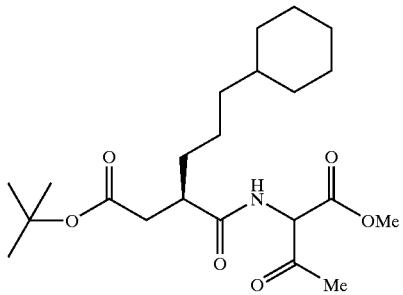

A solution of tert-butyl (3R)-6-cyclohexyl-3-({[2-hydroxy-1-(methoxycarbonyl)propyl]amino}carbonyl)hexanoate (Preparation 67) (6.48 g, 15.69 mmol) in dichloromethane (60 ml) was treated with Dess-Martin periodinane [1,1,1-triacetoxy-1,1-dihydro-1,2-benziodoxol-3(1H)-one] (7.32 g, 17.26 mmol) and the resulting mixture was stirred at room temperature under a nitrogen atmosphere for 1 hour. A solution of sodium thiosulphate (6 g in 50 ml water) and a saturated aqueous sodium hydrogen carbonate solution (50 ml) were then added to the mixture which was stirred for a further 10 minutes. The layers were separated and the aqueous layer was extracted with dichloromethane. The combined organic layers were sequentially washed with water and brine, dried over anhydrous magnesium sulphate, filtered and the solvent removed under reduced pressure. The residue was purified by column chromatography on silica gel eluting with a gradient system of pentane:ethyl acetate (100:0 to 90:10) to afford the title compound as a colourless oil (4.86 g)

MS: 412 (MH$^+$), 434 (MNa$^+$)

$^1$H-NMR (CDCl$_3$) δ: 6.82 (1H, br d), 5.21 (1H, m), 3.78 (3H, s), 2.72–2.52 (2H, m), 2.40–2.25 (4H, m), 1.72–1.53 (7H, m), 1.45–1.04 (17H, m), 0.83 (2H, m)

Preparation 69: Methyl 2-{(1R)-1-[2-(tert-butoxy)-2-oxoethyl]-4-cyclohexylbutyl}-5-methyl-1,3-oxazole-4-carboxylate

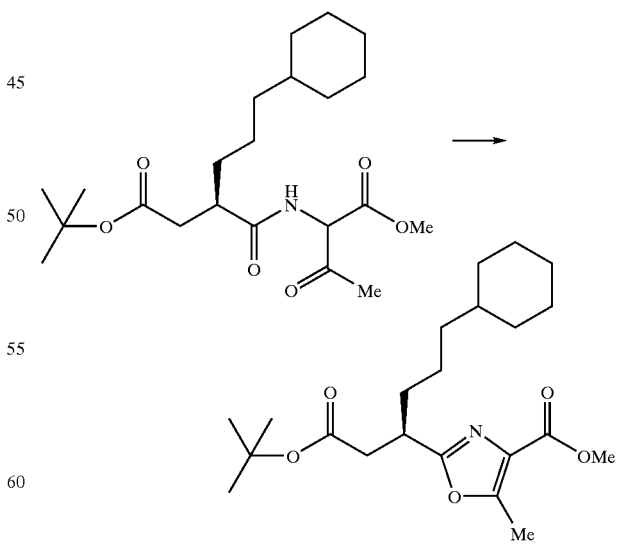

A suspension of triphenylphosphine (9.49 g, 36.18 mmol), iodine (7.98 g, 31.44 mmol) and triethylamine (8.49 ml, 60.75 mmol) in tetrahydrofuran was cooled to −78° C. then treated with tert-butyl (3R)-6-cyclohexyl-3-({[1-

(methoxycarbonyl)-2-oxopropyl]amino}carbonyl)
hexanoate (Preparation 68) (4.86 g, 11.80 mmol) over 15
minutes. The mixture was stirred at −78° C. for 30 minutes
then at 0–5° C. for 2 hours. The mixture was diluted with
water and extracted with dichloromethane. The combined
organic layers were dried over anhydrous magnesium
sulphate, filtered and the solvent removed under reduced
pressure. The residue was purified by column chromatography on silica gel eluting with a gradient system of ethyl
acetate:pentane (0:100 to 10:90) to afford the title compound
as a colourless oil (2.92 g).

MS: 394 (MH+), 416 (MNa+)

¹H-NMR (CDCl₃) δ: 3.89 (3H, s), 3.29 (1H, m), 2.74 (1H, dd, J=14, 6 Hz), 2.60–2.49 (4H, m), 1.79–1.54 (7H, m), 1.38 (9H, s), 1.31–1.05 (8H, m), 0.82 (2H, m)

Preparation 70: (3R)-6-Cyclohexyl-3-[4-(methoxycarbonyl)-5-methyl-1,3-oxazol-2-yl]hexanoic Acid

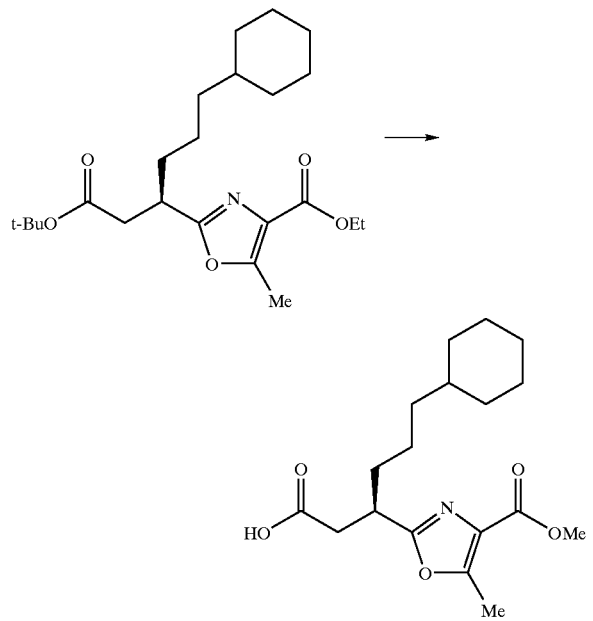

A solution of methyl 2-{(1R)-1-[2-(tert-butoxy)-2-oxoethyl]-4-cyclohexylbutyl}-5-methyl-1,3-oxazole-4-carboxylate (Preparation 69) (2.92 g, 7.43 mmol) in anhydrous dichloromethane (15 ml) was treated with trifluoroacetic acid (7.5 ml) and the resulting mixture was stirred at room temperature under a nitrogen atmosphere for 24 hours. The solvent was removed under reduced pressure and the residue was azeotroped with dichloromethane (×3). The residue was purified by column chromatography on silica gel eluting with a gradient system of ethyl acetate-:pentane (0:100 to 40:60) to afford the title compound as a colourless oil (2.50 g).

MS: 338 (MH+), 360 (MNa+)

Analysis: Found C, 62.90; H, 8.18; N, 3.93%; $C_{18}H_{27}NO_5$.0.3 EtOAc requires C, 63.38; H, 8.14; N, 3.85%

¹H-NMR (CDCl₃) δ: 3.86 (3H, s), 3.33 (1H, m), 2.92 (1H, dd, J=17, 8 Hz), 2.67 (1H, dd, J=17, 5 Hz), 2.58 (3H, s), 1.81–1.56 (7H, m), 1.34–1.03 (8H, m), 0.81 (2H, m)

Preparation 71: Methyl 2-((1R)-1-{2-[(benzyloxy)amino]-2-oxoethyl}-4-cyclohexylbutyl)-5-methyl-1,3-oxazole-4-carboxylate

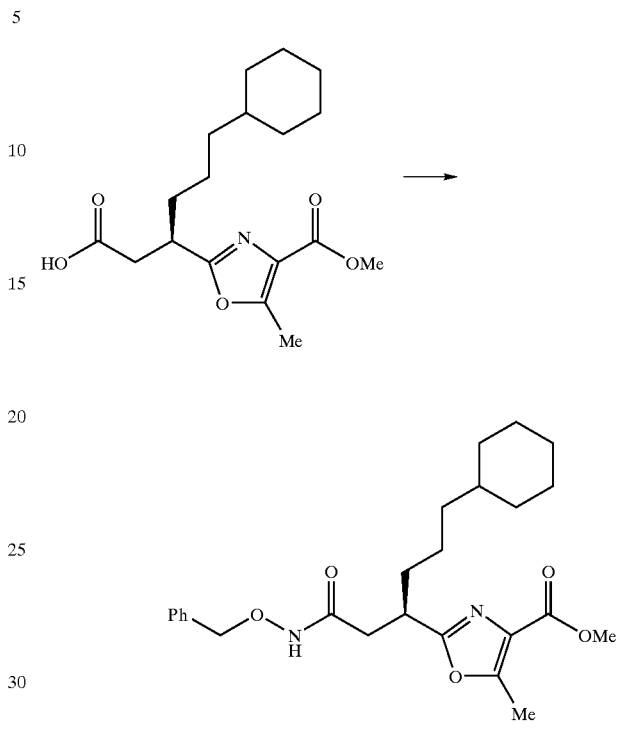

A solution of (3R)-6-cyclohexyl-3-[4-(methoxycarbonyl)-5-methyl-1,3-oxazol-2-yl]hexanoic acid (Preparation 70) (2.48 g, 7.36 mmol) was cooled to 0° and treated with 1-hydroxybenzotriazole hydrate (994 mg, 7.36 mmol), 1-[3-(dimethylamino)propyl]-3-ethylcarbodiimide hydrochloride (2.12 g, 11.06 mmol) and N-methylmorpholine (1.21 ml, 11.04 mmol). The mixture was stirred for 15 minutes then treated with O-benzylhydroxyamine (1.17 g, 7.36 mmol) and further N-methylmorpholine (0.81 ml, 7.36 mmol). The mixture was stirred for 1 hour being allowed to warm to room temperature over this time. The solvent was removed under reduced pressure and the residue was dissolved in ethyl acetate, washed sequentially with water, a saturated solution of sodium hydrogen carbonate and brine, dried over anhydrous magnesium sulphate, filtered and the solvent removed under reduced pressure to afford the title compound as a colourless oil (3.22 g)

MS: 443 (MH+), 465 (MNa+)

Analysis: Found C, 66.78; H, 7.77; N, 6.19%; $C_{25}H_{34}N_2O_5$.0.3 EtOAc requires C, 67.10; H, 7.82; N, 5.97%

¹H-NMR (CDCl₃) δ: 8.62 (1H, br s), 7.33 (5H, m), 4.84 (2H, s), 3.84 (3H, s), 3.36 (1H, m), 2.70–2.33 (5H, m), 1.78–1.54 (7H, m), 1.30–1.03 (8H, m), 0.82 (2H, m)

Preparation 72: 2-((1R)-1-{2-[(Benzyloxy)amino]-2-oxoethyl}-4-cyclohexylbutyl)-5-methyl-1,3-oxazole-4-carboxylic Acid

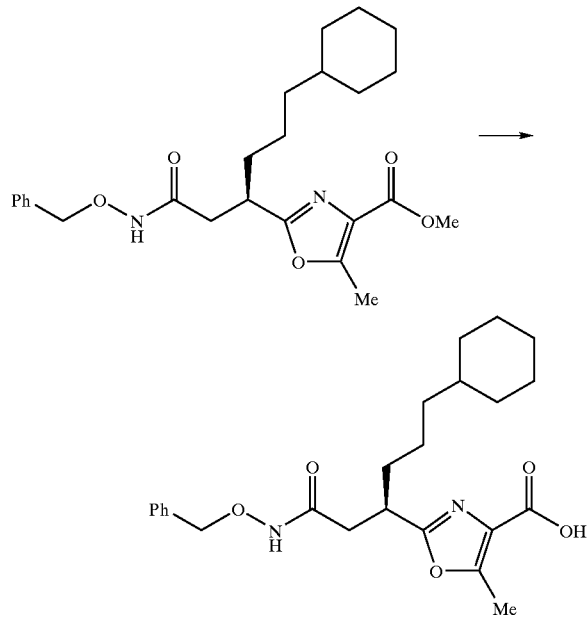

A solution of methyl 2-((1R)-1-{2-[(benzyloxy)amino]-2-oxoethyl}-4-cyclohexylbutyl)-5-methyl-1,3-oxazole-4-carboxylate (Preparation 71) (1.00 g, 2.26 mmol) in 1,4-dioxane (10 ml) was treated with an aqueous sodium hydroxide solution (1N, 1.5 ml) and stirred at room temperature for 4 hours. Further aqueous sodium hydroxide (1N, 3.0 ml) was added and the mixture was stirred for 20 hours. The solvent was removed under reduced pressure and the residue was dissolved in water and washed with ethyl acetate. The layers were separated and the aqueous layer was acidified with solid citric acid then extracted with ethyl acetate. The combined organic layers were dried over anhydrous magnesium sulphate, filtered and the solvent was removed under reduced pressure to afford the title compound as a white foam (0.83 g).

MS: 427 (MH$^-$)

$^1$H-NMR (CDCl$_3$) t: 7.34 (5H, m), 4.85 (2H, s), 3.40 (1H, m), 2.71–2.33 (5H, m), 1.76–1.51 (7H, m), 1.32–1.03 (8H, m), 0.83 (2H, m)

Preparation 73: 2-((1R)-1-{2-[(Benzyloxy)amino]-2-oxoethyl}-4-cyclohexylbutyl)-N,N,5-trimethyl-1,3-oxazole-4-carboxamide

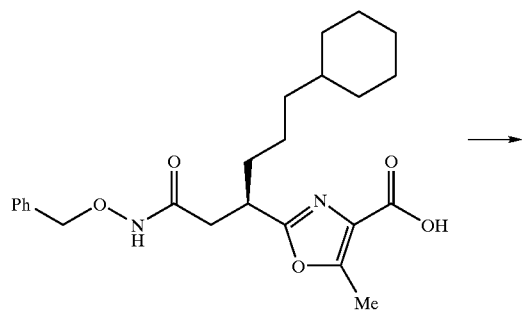

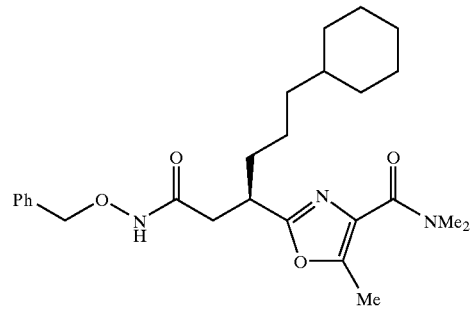

A solution of methyl 2-((1R)-1-{2-[(benzyloxy)amino]-2-oxoethyl}-4-cyclohexylbutyl)-5-methyl-1,3-oxazole-4-carboxylate (Preparation 72) (152 mg, 0.36 mmol) in dichloromethane (5 ml) was treated sequentially with 1-hydroxybenzotriazole hydrate (48 mg, 0.36 mmol), N-methylmorpholine (82 µl, 0.75 mmol), 1-[3-(dimethylamino)propyl]-3-ethylcarbodiimide hydrochloride (75 mg, 0.39 mmol) and dimethylamine hydrochloride (29 mg, 0.36 mmol) and the resulting mixture was stirred at room temperature under a nitrogen atmosphere for 17 hours. The solvent was removed under reduced pressure and the residue was dissolved in ethyl acetate and washed sequentially with water, a saturated aqueous solution of sodium hydrogen carbonate and brine, dried over anhydrous magnesium sulphate, filtered and the solvent removed under reduced pressure. The residue was purified by column chromatography on silica gel eluting with dichloromethane:methanol:0.88 ammonia (95:5:0.5) to afford the title compound as a colourless oil which crystallised on standing (109 mg).

MS: 456 (MH$^+$), 478 (MNa$^+$)

$^1$H-NMR (CDCl$_3$) δ: 8.53 (1H, br s), 7.34 (5H, m), 4.84 (2H, s), 3.36 (1H, m), 3.27–2.86 (6H, br m), 2.64–2.31 (5H, m), 1.74–1.50 (7H, m), 1.31–1.03 (8H, m), 0.82 (2H, m)

Preparation 74: 2-((1R)-1-{2-[(Benzyloxy)amino]-2-oxoethyl}-4-cyclohexylbutyl)-5-methyl-1,3-oxazole-4-carboxamide

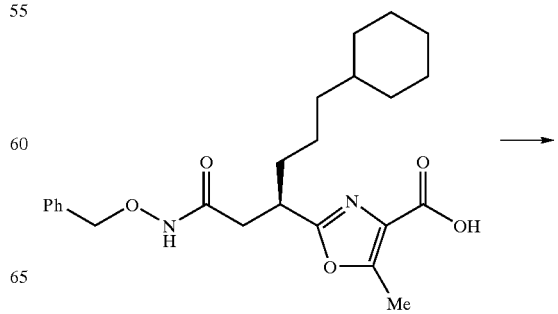

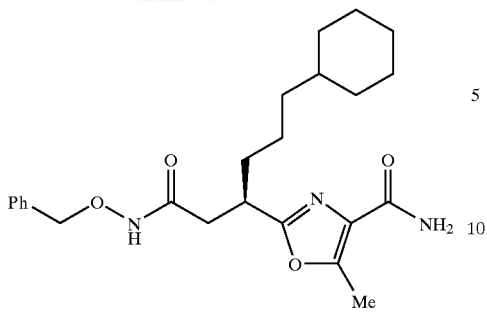

A solution of methyl 2-((1R)-1-{2-[(benzyloxy)amino]-2-oxoethyl}-4-cyclohexylbutyl)-5-methyl-1,3-oxazole-4-carboxylate (Preparation 72) (200 mg, 0.47 mmol) in dichloromethane (10 ml) was treated sequentially with 1-hydroxybenzotriazole hydrate (63 mg, 0.47 mmol), N-methylmorpholine (77 µl, 0.70 mmol) and 1-[3-(dimethylamino)propyl]-3-ethylcarbodiimide hydrochloride (134 mg, 0.70 mmol) and the resulting mixture was stirred at room temperature under a nitrogen atmosphere for 10 minutes. Concentrated ammonia solution (0.88, 50 µl, 1.00 mmol) was then added and the mixture was stirred for 17 hours. The mixture was diluted with dichloromethane and washed sequentially with water, a saturated aqueous solution of sodium hydrogen carbonate and brine, dried over anhydrous magnesium sulphate, filtered and the solvent removed under reduced pressure. The residue was then purified by column chromatography on silica gel eluting with dichloromethane:methanol:0.88 ammonia (97:3:0.3) to afford the title compound as a white solid (140 mg).

MS: 426(MH⁻)

Analysis: Found C, 67.45; H, 7.85; N, 9.64%; $C_{24}H_{33}N_3O_4$ requires C, 67.42; H, 7.78; N, 9.83%

¹H-NMR (CDCl₃) δ: 7.36 (5H, m), 4.86 (2H, s), 3.36 (1H, m), 2.72–2.37 (5H, m), 1.75–1.53 (7H, m), 1.42–1.05 (8H, m), 0.84 (2H, m).

Preparation 75: tert-Butyl (3R)-6-cyclohexyl-3-(3-{[3-(dimethylamino)-1-azetidinyl]carbonyl}-1,2,4-oxadiazol-5-yl)hexanoate

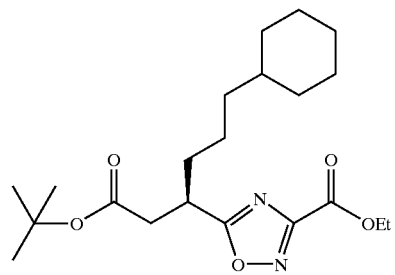

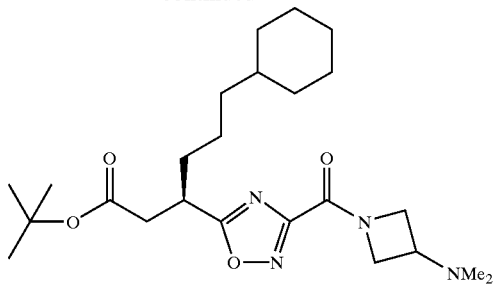

A solution of ethyl 5-{(1R)-1-[2-(tert-butoxy)-2-oxoethyl]-4-cyclohexylbutyl}-1,2,4-oxadiazole-3-carboxylate (Preparation 3) (360 mg, 0.91 mmol) and triethylamine (370 mg, 3.65 mmol) in ethanol (5 ml) was treated with N,N-dimethyl-3-azetidinamine (J.Med.Chem.;36; 801; 1993) (300 mg, 0.91 mmol) and the resulting mixture was heated at 80° C. under a nitrogen atmosphere for 16 hours. The mixture was partitioned between ethyl acetate (150 ml) and saturated aqueous ammonium chloride solution (150 ml). The organic layer was washed with saturated ammonium chloride solution (150 ml), water (150 ml) and brine (150 ml), dried over anhydrous sodium sulphate, filtered and the solvent removed under reduced pressure. The residue was purified by column chromatography on silica gel eluting with a gradient system of pentane:ethyl acetate:diethylamine (87.5:12.5:0.25) gradually changing to pentane:ethyl acetate:diethylamine (50:50:1) to afford the title compound as a colourless oil (355 mg).

MS: 449(MH⁺), 471 (MNa⁺)

¹H-NMR (CDCl₃) δ: 4.56 (1H, dd), 4.38 (1H, dd), 4.21 (1H, dd), 4.05 (1H,dd), 3.50 (1H, m), 3.17 (1H, m), 2.86 (1H, dd), 2.63 (1H, dd), 2.19 (6H, s), 1.78 (1H, m), 1.65 (6H, br t), 1.39 (9H, s), 1.08–1.28 (8H, m), 0.82 (2H, m).

Preparation 76: (3R)-6-Cyclohexyl-3-(3-{[3-(dimethylamino)-1-azetidinyl]carbonyl}-1,2,4-oxadiazol-5-yl)hexanoic Acid

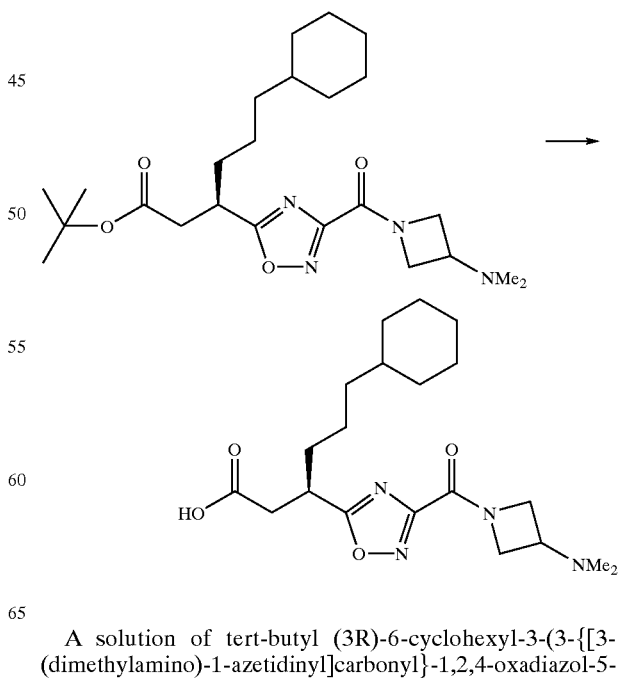

A solution of tert-butyl (3R)-6-cyclohexyl-3-(3-{[3-(dimethylamino)-1-azetidinyl]carbonyl}-1,2,4-oxadiazol-5- yl)hexanoate (Preparation 75) (340 mg, 0.76 mmol) in trifluoroacetic acid (10 ml) was stirred at room temperature for 2 hours. The solvent was removed under reduced pressure and the residue azeotroped from dichloromethane. The residue was dissolved in ethyl acetate (50 ml) and washed with saturated aqueous ammonium chloride solution (50 ml) and brine (50 ml), dried over anhydrous sodium sulphate, filtered and the solvent removed under reduced pressure to afford the title compound as a white solid (30 mg). The combined aqueous washes were extracted with dichloromethane, containing <10% methanol, (3×150 ml). The combined organic layers were dried over anhydrous sodium sulphate, filtered and the solvent removed under reduced pressure to afford the title compound as a white solid (180 mg), combined total mass 210 mg.

MS: 393 (MH$^+$), 415 (MNa$^+$)

$^1$H-NMR (CD$_3$OD) δ: 4.88 (1H, m), 4.70 (1H, m), 4.49 (1H, dd), 4.31 (1H, dd), 4.13 (1H, m), 3.05 (1H, m), 2.91 (1H, dd), 2.35 (6H, s), 2.79 (1H, dd), 1.78 (2H, q), 1.58–1.73 (5H, m), 1.09–1.3.5 (8H, m), 0.70–0.93 (2H, br q).

Preparation 77: tert-Butyl 3-(1,3-dioxo-1,3-dihydro-2H-isoindol-2-yl)-1-azetidinecarboxylate

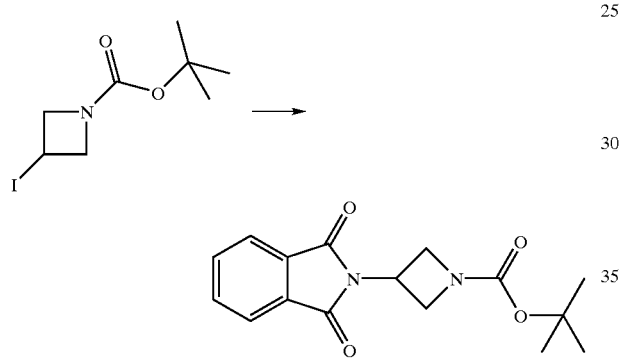

A solution of tert-butyl 3-iodocyclobutanecarboxylate (EP 992493) (5.0 g, 17.7 mmol) in dimethylformamide was treated with potassium phthalimide (5.0 g, 27.0 mmol) and heated at 100° C. for 18 hours. The reaction mixture was filtered, to remove the excess potassium phthalimide, which was washed with dimethylformamide (10 ml). The filtrate was concentrated under reduced pressure and the residue azeotroped with xylene (2×30 ml). The residue was purified by column chromatography on silica gel eluting with a gradient system of 95:5 (pentane:ethyl acetate) gradually changing to 55:45 (pentane:ethyl acetate) to afford the title compound as a white solid (3.78 g).

MS: 325 (MNa$^+$)

$^1$H-NMR (CDCl$_3$) δ: 7.84 (2H, m), 7.72 (2H, m), 5.01 (1H, m), 4.50 (2H, m), 4.20 (2H, m), 1.40 (9H, s).

Preparation 78: tert-Butyl 3-amino-1-azetidinecarboxylate

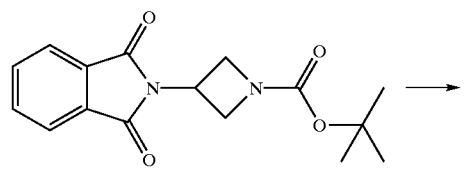

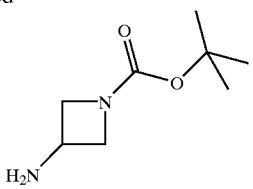

A solution of tert-butyl 3-(1,3-dioxo-1,3-dihydro-2H-isoindol-2-yl)-1-azetidinecarboxylate (Preparation 77) in methylamine in methanol (2M) (10 ml) was stirred in a sealed tube at 55° C. for 3 hours. On cooling a precipitate formed and the reaction mixture was concentrated under reduced pressure. The residue was dissolved in ethyl acetate (100 ml) and washed with water (100 ml, containing (2M) hydrochloric acid (3 ml)) and water (50 ml, containing (2M) hydrochloric acid (2 ml)). The combined aqueous was basified with (2M) sodium hydroxide solution (20 ml) and extracted with ethyl acetate (3×75 ml). The combined organic layers were dried over anhydrous magnesium sulphate, filtered and concentrated under reduced pressure. The residue was purified by column chromatography on silica gel eluting with a gradient system of 97.5:2.5:0.25 (dichloromethane:methanol:ammonia) gradually changing to 90:10:1 (dichloromethane:methanol:ammonia) to afford the title compound (935 mg) of approximately 90% purity, which was used in preparation without further purification.

MS: 173 (MH$^+$)

$^1$H-NMR (CDCl$_3$) δ: 4.11 (2H, m), 3.76 (1H, m), 3.57 (2H, m), 1.41 (9H, s).

Preparation 79: (3R)-3-[3-({[1-(tert-Butoxycarbonyl)-3-azetidinyl]amino}carbonyl)-1,2,4-oxadiazol-5-yl]-6-cyclohexylhexanoic Acid

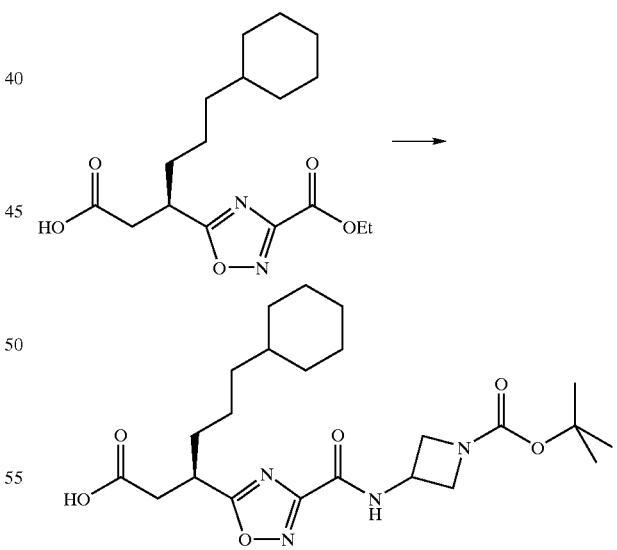

A solution of (3R)-6-cyclohexyl-3-[3-(ethoxycarbonyl)-1,2,4-oxadiazol-5-yl]hexanoic acid (Preparation 4) (480 mg, 1.42 mmol) and triethylamine (1 ml, 7.18 mmol) in ethanol (8 ml) was treated with tert-butyl 3-amino-1-azetidinecarboxylate (Preparation 78) (300 mg, 1.74 mmol) and the resulting mixture was heated at 80° C. under a nitrogen atmosphere for 18 hours. The solvent was removed under reduced pressure. The residue was purified by column chromatography on silica gel eluting with a gradient system of dichloromethane:methanol (99:1) gradually changing to dichloromethane:methanol (90:10) to afford the title compound contaminated with starting amine. The solid was dissolved in ethyl acetate and washed with hydrochloric acid (0.5M) (2×), water and brine, dried over magnesium sulphate, filtered and the solvent was removed under reduced pressure to afford the title compound as a sticky foam.

MS: 463 (M–H)⁻

$^1$H-NMR (CDCl$_3$) δ: 7.64 (1H, d), 4.80 (1H, m), 4.25 (2H, t), 3.88 (2H, dd), 3.97 (1H, dd), 2.79 (1H, dd), 1.57–1.80 (8H, m), 1.38 (9H, s), 1.03–1.20 (8H, m), 0.80 (2H, m).

Preparation 80: (3R)-3-[3-({3-[bis(tert-Butoxycarbonyl)amino]-1-azetidinyl}carbonyl)-1,2,4-oxadiazol-5-yl]-6-cyclohexylhexanoic Acid

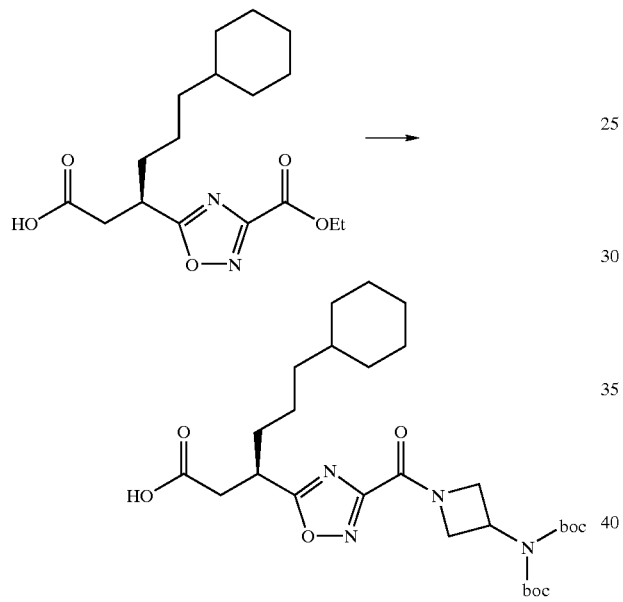

A solution of (3R)-6-cyclohexyl-3-[3-(ethoxycarbonyl)-1,2,4-oxadiazol-5-yl]hexanoic acid (Preparation 4) (480 mg, 1.26 mmol) and triethylamine (350 □l,2.50 mmol) in ethanol (8 ml) was treated with di(tert-butyl) 3-azetidinylimidodicarbonate (EP 153163, EP 106489) (1.00 g, 4.56 mmol) and the resulting mixture was heated at 80° C. under a nitrogen atmosphere for 18 hours. The solvent was removed under reduced pressure. The solid was dissolved in ethyl acetate and washed with water, to which the minimal amount of hydrochloric acid (2M) was added to reach pH 2, hydrochloric acid (0.5M) (2×), water and brine, dried over magnesium sulphate, filtered and the solvent was removed under reduced pressure. The residue was purified by column chromatography on silica gel eluting with a gradient system of dichloromethane:methanol (99:1) gradually changing to dichloromethane:methanol (90:10) to afford the title compound (440 mg).

MS: 563 (M–H)⁻

$^1$H-NMR (CDCl$_3$) δ: 4.78 (2H, m), 4.60 (1H, m), 4.45 (1H, t), 4.26 (1H, dd), 2.78 (1H, dd), 1.60–2.0 (7H, m), 1.49 (9H, s), 1.08–1.35 (8H, m), 0.82 (2H, m).

Preparation 81: tert-Butyl (3R)-6-cyclohexyl-3-(3-{[[2-(dimethylamino)ethyl](methyl)amino]carbonyl}-1,2,4-oxadiazol-5-yl)hexanoate

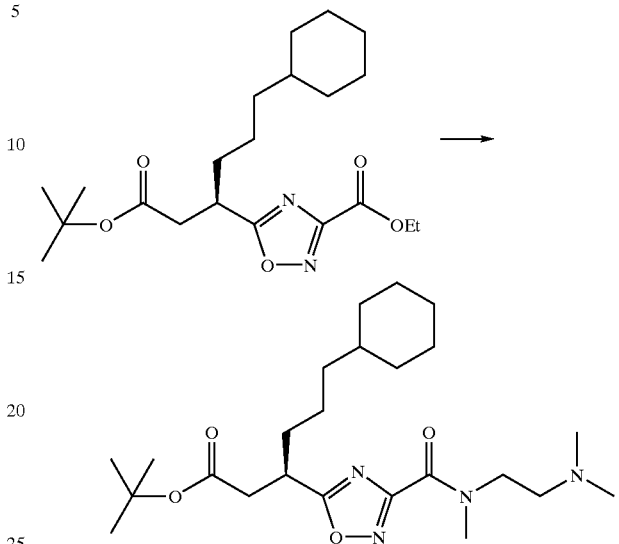

A solution of ethyl 5-{(1R)-1-[2-(tert-butoxy)-2-oxoethyl]-4-cyclohexylbutyl}-1,2,4-oxadiazole-3-carboxylate (Preparation 3) (560 mg, 1.42 mmol) in ethanol (2 ml) was treated with N,N,N'-trimethylethylenediamine (900 □1,0.91 mmol) and the resulting mixture was heated at 85° C. in a sealed tube for 4.5 hours. The solvent was removed under reduced pressure and the residue was purified by column chromatography on silica gel eluting with a system of 95:5:0.5 (dichloromethane:methanol:ammonia) to afford the title compound as a colourless oil (632 mg).

MS: 451 (MH⁺)

$^1$H-NMR (CDCl$_3$) δ: 3.64 (1H, br s), 3.51 (2H, m), 3.14 (3H, s), 2.83 (1H, dd), 2.65 (1H, dd), 2.43–2.60 (2H br d), 2.28 (3H, br s), 2.19 (3H, br s), 1.58–1.85 (7H, m), 1.39 (9H,s), 1.07–1.36 (8H, m), 0.84 (2H, m).

Preparation 82: (3R)-6-Cyclohexyl-3-(3-{[[2-(dimethylamino)ethyl](methyl)amino]carbonyl}-1,2,4-oxadiazol-5-yl)hexanoic Acid

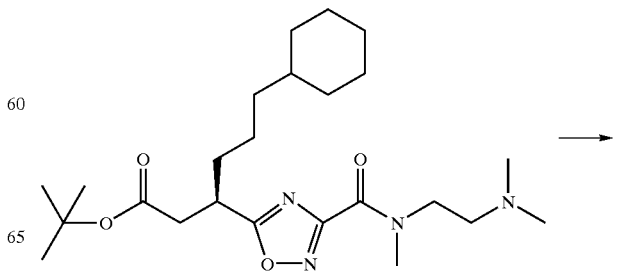

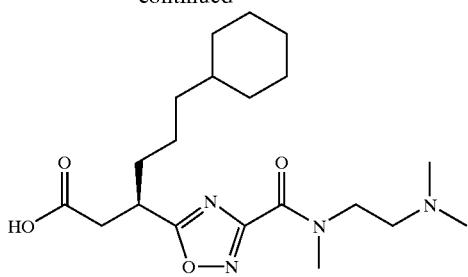

A solution of tert-butyl (3R)-6-cyclohexyl-3-(3-{[[2-(dimethylamino)ethyl](methyl)amino]carbonyl}-1,2,4-oxadiazol-5-yl)hexanoate (Preparation 81) (630 mg, 1.40 mmol) in dichloromethane (5 ml) was treated with trifluoroacetic acid (5 ml) and stirred at room temperature for 4 hours. The solvent was removed under reduced pressure and the residue azeotroped from dichloromethane. The residue was purified by column chromatography on silica gel eluting with a gradient system of 100:0 (dichloromethane:methanol) gradually changing to 90:10 (dichloromethane:methanol) to afford the title compound as a colourless gum (453 mg).

MS: 395 (MH+)

Analysis: Found, C, 46.50; H, 6.00; N, 9.13%; $C_{20}H_{34}N_4O_4 \cdot 2\ CF_3CO_2H$ requires C, 46.30; H, 5.83; N, 9.00%

$^1$H-NMR (CDCl$_3$) δ: 3.88 (1H, m), 3.76 (1H, m), 3.52 (1H, m), 3.05–3.40 (5H, m), 2.70–3.00 (7H, m), 1.57–1.90 (6H, m), 1.08–1.40 (7H, m), 0.84 (2H, m).

Preparation 83: tert-Butyl (3R)-6-cyclohexyl-3-(3-{[[3-(dimethylamino)propyl](methyl)amino]carbonyl}-1,2,4-oxadiazol-5-yl)hexanoate

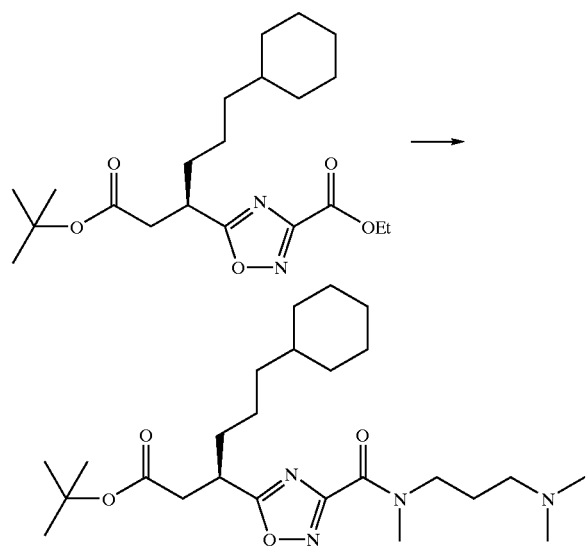

A solution of ethyl 5-{(1R)-1-[2-(tert-butoxy)-2-oxoethyl]-4-cyclohexylbutyl}-1,2,4-oxadiazole-3-carboxylate (Preparation 3) (550 mg, 1.40 mmol) in ethanol (2 ml) was treated with N,N,N'-trimethyl-1,3-propanediamine (1.02 ml, 7.00 mmol) and the resulting mixture was heated at 85° C. in a sealed tube for 3 hours. The solvent removed under reduced pressure. The residue was purified by column chromatography on silica eluting with a gradient system of 97:3:0.3 (dichloromethane:methanol:ammonia) gradually changing to 90:10:1 (dichloromethane:methanol:ammonia) to afford the title compound as a colourless oil (512 mg).

MS: 465 (MH+)

Analysis: Found, C, 64.44; H, 9.72; N, 12.07%; $C_{25}H_{44}N_4O_4$ requires C, 64.62; H, 9.54; N, 12.06%

$^1$H-NMR (CDCl$_3$) δ: 3.58 (1H, t), 3.50 (1H, t), 3.44 (1H, t), 3.09 (3H, d), 2.83 (1H, m), 2.64 (1H, dd), 2.35 (1H, t), 2.23 (3H, s), 2.20 (1H, m), 2.15 (3H, s), 1.58–1.88 (8H, m), 1.40 (9H, s), 1.06–1.37 (7H, m), 0.84 (2H, m).

Preparation 84: (3R)-6-Cyclohexyl-3-(3-{[[3-(dimethylamino)propyl](methyl)amino]carbonyl}-1,2,4-oxadiazol-5-yl)hexanoic Acid

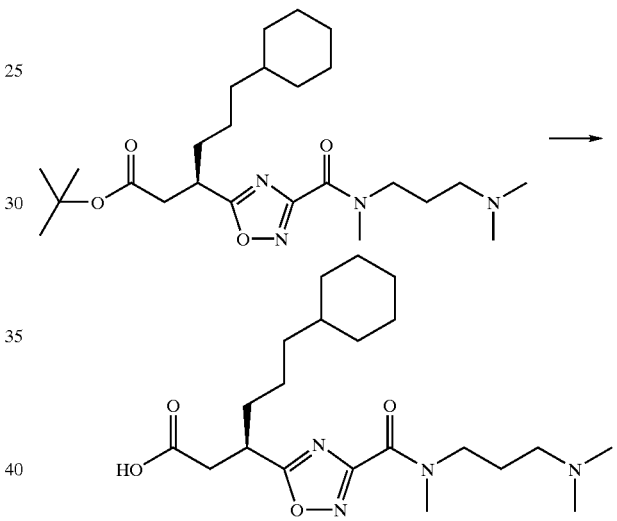

A solution of tert-butyl (3R)-6-cyclohexyl-3-(3-{[[3-(dimethylamino)propyl](methyl)amino]carbonyl}-1,2,4-oxadiazol-5-yl)hexanoate (Preparation 83) (500 mg, 1.08 mmol) in dichloromethane (5 ml) was treated with trifluoroacetic acid (5 ml) and stirred at room temperature for 4.5 hours. The solvent was removed under reduced pressure and the residue azeotroped from dichloromethane. The residue was purified by column chromatography on silica gel eluting with a gradient system of 100:0 (dichloromethane:methanol) gradually changing to 80:20 (dichloromethane:methanol) to afford the title compound as a colourless glass (595 mg).

MS: 409 (MH+)

Analysis: Found, C, 45.48; H, 5.84; N, 8.50%; $C_{21}H_{36}N_4O_4 \cdot 2\ CF_3CO_2H \cdot 2H_2O$ requires C, 45.87; H, 6.16; N, 8.56%

$^1$H-NMR (CDCl$_3$) δ: 3.52 (2H, m), 3.37 (1H, m), 3.09 (3H, m), 2.99 (2H, t), 2.81 (6H, s), 1.98 (2H, m), 1.58–1.90 (7H, m), 1.05–1.44 (8H, m), 0.88 (2H, m).

Preparation 85: tert-Butyl (3R)-6-cyclohexyl-3-[3-(hydroxymethyl)-1,2,4-oxadiazol-5-yl]hexanoate

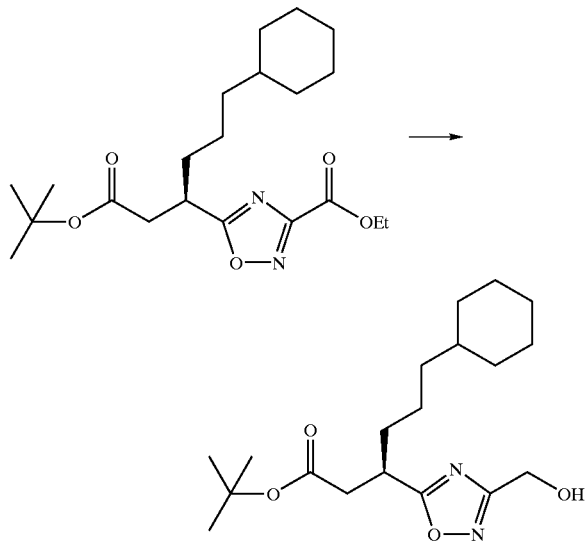

A solution of ethyl 5-{(1R)-1-[2-(tert-butoxy)-2-oxoethyl]-4-cyclohexylbutyl}-1,2,4-oxadiazol-3-carboxylate (Preparation 3) (15.2 g, 38.50 mmol) in ethanol (120 ml) was treated with portions of sodium borohydride (1.46 g, 38.50 mmol) and the resulting mixture was stirred at room temperature under a nitrogen atmosphere for 5 hours. Aqueous citric acid (5% w/v solution) was added slowly and the mixture was stirred at room temperature for a further 30 minutes. The organic solvent was removed under reduced pressure. The aqueous layer was diluted with water and extracted with ethyl acetate giving an emulsion. Anhydrous sodium chloride was added to break up the emulsion. The combined organic layers were washed with saturated sodium hydrogen carbonate solution and brine, dried over anhydrous sodium sulphate, filtered and the solvent removed under reduced pressure to afford the title compound as a colourless oil (13.4 g).

MS: 375 (MH$^+$)

$^1$H-NMR (CDCl$_3$) δ: 4.77 (2H, s), 3.46 (1H, m), 2.80 (1H, dd), 2.62 (1H, dd), 1.58–1.80 (7H, m), 1.39 (9H, s), 1.07–1.33 (8H, m), 0.82 (2H, m).

Preparation 86: tert-Butyl (3R)-6-cyclohexyl-3-{3-[(2-ethoxy-2-oxoethoxy)methyl]-1,2,4-oxadiazol-5-yl}hexanoate

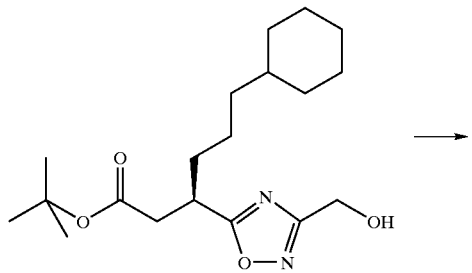

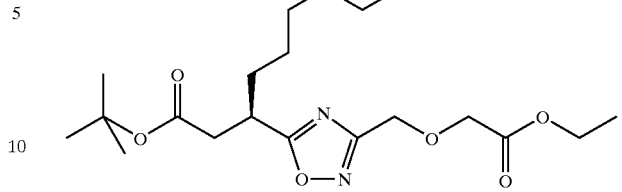

A suspension of sodium hydride 60% suspension in mineral oil (13 mg, 0.33 mmol) in anhydrous tetrahydrofuran (1 ml) was cooled to 0° C. and treated with a solution of tert-butyl (3R)-6-cyclohexyl-3-[3-(hydroxymethyl)-1,2,4-oxadiazol-5-yl]hexanoate (Preparation 85) (105 mg, 0.30 mmol) in anhydrous tetrahydrofuran (1 ml) and stirred under a nitrogen atmosphere for 1 hour. Ethyl bromoacetate (37 μl, 0.33 mmol) was added and the mixture was stirred for 18 hours, being allowed to warm to room temperature over this time. The reaction mixture was diluted with ethyl acetate and washed with water and brine, dried over anhydrous sodium sulphate, filtered and the solvent removed under reduced pressure. The solid was purified by column chromatography on silica gel eluting with a gradient system of pentane:ethyl acetate (99:1) to pentane:ethyl acetate (80:20) to afford the title compound as a colourless oil (84 mg).

MS: 461 (MNa$^+$)

Analysis: Found, C, 62.87; H, 8.77; N, 6.39%; C$_{23}$H$_{38}$N$_2$O$_6$ requires C, 62.99; H, 8.73; N, 6.39%

$^1$H-NMR (CDCl$_3$) δ: 4.75 (2H, s), 4.20 (4H, m), 3.45 (1H, m), 2.80 (1H, dd), 2.60 (1H, dd), 1.6–1.8 (7H, m), 1.40 (9H, s), 1.10–1.30 (11H, m), 0.94 (2H, m).

Preparation 87: (3R)-6-Cyclohexyl-3-{3-[(2-ethoxy-2-oxoethoxy)methyl]-1,2,4-oxadiazol-5-yl}hexanoic Acid

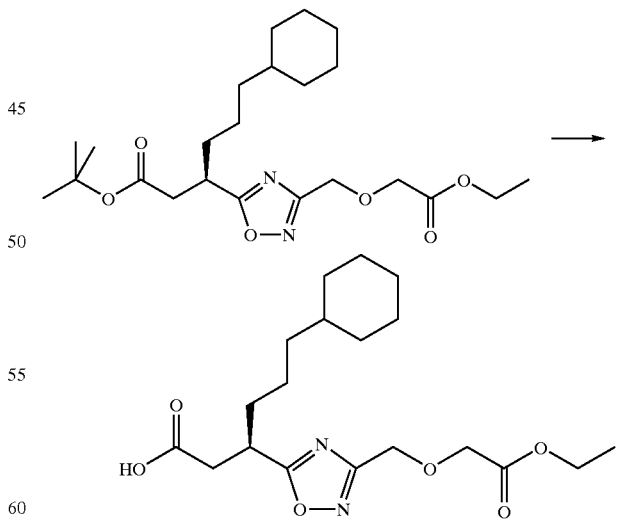

A solution of tert-butyl (3R)-6-cyclohexyl-3-{3-[(2-ethoxy-2-oxoethoxy)methyl]-1,2,4-oxadiazol-5-yl}hexanoate (Preparation 86) (500 mg, 1.08 mmol) in dichloromethane (7 ml) was treated with trifluoroacetic acid (3 ml) and stirred at room temperature for 5 hours. The solvent was removed under reduced pressure and the residue azeotroped from toluene and dichloromethane. The oil was purified by column chromatography on silica gel eluting with a gradient system of 100:0:0 (dichloromethane:methanol:acetic acid) gradually changing to 90:10:1 (dichloromethane:methanol:acetic acid) to afford the title compound as a colourless oil (374 mg).

MS: 383 (MH⁺)

Analysis: Found, C, 59.67; H, 7.91; N, 7.32%; $C_{19}H_{30}N_2O_6.0.05$ $H_2O.0.05$ $CH_2Cl_2$ requires C, 59.62; H, 7.90; N, 7.22%

$^1$H-NMR (CDCl$_3$) δ: 4.75 (2H, s), 4.20 (4H, m), 3.51 (1H, m), 2.98 (1H, dd), 2.75 (1H, dd), 1.60–1.80 (7H, m), 1.10–1.30 (11H, m), 0.82 (2H, m).

Preparation 88: tert-Butyl (3R)-6-cyclohexyl-3-{3-[(2-ethoxy-1-methyl-2-oxoethoxy)methyl]-1,2,4-oxadiazol-5-yl}hexanoate

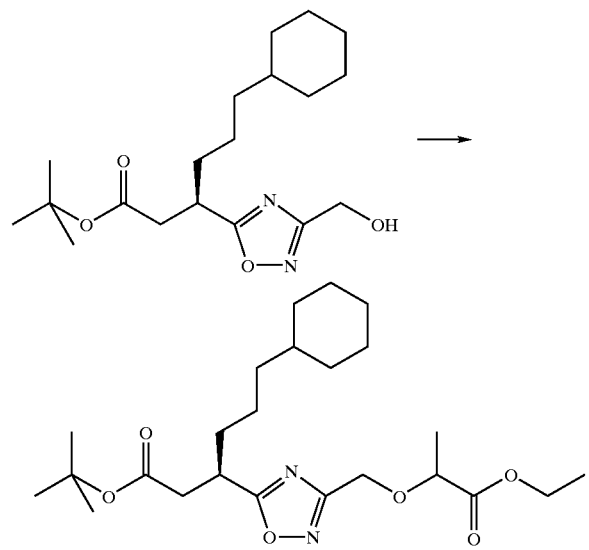

A suspension of sodium hydride 60% suspension in mineral oil (18 mg, 0.45 mmol) in anhydrous tetrahydrofuran (1 ml) was cooled to 0° C. and treated with a solution of tert-butyl (3R)-6-cyclohexyl-3-[3-(hydroxymethyl)-1,2,4-oxadiazol-5-yl]hexanoate (Preparation 85) (142 mg, 0.40 mmol) in anhydrous tetrahydrofuran (1 ml) and stirred under a nitrogen atmosphere for 0.5 hours. Ethyl 2-bromopropionate (37 μl, 0.33 mmol) was added and the mixture was stirred for 2 days, being allowed to warm to room temperature over this time. The reaction mixture was diluted with ethyl acetate and washed with water and brine, dried over anhydrous sodium sulphate, filtered and the solvent removed under reduced pressure. The oil was purified by column chromatography on silica gel eluting with a gradient system of pentane:ethyl acetate (99:1) to pentane:ethyl acetate (0:100) to afford the title compound as a colourless oil (90 mg).

MS: 475 (MNa⁺)

Analysis: Found, C, 63.57; H, 8.93; N, 6.19%; $C_{24}H_{40}N_2O_6$ requires C, 63.69; H, 8.91; N, 6.19%

$^1$H-NMR (CDCl$_3$) δ: 4.79 (1H, d), 4.58 (1H, d), 4.20 (3H, m), 3.45 (1H, m), 2.78 (1H, dd), 2.60 (1H, dd), 1.60–1.80 (7H, m), 1.42 (3H, d), 1.35 (9H, s), 1.10–1.30 (11H, m), 0.83 (2H, m)

Preparation 89: (3R)-6-Cyclohexyl-3-{3-[(2-ethoxy-1-methyl-2-oxoethoxy)methyl]-1,2,4-oxadiazol-5-yl}hexanoic Acid

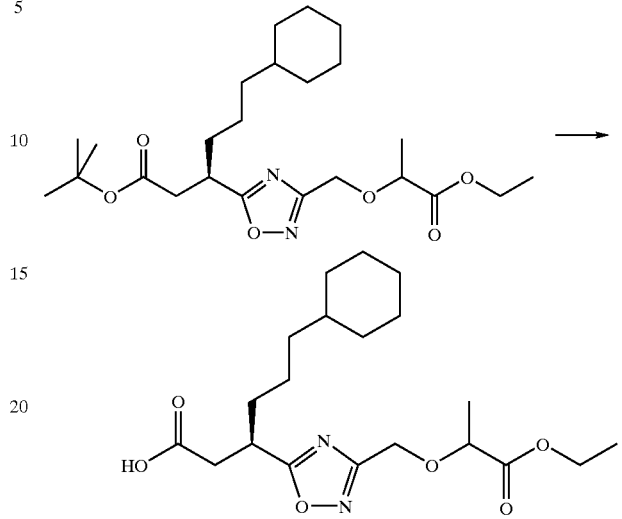

A solution of tert-butyl (3R)-6-cyclohexyl-3-{3-[(2-ethoxy-1-methyl-2-oxoethoxy)methyl]-1,2,4-oxadiazol-5-yl}hexanoate (Preparation 88) (480 mg, 1.06 mmol) in dichloromethane (8 ml) was treated with trifluoroacetic acid (3.5 ml) and stirred at room temperature for 5 hours. The solvent was removed under reduced pressure and the residue azeotroped from toluene and dichloromethane. The oil was purified by column chromatography on silica gel eluting with a gradient system of 100:0:0 (dichloromethane:methanol:acetic acid) gradually changing to 95:5:0.5 (dichloromethane:methanol:acetic acid) to afford the title compound as a colourless oil (395 mg).

MS: 419 (MNa⁺)

Analysis: Found, C, 60.03; H, 8.21; N, 6.97%; $C_{20}H_{32}N_2O_6.0.2$ $CH_2Cl_2$ requires C, 60.04; H, 8.16; N, 7.00%

$^1$H-NMR (CDCl$_3$) δ: 4.80 (1H, d), 4.58 (1H, d), 4.10–4.30 (3H, m), 3.50 (1H, m), 2.98 (1H, dd), 2.75 (1H, dd), 1.60–1.80 (7H, m), 1.45 (3H, d), 1.10–1.30 (11H, m), 0.83 (2H, m).

Preparation 90: tert-Butyl (3R)-3-{3-[(2-amino-2-oxoethoxy)methyl]-1,2,4-oxadiazol-5-yl}-6-cyclohexylhexanoate

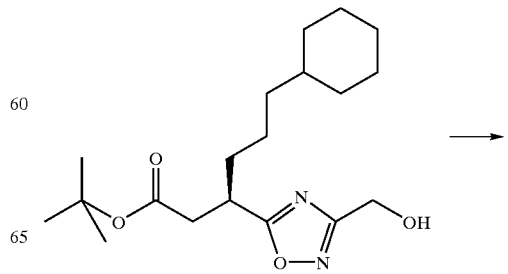

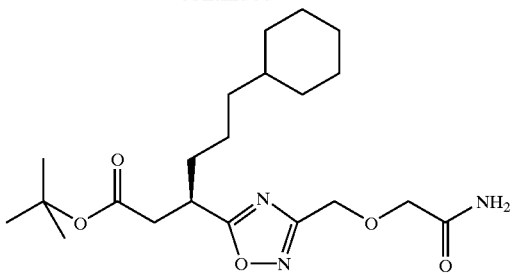

A suspension of sodium hydride 60% suspension in mineral oil (51 mg, 1.28 mmol) in anhydrous tetrahydrofuran (3 ml) was cooled to 0° C. and treated with a solution of tert-butyl (3R)-6-cyclohexyl-3-[3-(hydroxymethyl)-1,2,4-oxadiazol-5-yl]hexanoate (Preparation 85) (105 mg, 0.30 mmol) in anhydrous tetrahydrofuran (3 ml) and stirred under a nitrogen atmosphere for 30 minutes. 2-Bromoacetamide (235 mg, 1.70 mmol) was added and the mixture was allowed to warm to room temperature and then heated at 40° C. for 15 hours. The cooled reaction mixture was diluted with ethyl acetate and washed with water and brine, dried over anhydrous sodium sulphate, filtered and the solvent removed under reduced pressure. The solid was purified by column chromatography on silica gel eluting with a gradient system of pentane:ethyl acetate (99:1) to pentane:ethyl acetate (0:100) to afford the title compound as a colourless oil (330 mg).

MS: 432 (MNa$^+$)

$^1$H-NMR (CDCl$_3$) δ: 4.68 (2H, s), 4.10 (2H, s), 3.46 (1H, m), 2.79 (1H, dd), 2.6 (1H, dd), 1.6–1.8 (7H, m), 1.40 (9H, s), 1.10–1.30 (8H, m), 0.84 (2H, m).

Preparation 91: (3R)-3-{3-[(2-Amino-2-oxoethoxy)methyl]-1,2,4-oxadiazol-5-yl}-6-cyclohexylhexanoic Acid

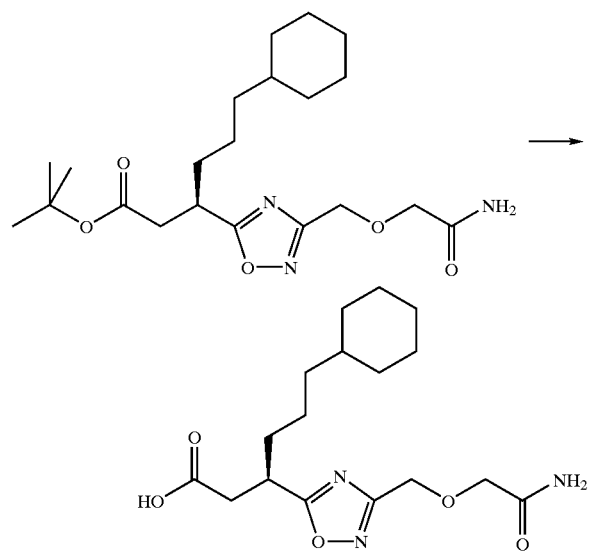

A solution of tert-butyl (3R)-3-{3-[(2-amino-2-oxoethoxy)methyl]-1,2,4-oxadiazol-5-yl}-6-cyclohexylhexanoate (Preparation 90) (280 mg, 0.86 mmol) in dichloromethane (7 ml) was treated with trifluoroacetic acid (3 ml) and stirred at room temperature for 4 hours. The solvent was removed under reduced pressure and the residue azeotroped from toluene and dichloromethane. The oil was purified by column chromatography on silica gel eluting with a gradient system of 100:0:0 (dichloromethane:methanol:acetic acid) gradually changing to 90:10:1 (dichloromethane:methanol:acetic acid) to afford a colourless oil which was triturated with diethyl ether and filtered to afford the title compound (155 mg).

MS: 376 (MNa$^+$)

$^1$H-NMR (CDCl$_3$) δ: 6.60–6.80 (2H, br d) 4.70 (2H, s), 4.08 (2H, dd), 3.48 (1H, m), 2.85 (1H, dd), 2.73 (1H, dd), 1.60–1.80 (7H, m), 1.10–1.40 (8H, m), 0.82 (2H, m).

Preparation 92: tert-Butyl (3R)-6-cyclohexyl-3-[3-({[(4-methylphenyl)sulfonyl]oxy}methyl)-1,2,4-oxadiazol-5-yl]hexanoate

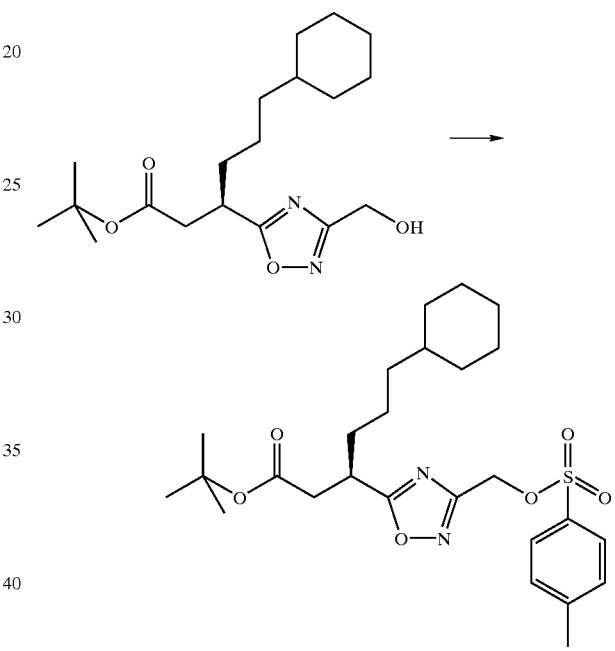

A suspension of sodium hydride 60% suspension in mineral oil (1.52 g, 38.00 mmol) in anhydrous tetrahydrofuran (30 ml) was cooled to 0° C. and treated with a solution of tert-butyl (3R)-6-cyclohexyl-3-[3-(hydroxymethyl)-1,2,4-oxadiazol-5-yl]hexanoate (Preparation 85) (13.40 g, 38.00 mmol) in anhydrous tetrahydrofuran (120 ml) and stirred under a nitrogen atmosphere for 30 minutes. p-Toluene sulphonyl chloride (7.25 g, 38.00 mmol) was added portionwise and the mixture was allowed to warm to room temperature over 18 hours. The solvent was removed under reduced pressure The residue was dissolved in ethyl acetate and washed with water, saturated sodium hydrogen carbonate solution and brine, dried over anhydrous sodium sulphate, filtered and the solvent removed under reduced pressure. The oil was purified by column chromatography on silica gel eluting with dichloromethane to afford the title compound (10.75 g).

MS: 529 (MNa$^+$)

$^1$H-NMR (CDCl$_3$) δ: 7.80 (2H, d), 7.33 (2H, d), 5.12 (2H, s), 3.40 (1H, m), 2.72 (1H, dd), 2.58 (1H, dd), 2.43 (3H, s), 1.56–1.78 (7H, m), 1.35 (9H, s), 1.05–1.30 (8H, m), 0.82 (2H, m).

Preparation 93: 1-tert-Butyl 3-ethyl 2-({5-[(1R)-1-(2-tert-butoxy-2-oxoethyl)-4-cyclohexylbutyl]-1,2,4-oxadiazol-3-yl}methyl)malonate

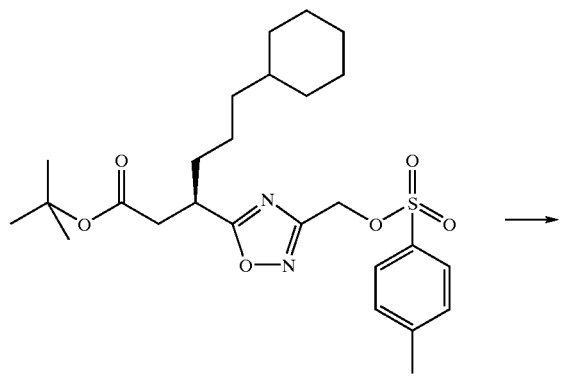

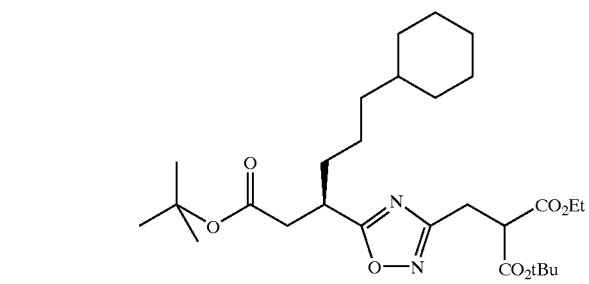

A suspension of sodium hydride 60% suspension in mineral oil (35 mg, 38.00 mmol) in anhydrous tetrahydrofuran (3 ml) was cooled to 0° C. and treated with tert-butylethyl malonate (13.40 g, 38.00 mmol), stirred under a nitrogen atmosphere for 5 minutes and then allowed to warm to room temperature. A solution of tert-butyl (3R)-6-cyclohexyl-3-[3-({[(4-methylphenyl)sulfonyl]oxy}methyl)-1,2,4-oxadiazol-5-yl]hexanoate (Preparation 92) (400 mg, 0.78 mmol) in anhydrous tetrahydrofuran (3 ml) was added and the mixture was stirred at room temperature for 18 hours. The solvent was removed under reduced pressure. The residue was dissolved in ethyl acetate and washed with water and brine, dried over anhydrous sodium sulphate, filtered and the solvent removed under reduced pressure to afford the title compound as a colourless oil (518 mg) of approximately 70% purity which was used without further purification.

MS: 546 (MNa$^+$)

$^1$H-NMR (CDCl$_3$) δ: 4.20 (2H, m), 3.80 (1H, t), 3.40 (1H, m), 3.25 (2H, d), 2.75 (1H, dd), 2.59 (1H, dd), 1.60–1.75 (7H, m), 1.43 (9H, s), 1.39 (9H, s), 1.10–1.30 (11H, m), 0.83 (2H, m).

Preparation 94: (3R)-6-Cyclohexyl-3-[3-(3-ethoxy-3-oxopropyl)-1,2,4-oxadiazol-5-yl]hexanoic Acid

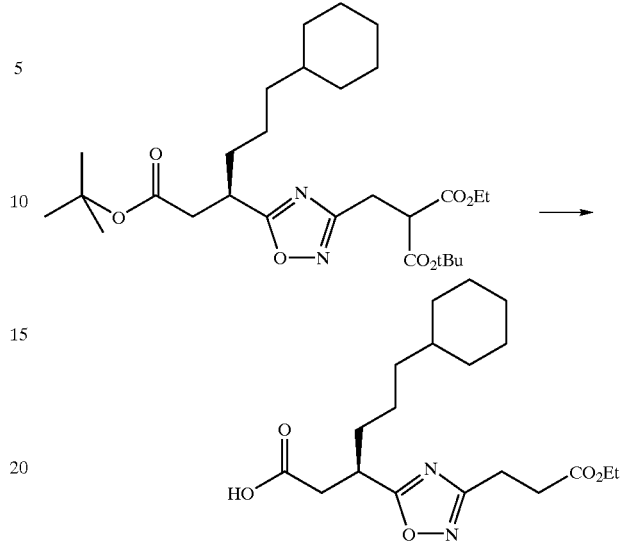

A solution of 1-tert-butyl 3-ethyl 2-({5-[(1R)-1-(2-tert-butoxy-2-oxoethyl)-4-cyclohexylbutyl]-1,2,4-oxadiazol-3-yl}methyl)malonate (Preparation 93) (510 mg, 0.79 mmol) in dichloromethane (10 ml) was treated with trifluoroacetic acid (5 ml) and stirred at room temperature for 5 hours. The solvent was removed under reduced pressure and the residue azeotroped from toluene. The solid was dissolved in xylene (10 ml) and heated at 140° C. for 7 hours. The solvent was removed under reduced pressure. The oil was purified by column chromatography on silica gel eluting with a gradient system of 95:5:0 (dichloromethane:isopropyl alcohol:acetic acid) gradually changing to 90:10:1 (dichloromethane:isopropyl alcohol:acetic acid) to afford the title compound as a colourless oil (117 mg).

MS: 389 (MNa$^+$)

$^1$H-NMR (CDCl$_3$) δ: 4.12 (2H, q), 3.48 (1H, m), 3.03 (2H, t), 2.92 (1H, dd), 2.75 (3H, m), 1.60–1.80 (7H, m), 1.10–1.35 (11H, m), 0.82 (2H, m).

Preparation 95: tert-Butyl (3R)-3-[({[(Z)-1-amino-2-(propylsulfonyl)ethylidene]amino}oxy)carbonyl]-6-cyclohexylhexanoate

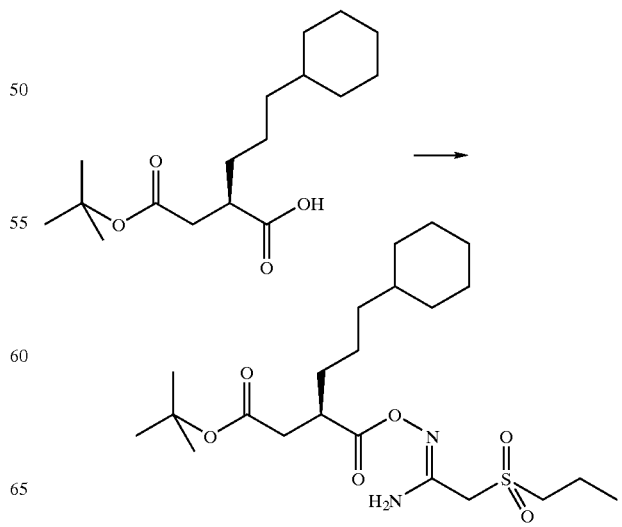

A solution of (2R)-2-(2-tert-butoxy-2-oxoethyl)-5-cyclohexylpentanoic acid (Preparation 1) (500 mg, 1.67 mmol), 1-(3-dimethylaminopropyl)-3-ethylcarbodiimide hydrochloride (354 mg, 1.85 mmol), N-methylmorpholine (203 □1,1.85 mmol) and 1-hydroxybenzotriazole hydrate (227 mg, 1.67 mmol) in dichloromethane (20 ml) was treated with (1Z)-N'-hydroxy-2-(propylsulfonyl)ethanimidamide (300 mg, 1.67 mmol) and stirred at room temperature for 18 hours. The reaction mixture was diluted with water (10 ml) and stirred for 20 minutes. The layers were separated via a 5 micron filter cartridge. The organic solvent was removed under reduced pressure to afford the title compound as a yellow solid (760 mg).

MS: 483 (MNa$^+$)

$^1$H-NMR (CDCl$_3$) δ: 5.62 (2H, br s), 3.82 (2H, d), 3.15 (2H, m), 2.83 (1H, m), 2.65 (1H, dd), 2.42 (1H, dd), 1.90 (2H, m), 1.57–1.80 (8H, m), 1.45 (9H, s), 1.10–1.30 (7H, m), 1.08 (3H, t), 0.83 (2H, m).

Preparation 96: tert-Butyl (3R)-6-cyclohexyl-3-{3-[(propylsulfonyl)methyl]-1,2,4-oxadiazol-5-yl}hexanoate

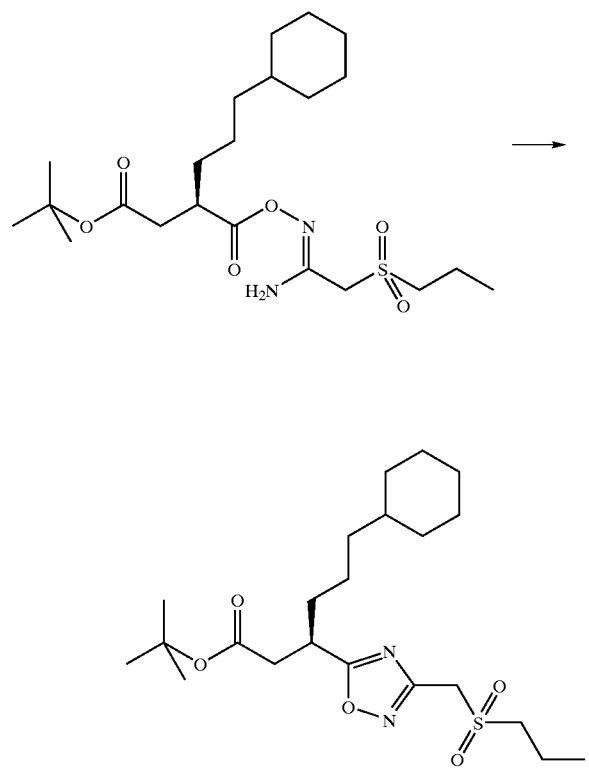

A solution of tert-butyl (3R)-3-[({[(Z)-1-amino-2-(propylsulfonyl)ethylidene]amino}oxy)carbonyl]-6-cyclohexylhexanoate (Preparation 95) (760 mg, 1.60 mmol) in xylene (15 ml) was heated at 130° C. for 28 hours. After cooling to room temperature the reaction mixture was purified by column chromatography on silica gel eluting with a gradient system of 100:0 (pentane:ethyl acetate) gradually changing to 70:30 (pentane:ethyl acetate) to afford the title compound as a yellow oil (400 mg).

MS: 441 (MH$^+$)

$^1$H-NMR (CDCl$_3$) δ: 4.32 (2H, s), 3.48 (1H, m), 3.13 (2H, dd), 2.80 (1H, dd), 2.65 (1H, dd), 1.92 (2H, m), 1.60–1.80 (7H, m), 1.40 (9H, s), 1.10–1.35 (11H, m), 0.82 (2H, m).

Preparation 97: (3R)-6-Cyclohexyl-3-{3-[(propylsulfonyl)methyl]-1,2,4-oxadiazol-5-yl}hexanoic Acid

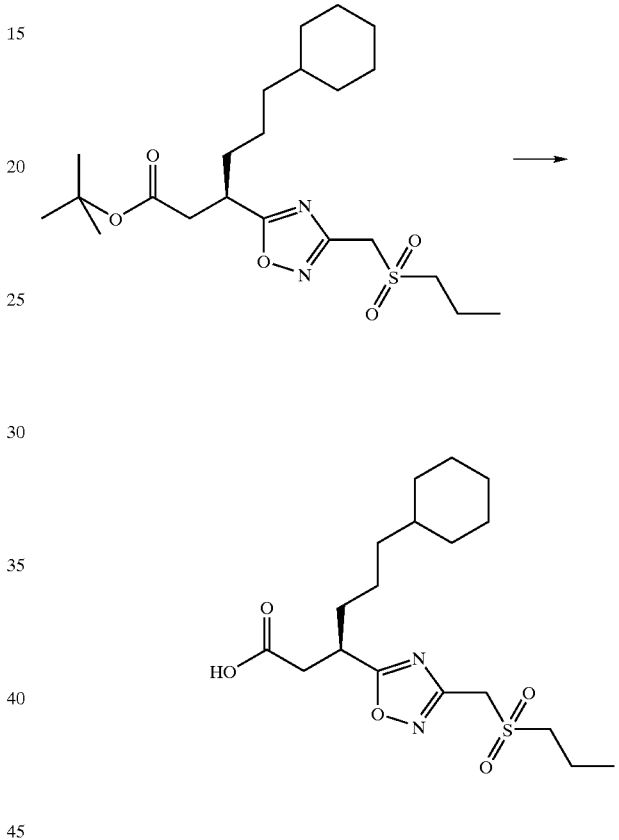

A solution of tert-butyl (3R)-6-cyclohexyl-3-{3-[(propylsulfonyl)methyl]-1,2,4-oxadiazol-5-yl}hexanoate (Preparation 96) (371 mg, 0.84 mmol) in hydrogen chloride in 1,4-dioxan (4M) (4 ml) was stirred at room temperature for 24 hours. The solvent was removed under reduced pressure. The solid was dissolved in fresh hydrogen chloride in 1,4-dioxan (4M) and stirred at room temperature for 3 hours. The solvent was removed under reduced pressure. The residue was dissolved in ethyl acetate and washed with saturated sodium hydrogen carbonate solution and brine, dried over anhydrous magnesium sulphate, filtered and the solvent was removed under reduced pressure to afford the title compound as a yellow oil (313 mg).

MS: 385 (M−H)$^-$ $^1$H-NMR (DMSO) δ: 4.70 (2H, s), 3.43 (1H, m), 2.75 (2H, t), 2.52 (2H, obs), 1.75 (2H, m), 1.50–1.70 (7H, m), 1.05–1.30 (9H, m), 0.97 (3H, t), 0.80 (2H, m).

Preparation 98: 2-((1R)-1-{2-[(Benzyloxy)amino]-2-oxoethyl}-4-cyclohexylbutyl)-N-[2-(dimethylamino)ethyl]-5-methyl-1,3-oxazole-4-carboxamide

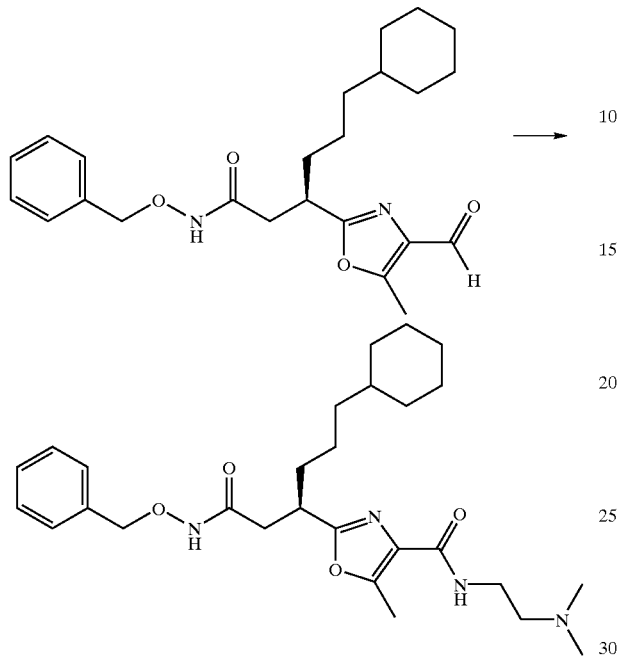

Preparation 99: Methyl ({[2-((1R)-1-{2-[(benzyloxy)amino]-2-oxoethyl}-4-cyclohexylbutyl)-5-methyl-1,3-oxazol-4-yl]carbonyl}amino)acetate

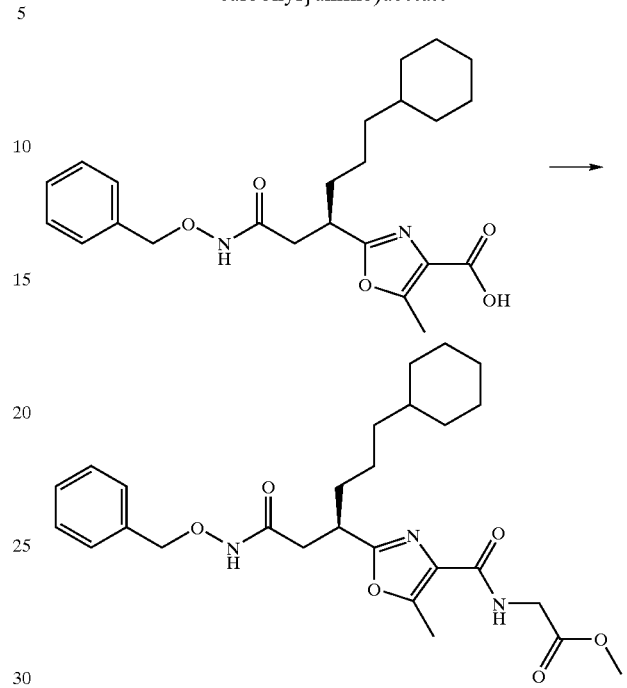

A solution 2-((1R)-1-{2-[(benzyloxy)amino]-2-oxoethyl}-4-cyclohexylbutyl)-5-methyl-1,3-oxazole-4-carboxylic acid (Preparation 72) (200 mg, 0.47 mmol), N-methylmorpholine (77 □1,0.70 mmol), 1-hydroxybenzotriazole hydrate (63 mg, 0.47 mmol) and 1-(3-dimethylaminopropyl)-3-ethylcarbodiimide hydochloride (134 mg, 0.70 mmol) in dichloromethane (10 ml) was treated with N,N-dimethylethylenediamine (56 □1,0.51 mmol) and stirred at room temperature for 18 hours. The reaction mixture was diluted with dichloromethane and washed with water, saturated sodium hydrogen carbonate solution and brine, dried over anhydrous magnesium sulphate, filtered and the solvent removed under reduced pressure. The residue was purified by column chromatography on silica gel eluting with a system of 94:4:0.4 (dichloromethane:methanol:ammonia) to afford the title compound as a white solid (216 mg).

MS: 499 (MH$^+$)

Analysis: Found, C, 67.24; H, 8.60; N, 11.25%; $C_{28}H_{42}N_4O_4$ requires C, 67.44; H, 8.49; N, 11.24%

$^1$H-NMR (CDCl$_3$) δ: 7.35 (5H, br s), 7.10 (1H, br s), 4.85 (2H, s), 3.45 (2H, q), 3.35 (1H, m), 2.59 (3H, s), 2.46 (2H, t), 2.24 (6H, s), 1.60–1.75 (7H, m), 1.10–1.30 (7H, m), 0.85 (2H, m).

A solution 2-((1R)-1-{2-[(benzyloxy)amino]-2-oxoethyl}-4-cyclohexylbutyl)-5-methyl-1,3-oxazole-4-carboxylic acid (Preparation 72) (230 mg, 0.53 mmol), N-methylmorpholine (61 □1,0.56 mmol), 1-hydroxybenzotriazole hydrate (68 mg, 0.53 mmol) and 1-(3-dimethylaminopropyl)-3-ethylcarbodiimide hydrochloride (107 mg, 0.56 mmol) in dichloromethane (10 ml) was treated with a solution of glycine methyl ester hydrochloride (70 mg, 0.56 mmol) and N-methylmorpholine (61 o1,0.56 mmol) in dichloromethane (2 ml) and stirred at room temperature for 18 hours. The reaction mixture was diluted with dichloromethane and washed with water, saturated sodium hydrogen carbonate solution and brine, dried over anhydrous magnesium sulphate, filtered and the solvent removed under reduced pressure. The residue was purified by column chromatography on silica gel eluting with a gradient system of 100:0:0 (dichloromethane:methanol:ammonia) gradually changing to 98:2:0.2 (dichloromethane:methanol:ammonia) to afford the title compound as a white solid (160 mg).

MS: 522 (MNa$^+$)

$^1$H-NMR (CDCl$_3$) δ: 7.44 (1H, br s), 7.35 (5H, s), 5.11 (1H, s), 4.87 (2H, s), 4.12 (2H, d), 3.77 (3H, s), 3.37 (1H, m), 2.70 (1H, m), 2.56 (3H, s), 2.45 (1H, m), 1.55–1.1.80 (7H, m), 1.05–1.40 (8H, m), 0.83 (2H, m).

Preparation 100: ({[2-((1R)-1-{2-[(Benzyloxy)amino]-2-oxoethyl}-4-cyclohexylbutyl)-5-methyl-1,3-oxazol-4-yl]carbonyl}amino)acetic Acid

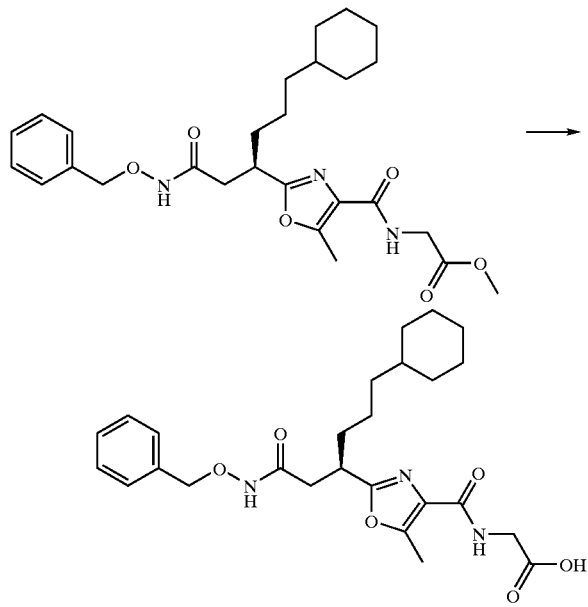

A solution of methyl ({[2-((1R)-1-{2-[(benzyloxy)amino]-2-oxoethyl}-4-cyclohexylbutyl)-5-methyl-1,3-oxazol-4-yl]carbonyl}amino)acetate (Preparation 99) (158 mg, 0.32 mmol) in 1,4-dioxan (5 ml) was treated with sodium hydroxide solution (1M) (470 □1,0.47 mmol). The mixture was stirred for 1 hour under a nitrogen atmosphere. The reaction mixture was diluted in water and washed with ethyl acetate. The aqueous layer was acidified with solid citric acid and extracted with ethyl acetate. The organic layers were dried over anhydrous magnesium sulphate, filtered and the solvent removed under reduced pressure to afford the title compound (61 mg).

MS: 484 (M–H)⁻

¹H-NMR (CDCl₃) δ: 7.35 (5H, br s), 4.85 (2H, s), 4.17 (2H, d), 3.39 (1H, m), 2.60 (3H, s), 2.43 (1H, m), 1.55–1.75 (7H, m), 1.10–1.35 (9H, m), 0.85 (2H, m).

Accurate Mass: 486.26 (MH⁺)

Preparation 101: tert-Butyl (3R)-3-[({[(Z)-1,2-diamino-2-oxoethylidene]amino}oxy)carbonyl]-6-cyclohexylhexanoate

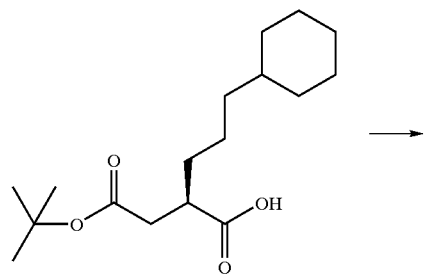

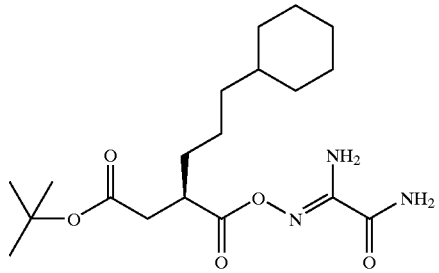

(R)-2-[2-(tert-Butoxy)-2-oxoethyl]-5-cyclohexylpentanoic acid (Preparation 1) (3.47 g, 11.6 mmol) in dimethylformamide (21 ml) was treated with 1,1'-carbonyldiimidazole (1.97 g, 12.2 mmol) and the mixture was stirred at ambient temperature for 1 hour. N-Dimethylaminopyridine (1.43 g, 11.7 mmol) was then added in one portion, followed by the addition of 2-amino-2-(hydroxyimino)acetamide (1.25 g, 12.1 mmol, Helv.Chim.Acta; 47; 1964; 33–46). The resulting mixture was stirred at room temperature for 24 hours. The mixture was partitioned between ethyl acetate and a 10% solution of citric acid in demineralised water. The layers were separated and the aqueous phase was extracted with ethyl acetate. The combined organic layers were washed with demineralised water (×4) and brine, dried over anhydrous magnesium sulfate, filtered and the solvent removed under reduced pressure. The residue was crystallised from n-hexane, the precipitate was collected by filtration and dried in vacuo to afford the title compound as a colourless solid (3.30 g, 74% yield).

MS: 382 [(M–H)]⁻

¹H-NMR (CDCl₃) δ: 7.04 (1H, br s), 5.73 (2H, br s), 5.46 (1H, br s), 2.90 (1H, m), 2.68 (1H, dd, J=15, 12 Hz), 2.45 (1H, dd, J=18, 6 Hz), 1.63–1.74 (9H, m), 1.55–1.50 (1H, m), 1.43 (9H, s), 1.37–1.10 (5H, m), 0.93–0.82 (2H, m)

Preparation 102: tert-butyl (3R)-6-cyclohexyl-3-[3-(1H-imidazol-2-ylmethyl)-1,2,4-oxadiazol-5-yl]hexanoate

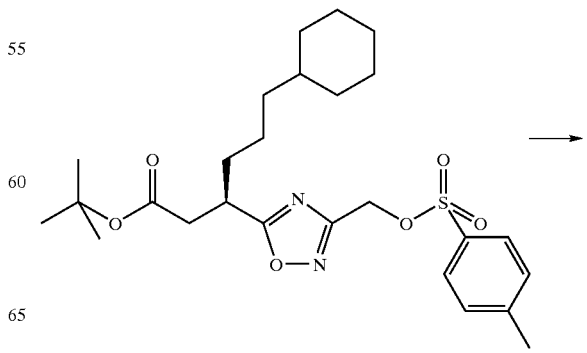

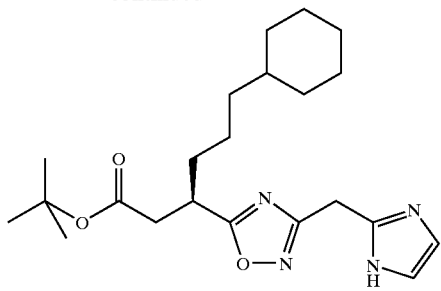

A solution of tert-butyl 1H-imidazole-1-carboxylate (133 mg, 0.79 mmol) in anhydrous tetrahydrofuran (2 ml), cooled to −78° C., treated with n-butyl lithium, 2.5M in hexanes (320 μl, 0.79 mmol) and stirred under a nitrogen atmosphere for 1 hour. A solution of tert-butyl (3R)-6-cyclohexyl-3-[3-({[(4-methylphenyl)sulfonyl]oxy}methyl)-1,2,4-oxadiazol-5-yl]hexanoate (Preparation 92) (400 mg, 0.79 mmol) in anhydrous tetrahydrofuran (2 ml) was added slowly and the mixture was allowed to warm to room temperature and stirred at this temperature for 18 hours. The reaction mixture was partitioned between ethyl acetate (30 ml) and water (30 ml). The organic layer was washed once more with water (20 ml), dried over anhydrous sodium sulphate, filtered and the solvent removed under reduced pressure to afford the title compound as a pale yellow oil (307 mg).

MS: 403 (MH$^+$)

Analysis: Found, C, 65.61; H, 8.91; N, 11.78%; $C_{22}H_{34}N_4O_3$ requires C, 65.64; H, 8.51; N, 13.92%

$^1$H-NMR (CDCl$_3$) δ: 7.59 (1H, s), 7.07 (1H, s), 7.01 (1H, s), 5.28 (2H, s), 3.40 (1H, m), 2.76 (1H, dd), 2.60 (1H, dd), 1.40–1.80 (10H, m), 1.10–1.40 (12H, m), 0.88 (4H, m).

Preparation 103: (3R)-6-cyclohexyl-3-[3-(1H-imidazol-2-ylmethyl)-1,2,4-oxadiazol-5-yl]hexanoic Acid

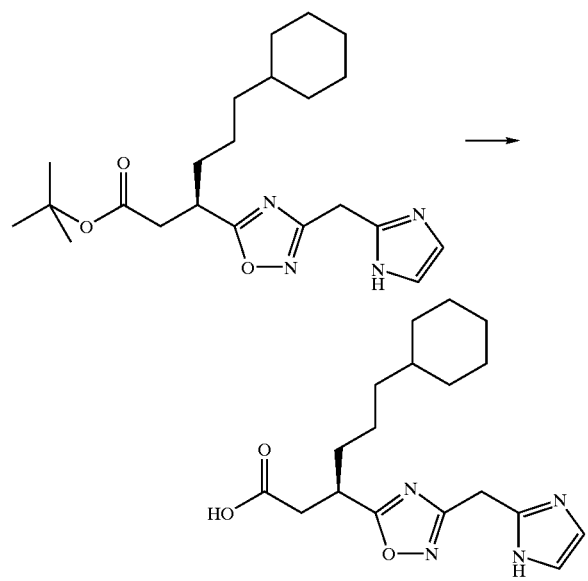

tert-butyl (3R)-6-cyclohexyl-3-[3-(1H-imidazol-2-ylmethyl)-1,2,4-oxadiazol-5-yl]hexanoate (Preparation 102) (530 mg, 1.32 mmol) was treated with trifluoroacetic acid (10 ml) and stirred at room temperature for 1.5 hours. The solvent was removed under reduced pressure and the residue azeotroped from toluene (3×30 ml) and dichloromethane (2×30 ml) to afford the title compound (609 mg).

MS: 347 (MH$^+$)

Analysis: Found, C, 48.81; H, 5.61; N, 10.40%; $C_{18}H_{26}N_4O_3$. 1.5CF$_3$CO$_2$H. 0.13H$_2$O requires C, 48.52; H, 5.38; N, 10.78%

$^1$H-NMR (CDCl$_3$) δ: 8.80 (1H, s), 7.38 (1H, s), 7.28 (1H, s), 5.41 (2H, s), 3.48 (1H, m), 2.70–2.95 (2H, m), 1.50–1.80 (7H, m), 1.10–1.40 (8H, m), 0.85 (2H, m).

Preparation 104: tert-butyl (3R)-3-[({[(Z)-1-amino-2-(4-pyridinyl)ethylidene]amino}oxy)carbonyl]-6-cyclohexylhexanoate

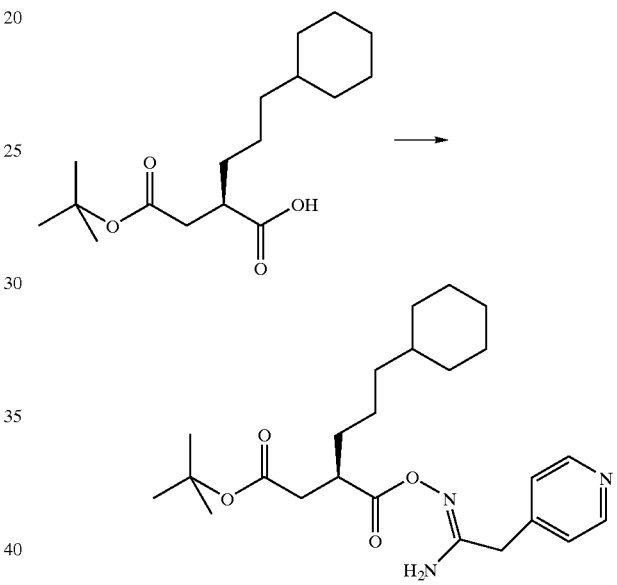

A solution of (2R)-2-(2-tert-butoxy-2-oxoethyl)-5-cyclohexylpentanoic acid (Preparation 1) (500 mg, 1.67 mmol) in dichloromethane (20 ml) was treated with 1-(3-dimethylaminopropyl)-3-ethylcarbodiimide hydrochloride (354 mg, 1.85 mmol), N-methylmorpholine (203 μl, 1.85 mmol) and 1-hydroxybenzotriazole hydrate (227 mg, 1.67 mmol). (1Z)-N'-hydroxy-2-(4-pyridinyl)ethanimidamide (WO 9600720) (374 mg, 1.67 mmol) followed by N-methylmorpholine (369 μl, 3.34 mmol) were added to the reaction mixture which was stirred at room temperature for 18 hours. The reaction mixture was diluted with water (10 ml) and stirred for 20 minutes. The layers were separated via a 5 micron filter cartridge. The organic solvent was removed under reduced pressure to afford the title compound as a yellow oil (840 mg). This was used without further purification in the following step.

MS: 454 (MNa$^+$)

$^1$H-NMR (CDCl$_3$) δ: 8.58 (2H, d), 7.28 (2H, d), 4.90 (1H, br s), 3.57 (2H, s), 2.85 (1H, m), 2.40 (2H, m), 1.60–1.80 (6H, m), 1.30–1.60 (12H, m), 1.10–1.30 (6H, m), 0.87 (2H, m).

Preparation 105: tert-butyl (3R)-6-cyclohexyl-3-[3-(4-pyridinylmethyl)-1,2,4-oxadiazol-5-yl]hexanoate

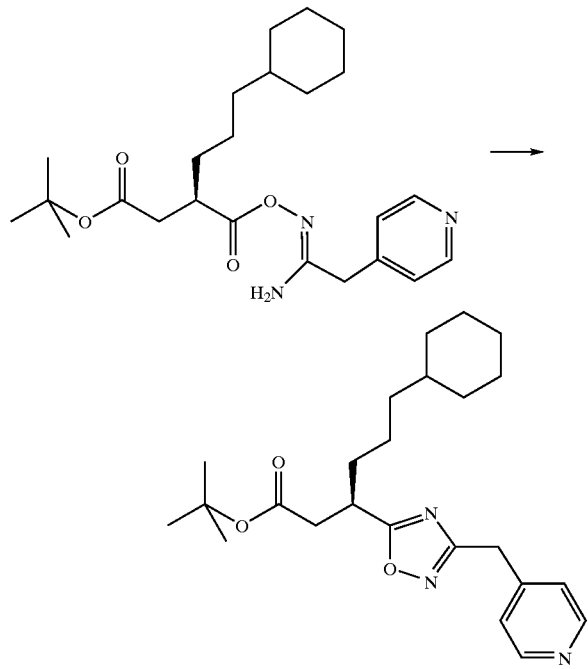

A solution of tert-butyl (3R)-3-[({[(Z)-1-amino-2-(4-pyridinyl)ethylidene]amino}oxy)carbonyl]-6-cyclohexylhexanoate (Preparation 104) (840 mg, 1.60 mmol) in xylene (15 ml) was heated at 130° C. for 4.5 hours. After cooling to room temperature the reaction mixture was purified by column chromatography on silica gel eluting with a gradient system of 90:10 (pentane:ethyl acetate) gradually changing to 50:50 (pentane:ethyl acetate) to afford the title compound as a yellow oil (420 mg).

MS: 436 (MNa$^+$)

Analysis: Found, C, 69.38; H, 8.69; N, 9.72%; $C_{24}H_{35}N_3O_3$.0.1 EtOAc requires C, 69.39; H, 8.45; N, 9.72%

$^1$H-NMR (CDCl$_3$) δ: 8.54 (2H, d), 7.21 (2H, d), 4.03 (2H, s), 3.40 (1H, m), 2.77 (1H, dd), 2.60 (1H, m), 1.60–1.80 (8H, m), 1.35 (9H, s), 1.10–1.30 (7H, m), 0.82 (2H, m).

Preparation 106: (3R)-6-cyclohexyl-3-[3-(4-pyridinylmethyl)-1,2,4-oxadiazol-5-yl]hexanoic Acid

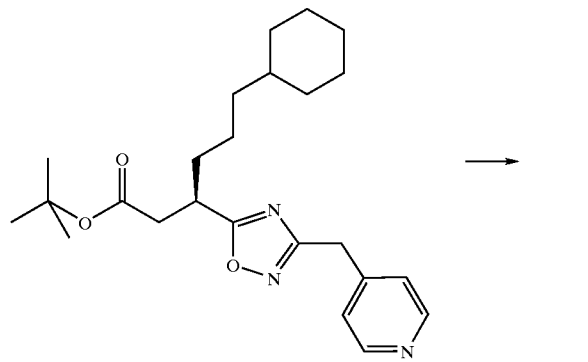

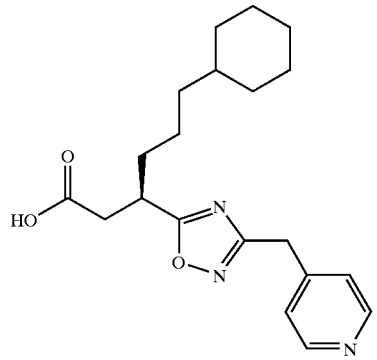

A solution of tert-butyl (3R)-6-cyclohexyl-3-[3-(4-pyridinylmethyl)-1,2,4-oxadiazol-5-yl]hexanoate (Preparation 105) (400 mg, 0.97 mmol) in hydrogen chloride in 1,4-dioxan (4M) (5 ml) was stirred at room temperature for 24 hours. The solvent was removed under reduced pressure. The solid was dissolved in fresh hydrogen chloride in 1,4-dioxan (4M) and stirred at room temperature for 3 hours. The solvent was removed under reduced pressure to afford the title compound as a yellow oil (390 mg).

MS: 356 (M–H)$^-$

Analysis: Found, C, 59.65; H, 7.34; N, 9.62%; $C_{20}H_{27}N_3O_3$.HCl.0.35H$_2$O.0.25Dioxan requires C, 59.74; H, 7.33; N, 9.95%

$^1$H-NMR (DMSO) δ: 8.75 (2H, d), 7.78 (2H, d), 4.40 (2H, s), 3.40 (1H, m), 2.75 (2H, m), 1.50–1.70 (7H, m), 1.00–1.25 (8H, m), 0.89 (2H, m).

Preparation 107: tert-butyl (3R)-3-[({[(Z)-1-amino-2-(3-pyridinyl)ethylidene]amino}oxy)carbonyl]-6-cyclohexylhexanoate

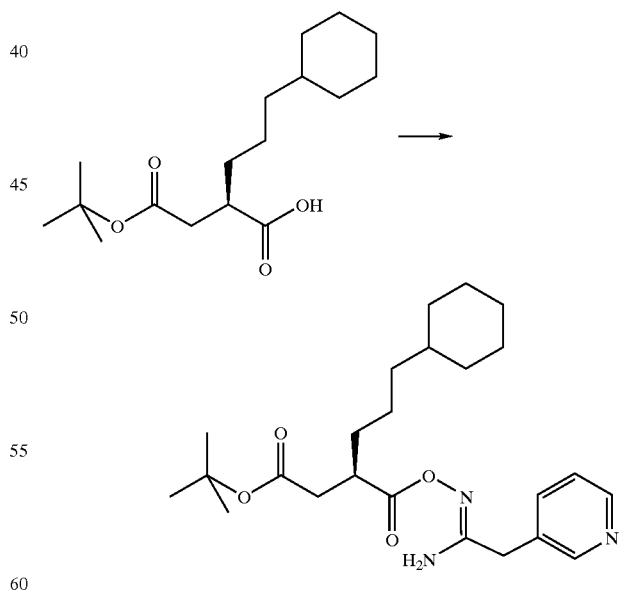

A solution of (2R)-2-(2-tert-butoxy-2-oxoethyl)-5-cyclohexylpentanoic acid (Preparation 1) (500 mg, 1.67 mmol) in dichloromethane (20 ml) was treated with 1-(3-dimethylaminopropyl)-3-ethylcarbodiimide hydrochloride (354 mg, 1.85 mmol), N-methylmorpholine (203 μl, 1.85 mmol) and 1-hydroxybenzotriazole hydrate (227 mg, 1.67 mmol). (1Z)-N'-hydroxy-2-(3-pyridinyl)ethanimidamide (WO 9600720) (374 mg, 1.67 mmol) followed by N-methylmorpholine (369 µl, 3.34 mmol) were added to the reaction mixture which was stirred at room temperature for 18 hours. The reaction mixture was diluted with water (10 ml) and stirred for 20 minutes. The layers were separated via a 5 micron filter cartridge. The organic solvent was removed under reduced pressure to afford the title compound as a yellow oil (835 mg). This was used without further purification in the following step.

MS: 432 (MH$^+$)

$^1$H-NMR (CDCl$_3$) δ: 8.55 (2H, d), 7.70 (1H, d), 7.28 (1H, d), 4.90 (2H, br s), 3.70 (2H, m), 2.85 (1H, m), 2.40 (2H, m), 1.60–1.80 (7H, m), 1.40 (9H, s), 1.10–1.30 (8H, m), 0.83 (2H, m).

Preparation 108: tert-butyl (3R)-6-cyclohexyl-3-[3-(3-pyridinylmethyl)-1,2,4-oxadiazol-5-yl]hexanoate

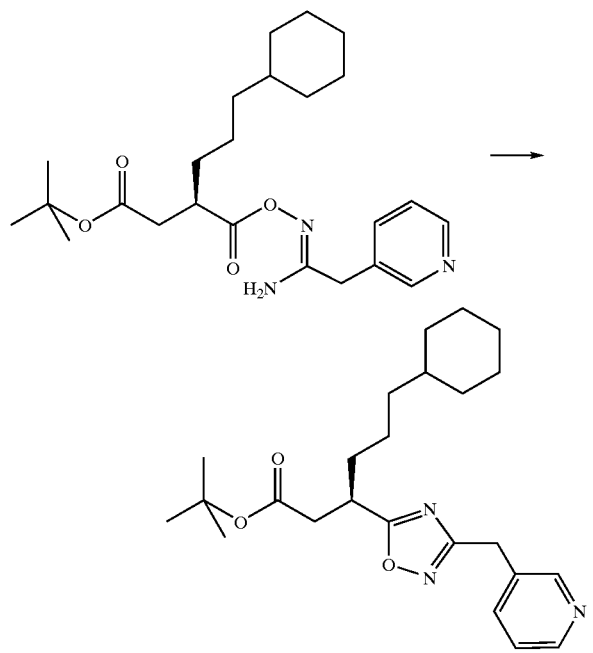

A solution of tert-butyl (3R)-3-[({[(Z)-1-amino-2-(3-pyridinyl)ethylidene]amino}oxy)carbonyl]-6-cyclohexylhexanoate (Preparation 107) (835 mg, 1.60 mmol) in xylene (15 ml) was heated at 130° C. for 4.5 hours. After cooling to room temperature the reaction mixture was purified by column chromatography on silica gel eluting with a gradient system of 90:10 (pentane:ethyl acetate) gradually changing to 50:50 (pentane:ethyl acetate) to afford the title compound as a yellow oil (443 mg).

MS: 436 (MNa$^+$)

$^1$H-NMR (CDCl$_3$) δ: 8.60 (1H, s), 8.50 (1H, d), 7.62 (1H, d), 7.21 (1H, m), 4.05 (2H, s), 3.41 (1H, m), 2.77 (1H, dd), 2.58 (1H, m), 1.60–1.75 (8H, m), 1.35 (9H, s), 1.10–1.25 (7H, m), 0.82 (2H, m).

Preparation 109: (3R)-6-cyclohexyl-3-[3-(3-pyridinylmethyl)-1,2,4-oxadiazol-5-yl]hexanoic Acid

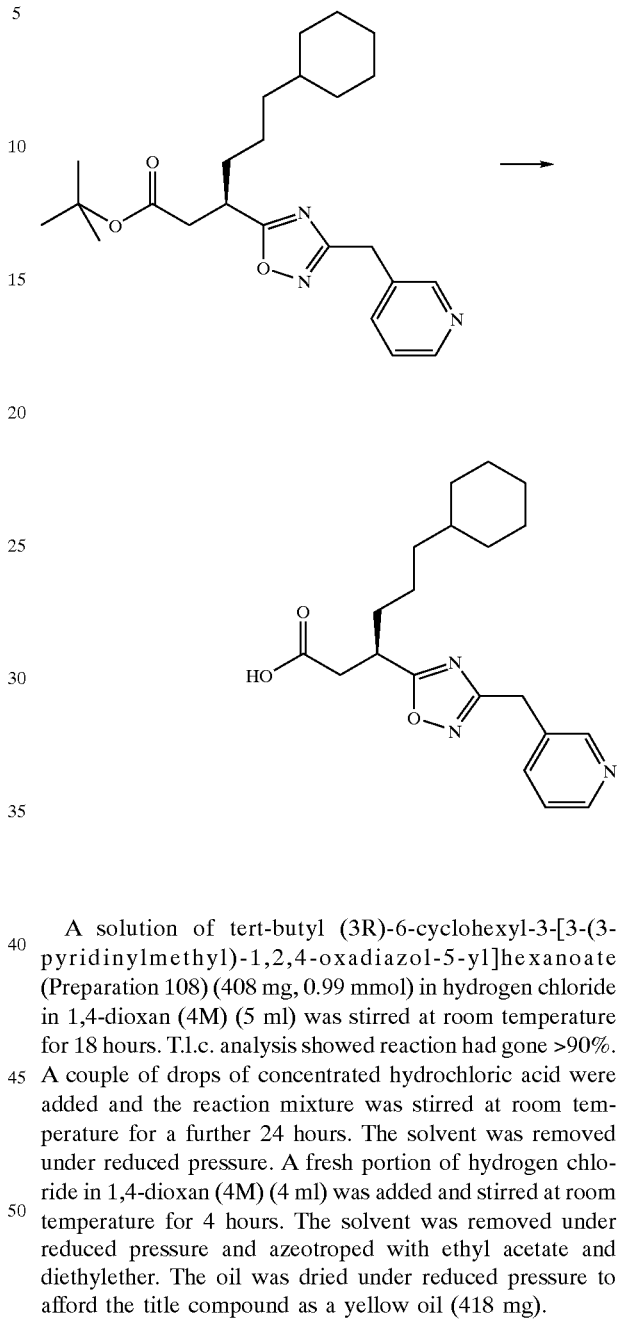

A solution of tert-butyl (3R)-6-cyclohexyl-3-[3-(3-pyridinylmethyl)-1,2,4-oxadiazol-5-yl]hexanoate (Preparation 108) (408 mg, 0.99 mmol) in hydrogen chloride in 1,4-dioxan (4M) (5 ml) was stirred at room temperature for 18 hours. T.l.c. analysis showed reaction had gone >90%. A couple of drops of concentrated hydrochloric acid were added and the reaction mixture was stirred at room temperature for a further 24 hours. The solvent was removed under reduced pressure. A fresh portion of hydrogen chloride in 1,4-dioxan (4M) (4 ml) was added and stirred at room temperature for 4 hours. The solvent was removed under reduced pressure and azeotroped with ethyl acetate and diethylether. The oil was dried under reduced pressure to afford the title compound as a yellow oil (418 mg).

MS: 356 (M−H)$^-$

Analysis: Found, C, 59.07; H, 7.43; N, 8.71%; $C_{20}H_{27}N_3O_3$.HCl.0.4H$_2$O.0.7Dioxan requires C, 59.17; H, 7.49; N, 9.08%

$^1$H-NMR (DMSO) δ: 8.72 (1H, s), 8.63 (1H, d) 8.10 (1H, d), 7.69 (1H, t), 4.25 (2H, s), 3.38 (1H, m), 2.67 (2H, t), 1.50–1.70 (7H, m), 1.00–1.25 (8H, m), 0.79 (2H, m).

Preparation 110: (4S)-4-isopropyl-3-(4-pentenoyl)-1,3-oxazolidin-2-one

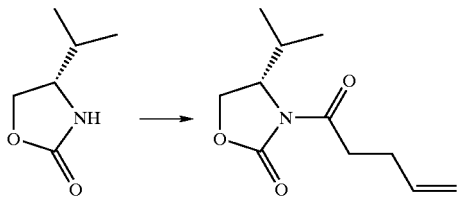

A solution of (4S)-4-isopropyl-1,3-oxazolidin-2-one (26 g, 0.2 mol) in anhydrous tetrahydrofuran (600 ml) was cooled to −78° C. under a nitrogen atmosphere and treated with n-butyl lithium, 2.5M in hexanes (80 ml, 0.2 mol) keeping the temperature below −65° C. Once the addition was complete the reaction mixture was allowed to warm to −55° C. and stirred at this temperature for 30 minutes. The mixture was cooled back down to −78° C. and treated dropwise with a solution of 4-pentenoyl chloride (23.7 g, 0.2 mol) in anhydrous tetrahydrofuran (100 ml). After stirring at −78° C. for 30 minutes the reaction mixture was allowed to warm to room temperature. Saturated aqueous ammonium chloride solution (1 L) was added and the mixture was extracted with ethyl acetate (2×). The combined organic extracts were dried over anhydrous magnesium sulphate, filtered and the solvent removed under reduced pressure. The oil was purified by column chromatography on silica gel eluting with a solvent gradient of 100:0 (pentane:ethyl acetate) gradually changing to 70:30 (pentane:ethyl acetate) to afford the title compound as a yellow oil (36.3 g).

MS: 229 (MNH$_4^+$)

$^1$H-NMR (CDCl$_3$) δ: 5.85 (1H, m), 5.10 (1H, d), 5.02 (1H, d), 4.41 (1H, m), 4.22 (2H, m), 3.11 (1H, m), 2.98 (1H, m), 2.30–2.45 (3H, m), 0.92 (3H, d), 0.85 (3H, d).

Preparation 111: tert-butyl (3R)-3-{[(4S)-4-isopropyl-2-oxo-1,3-oxazolidin-3-yl]carbonyl}-5-hexenoate

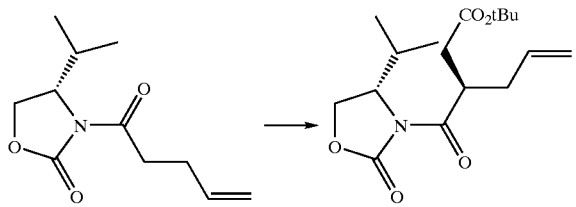

A solution of (4S)-4-isopropyl-3-(4-pentenoyl)-1,3-oxazolidin-2-one (Preparation 110) (36 g, 0.17 mol) in anhydrous tetrahydrofuran (650 ml), under a nitrogen atmosphere, at −78° C., was treated dropwise with sodium bis(trimethylsilyl)amide, 1M in tetrahydrofuran (188 ml, 0.19 mol) over 1.5 hours, keeping the temperature below −65° C. The mixture was stirred at −78° C. for 30 minutes and then allowed to warm to room temperature. The mixture was poured into saturated aqueous ammonium chloride solution (500 ml) and extracted with diethylether. The organic extract was washed with water and brine, dried over anhydrous magnesium sulphate, filtered and the solvent removed under reduced pressure. The brown slurry was triturated with hexane, filtered and washed with cold hexane. The white solid was dried under reduced pressure to afford the title compound (35.8 g).

MS: 343 (MNH$_4^+$)

$^1$H-NMR (CDCl$_3$) δ: 5.78 (1H, m), 5.08 (1H, d), 5.02 (1H, s), 4.40 (1H, m), 4.18–4.30 (3H, m), 2.77 (1H, dd), 2.30–2.45 (3H, m), 2.18 (1H, m), 1.41 (9H, s), 0.91 (6H, t).

Preparation 112: (2R)-2-(4,4-dimethyl-2-oxopentyl)-4-pentenoic Acid

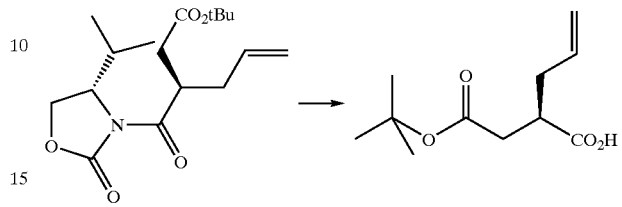

A solution of tert-butyl (3R)-3-{[(4S)-4-isopropyl-2-oxo-1,3-oxazolidin-3-yl]carbonyl}-5-hexenoate (Preparation 111) (37.5 g, 0.11 mol) in 1,4-dioxan (190 ml), under a nitrogen atmosphere, was treated with a solution of lithium hydroxide monohydrate (7.3 g, 0.17 mol) in water (75 ml). The mixture was stirred at room temperature for 18 hours. Further lithium hydroxide monhydrate (2.42 g, 0.06 mol) was added and the mixture partitioned between ethyl acetate and water. The aqueous layer was acidified with hydrochloric acid (2M) (250 ml) and extracted with ethyl acetate. The organic extract was washed with brine, dried over anhydrous magnesium sulphate, filtered and the solvent removed under reduced pressure. The oil was purified by column chromatography on silica gel eluting with 50:50 (pentane:ethyl acetate) to afford the title compound as a colourless oil (14.2 g).

MS: 232 (MNH$_4^+$)

$^1$H-NMR (CDCl$_3$) δ: 5.77 (1H, m), 5.12 (1H, d), 5.08 (1H, s), 2.90 (1H, m), 2.60 (1H, dd), 2.25–2.55 (3H, m), 1.43 (9H, s).

Preparation 113: Ethyl (2S)-2-{[(2R)-2-(4,4-dimethyl-2-oxopentyl)-4-pentenoyl]amino}-3-hydroxypropanoate

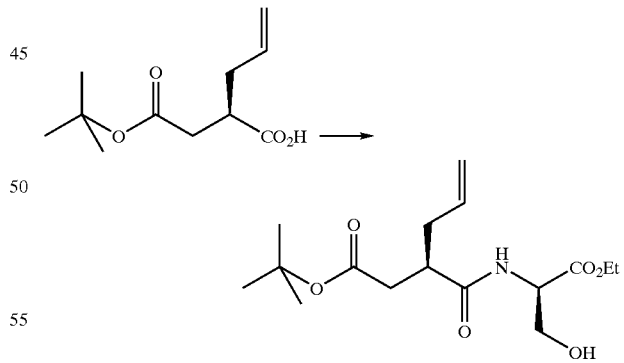

A solution (2R)-2-(4,4-dimethyl-2-oxopentyl)-4-pentenoic acid (Preparation 112) (15.91 g, 74.3 mmol), 1-hydroxybenzotriazole hydrate (11.00 g, 81.4 mmol), L-serine ethylester hydrochloride (13.84 g, 81.6 mmol) and N,N-diisopropylethylamine (27 ml, 156.0 mmol) in dichloromethane (280 ml) was treated with 1-(3-dimethylaminopropyl)-3-ethylcarbodiimide hydrochloride (15.67 g, 81.7 mmol) and stirred at room temperature for 18 hours under a nitrogen atmosphere. The reaction mixture was diluted with dichloromethane and washed with water, aqueous citric acid (2M), saturated sodium hydrogen carbonate solution and brine, dried over anhydrous sodium sulphate and filtered. The solvent was removed under reduced pressure to afford the title compound as a yellow oil (23.8 g).

MS: 330 (MH$^+$)

$^1$H-NMR (CDCl$_3$) δ: 6.50 (1H, br d), 5.77 (1H, m), 5.10 (2H, s+d), 4.59 (1H, m), 4.22 (2H, q), 4.02 (1H, br d), 3.84 (1H, br d), 2.85 (1H, br s), 2.55–2.70 (2H, m), 2.40 (2H, m), 2.18 (1H, m), 1.40 (9H, s), 1.30 (3H, t).

Preparation 114: Ethyl (4S)-2-[(1R)-1-(4,4-dimethyl-2-oxopentyl)-3-butenyl]-4,5-dihydro-1,3-oxazole-4-carboxylate

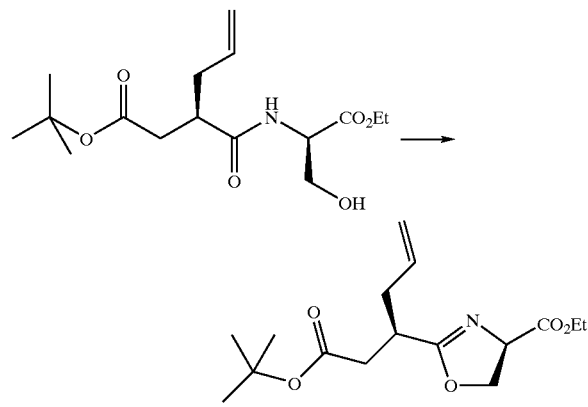

A solution of ethyl (2S)-2-{[(2R)-2-(4,4-dimethyl-2-oxopentyl)-4-pentenoyl]amino}-3-hydroxypropanoate (Preparation 113) (23.8 g, 72.3 mmol) in anhydrous tetrahydrofuran (300 ml), under a nitrogen atmosphere, was treated with (methoxycarbonylsulfamoyl)triethylammonium hydroxide triethylamine hydrochloride salt (43.5 g, 79.4 mmol) and stirred at reflux for 1.5 hours. After allowing to cool to room temperature the mixture was filtered, washed with ethyl acetate and the filtrate was concentrated under reduced pressure. The oil was purified by column chromatography on silica gel eluting with a solvent gradient of 80:20 (hexane:diethylether) gradually changing to 50:50 (hexane:diethylether) to afford the title compound as a colourless oil (11.0 g).

MS: 312 (MH$^+$)

$^1$H-NMR (CDCl$_3$) δ: 5.73 (1H, m), 5.05 (2H, s+d), 4.66 (1H, m), 4.42 (1H, t), 4.38 (1H, t), 4.20 (2H, m), 3.95 (1H, m), 2.60 (1H, dd), 2.30–2.50 (3H, m), 1.41 (9H, s), 1.28 (3H, t).

Preparation 115: Ethyl 2-[(1R)-1-(4,4-dimethyl-2-oxopentyl)-3-butenyl]-1,3-oxazole-4-carboxylate

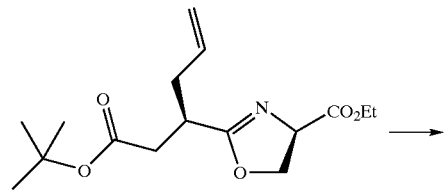

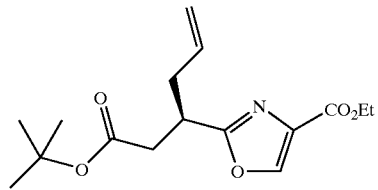

A suspension of copper (II) bromide (50.6 g, 226.6 mmol) and hexamethylenetetramine (31.6 g, 225.5 mmol) in dichloromethane (250 ml), under a nitrogen atmosphere, was treated with 1,8-diazabicyco[5.4.0]undec-7-ene (33 ml, 220.7 mmol). The mixture was cooled to 0° C. and treated with a solution of ethyl (4S)-2-[(1R)-1-(4,4-dimethyl-2-oxopentyl)-3-butenyl]-4,5-dihydro-1,3-oxazole-4-carboxylate (Preparation 114) (17.6 g, 56.4 mmol) in dichloromethane (250 ml) via a cannula. The reaction mixture was allowed to warm to room temperature and stirred for 18 hours. The solvent was removed under reduced pressure and the residue was azeotroped with ethyl acetate. The residue was dissolved in ethyl acetate and washed with a 1:1 mixture of 0.880 ammonia solution:saturated aqueous ammonium chloride solution (×2), water, hydrochloric acid (2M) (×3), saturated aqueous sodium hydrogen carbonate solution and brine. The solvent was removed under reduced pressure. The oil was purified by column chromatography on silica gel eluting with a solvent gradient of 95:5 (hexane:diethylether) gradually changing to 50:50 (hexane:diethylether) to afford the title compound as a colourless oil (11.5 g).

MS: 310 (MH$^+$)

$^1$H-NMR (CDCl$_3$) δ: 8.10 (1H, s), 5.70 (1H, m), 5.01 (2H, s+d), 4.37 (2H, q), 3.45 (1H, m), 2.79 (1H, dd), 2.50–2.65 (2H, m), 2.45 (1H, m), 1.30–1.45 (12H, s+t).

Preparation 116: 2-[(1R)-1-(2-tert-butoxy-2-oxoethyl)-3-butenyl]-1,3-oxazole-4-carboxylic Acid

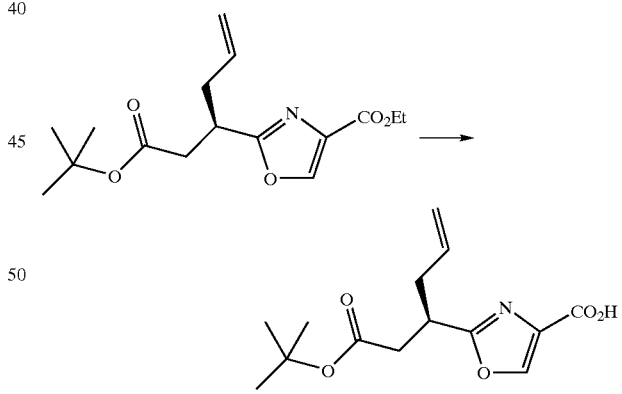

Two identical reactions were put on each containing the following: A solution of ethyl 2-[(1R)-1-(4,4-dimethyl-2-oxopentyl)-3-butenyl]-1,3-oxazole-4-carboxylate (Preparation 115) (4.0 g, 12.9 mmol) in 1,4-dioxan (40 ml) and water (20 ml) was cooled to 0° C. and treated with lithium hydroxide monohydrate (0.8 g, 19.0 mmol). The mixture was stirred at 0° C. for 4 hours. Further lithium hydroxide monhydrate (0.8 g, 19.0 mmol) was added and stirred at 0° C. for 10 minutes. The two reactions were combined and partitioned between ethyl acetate and water. The aqueous layer was neutralised with citric acid (16.3 g, 38.0 mmol) and extracted with ethyl acetate (×3). The combined organic extracts were washed with water and brine, dried over anhydrous sodium sulphate, filtered and the solvent removed under reduced pressure to afford the title compound as a colourless oil (8.3 g).

MS: 282 (MH$^+$)

$^1$H-NMR (CDCl$_3$) δ: 8.10 (1H, s), 5.70 (1H, m), 5.01 (2H, s+d), 3.47 (1H, m), 2.80 (1H, dd), 2.62 (1H, dd), 2.57 (1H, m), 2.45 (1H, m), 1.38 (9H, s).

Preparation 117: tert-butyl (3R)-3-{4-[(dimethylamino)carbonyl]-1,3-oxazol-2-yl}-5-hexenoate

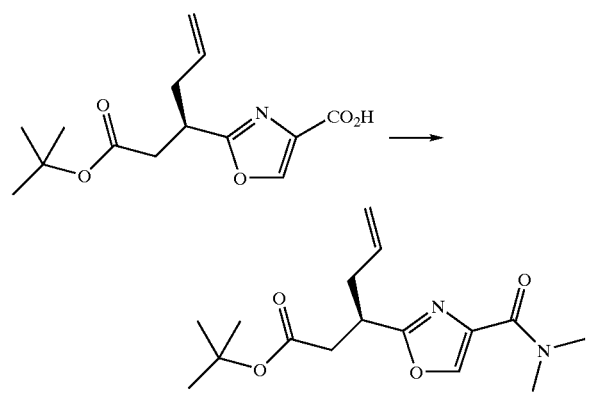

A solution of 2-[(1R)-1-(2-tert-butoxy-2-oxoethyl)-3-butenyl]-1,3-oxazole-4-carboxylic acid (Preparation 116) (10.77 g, 38.3 mmol) in dichloromethane (250 ml), at 0° C., was treated with 1-hydroxybenzotriazole hydrate (5.75 g, 42.6 mmol), dimethylamine hydrochloride (3.45 g, 42.3 mmol) and N,N-diisopropylethylamine (13 ml, 75.13 mmol) and lastly 1-(3-dimethylaminopropyl)-3-ethylcarbodiimide hydrochloride (8.10 g, 42.3 mmol), allowed to warm to room temperature and stirred for 20 hours under a nitrogen atmosphere. The reaction mixture was diluted with dichloromethane and washed with saturated sodium hydrogen carbonate solution, aqueous citric acid (10%), water and brine, dried over anhydrous sodium sulphate and filtered. The solvent was removed under reduced pressure. The oil was purified by column chromatography on silica gel eluting with a solvent gradient of 7:3 (pentane:ethyl acetate) gradually changing to 1:1 (pentane:ethyl acetate) to afford the title compound as a colourless oil (9.9 g).

MS: 309 (MH$^+$)

Analysis: Found, C, 61.31; H, 7.89; N, 8.92%; C$_{16}$H$_{24}$N$_2$O$_4$·0.2H$_2$O requires C, 61.60; H, 7.88; N, 8.98%

$^1$H-NMR (CDCl$_3$) δ: 8.00 (1H, s), 5.70 (1H, m), 5.02 (2H, s+d), 3.40 (1H, m), 3.30 (3H, br s), 3.03 (3H, br s), 2.75 (1H, m), 2.38 (1H, dd), 2.50 (1H, t), 2.43 (1H, m), 1.39 (9H, s).

Preparation 118: tert-butyl (3R)-3-{4-[(dimethylamino)carbonyl]-1,3-oxazol-2-yl}-5-oxopentanoate

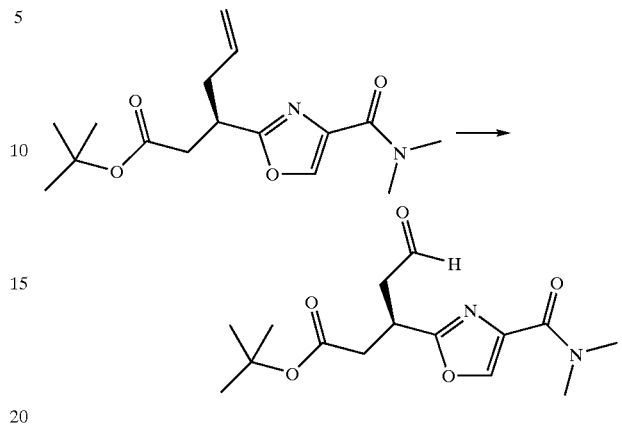

A solution of tert-butyl (3R)-3-{4-[(dimethylamino)carbonyl]-1,3-oxazol-2-yl}-5-hexenoate (Preparation 117) (1.0 g, 3.24 mmol) in acetone (20 ml) and water (20 ml) was treated with osmium tetroxide, 2.5% wt in tert-butanol (500 μl, 0.04 mmol) and stirred at room temperature for 5 minutes. Sodium periodate (2.13 g, 10.00 mmol) was added and the reaction mixture stirred for 2 hours. The reaction mixture was partitioned between ethyl acetate and aqueous sodium thiosulphate solution (20% wt). The organic layer was washed with water (×2) and brine, dried over anhydrous sodium sulphate and filtered. The solvent was removed under reduced pressure to afford the title compound as a colourless oil (866 mg).

MS: 311 (MH$^+$)

Analysis: Found, C, 56.13; H, 7.13; N, 8.66%; C$_{15}$H$_{22}$N$_2$O$_5$·0.6H$_2$O requires C, 56.10; H, 7.28; N, 8.72%

$^1$H-NMR (CDCl$_3$) δ: 9.78 (1H, s), 8.01 (1H, s), 3.87 (1H, m), 3.29 (3H, br s), 3.03 (4H, br s), 2.70–2.90 (2H, m), 2.64 (1H, dd), 1.39 (9H, s).

Preparation 119: tert-butyl (3R,5Z)-6-cyclobutyl-3-{4-[(dimethylamino)carbonyl]-1,3-oxazol-2-yl}-5-hexenoate

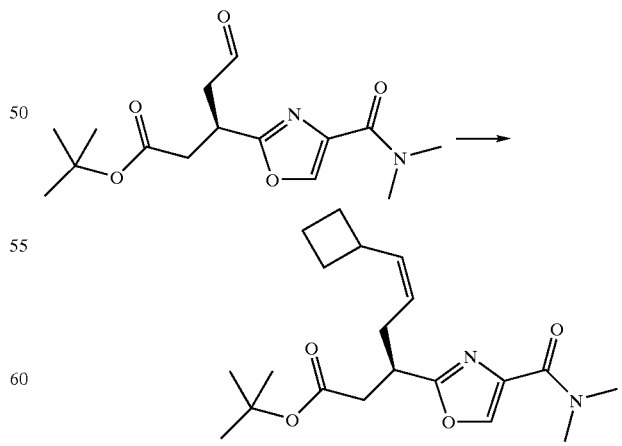

A suspension of (cyclobutylmethyl)(triphenyl)phosphonium bromide (Preparation 122) (680 mg, 1.65 mmol) in anhydrous tetrahydrofuran (13 ml), under a nitrogen atmosphere, at 0° C., was treated with sodium bis (trimethylsilyl)amide 1M in tetrahydrofuran (1.65 ml, 1.65 mmol) over a period of 5 minutes. The bright orange mixture was stirred at 0° C. for 1 hour. A solution of tert-butyl (3R)-3-{4-[(dimethylamino)carbonyl]-1,3-oxazol-2-yl}-5-oxopentanoate (Preparation 118) (428 mg, 1.38 mmol) in toluene (4 ml) was added to the mixture and stirred at 0° C. for 30 minutes and allowed to warm to room temperature for a further 30 minutes. Water (2 ml) was added and the solvents were removed under reduced pressure. The residue was dissolved in ethyl acetate and washed with dilute aqueous of potassium sodium tartrate solution and brine, dried over anhydrous sodium sulphate, filtered and the solvent removed under reduced pressure. The oil was purified by column chromatography on silica gel eluting with a solvent gradient of 9:1 (hexane:ethyl acetate) gradually changing to 1:1 (hexane:ethyl acetate) to afford the title compound as a colourless oil (282 mg).

MS: 363 (MH+)

Analysis: Found, C, 65.95; H, 8.35; N, 7.72%; $C_{20}H_{30}N_2O_4 \cdot 0.1H_2O$ requires C, 65.95; H, 8.36; N, 7.69%

$^1$H-NMR (CDCl$_3$) δ: 8.00 (1H, s), 5.55 (1H, t), 5.11 (1H, q), 3.00–3.40 (8H, m), 2.73 (1H, dd), 2.56 (1H, dd), 2.30–2.50 (2H, m), 2.08 (2H, m), 1.70–1.90 (4H, m), 1.38 (9H, s).

Preparation 120: tert-butyl (3R)-6-cyclobutyl-3-{4-[(dimethylamino)carbonyl]-1,3-oxazol-2-yl}hexanoate

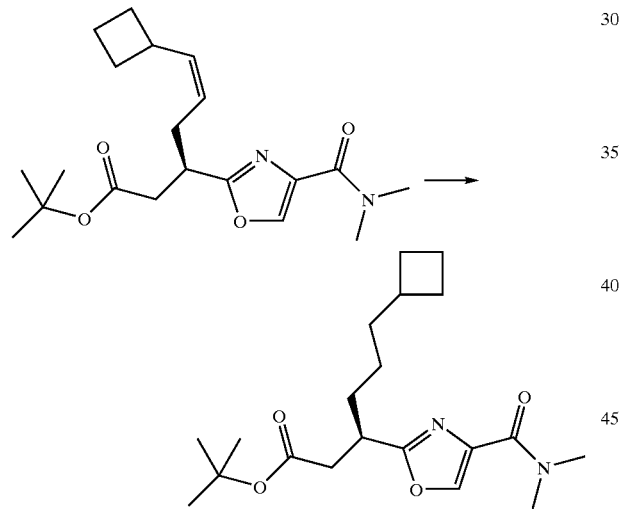

A solution of tert-butyl (3R,5Z)-6-cyclobutyl-3-{4-[(dimethylamino)carbonyl]-1,3-oxazol-2-yl}-5-hexenoate (Preparation 119) (260 mg, 0.72 mmol) in ethanol (15 ml) was treated with palladium hydroxide (250 mg) followed by ammonium formate (500 mg) and the mixture was stirred at reflux for 3 hours. The reaction mixture was allowed to cool to room temperature and was filtered through arbacel. The solvent was removed under reduced pressure. The residue was dissolved in ethyl acetate and washed with water and brine, dried over anhydrous sodium sulphate and filtered. The solvent was removed under reduced pressure to afford the title compound as a colourless oil (246 mg).

MS: 366 (MH+)

$^1$H-NMR (CDCl$_3$) δ: 8.17 (1H, s), 3.31 (4H, m), 3.05 (3H, m), 2.70 (1H, dd), 2.59 (1H, dd), 2.22 (1H, m), 2.00 (2H, m), 1.60–1.90 (4H, m), 1.55 (2H, m), 1.30–1.40 (11H, m) 1.07 (2H, m).

Preparation 121: (3R)-6-cyclobutyl-3-{4-[(dimethylamino)carbonyl]-1,3-oxazol-2-yl}hexanoic Acid

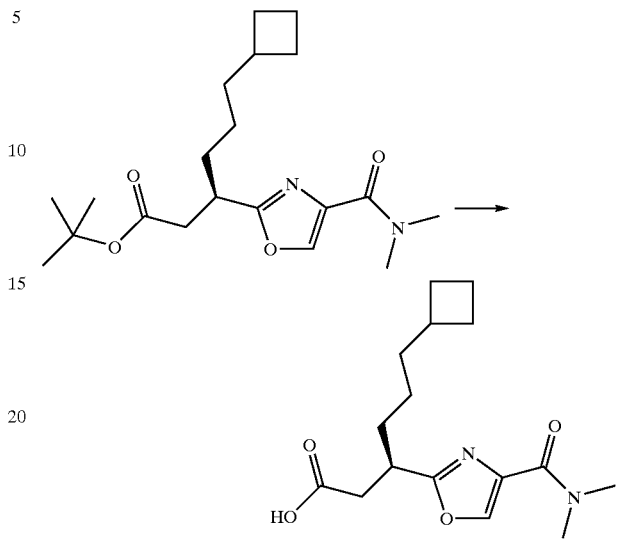

A solution of tert-butyl (3R)-6-cyclobutyl-3-{4-[(dimethylamino)carbonyl]-1,3-oxazol-2-yl}hexanoate (Preparation 120) (240 mg, 0.66 mmol) in dichloromethane (4 ml) was treated with trifluoroacetic acid (1.2 ml) and stirred at room temperature for 4 hours. The solvent was removed under reduced pressure and the residue azeotroped from toluene and dichloromethane. The oil was purified by column chromatography on silica gel eluting with 97:3:0.3 (dichloromethane:methanol:acetic acid) to afford the title compound as a white solid (161 mg).

MS: 309 (MH+)

$^1$H-NMR (CDCl$_3$) δ: 8.05 (1H, s), 3.33 (4H, m), 3.05 (3H, m), 2.87 (1H, dd), 2.67 (1H, dd), 2.20 (1H, m), 1.99 (2H, m), 1.60–1.90 (4H, m), 1.52 (2H, m), 1.36 (2H, m) 1.07 (2H, m).

Preparation 122: (cyclobutylmethyl)(triphenyl)phosphonium Bromide

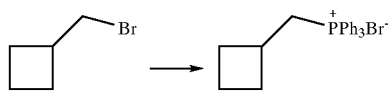

A solution of (bromomethyl)cyclobutane (4.5 ml, 0.04 mol) in toluene (50 ml) was treated with triphenylphosphine (10.56 g, 0.04 mol) and the mixture stirred at reflux, under a nitrogen atmosphere, for 2 days. The mixture was allowed to cool to room temperature and treated with hexane (50 ml). The solvent was decanted off and further hexane added. The solvent was decanted off again. The solid was washed with diethyl ether (×2) and dried under reduced pressure to afford the title compound as a white solid (6.34 g).

MS: 332 (MH+)

Analysis: Found, C, 67.13; H, 5.88; N, 0.00%; $C_{23}H_{24}PBr$ requires C, 67.16; H, 5.88; N, 0.00%

$^1$H-NMR (d$_6$-DMSO) δ: 7.65–7.90 (15H, m), 3.74 (2H, m), 2.62 (1H, br m), 1.60–1.80 (6H, m).

What is claimed is:

1. A compound of the formula formula:

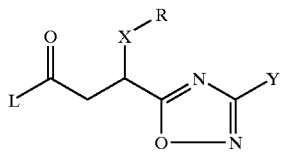

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y is represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

L is suitable leaving group represented by a substituent selected from the group consisting of halide, $C^{1-4}$ halogen, alkylsulphonate, or arylsulphonate;

and the pharmaceutically acceptable salts, solvates (including hydrates)L and prodrugs thereof.

2. A compound of the formula:

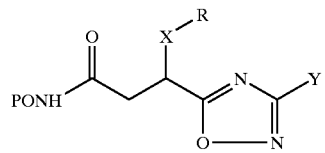

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y is represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

P is suitable O-protecting group;

and the pharmaceutically acceptable salts, solvates (including hydrates)L and prodrugs thereof.

3. A compound of the formula:

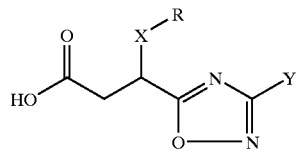

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y is represented by H, $C_{1-4}$ alkyl (optionally substituted by one or more substituents independently selected from halogen, $S(O)_p R^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

and the pharmaceutically acceptable salts, solvates (including hydrates)L and prodrugs thereof.

4. A compound of the formula:

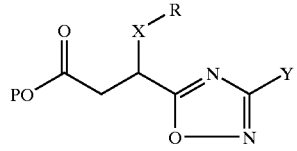

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y is represented by H, $C_{1-4}$ alkyl (optionally substituted by one or more substituents independently selected from halogen, $S(O)_p R^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

P is represented by a O-protecting group, and the pharmaceutically acceptable salts, solvates (including hydrates) and prodrugs thereof.

5. A compound of the formula:

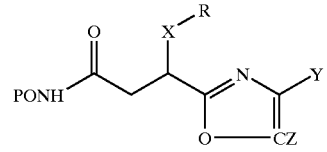

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y and Z are each represented by H, $C_{1-4}$ alkyl (optionally substituted by one or more substituents independently selected from halogen, $S(O)_p R^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

P is a suitable O-protecting group;

and the pharmaceutically acceptable salts, solvates (including hydrates) and prodrugs thereof.

6. A compound of the formula:

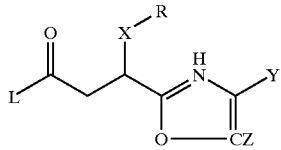

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y and Z are each represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

L is suitable leaving group represented by a substituent selected from the group consisting of halide, $C^{1-4}$ halogen, alkylsulphonate, and arylsulphonate;

and the pharmaceutically acceptable salts, solvates (including hydrates) and prodrugs thereof.

7. A compound of the formula:

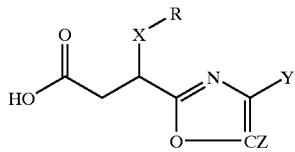

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y and Z are each represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^5$;

p is 0, 1 or 2;

and the pharmaceutically acceptable salts, solvates (including hydrates) and prodrugs thereof.

8. A compound of the formula:

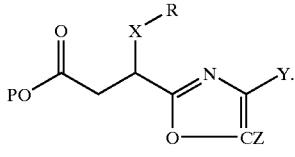

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y and Z are each represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^0$;

p is 0, 1 or 2; P is a suitable O-protecting group;

and the pharmaceutically acceptable salts, solvates (including hydrates) and prodrugs thereof.

9. A compound of the formula:

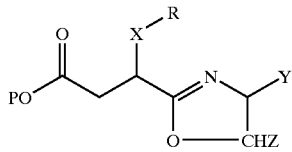

wherein:

X is $C_{1-6}$ alkylene or $C_{2-6}$ alkenylene, each of which is optionally substituted by one or more fluorine atoms;

R is aryl or $C_{3-8}$ cycloalkyl optionally substituted by one or more fluorine atoms;

Y and Z are each represented by H, $C_{1-4}$ alkyl (optionally substituted by one or more substituents independently selected from halogen, $S(O)_pR^6$, $OR^5$, $CONR^1R^2$, $CO_2R^7$ and aryl-), $C_{1-4}$ alkanoyl optionally substituted by one or more halogen, $C_{1-4}$ alkoxycarbonyl optionally substituted by one or more halogen, or $CONR^1R^2$;

$R^1$ and $R^2$ are each independently selected from H, $C_{3-8}$ cycloalkyl, $C_{1-4}$ alkyl either of which may optionally be substituted by one or more substituents selected from $C_{3-8}$ cycloalkyl, aryl, $CO_2H$, $CO_2R^5$ and/or $NR^3R^4$, or $R^1$ and $R^2$ can be taken together with the nitrogen to which they are attached to represent a 4- to 6-membered heterocyclic ring optionally containing one or two further hetero atoms in the ring independently selected from N, O and S, which heterocyclic ring is optionally benzo- or pyrido-fused, and which heterocyclic ring is optionally substituted by one or more substituents selected from $C_{1-4}$ alkyl, $CO_2H$, $CO_2R^5$, aryl and/or $NR^3R^4$;

$R^3$ and $R^4$ are each independently selected from H, $C_1$–$C_4$ alkyl or $C_{1-4}$ alkoxycarbonyl, either of which may optionally substituted by one or more halogen, or $R^3$ and $R^4$ can be taken together with the nitrogen atom to which they are attached to represent a morpholine, piperidine, azetidine or piperazine (optionally N-substituted by $C_{1-4}$ alkyl) moiety;

$R^5$ is $C_{1-4}$ alkyl optionally substituted by $CO_2R^7$ or $CONR^3R^4$, or $R^5$ is aryl;

$R^6$ is $C_{1-4}$ alkyl optionally substituted by one or more halogen, or $R^6$ is aryl;

$R^7$ is H or $R^6$;

p is 0, 1 or 2;

P is a suitable O-protecting group;

and the pharmaceutically acceptable salts, solvates (including hydrates) and prodrugs thereof.

10. A compound according to claim 3 selected from the group consisting of a) (3R)-6-cyclohexy-3-3-[3-(ethoxycarbonyl)-1-2,4-oxadiazol-5-yl]hexanoic acid;

b) (3R)-3-[3-(aminocarbonyl)-1,2,4-oxadiazol-5-yl]-6-cyclohexylhexanoic acid;

c) (3R)-6-cyclohexyl-3-{3-[(methylamino)carbonyl]-1,2,4-oxadiazol-5-yl}hexanoic acid;

d) (3R)-6-cyclohexyl-3-{3-[(propylamino)carbonyl]-1,2,4-oxadiazol-5-yl}hexanoic acid;

e) (3R)-6-cyclohexyl-3-{3-[(dimethtlamino)carbonyl]-1,2,4-oxadiazol-5-yl}hexanoic acid;

f) (3R)-6-cyclohexyl-3-(3-{[4-(dimethylamino)-1-piperidinyl]carbonyl}-1,2,4-oxadiazol-5-yl)hexanoic acid;

g) (3R)-6-cyclohexyl-3-(3-{[3(4-morpholinyl)-1-azetidinyl]carbonyl)-1,2,4-oxadiazol-5-yl)hexanoic acid:

h) (3R)-6-cyclohexyl-3-(3-([4-(pyridinyl)-1-piperldinyl])carbonyl}-1,2,4-oxadiazol-5-yl)hexanoic acid;

i) (3R)-6-cyclohexyl-3-(3-{[methyl(2-pyridinlymethyl)amino]carbonyl}-1,2,4-oxadiazol-5-yl)hexanoic acid;

j) (3R)-6-cyclohexyl-3-(3-{[3-(methoxycarbonyl)-1-azetidinyl]carbonyl}-1,2,4oxadiazol-5-yl)hexanoic acid;

k) (3R)-6-cyclohexyl-3-(3-methyl-1,2,4-oxadiazol-5-yl) hexanoic acid;

l) (3R)-6-cyclohexyl-3-(3-ispropyl-1,2,4-oxadiazol-5-yl) hexanoic acid;

m) of (3R)-6-cyclohexyl-3-[3-(3-(methoxymethyl)-1,2,4-oxadiazol-5-y]hexanoic acid;

n) (3R)-6-cyclohexyl-3-[3-(2-methoxyethyl)-1,2,4-oxadiazol-5-yl]hexanoic acid;

o) (3R)-6-cyclohexyl-3-{3-[2-oxo-2-(1-pyrrolidinyl) ethyl]-1,2,4-oxadiazol-5-yl}hexanoic acid;

p) (3R)-6-cyclohexyl-3-{3[(phenylsulfonyl)methyl]-1,2,4-oxadiazol-5-yl}hexanoic acid;

q) (3R)-3-{3-[(4-chlorophenoxy)methyl]-1,2,4-oxadiazol-5-yl}-6-cyclohexylhexanoic acid;

r) (3R)-8-cyclohexyl-3-[3-(2pyridinylmethyl)-1,2,4-oxadiazol-5-yl]hexanoic acid;

s) (3R)-6-cyclohexyl-3-[3-(1-pyrrolidinylcarbonyl)-1,2,4-oxadiazol-5-yl]hexanoic acid;

t) (3R)-6-cyclohexyl-3-(3-{[(2-methoxy-2-oxoethyl)(methyl)amino]carbonyl}-1,2,4-oxadiazol-5-yl)gexanoic acid:

u) of (3R)-6-cyclohexyl-3-{3-([3-dimethylamino)-1-azetidinyl]carbonyl}-1,2,4-oxadiazol-5-yl)hexanoic acid;

v) (3R)-3-[3-({[tert-butoxycarbonyl)- 3-azetidinyl]amino}carbonyl)-1,2,4-oxadiazol-5-yl]-6-cyclohexylhexanoic acid;

w) (3R)-3-[3-({bis(tert-butoxtycarbonyl)amino]-1-azetidinyl)carbonyl)-1,2,4-oxadiazol-5-yl]-6-cyclohexylhexanoic acid;

x) (3R)-6-cyclohexyl-3(3-{([2-dimethylamino)ethyl](methyl)amino)carbonyl}-1,2,4-oxadiazol-5-yl)hexanoic acid;

y) (3R)-6-cyclohexyl-3-(3-{([3-(dimethylamino)propyl](methyl)amino]-1,2,4-oxadiazol-5-yl}hexanoic acid;

z) (3R)-6-cyclohexyl-3-{3[(2-ethoxy-2-oxoethoxy)methyl]-,1,2,4-oxadiazol-5-yl)hexanoic acid aa) (3R)-6-cyclohexyl-3-{3-[(2-ethoxy-1-methyl-2-oxoethoxy)methyl]1,2,4-oxadiazol-5-yl}hexanoic acid;

bb) (3R)-3-{3-[(2-amino-2-oxoethoxy-1-methyl]1,2,4-oxadiazol-5-yl)-6-cyclohexylhexanoic acid;

cc) 3R)-6-cyclohexyl-3-[3-(3-ethoxy-3-oxopropyl )-1,2,4-oxadiazol-5-yl]hexanoic acid;

dd) (3R)-6-cyclohexyl-3-{3-[(propylsulfonly)methyl-1,2,4-oxadiazol-5-yl}hexanoic acid;

ee) (3R)-6-cyclohexyl-3-[3-(1H-imidazol-2-ylmethyl)-1,2,4-oxadiazol-5-yl]hexanoic acid, and;

ff) (3R)-6-cyclohexyl-3-[3-(4-pyridinylmethyl)-1,2,4-oxadiazol-5-yl]hexanoic acid.

11. A compound according to claim 7 selected from the group consisting of a) (3R)-6-cyclohexyl-3-[4-(ethoxycarbonyl)-1,3-axazol-2-yl]hexanoic acid; and b) (3R)-6-cyclotbuyl-3-{4-[dimethylamino)carbonyl]-1,3-oxazol-2-yl}hexanoic acid.

* * * * *